US009931104B2

(12) United States Patent
Rhad et al.

(10) Patent No.: US 9,931,104 B2
(45) Date of Patent: Apr. 3, 2018

(54) BIOPSY DEVICE TARGETING FEATURES

(71) Applicant: Devicor Medical Products, Inc., Cincinnati, OH (US)

(72) Inventors: Edward A. Rhad, Fairfield, OH (US); Kevin M. Fiebig, Cincinnati, OH (US); Andrew P. Nock, Dayton, OH (US); Khayrollah Taherkhani, Cincinnati, OH (US); Jessica P. Leimbach, Cincinnati, OH (US); Patrick A. Mescher, Bellbrook, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 288 days.

(21) Appl. No.: 14/335,051

(22) Filed: Jul. 18, 2014

(65) Prior Publication Data
US 2015/0025414 A1    Jan. 22, 2015

Related U.S. Application Data

(60) Provisional application No. 61/928,089, filed on Jan. 16, 2014, provisional application No. 61/856,157, filed on Jul. 19, 2013.

(51) Int. Cl.
*A61B 10/00*    (2006.01)
*A61B 10/02*    (2006.01)
(Continued)

(52) U.S. Cl.
CPC ...... *A61B 10/0266* (2013.01); *A61B 17/3403* (2013.01); *A61B 17/3421* (2013.01);
(Continued)

(58) Field of Classification Search
CPC ............ A61B 10/0275; A61B 10/0266; A61B 2010/0208
(Continued)

(56) References Cited

U.S. PATENT DOCUMENTS 5,368,046 A * 11/1994 Scarfone .............. A61B 10/025
600/567
5,526,822 A    6/1996 Burbank et al.
(Continued)

FOREIGN PATENT DOCUMENTS

WO    WO 2009/067648    5/2009

OTHER PUBLICATIONS

International Search Report and Written Opinion dated Nov. 5, 2014 for Application No. PCT/US2014/047183.
(Continued)

*Primary Examiner* — Daniel Cerioni
(74) *Attorney, Agent, or Firm* — Frost Brown Todd LLC

(57) ABSTRACT

An apparatus for guiding a biopsy instrument into tissue of a patent comprises a cannula, a guide device, a support structure, and a locking assembly. At least a portion of the biopsy instrument is insertable into the cannula. The guide device comprises at least one guide hole. The at least one guide hole is configured to receive the cannula. The support structure is configured to position the guide device relative to a breast of a patent. The locking assembly comprises a lock arm that is configured to engage the cannula to restrict translational movement of the cannula within the guide hole of the guide device.

20 Claims, 117 Drawing Sheets

(51) Int. Cl.
  *A61B 17/34* (2006.01)
  *A61B 90/17* (2016.01)
  *A61B 90/11* (2016.01)

(52) U.S. Cl.
  CPC .............. *A61B 90/11* (2016.02); *A61B 90/17* (2016.02); *A61B 2017/346* (2013.01); *A61B 2017/3409* (2013.01); *A61B 2017/3411* (2013.01); *A61B 2017/3454* (2013.01)

(58) Field of Classification Search
  USPC ........................................................ 600/567
  See application file for complete search history.

(56) References Cited

U.S. PATENT DOCUMENTS

| | | | |
|---|---|---|---|
| 5,928,164 | A | 7/1999 | Burbank et al. |
| 6,017,316 | A | 1/2000 | Ritchart et al. |
| 6,086,544 | A | 4/2000 | Hibner et al. |
| 6,162,187 | A | 12/2000 | Buzzard et al. |
| 6,432,065 | B1 | 8/2002 | Burdorff et al. |
| 6,626,849 | B2 | 9/2003 | Huitema et al. |
| 6,752,768 | B2 | 6/2004 | Burdorff et al. |
| 7,442,171 | B2 | 10/2008 | Stephens et al. |
| 7,507,210 | B2 | 3/2009 | Hibner et al. |
| 7,648,466 | B2 | 1/2010 | Stephens et al. |
| 7,730,628 | B2 | 6/2010 | Hoffman |
| 7,831,290 | B2 | 11/2010 | Hughes et al. |
| 7,837,632 | B2 | 11/2010 | Stephens et al. |
| 7,854,706 | B2 | 12/2010 | Hibner |
| 7,914,464 | B2 | 3/2011 | Burdorff et al. |
| 7,938,786 | B2 | 5/2011 | Ritchie et al. |
| 8,083,687 | B2 | 12/2011 | Parihar |
| 8,118,755 | B2 | 2/2012 | Hibner et al. |
| 8,206,316 | B2 | 6/2012 | Hibner et al. |
| 8,241,226 | B2 | 8/2012 | Hibner et al. |
| 8,246,551 | B2 | 8/2012 | Miller et al. |
| 8,277,394 | B2 | 10/2012 | Hibner |
| 8,328,732 | B2 | 12/2012 | Parihar et al. |
| 8,454,531 | B2 | 6/2013 | Speeg et al. |
| 8,568,333 | B2 | 10/2013 | Hibner et al. |
| 8,702,623 | B2 | 4/2014 | Parihar et al. |
| 8,764,680 | B2 | 7/2014 | Rhad et al. |
| 8,801,742 | B2 | 8/2014 | Rhad et al. |
| 8,858,465 | B2 | 10/2014 | Fiebig |
| 8,932,233 | B2 | 1/2015 | Haberstich et al. |
| 8,938,285 | B2 | 1/2015 | Fiebig et al. |
| 9,095,326 | B2 | 8/2015 | Ritchie et al. |
| 2005/0054947 | A1* | 3/2005 | Goldenberg ....... A61B 10/0233 600/567 |
| 2006/0074345 | A1 | 4/2006 | Hibner |
| 2008/0214955 | A1 | 9/2008 | Speeg et al. |
| 2009/0131821 | A1 | 5/2009 | Speeg et al. |
| 2010/0152610 | A1 | 6/2010 | Parihar et al. |
| 2010/0160811 | A1 | 6/2010 | Parihar et al. |
| 2010/0160819 | A1 | 6/2010 | Parihar et al. |
| 2010/0160823 | A1* | 6/2010 | Parihar .............. A61B 10/0275 600/567 |
| 2011/0092849 | A1* | 4/2011 | Deshmukh ............ A61B 90/17 600/562 |
| 2011/0092850 | A1* | 4/2011 | Kulkarni ................ A61B 90/11 600/562 |
| 2012/0065542 | A1 | 3/2012 | Hibner et al. |
| 2013/0053724 | A1 | 2/2013 | Fiebig et al. |
| 2013/0144188 | A1 | 6/2013 | Fiebig et al. |
| 2013/0324882 | A1 | 12/2013 | Mescher |

OTHER PUBLICATIONS

U.S. Appl. No. 61/566,793, filed Dec. 5, 2011.
U.S. Appl. No. 61/771,202, filed Mar. 1, 2013.
U.S. Appl. No. 61/856,157, filed Jul. 19, 2013.
U.S. Appl. No. 61/928,089, filed Jan. 16, 2014.
Extended European Search Report dated Dec. 16, 2016 for Application No. 14825919.5, 8 pgs.
Australian Office Action dated Nov. 2, 2017 for Application No. 2014290446, 6 pgs.
Korean Office Action dated Jan. 3, 2018 for Application No. 10-2016-7004025, 5 pgs.

* cited by examiner

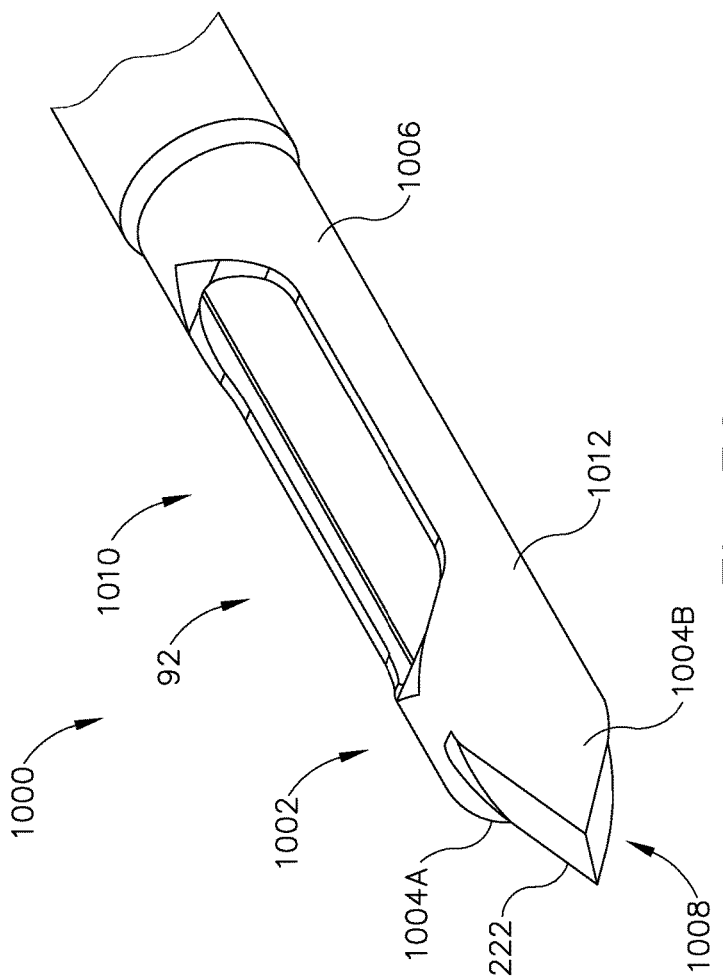

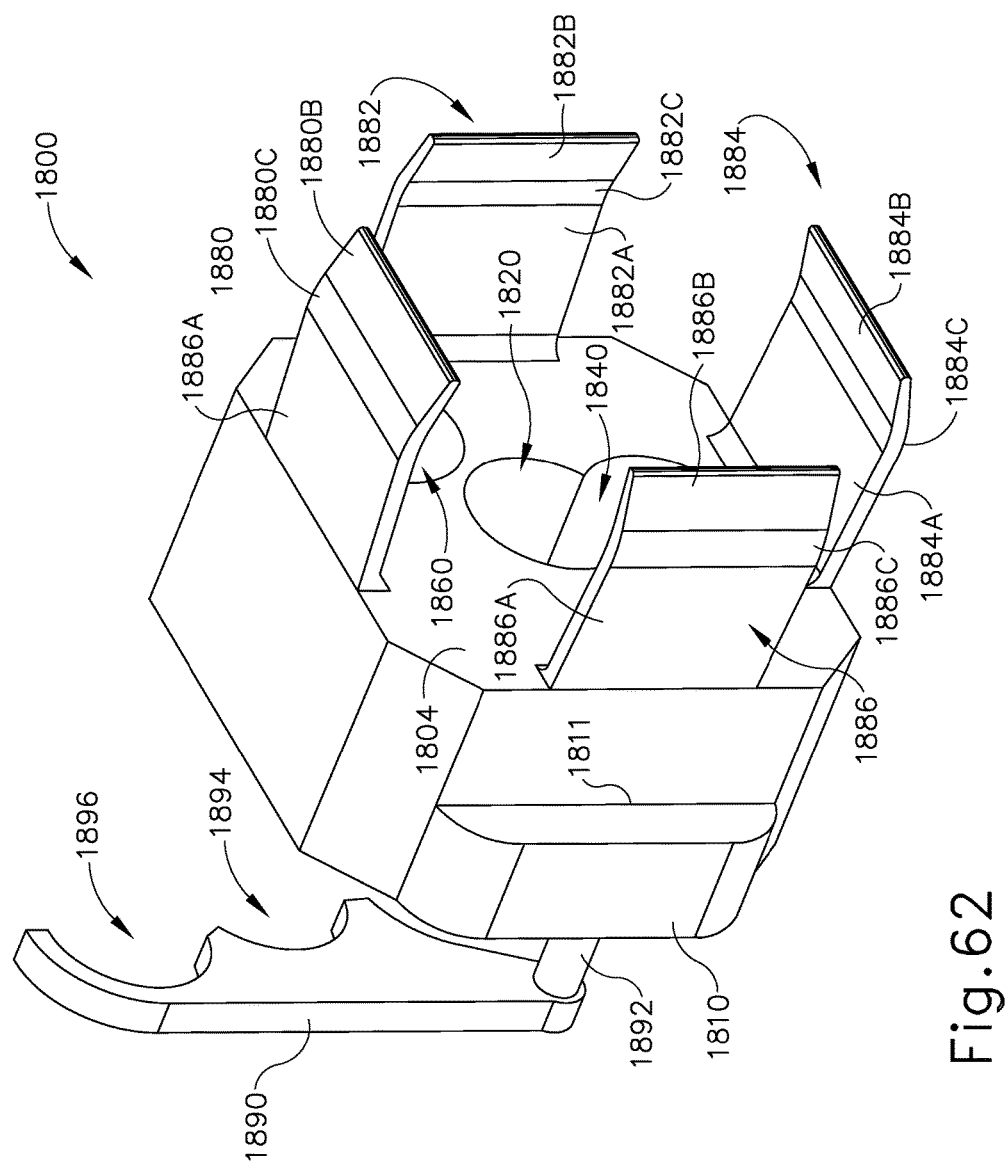

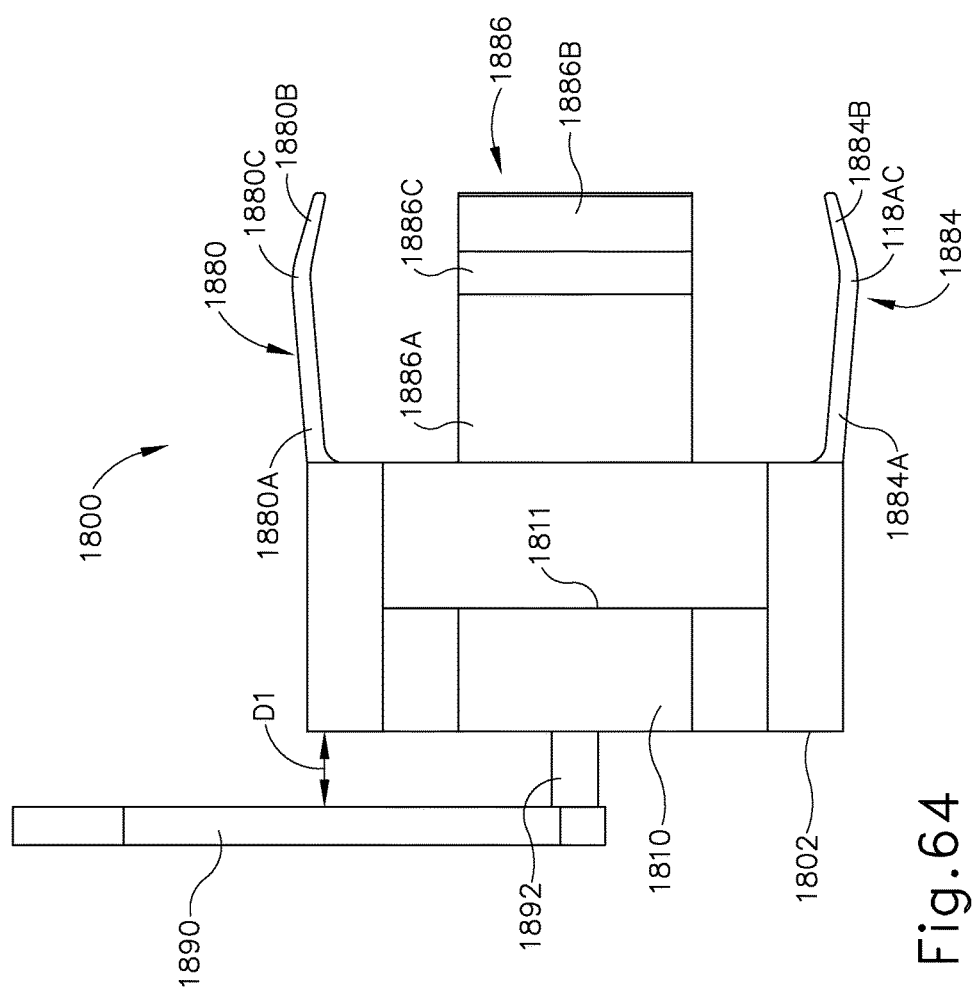

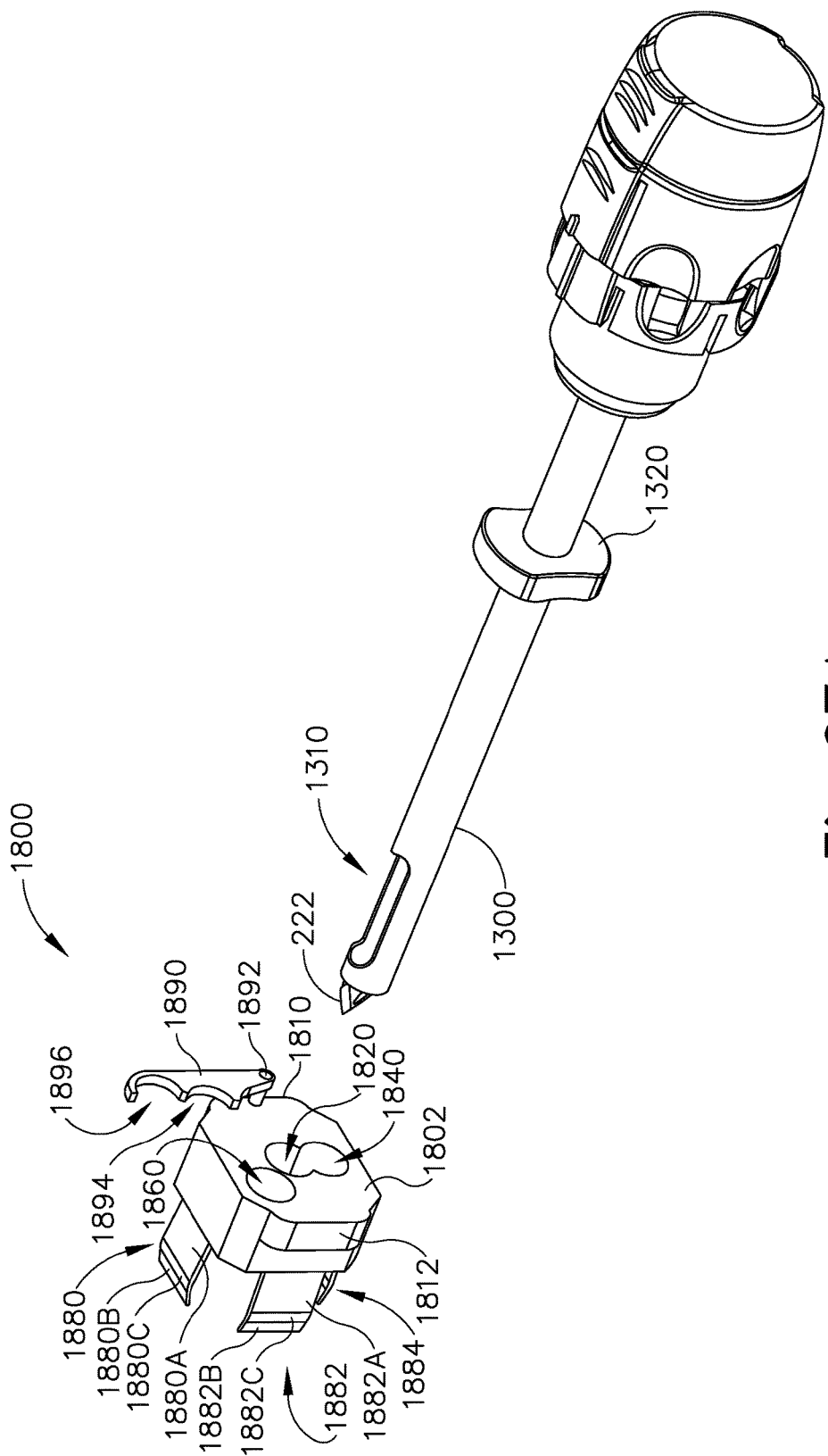

BIOPSY DEVICE TARGETING FEATURES

PRIORITY

This application claims priority to U.S. Provisional Application Ser. No. 61/928,089, filed Jan. 16, 2014, entitled "Biopsy Device Targeting Features," the disclosure of which is incorporated by reference herein. This application also claims priority to U.S. Provisional Application Ser. No. 61/856,157, filed Jul. 19, 2013, entitled "Biopsy Device Targeting Features," the disclosure of which is incorporated by reference herein.

BACKGROUND

Biopsy samples have been obtained in a variety of ways in various medical procedures including open and percutaneous methods using a variety of devices. Biopsy devices may be used under stereotactic guidance, ultrasound guidance, MRI guidance, PEM guidance, BSGI guidance, or otherwise.

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "MRI Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; and U.S. Pat. No. 8,118,755, entitled "Biopsy Sample Storage," issued Feb. 21, 2012. The disclosure of each of the above-cited U.S. patents is incorporated by reference herein.

Additional exemplary biopsy devices and biopsy system components are disclosed in U.S. Pat. Pub. No. 2006/0074345, entitled "Biopsy Apparatus and Method," published Apr. 6, 2006; U.S. Pat. Pub. No. 2008/0146962, entitled "Biopsy System with Vacuum Control Module," published Jun. 19, 2008; U.S. Pat. Pub. No. 2008/0214955, entitled "Presentation of Biopsy Sample by Biopsy Device," published Sep. 4, 2008; U.S. Pat. Pub. No. 2008/0221480, entitled "Biopsy Sample Storage," published Sep. 11, 2008, issued as U.S. Pat. No. 8,118,755 on Feb. 21, 2012; U.S. Pat. Pub. No. 2009/0131821, entitled "Graphical User Interface For Biopsy System Control Module," published May 21, 2009; U.S. Pat. Pub. No. 2009/0131820, entitled "Icon-Based User Interface on Biopsy System Control Module," published May 21, 2009, issued as U.S. Pat. No. 8,454,531 on Jun. 4, 2013; U.S. Pat. Pub. No. 2010/0113973, entitled "Biopsy Device with Rotatable Tissue Sample Holder," published May 6, 2010, issued as U.S. Pat. No. 8,241,226 on Aug. 14, 2012; U.S. Pat. Pub. No. 2010/0152610, entitled "Hand Actuated Tetherless Biopsy Device with Pistol Grip," published Jun. 17, 2010; U.S. Pat. Pub. No. 2010/0160819, entitled "Biopsy Device with Central Thumbwheel," published Jun. 24, 2010; U.S. Pat. Pub. No. 2010/0160824, entitled "Biopsy Device with Discrete Tissue Chambers," published Jun. 24, 2010, issued as U.S. Pat. No. 8,702,623 on Apr. 22, 2014; U.S. Pat. Pub. No. 2010/0317997, entitled "Tetherless Biopsy Device with Reusable Portion," published Dec. 16, 2010, issued as U.S. Pat. No. 8,206,316 on Jun. 26, 2012; U.S. Pat. Pub. No. 2012/0109007, entitled "Handheld Biopsy Device with Needle Firing," published May 3, 2012; U.S. Non-Provisional patent application Ser. No. 13/086,567, entitled "Biopsy Device with Motorized Needle Firing," filed Apr. 14, 2011, published as U.S. Pat. Pub. No. 2012/0265095 on Oct. 18, 2012; U.S. Non-Provisional patent application Ser. No. 13/150,950, entitled "Needle Assembly and Blade Assembly for Biopsy Device," filed Jun. 1, 2011, published as U.S. Pat. Pub. No. 2012/0310110 on Dec. 6, 2012; U.S. Non-Provisional patent application Ser. No. 13/205,189, entitled "Access Chamber and Markers for Biopsy Device," filed Aug. 8, 2011, published as U.S. Pat. Pub. No. 2013/0041256 on Feb. 14, 2013; U.S. Non-Provisional patent application Ser. No. 13/218,656, entitled "Biopsy Device Tissue Sample Holder with Bulk Chamber and Pathology Chamber," filed Aug. 26, 2011, published as U.S. Pat. Pub. No. 2013/0053724 on Feb. 28, 2013; U.S. Provisional Patent App. No. 61/566,793, entitled "Biopsy Device With Slide-In Probe," filed Dec. 5, 2011; and U.S. Non-Provisional patent application Ser. No. 13/483,235, entitled "Control for Biopsy Device," filed May 30, 2012, published as U.S. Pat. Pub. No. 2013/0324882 on Dec. 5, 2013. The disclosure of each of the above-cited U.S. patent application Publications, U.S. Non-Provisional patent applications, and U.S. Provisional patent applications is incorporated by reference herein.

In U.S. Pat. Pub. No. 2005/0283069, entitled "MRI Biopsy Device Localization Fixture" published Dec. 22, 2005, the disclosure of which is incorporated by reference herein, a localization mechanism, or fixture, is described that is used in conjunction with a breast coil for breast compression and for guiding a core biopsy instrument during prone biopsy procedures in both open and closed Magnetic Resonance Imaging (MRI) machines. The localization fixture includes a three-dimensional Cartesian positionable guide for supporting and orienting an MRI-compatible biopsy instrument, and, in particular, a cannula/sleeve to a biopsy site of suspicious tissues or lesions. Another merely illustrative localization mechanism used for guiding a core biopsy instrument is disclosed in U.S. Pat. No. 7,507,210, entitled "Biopsy Cannula Adjustable Depth Stop," issued Mar. 24, 2009, the disclosure of which is incorporated by reference herein. The localization mechanism includes a grid plate configured to removably receive a guide cube capable of supporting and orienting an MRI-compatible biopsy instrument. For instance, a combination of an obturator and targeting cannula/sleeve may be introduced through a breast to a biopsy site via the guide cube, with proper positioning confirmed using MRI imaging. The obturator may then be removed and the needle of a biopsy device may then be inserted through the targeting cannula/sleeve to reach the targeted lesion.

A Z-stop may enhance accurate insertion, and prevent over-insertion or inadvertent retraction of a biopsy device targeting cannula/sleeve and obturator. In particular, a Z-stop may engage the localization fixture or cube at a distance from the patient set to restrict the depth of insertion of a biopsy device needle into a patient. Merely illustrative z-stop examples are disclosed in U.S. Pat. No. 7,507,210, entitled "Biopsy Cannula Adjustable Depth Stop," issued Mar. 24, 2009, the disclosure of which is incorporated by reference herein.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

FIG. 30 depicts a partial perspective view of the cannula and obturator of FIG. 29;

FIG. 62 depicts another perspective view of the guide cube of FIG. 61;

FIG. 64 depicts a side elevational view of the guide cube of FIG. 61;

FIG. 67A depicts a perspective view of the guide cube of FIG. 61 with the locking feature of FIG. 63A in the first rotational position of FIG. 63A, and with a cannula in a first longitudinal position;

Figure 1:
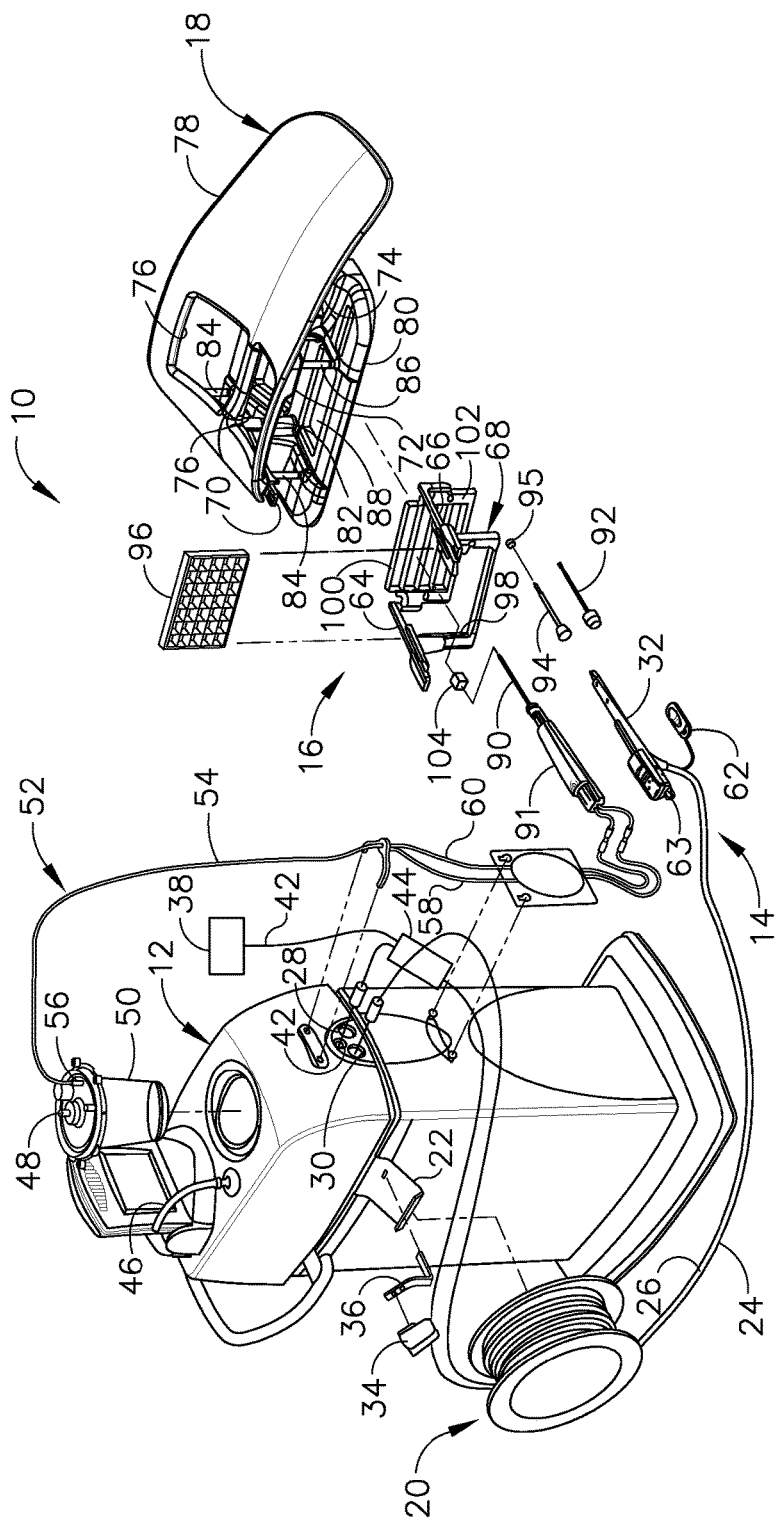
FIG. 1 depicts a perspective view of a biopsy system including a control module remotely coupled to a biopsy device, and including a localization fixture with a lateral grid plate used in conjunction with a rotatable cube to position an obturator or a probe of the biopsy device to a desired insertion depth as set by a ring stop.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Overview of Exemplary MRI Biopsy Control Module

Figure 2:
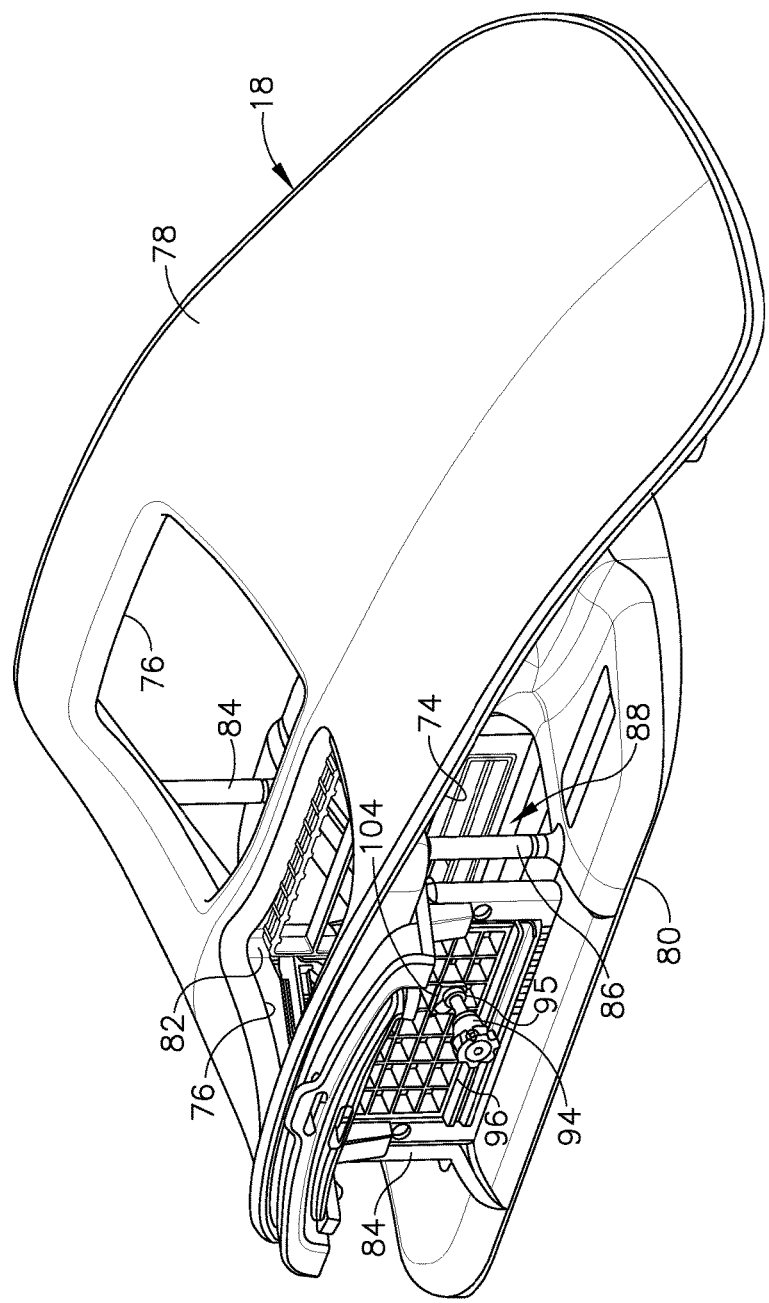
FIG. 2 depicts a perspective view of a breast coil receiving the localization fixture of FIG. 1.
Figure 3:
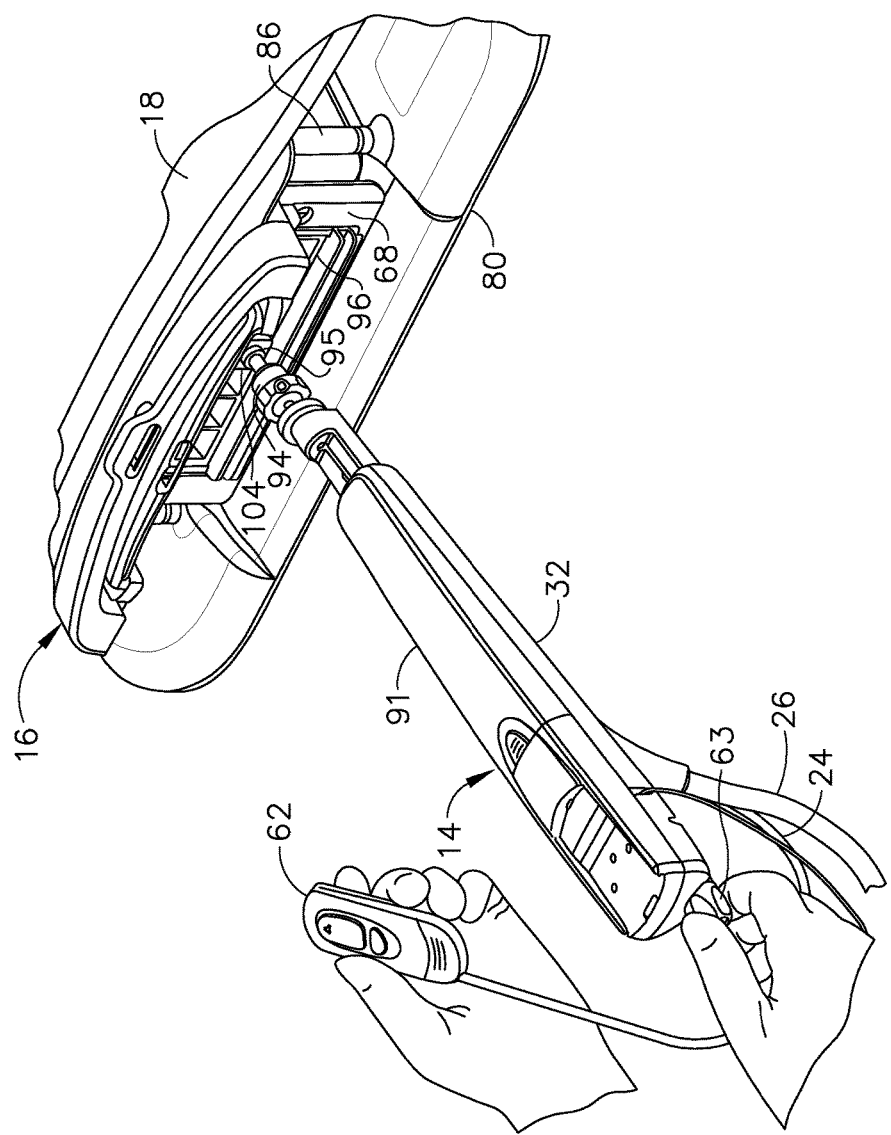
FIG. 3 depicts a perspective view of the biopsy device inserted through the rotatable cube within the cube plate of the localization fixture attached to the breast coil of FIG. 2.

In FIGS. 1-3, MRI compatible biopsy system (10) has control module (12) that may be placed outside of a shielded room containing an MRI machine (not shown) or at least spaced away to mitigate detrimental interaction with its strong magnetic field and/or sensitive radio frequency (RF) signal detection antennas. As described in U.S. Pat. No. 6,752,768, which is hereby incorporated by reference in its entirety, a range of preprogrammed functionality may be incorporated into control module (12) to assist in taking tissue samples. Control module (12) controls and powers biopsy device (14) that is used with localization assembly (15). Biopsy device (14) is positioned and guided by localization fixture (16) attached to breast coil (18) that may be placed upon a gantry (not shown) of a MRI or other imaging machine.

In the present example, control module (12) is mechanically, electrically, and pneumatically coupled to biopsy device (14) so that components may be segregated that need to be spaced away from the strong magnetic field and the sensitive RF receiving components of a MRI machine. Cable management spool (20) is placed upon cable management attachment saddle (22) that projects from a side of control module (12). Wound upon cable management spool (20) is paired electrical cable (24) and mechanical cable (26) for communicating control signals and cutter rotation/advancement motions respectively. In particular, electrical and mechanical cables (24, 26) each have one end connected to respective electrical and mechanical ports (28, 30) in control module (12) and another end connected to holster portion (32) of biopsy device (14). Docking cup (34), which may hold holster portion (32) when not in use, is hooked to control module (12) by docking station mounting bracket (36). It should be understood that such components described above as being associated with control module (12) are merely optional.

Interface lock box (38) mounted to a wall provides tether (40) to lockout port (42) on control module (12). Tether (40) is uniquely terminated and of short length to preclude inadvertent positioning of control module (12) too close to a MRI machine or other machine. In-line enclosure (44) may register tether (40), electrical cable (24) and mechanical cable (26) to their respective ports (42, 28, 30) on control module (12).

Vacuum assist is provided by first vacuum line (46) that connects between control module (12) and outlet port (48) of vacuum canister (50) that catches liquid and solid debris. Tubing kit (52) completes the pneumatic communication between control module (12) and biopsy device (14). In particular, second vacuum line (54) is connected to inlet port (56) of vacuum canister (50). Second vacuum line (54) divides into two vacuum lines (58, 60) that are attached to biopsy device (14). With biopsy device (14) installed in holster portion (32), control module (12) performs a functional check. Saline may be manually injected into biopsy device (14) or otherwise introduced to biopsy device (14), such as to serve as a lubricant and to assist in achieving a vacuum seal and/or for other purposes. Control module (12) actuates a cutter mechanism (not shown) in biopsy device (14), monitoring full travel of a cutter in biopsy device (14) in the present example. Binding in mechanical cable (26) or within biopsy device (14) may optionally monitored with reference to motor force exerted to turn mechanical cable (26) and/or an amount of twist in mechanical cable (26) sensed in comparing rotary speed or position at each end of mechanical cable (26).

Remote keypad (62), which is detachable from holster portion (32), communicates via electrical cable (24) to control panel (12) to enhance clinician control of biopsy device (14) in the present example, especially when controls that would otherwise be on biopsy device (14) itself are not readily accessible after insertion into localization fixture (16) and/or placement of control module (12) is inconveniently remote (e.g., 30 feet away). However, as with other components described herein, remote keypad (62) is merely optional, and may be modified, substituted, supplemented, or omitted as desired. In the present example, aft end thumbwheel (63) on holster portion (32) is also readily accessible after insertion to rotate the side from which a tissue sample is to be taken.

Of course, the above-described control module (12) is merely one example. Any other suitable type of control module (12) and associated components may be used. By way of example only, control module (12) may instead be configured and operable in accordance with the teachings of U.S. Pub. No. 2008/0228103, entitled "Vacuum Timing Algorithm for Biopsy Device," published Sep. 18, 2008, the disclosure of which is incorporated by reference herein. As another merely illustrative example, control module (12) may instead be configured and operable in accordance with the teachings of U.S. patent application Ser. No. 12/337,814, entitled "Control Module Interface for MRI Biopsy Device," filed Dec. 18, 2008, the disclosure of which is incorporated by reference herein. Alternatively, control module (12) may have any other suitable components, features, configurations, functionalities, operability, etc. Other suitable variations of control module (12) and associated components will be apparent to those of ordinary skill in the art in view of the teachings herein.

II. Exemplary Localization Assembly

Left and right parallel upper guides (64, 66) of localization framework (68) are laterally adjustably received respectively within left and right parallel upper tracks (70, 72) attached to under side (74) and to each side of a selected breast aperture (76) formed in patient support platform (78) of breast coil (18). Base (80) of breast coil (18) is connected by centerline pillars (82) that are attached to patient support platform (78) between breast apertures (76). Also, a pair of outer vertical support pillars (84, 86) on each side spaced about a respective breast aperture (76) respectively define lateral recess (88) within which localization fixture (16) resides.

It should be appreciated that the patient's breasts hang pendulously respectively into breast apertures (76) within lateral recesses (88) in the present example. For convenience, herein a convention is used for locating a suspicious lesion by Cartesian coordinates within breast tissue referenced to localization fixture (16) and to thereafter selectively position an instrument, such as needle (90) of probe (91) that is engaged to holster portion (32) to form biopsy device (14). Of course, any other type of coordinate system or targeting techniques may be used. To enhance hands-off use of biopsy system (10), especially for repeated re-imaging within the narrow confines of a closed bore MRI machine, biopsy system (10) may also guide obturator (92) encompassed by cannula (94). Depth of insertion is controlled by depth stop device (95) longitudinally positioned on either needle (90) or cannula (94). Alternatively, depth of insertion may be controlled in any other suitable fashion.

This guidance is specifically provided by a lateral fence in the present example, depicted as grid plate (96), which is received within laterally adjustable outer three-sided plate bracket (98) attached below left and right parallel upper guides (64, 66). Similarly, a medial fence with respect to a medial plane of the chest of the patient, depicted as medial plate (100), is received within inner three-sided plate bracket (102) attached below left and right parallel upper guides (64, 66) close to centerline pillars (82) when installed in breast coil (18). To further refine the insertion point of the instrument (e.g., needle (90) of probe (91), obturator/cannula (92, 94), etc.), guide cube (104) may be inserted into grid plate (96).

In the present example, the selected breast is compressed along an inner (medial) side by medial plate (100) and on an outer (lateral) side of the breast by grid plate (96), the latter defining an X-Y plane. The X-axis is vertical (sagittal) with respect to a standing patient and corresponds to a left-to-right axis as viewed by a clinician facing the externally exposed portion of localization fixture (16). Perpendicular to this X-Y plane extending toward the medial side of the breast is the Z-axis, which typically corresponds to the orientation and depth of insertion of needle (90) or obturator/cannula (92, 94) of biopsy device (14). For clarity, the term Z-axis may be used interchangeably with "axis of penetration", although the latter may or may not be orthogonal to the spatial coordinates used to locate an insertion point on the patient. Versions of localization fixture (16) described herein allow a non-orthogonal axis of penetration to the X-Y axis to a lesion at a convenient or clinically beneficial angle.

It should be understood that the above-described localization assembly (15) is merely one example. Any other suitable type of localization assembly (15) may be used, including but not limited to localization assemblies (15) that use a breast coil (18) and/or localization fixture (16) different from those described above. Other suitable components, features, configurations, functionalities, operability, etc. for a localization assembly (15) will be apparent to those of ordinary skill in the art in view of the teachings herein.

III. Exemplary Biopsy Device

As shown in FIG. 1, one version of biopsy device (14) may comprise holster portion (32) and probe (91). Exemplary holster portion (32) was discussed previously in the above section addressing control module (12). The following paragraphs will discuss probe (91) and associated components and devices in further detail.

Figure 7:
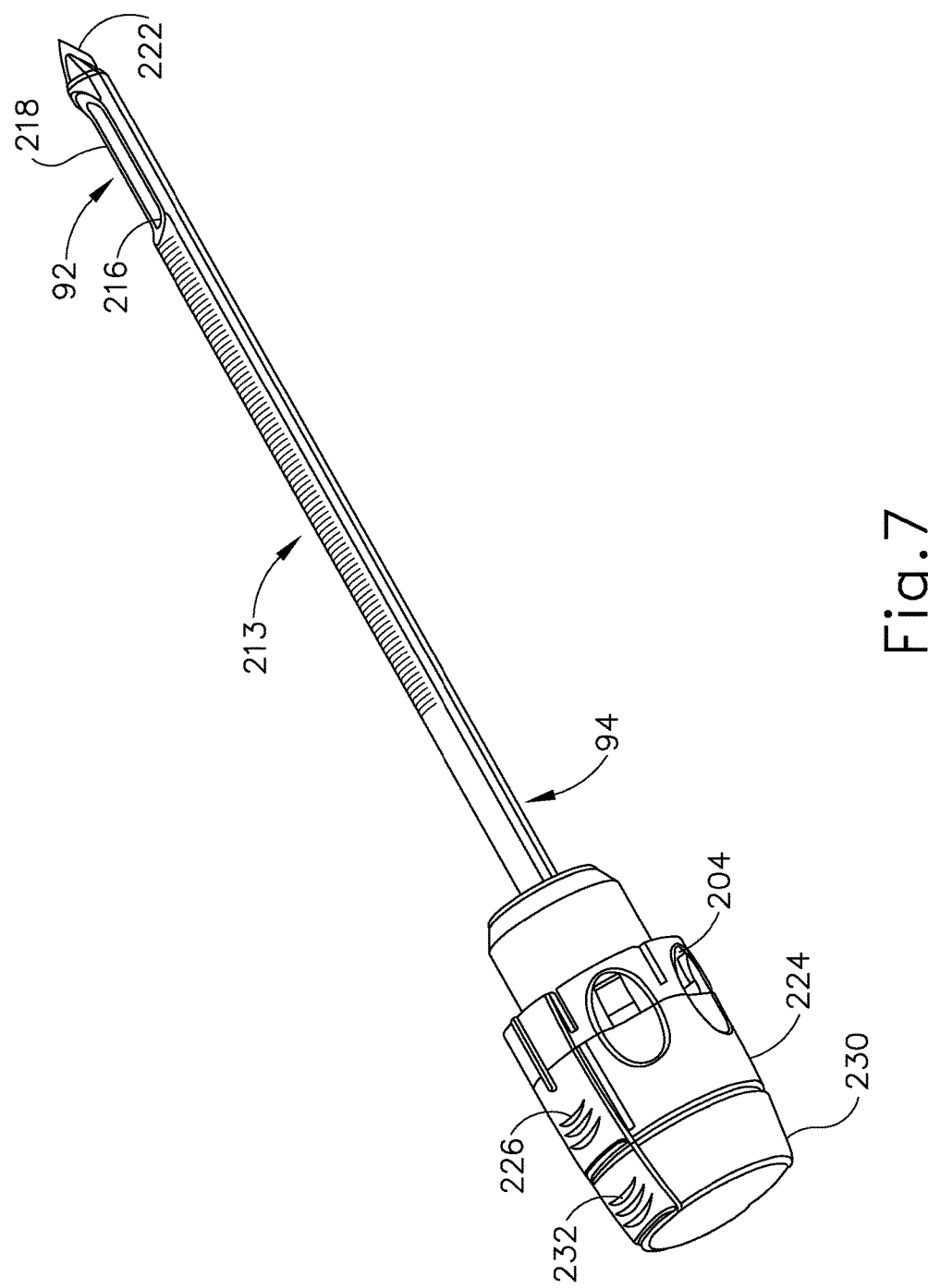
FIG. 7 depicts a perspective view of a obturator and cannula of the biopsy system of FIG. 1.
Figure 8:
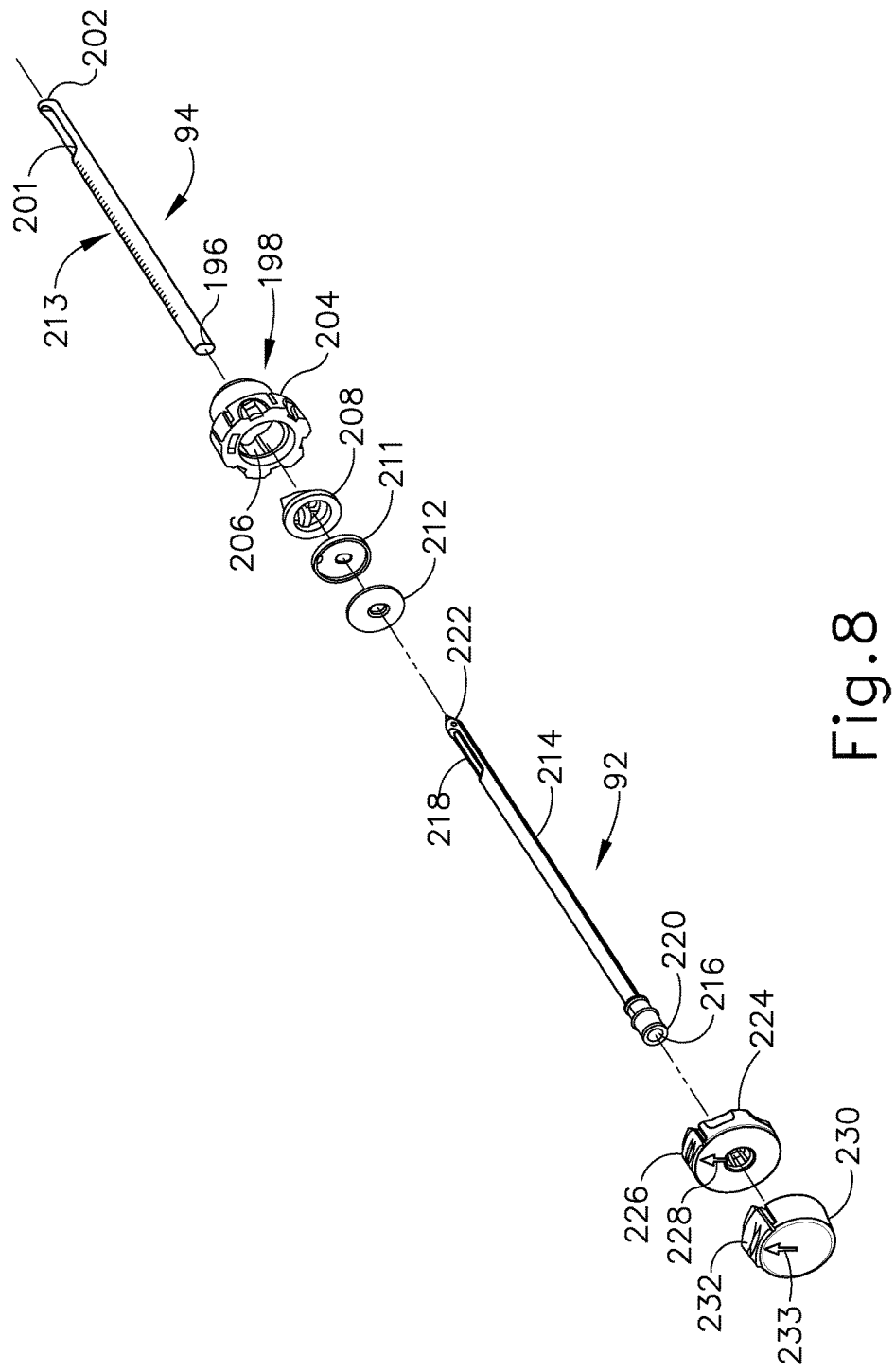
FIG. 8 depicts a perspective exploded view of the obturator and cannula of FIG. 7.
Figure 9:
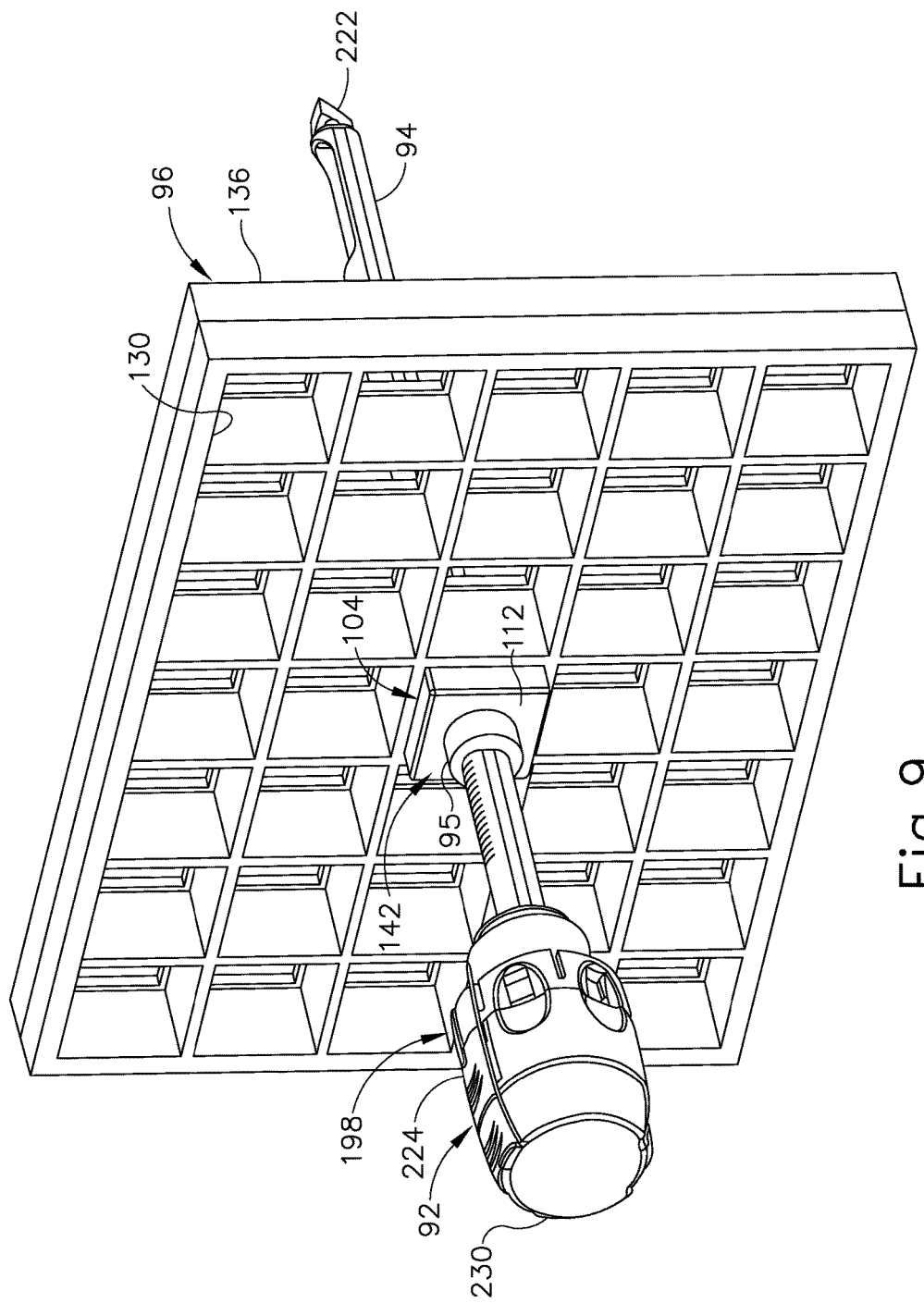
FIG. 9 depicts a perspective view of the obturator and cannula of FIG. 7 with a depth stop device of FIG. 1 inserted through the guide cube and grid plate of FIG. 6.

In the present example, cannula (94) and obturator (92) are associated with probe (91). In particular, and as shown in FIGS. 7, 8, and 9, obturator (92) is slid into cannula (94) and the combination is guided through guide cube (104) to the biopsy site within the breast tissue. As shown in FIG. 3, obturator (92) is then withdrawn from cannula (94), then needle (90) of probe (91) is inserted in cannula (94), and then biopsy device (14) is operated to acquire one or more tissue samples from the breast via needle (90).

Cannula (94) of the present example is proximally attached to cylindrical hub (198) and cannula (94) includes lumen (196) and lateral aperture (201) proximate to open distal end (202). Cylindrical hub (198) has exteriorly presented thumbwheel (204) for rotating lateral aperture (201). Cylindrical hub (198) has interior recess (206) that encompasses duckbill seal (208), wiper seal (211) and seal retainer (212) to provide a fluid seal when lumen (196) is empty and for sealing to inserted obturator (92). Longitudinally spaced measurement indicia (213) along an outer surface of cannula (94) visually, and perhaps physically, provide a means to locate depth stop device (95) of FIG. 1.

Obturator (92) of the present example incorporates a number of components with corresponding features. Shaft (214) includes fluid lumen (216) that communicates between imageable side notch (218) and proximal port (220). Shaft (214) is longitudinally sized such that piercing tip (222) extends out of distal end (202) of cannula (94). Obturator thumbwheel cap (224) encompasses proximal port (220) and includes locking feature (226), which includes visible angle indicator (228), that engages cannula thumbwheel (204) to ensure that imageable side notch (218) is registered to lateral aperture (201) in cannula (94). Obturator seal cap (230) may be engaged proximally into obturator thumbwheel cap (224) to close fluid lumen (216). Obturator seal cap (230) of the present example includes locking or locating feature (232) that includes visible angle indicator (233) that corresponds with visible angle indicator (228) on obturator thumbwheel cap (224), which may be fashioned from either a rigid, soft, or elastomeric material. In FIG. 9, guide cube (104) has guided obturator (92) and cannula (94) through grid plate (96).

While obturator (92) of the present example is hollow, it should be understood that obturator (92) may alternatively have a substantially solid interior, such that obturator (92) does not define an interior lumen. In addition, obturator (92) may lack side notch (218) in some versions. Other suitable components, features, configurations, functionalities, operability, etc. for an obturator (92) will be apparent to those of ordinary skill in the art in view of the teachings herein. Likewise, cannula (94) may be varied in a number of ways. For instance, in some other versions, cannula (94) has a closed distal end (202). As another merely illustrative example, cannula (94) may have a closed piercing tip (222) instead of obturator (92) having piercing tip (222). In some such versions, obturator (92) may simply have a blunt distal end; or the distal end of obturator (92) may have any other suitable structures, features, or configurations. Other suitable components, features, configurations, functionalities, operability, etc. for a cannula (94) will be apparent to those of ordinary skill in the art in view of the teachings herein. Furthermore, in some versions, one or both of obturator (92) or cannula (94) may be omitted altogether. For instance, needle (90) of probe (91) may be directly inserted into a guide cube (104), without being inserted into guide cube (104) via cannula (94).

Another component that may be used with probe (91) (or needle (90)) is depth stop (95). Depth stop may be of any suitable configuration that is operable to prevent cannula (94) and obturator (92) (or needle (90)) from being inserted further than desired. For instance, depth stop (95) may be positioned on the exterior of cannula (94) (or needle (90)), and may be configured to restrict the extent to which cannula (94) is inserted into a guide cube. It should be understood that such restriction by depth stop (95) may further provide a limit on the depth to which the combination of cannula (94) and obturator (92) (or needle (90)) may be inserted into the patient's breast. Furthermore, it should be understood that such restriction may establish the depth within the patient's breast at which biopsy device (14) acquires one or more tissue samples after obturator (92) has been withdrawn from cannula (94) and needle (90) has been inserted in cannula (94). Exemplary depth stops (95) that may be used with biopsy system (10) are described in U.S. Pub. No. 2007/0255168, entitled "Grid and Rotatable Cube Guide Localization Fixture for Biopsy Device," published Nov. 1, 2007, and incorporated by reference herein as mentioned previously.

In the present example, and as noted above, biopsy device (14) includes a needle (90) that may be inserted into cannula (94) after the combination of cannula (94) and obturator (92) has been inserted to a desired location within a patient's breast and after obturator (92) has been removed from cannula (94). Needle (90) of the present example comprises a lateral aperture (not shown) that is configured to substantially align with lateral aperture (201) of cannula (94) when needle (90) is inserted into lumen (196) of cannula (94). Probe (91) of the present example further comprises a rotating and translating cutter (not shown), which is driven by components in holster (32), and which is operable to sever tissue protruding through lateral aperture (201) of cannula (94) and the lateral aperture of needle (90). Severed tissue samples may be retrieved from biopsy device (14) in any suitable fashion.

Figure 10:
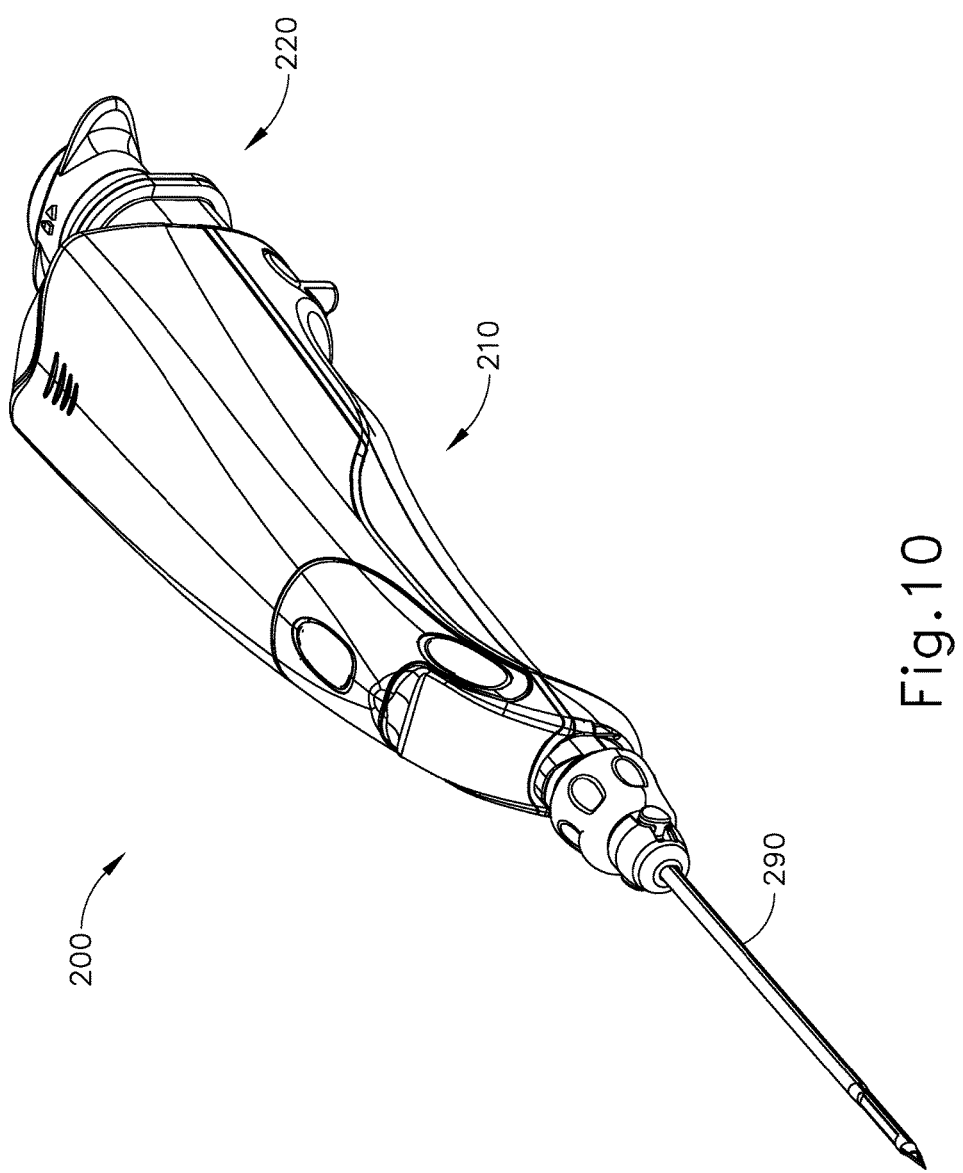
FIG. 10 depicts a perspective view of an exemplary alternative biopsy device that may be used with the biopsy system of FIG. 1.

It should be understood that although biopsy system (10) is discussed above as utilizing disposable probe assembly (91), other suitable probe assemblies and biopsy device assemblies may be utilized. By way of example only, a biopsy device such as the biopsy device (200) shown in FIG. 10 may be used in biopsy system (10). Biopsy device (200) of this example comprises a needle (290) extending distally from a handpiece (210); and a tissue sample holder (220) disposed at a proximal end of handpiece (210). Needle (290) is configured to operate substantially similar to needle (90) discussed above. For instance, needle (290) is configured to cooperate with a cutter to obtain tissue samples from a biopsy site. Tissue sample holder (220) is configured to store tissue samples received through needle (290). By way of example only, biopsy device (200) may be configured in accordance with at least some of the teachings of U.S. Pat. No. 8,206,316, entitled "Tetherless Biopsy Device with Reusable Portion," issued Jun. 26, 2012, the disclosure of which is incorporated by reference herein; U.S. Pat. No. 8,277,394, entitled "Multi-Button Biopsy Device," issued Oct. 2, 2012, the disclosure of which is incorporated by reference herein; and/or U.S. Pub. No. 2012/0065542, entitled "Biopsy Device Tissue Sample Holder with Removable Tray," published Mar. 15, 2012, the disclosure of which is incorporated by reference herein.

Figure 11:
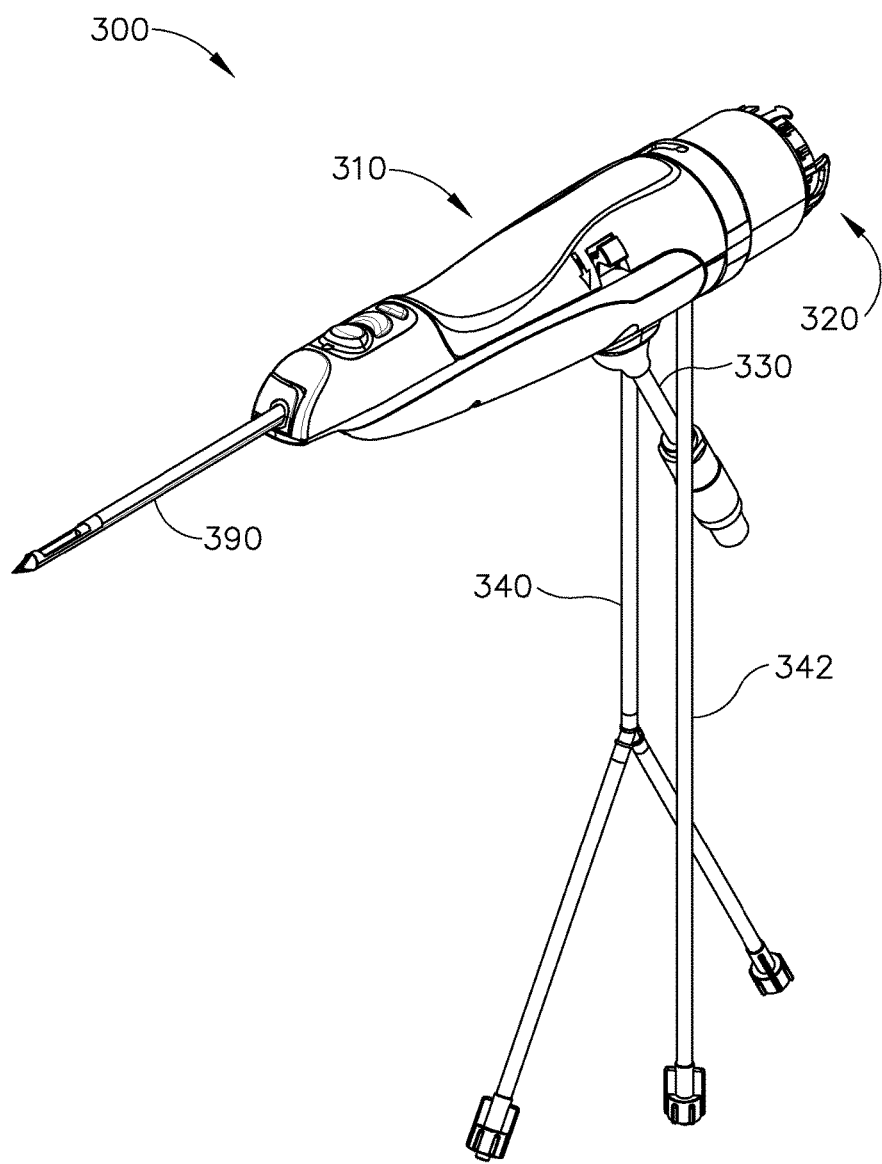
FIG. 11 depicts a perspective view of another exemplary alternative biopsy device that may be used with the biopsy system of FIG. 1.

As yet another merely illustrative example, a biopsy device such as the biopsy device (300) shown in FIG. 11 may be used in biopsy system (10). Biopsy device (300) of this example comprises a needle (390) extending distally from a handpiece (310) and a tissue sample holder (320) disposed at a proximal end of handpiece (310). Needle (290) is configured to operate substantially similar to needle (90) discussed above. For instance, needle (390) is configured to cooperate with a cutter to obtain tissue samples from a biopsy site. Tissue sample holder (320) is configured to store tissue samples received through needle (390). A cable (330) provides communication of electrical power, commands, etc. while conduits (340, 342) provide fluid communication. By way of example only, biopsy device (300) may be configured in accordance with at least some of the teachings of U.S. Pub. No. 2010/0160824, the disclosure of which is incorporated by reference herein; U.S. Non-Provisional patent application Ser. No. 13/693,671, entitled "Biopsy Device with Slide-In Probe," filed Dec. 4, 2012, the disclosure of which is incorporated by reference herein; U.S. Non-Provisional patent application Ser. No. 13/483,235, entitled "Control for Biopsy Device," filed May 30, 2012, the disclosure of which is incorporated by reference herein; and/or U.S. Provisional Patent App. No. 61/771,212, entitled "Biopsy System with Graphical User Interface," filed Mar. 1, 2013, the disclosure of which is incorporated by reference herein.

Still other suitable forms of biopsy devices that may be used in conjunction with the various alternative components of system (10) as described herein will be apparent to those of ordinary skill in the art.

IV. Exemplary Guide Cube

In some versions, a guide cube may comprise a body defined by one or more edges and faces. The body may include one or more guide holes or other types of passages that extend between faces of the guide cube and that may be used to guide an instrument such as a biopsy device (14) or a portion of a biopsy device (14) (e.g., needle (90) of biopsy device (14), a combination of cannula (94) and obturator (92), etc.). Guide cubes may be rotatable about one, two, or three axes to position the one or more guide holes or passages of the guide cube into a desired position.

Figure 4:
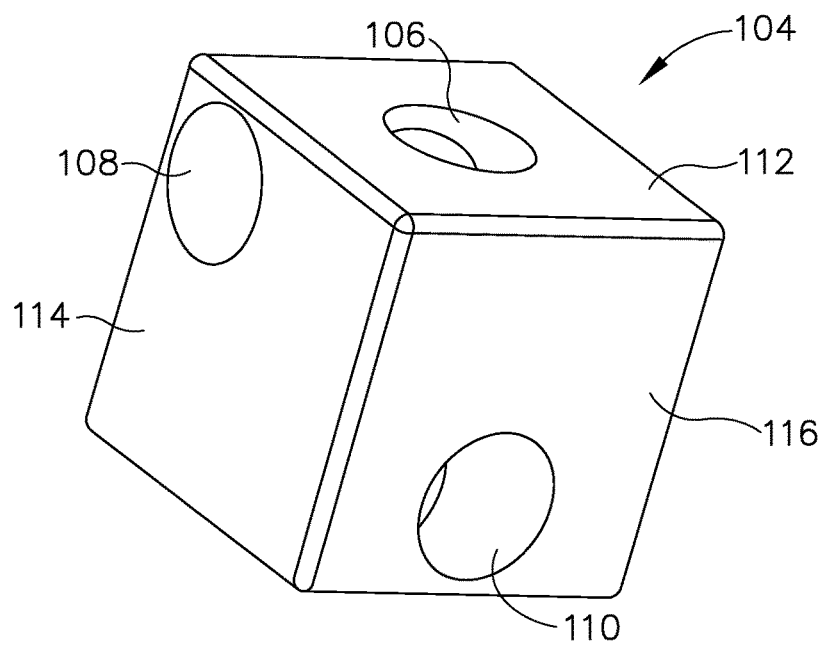
FIG. 4 depicts a perspective view of a two-axis rotatable guide cube of the biopsy system of FIG. 1.
Figure 5:
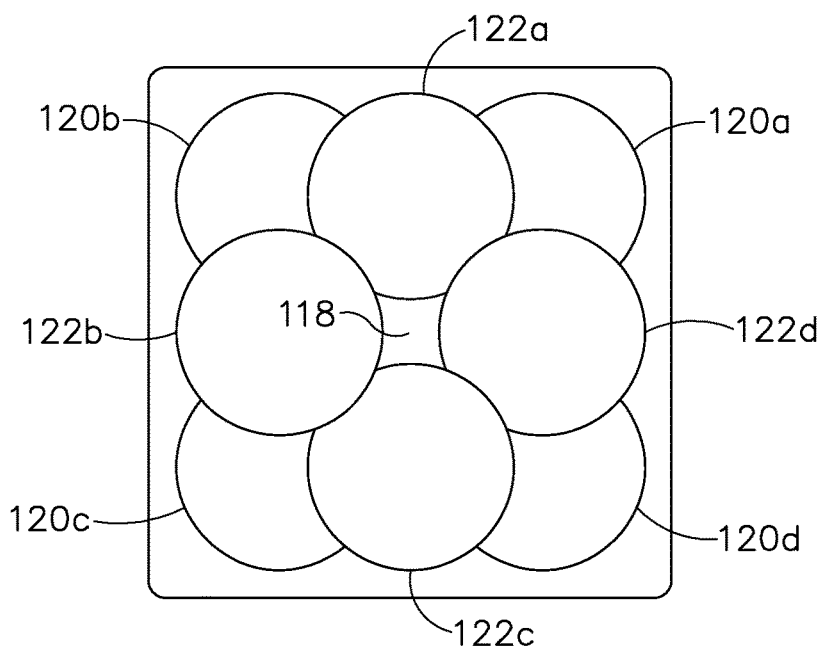
FIG. 5 depicts a diagram of nine guide positions achievable by the two-axis rotatable guide cube of FIG. 4.

In FIG. 4, guide cube (104) includes a central guide hole (106), a corner guide hole (108), and an off-center guide hole (110) that pass orthogonally to one another between respective opposite pairs of faces (112, 114, 116). By selectively rotating guide cube (104) in two axis, one of pairs of faces (112, 114, 116) may be proximally aligned to an unturned position and then selected proximal face (112, 114, 116) optionally rotated a quarter turn, half turn, or three quarter turn. Thereby, one of nine guide positions (118) (i.e., using central guide hole (106)), (120a-120d) (i.e., corner guide hole (108)), (122a-122d) (i.e., using off-center guide hole (110)) may be proximally exposed as depicted in FIG. 5.

Figure 6:
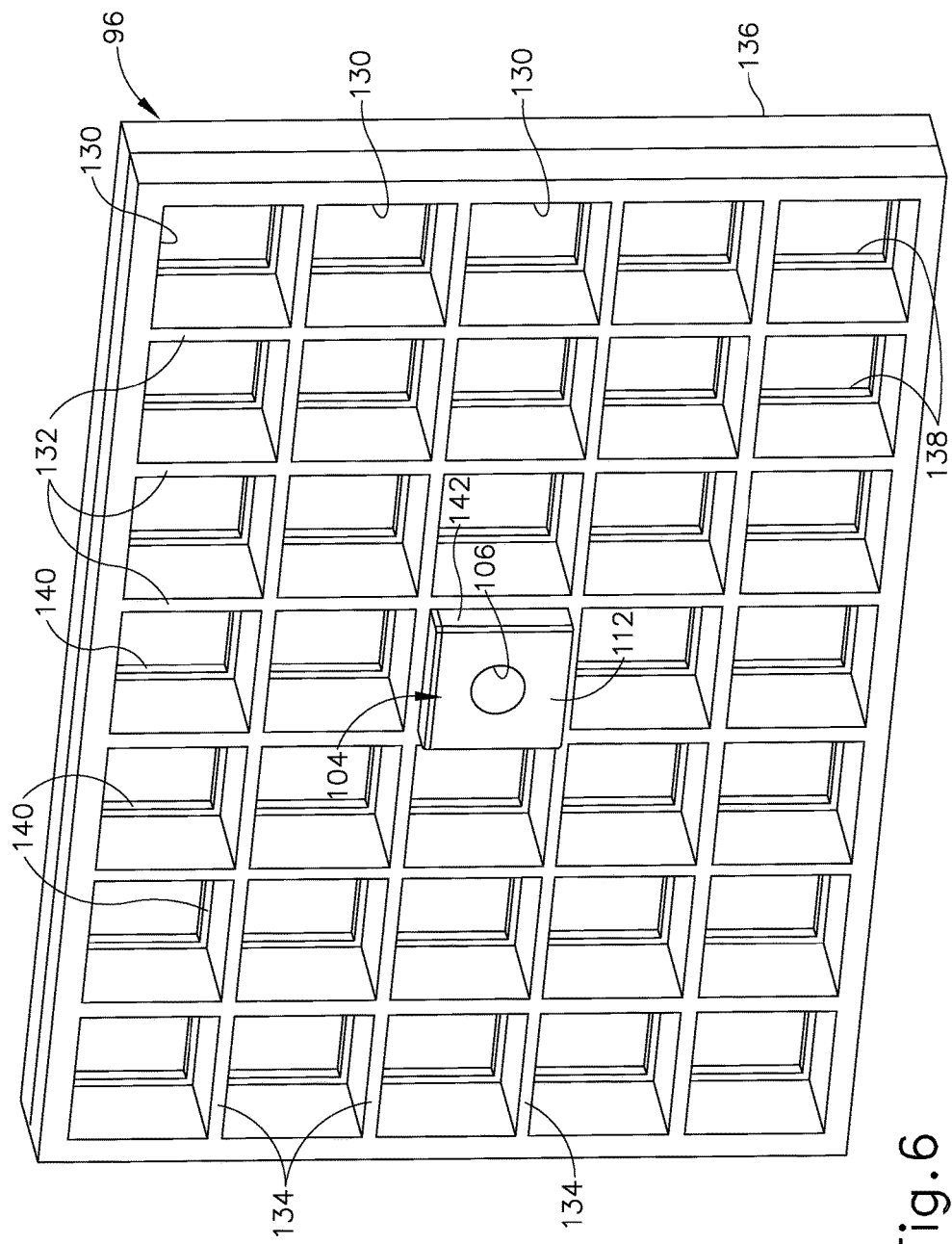
FIG. 6 depicts a perspective view of a two-axis rotatable guide cube into a lateral grid with the backing of the localization fixture of FIG. 1.

In FIG. 6, two-axis rotatable guide cube (104) is sized for insertion from a proximal side into one of a plurality of square recesses (130) in grid plate (96), which are formed by intersecting vertical bars (132) and horizontal bars (134). Guide cube (104) is prevented from passing through grid plate (96) by backing substrate (136) attached to a front face of grid plate (96). Backing substrate (136) includes respective square opening (138) centered within each square recess (130), forming lip (140) sufficient to capture the front face of guide cube (104), but not so large as to obstruct guide holes (104, 106, 108). The depth of square recesses (130) is less than guide cube (104), thereby exposing a proximal portion (142) of guide cube (104) for seizing and extraction from grid plate (96). It will be appreciated by those of ordinary skill in the art based on the teachings herein that backing substrate (136) of grid plate (96) may be omitted altogether in some versions. In some such versions without backing substrate (136) other features of a guide cube, as will be discussed in more detail below, may be used to securely and removably fit a guide cube within a grid plate. However, such other features may also be used in combination with a grid plate having backing substrate (136), such as grid plate (96), instead of partially or wholly omitting backing substrate (136).

V. Exemplary Alternative Targeting Cannulas and Obturators

As a variation of obturator (92) and cannula (94) discussed above, obturator (92) and cannula (94) may be arranged such that a distal end of obturator (92) and cannula (94) present a distal tip having a more effective profile. Among other benefits, such a profile may make insertion of obturator (92) and cannula (94) into a patient's breast easier by reducing the force required to penetrate tissue. Such a profile may also make rotation of obturator (92) and cannula (94) within the patient's breast easier by reducing the force required to rotate obturator (92) and/or cannula (94) within a patient's breast. Various examples of how obturator (92) and cannula (94) may be reconfigured to present a distal tip having a more effective profile will be described in greater detail below; while other examples will be apparent to those of ordinary skill in the art according to the teachings herein. It should be understood that the obturator and cannula examples described below may function substantially similar to obturator (92) and cannula (94) described above. In particular, the obturator and cannula examples described below may be used to assist in biopsy device needle targeting within a patient's breast using MRI guidance. It should be understood that the cannula tip examples discussed below may be used with any of the biopsy devices discussed above or disclosed herein.

A. First Exemplary Alternative Obturator and Cannula Tip

Figure 12:
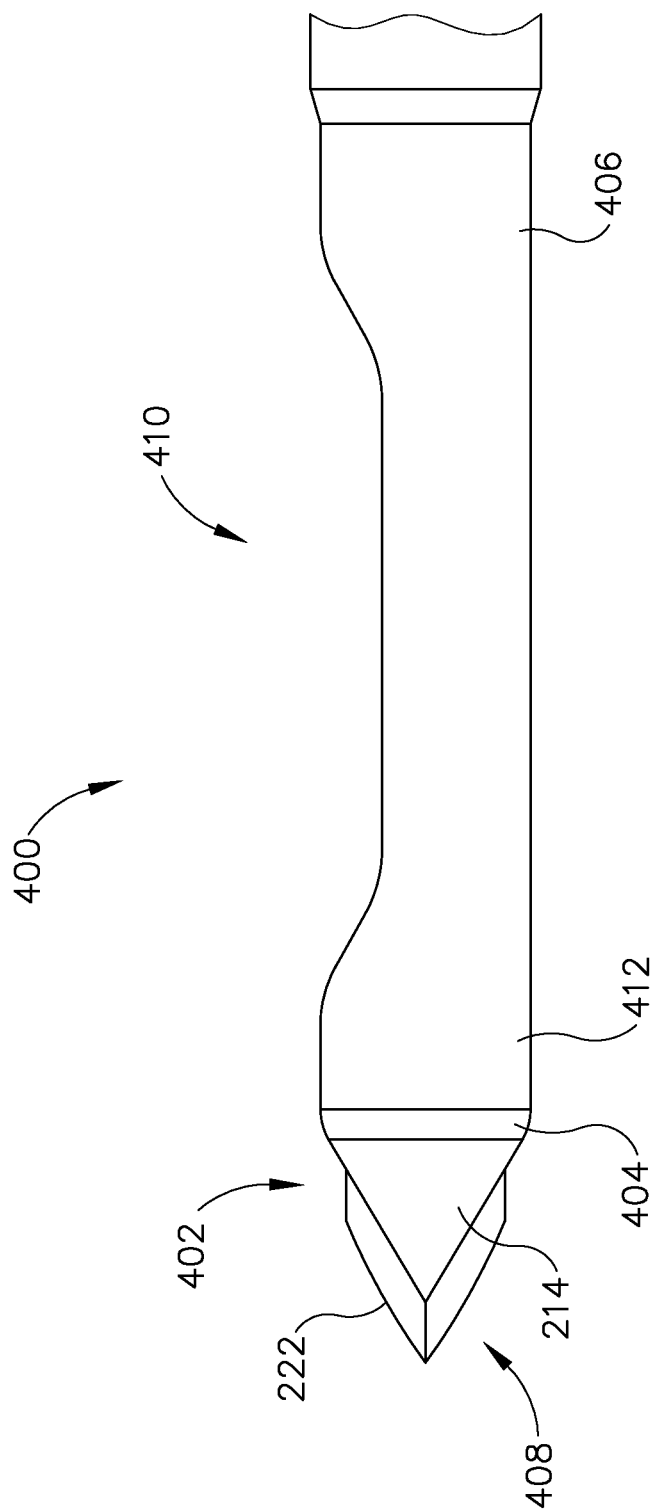
FIG. 12 depicts a partial side elevational view of an exemplary alternative cannula with an obturator disposed therein, that may be used with the biopsy system of FIG. 1.
Figure 13:
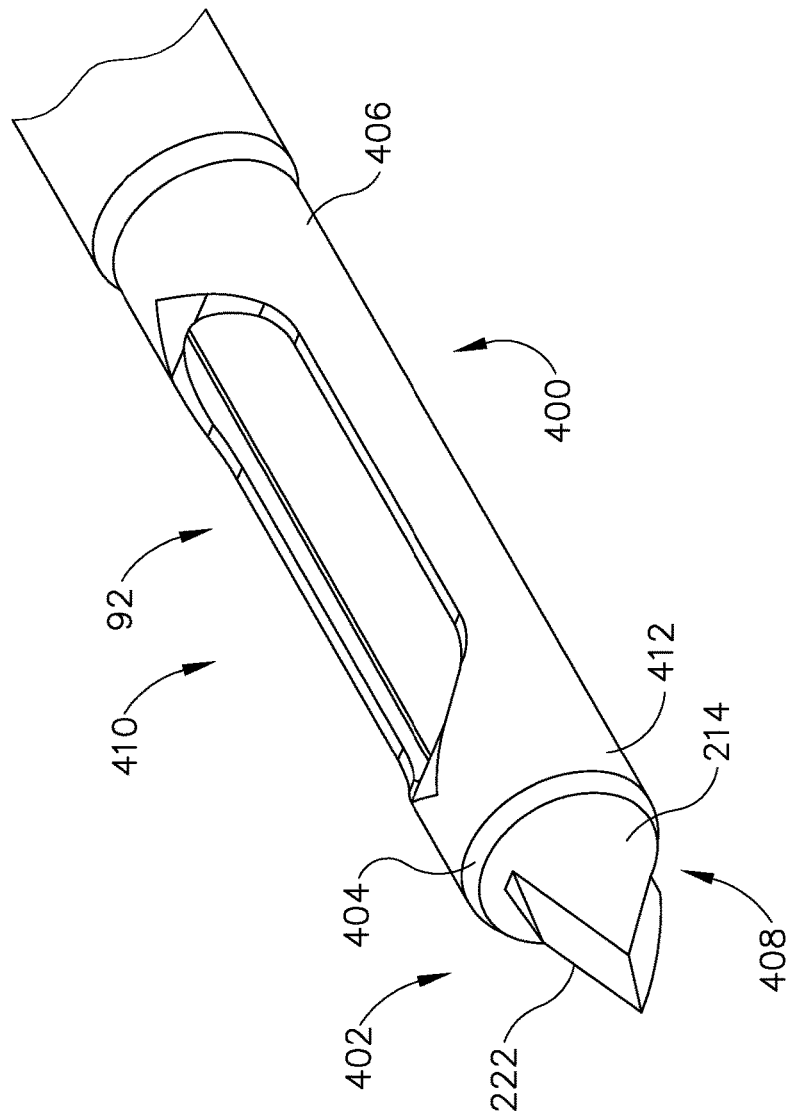
FIG. 13 depicts a partial perspective view of the cannula and obturator of FIG. 12.

FIGS. 12-13 show one merely exemplary variation of a cannula (400). Cannula (400) is configured to function substantially similar to cannula (94) described above. For instance, cannula (400) is configured to receive obturator (92) and the combination is configured to be guided through a guide cube to a biopsy site within a patient's breast. Cannula (400) includes a hollow shaft (406) that is proximally attached to a cylindrical hub (not shown) and has a lateral aperture (410) proximal to an opening (408) defined within a distal end (402) of cannula (400). As best seen in FIG. 13, distal end (402) of cannula (400) comprises a beveled edge (404) which extends from an exterior surface (412) of cannula (400) to opening (408). Beveled edge (404) extends along a plane that is perpendicular to a longitudinal axis defined by hollow shaft (406). Shaft (214) of obturator (92) is longitudinally sized such that piercing tip (222) extends out of opening (408) of cannula (400). Beveled edge (404) is configured to house a portion of piercing tip (222) and to provide an angular transition from piercing tip (222) and opening (408) to exterior surface (412). Such an angular transition creates a more streamlined profile which may reduce the force required to insert cannula (400) and obturator (92) into a patient's breast. Such an angular transition may also reduce the force required to rotate cannula (400) and obturator (92) in a patient's breast.

B. Second Exemplary Alternative Obturator and Cannula Tip

Figure 14:
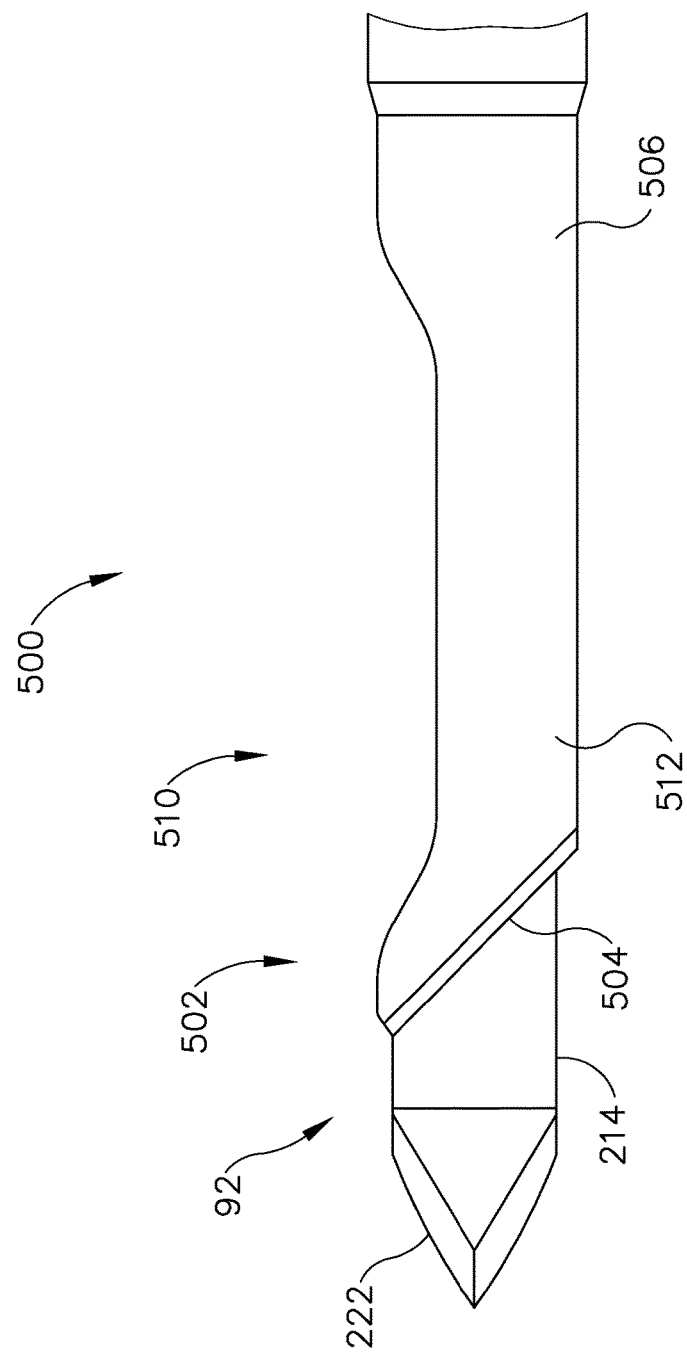
FIG. 14 depicts a partial side elevational view of another exemplary alternative cannula with an angled open end and an obturator disposed therein, that may be used with the biopsy system of FIG. 1.
Figure 15:
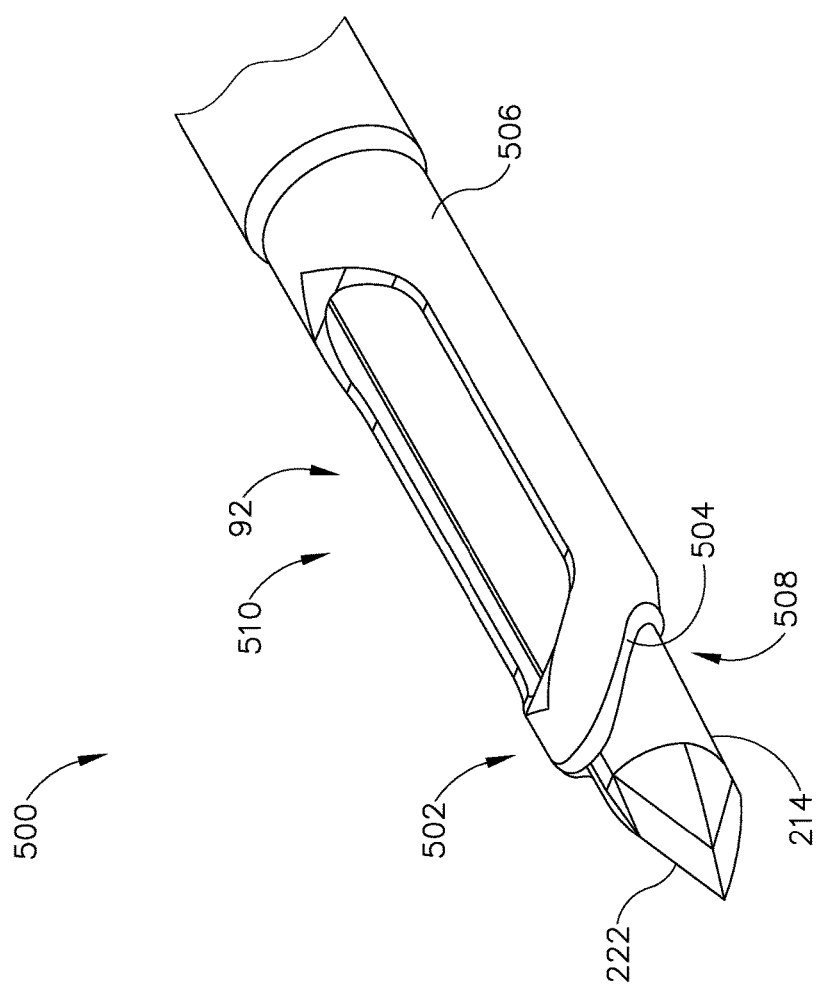
FIG. 15 depicts a partial perspective view of the cannula and obturator of FIG. 14.

FIGS. 14-15 show another merely exemplary variation of a cannula (500). Cannula (500) is configured to function substantially similar to cannula (94) described above. For instance, cannula (500) is configured to receive obturator (92) and the combination is configured to be guided through a guide cube to a biopsy site within a patient's breast. Cannula (500) includes a hollow shaft (506) that is proximally attached to a cylindrical hub (not shown) and has a lateral aperture (510) proximal to an opening (508) defined within a distal end (502) of cannula (500). As best seen in FIG. 14, opening (508) defines a slanted edge (504). Slanted edge (504) extends proximally from a top of cannula (500) to a bottom of cannula (500) along a plane that is oblique to a longitudinal axis defined by hollow shaft (506). Shaft (214) of obturator (92) is longitudinally sized such that piercing tip (222) extends out of opening (508) of cannula (500). Slanted edge (504) may be beveled or chamfered to provide a smoother transition between an exterior surface of shaft (214) and an exterior surface (512) of cannula (500). Slanted edge (504) creates a more streamlined profile which may reduce the force required to insert cannula (500) and obturator (92) into a patient's breast. Such a streamlined profile may also reduce the force required to rotate cannula (500) and obturator (92) in a patient's breast.

C. Third Exemplary Alternative Obturator and Cannula Tip

Figure 16:
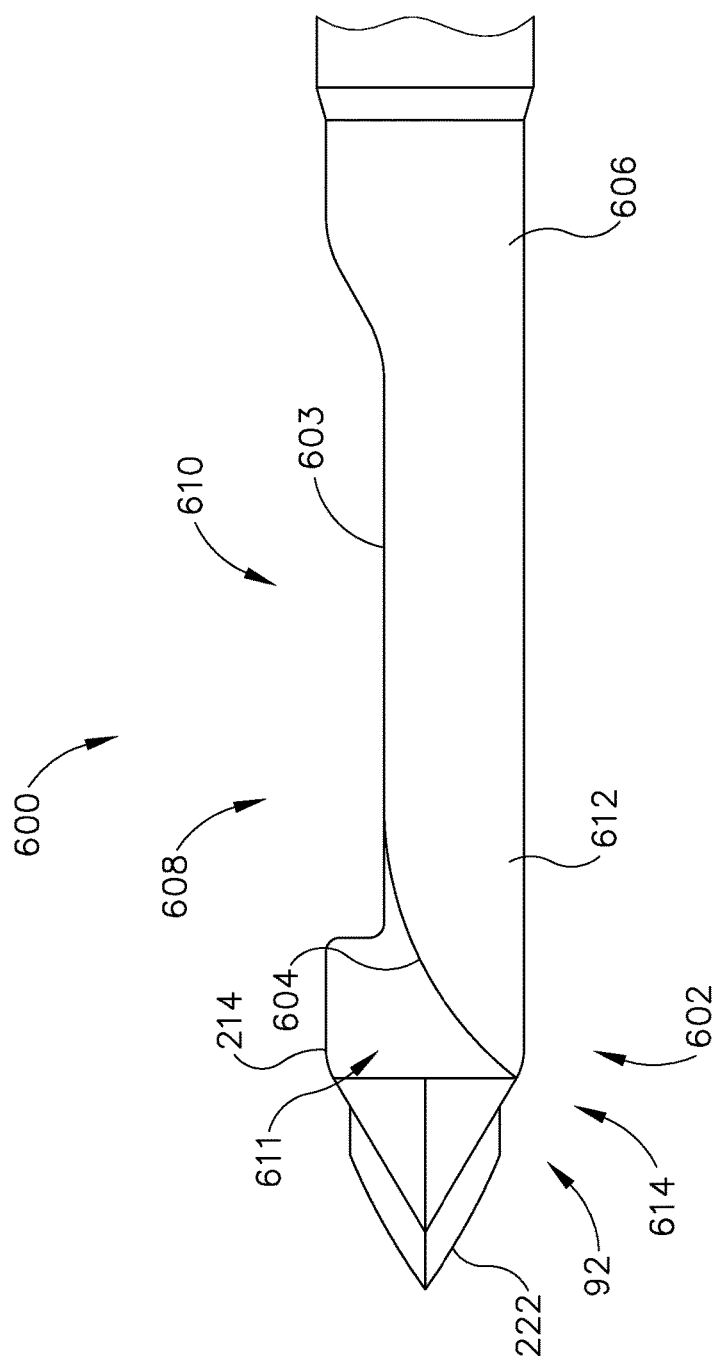
FIG. 16 depicts a partial side elevational view of yet another exemplary alternative cannula with a lateral opening having an angled distal portion and an obturator disposed therein, that may be used with the biopsy system of FIG. 1.
Figure 17:
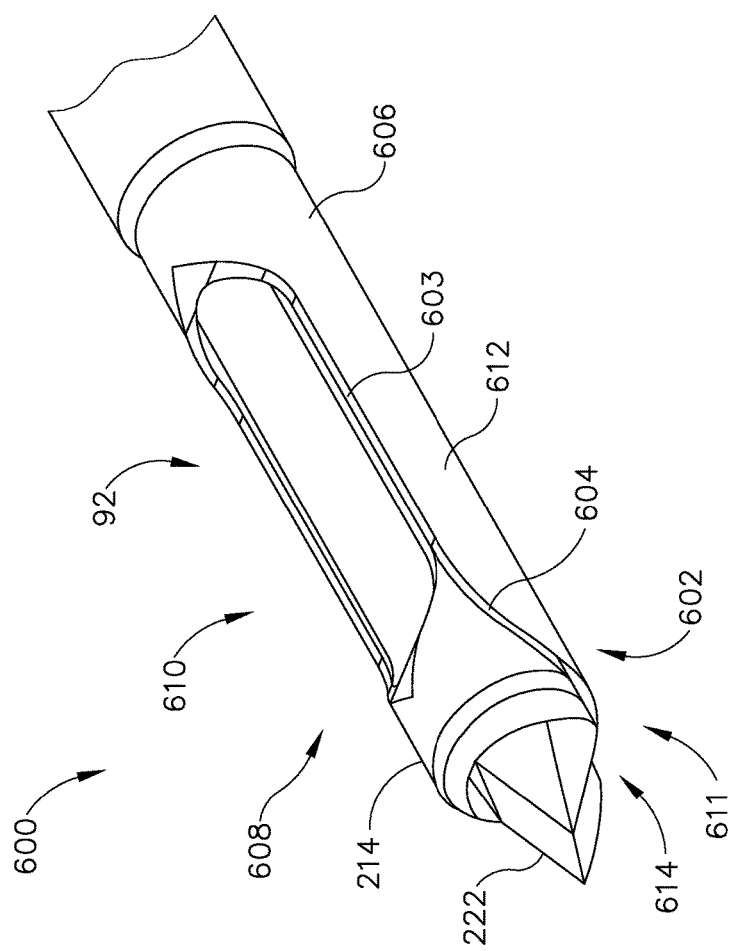
FIG. 17 depicts a partial perspective view of the cannula and obturator of FIG. 16.

FIGS. 16-17 show yet another merely exemplary variation of a cannula (600). Cannula (600) is configured to function substantially similar to cannula (94) described above. For instance, cannula (600) is configured to receive obturator (92) and the combination is configured to be guided through a guide cube to a biopsy site within a patient's breast. Cannula (600) includes a hollow shaft (606) that is proximally attached to a cylindrical hub (not shown) and has an opening (608) defined within a distal end (602) of cannula (600). As best seen in FIG. 16, opening (608) presents a shovel-like profile defined by a lateral portion (610) and a distal portion (611). Lateral portion (610) is defined by longitudinally extending lateral edges (603), which are positioned to run alongside the lateral boundary of side notch (218) when obturator (92) is inserted in cannula (600); and alongside the lateral boundary of the lateral aperture of a biopsy needle when a biopsy needle is inserted in cannula (600). Distal portion (611) of opening (608) is defined by a slanted edge (604), which extends distally from lateral edges (603) of opening (608) to a bottom of cannula (600) along a plane that is oblique to a longitudinal axis defined by hollow shaft (606). Shaft (214) of obturator (92) is longitudinally sized such that piercing tip (222) extends out of opening (608) of cannula (600). A bottom portion (614) of slanted edge (604) is configured to form a continuous profile with piercing tip (222). Slanted edge (604) may be beveled or chamfered to provide a smoother transition between an exterior surface of shaft (214) and an exterior surface (612) of cannula (600). Slanted edge (604) creates a more streamlined profile which may reduce the force required to insert cannula (600) and obturator (92) into a patient's breast. Such a streamlined profile may also reduce the force required to rotate cannula (600) and obturator (92) in a patient's breast.

D. Fourth Exemplary Alternative Obturator and Cannula Tip

Figure 18:
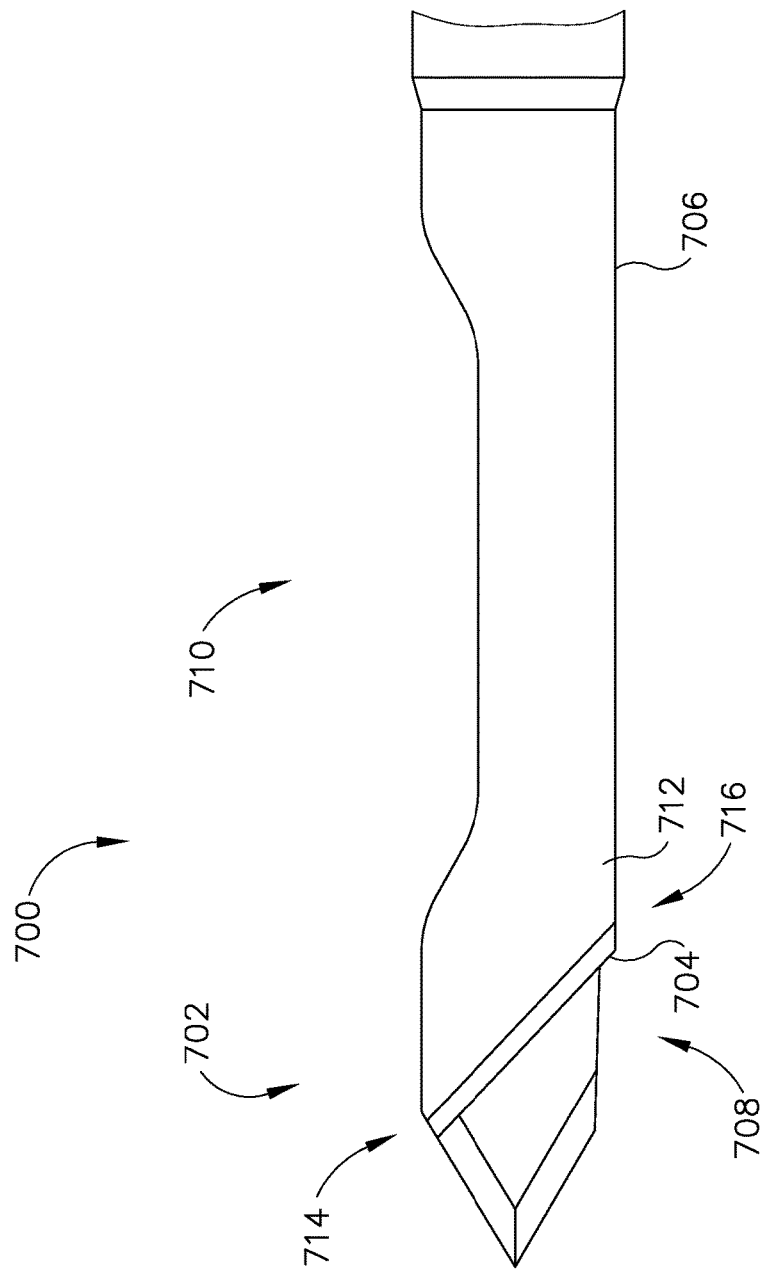
FIG. 18 depicts a partial side elevational view of yet another exemplary alternative cannula with an angled open end and an obturator disposed therein, that may be used with the biopsy system of FIG. 1.

FIG. 18 shows yet another merely exemplary variation of a cannula (700). Cannula (700) is configured to function substantially similar to cannula (94) described above. For instance, cannula (700) is configured to receive obturator (92) and the combination is configured to be guided through a guide cube to a biopsy site within a patient's breast. Cannula (700) includes a hollow shaft (706) that is proximally attached to a cylindrical hub (not shown) and has a lateral aperture (710) proximal to an opening (708) defined within a distal end (702) of cannula (700). As seen in FIG. 18, opening (708) defines a slanted edge (704). Slanted edge (704) extends proximally from a top of cannula (700) to a bottom of cannula (700) along a plane that is oblique to a longitudinal axis defined by hollow shaft (706). Shaft (214) of obturator (92) is longitudinally sized such that piercing tip (222) extends out of opening (708) of cannula (700). A top portion (714) of slanted edge (704) is configured to form a continuous profile with piercing tip (222). Slanted edge (704) may be beveled or chamfered to provide a smoother transition between an exterior surface of shaft (214) and an exterior surface (712) of cannula (700). Slanted edge (704) creates a more streamlined profile which may reduce the force required to insert cannula (700) and obturator (92) into a patient's breast. Such a streamlined profile may also reduce the force required to rotate cannula (700) and obturator (92) in a patient's breast. It should be understood that, although only top portion (714) of the present example is configured to form a continuous profile with piercing tip (222), a bottom portion (716) of cannula (700) may be configured to form a continuous profile with piercing tip (222) in addition to or in lieu of top portion (714).

E. Fifth Exemplary Alternative Obturator and Cannula Tip

Figure 19:
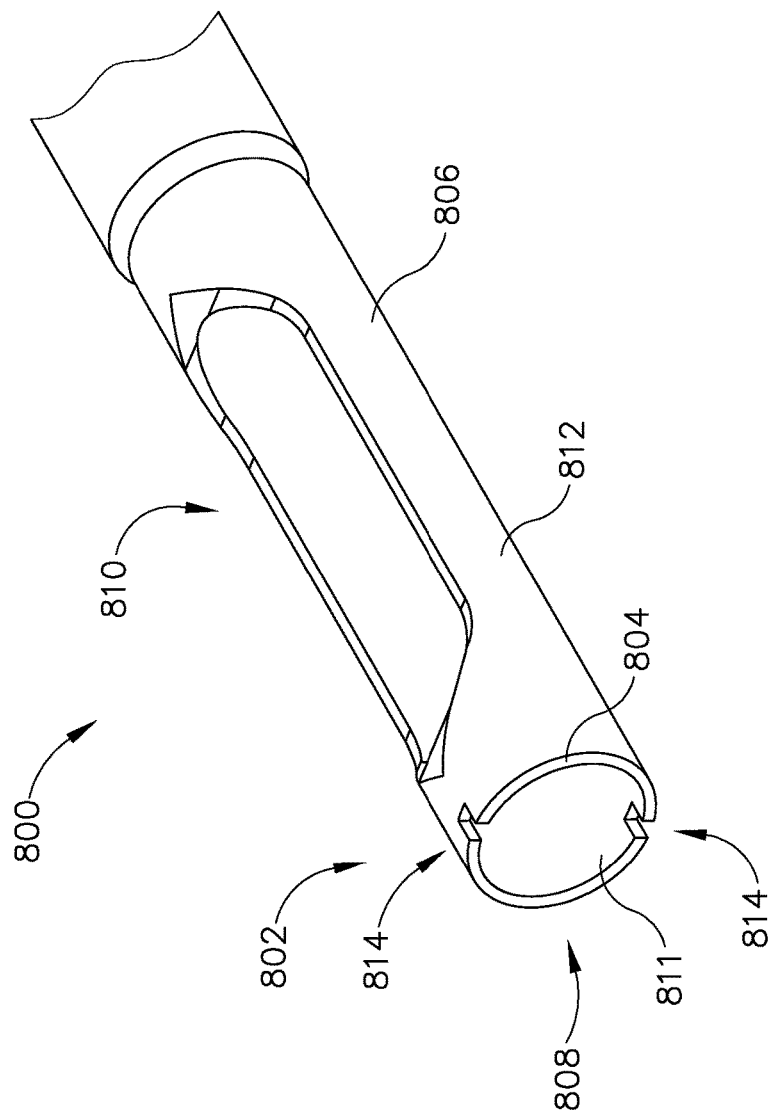
FIG. 19 depicts a partial perspective view of yet another exemplary alternative cannula with an open end and a pair of longitudinal openings, that may be used with the biopsy system of FIG. 1.
Figure 20:
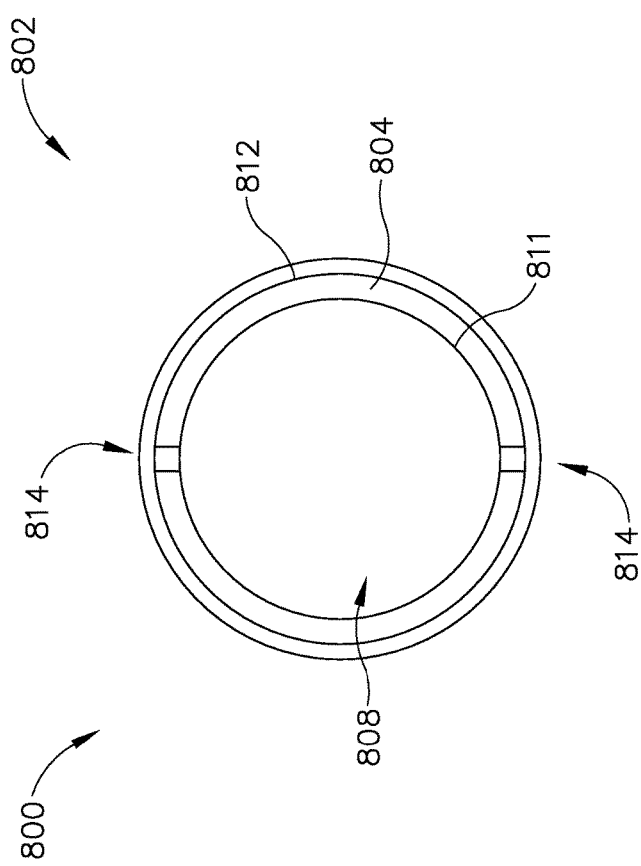
FIG. 20 depicts a front elevational view of the cannula of FIG. 19.

FIGS. 19-22 show yet another merely exemplary variation of a cannula (800). Cannula (800) is configured to function substantially similar to cannula (94) described above. For instance, cannula (800) is configured to receive obturator (92) and the combination is configured to be guided through a guide cube to a biopsy site within a patient's breast. Cannula (800) includes a hollow shaft (806) that is proximally attached to a cylindrical hub (not shown) and has a lateral aperture (810) proximal to an opening (808) defined within a distal end (802) of cannula (800). Opening (808) is bounded by an edge (804). As best seen in FIGS. 19-20, distal end (802) presents a pair of recessed-longitudinal openings (814) defined in a top and bottom of edge (804) of cannula (800) and extending from an interior surface (811) of cannula (800) to an exterior surface (812) of cannula (800). Shaft (214) of obturator (92) is longitudinally sized such that piercing tip (222) extends out of opening (808) of cannula (800).

Figure 21:
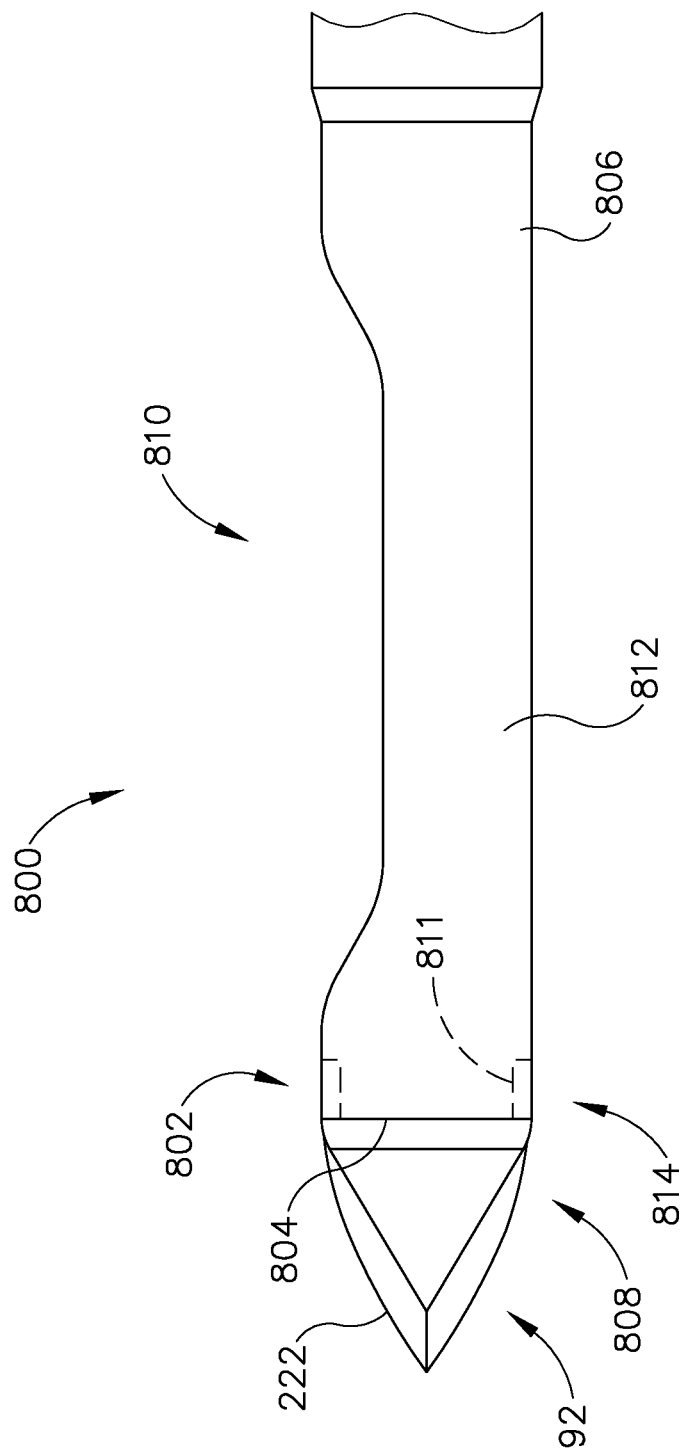
FIG. 21 depicts a partial side elevational view of the cannula of FIG. 19 with an obturator inserted therein.
Figure 22:
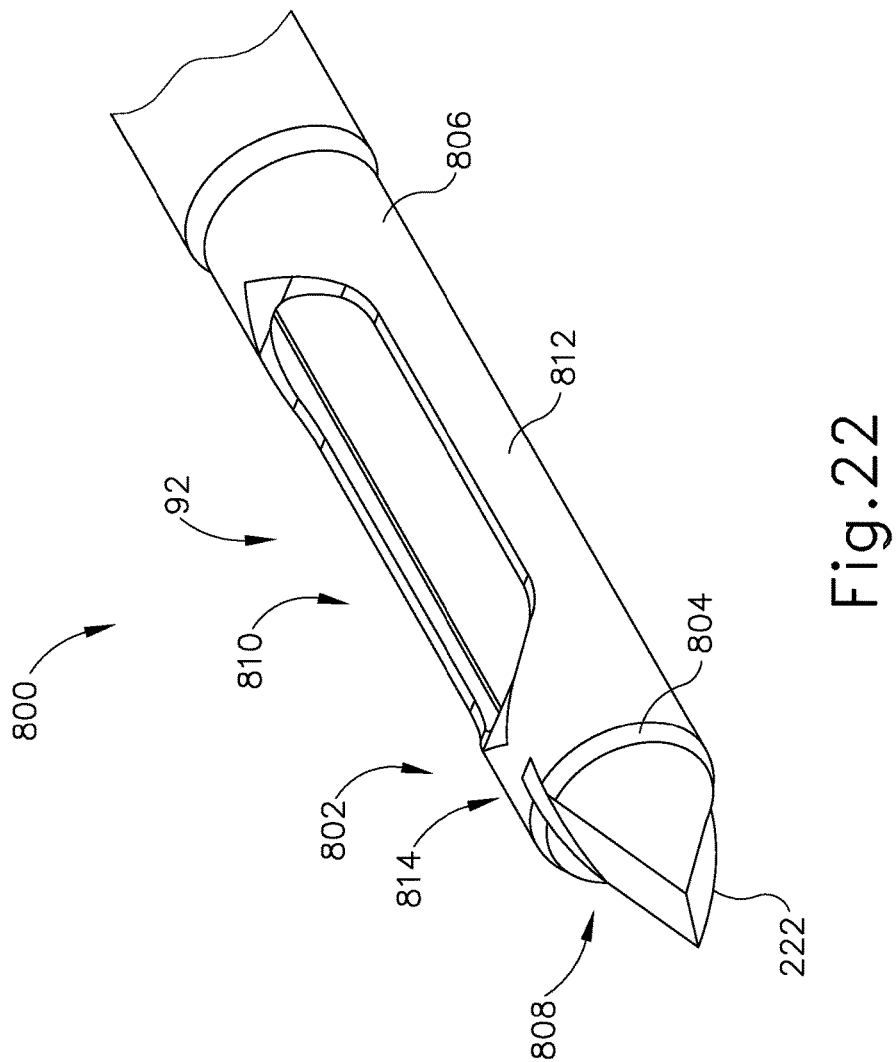
FIG. 22 depicts a partial perspective view of the cannula and obturator of FIG. 21.
Figure 23:
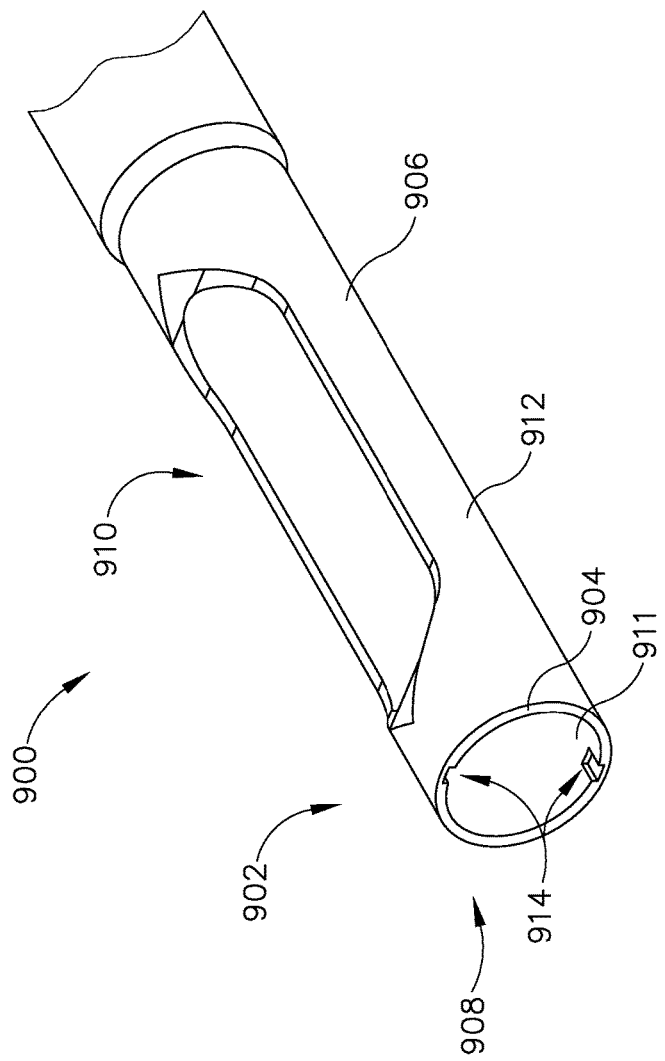
FIG. 23 depicts a partial perspective view of yet another exemplary alternative cannula with an open end and a pair of longitudinal recesses, that may be used with the biopsy system of FIG. 1.

As shown in FIGS. 21-22, each opening of pair of openings (814) is configured to receive a top edge and a bottom edge of piercing tip (222) such that the top edge and the bottom edge of piercing tip (222) are substantially aligned with an exterior surface (812) of cannula (800). Edge (804) may be beveled or chamfered to provide a smoother transition between an exterior surface of shaft (214) and exterior surface (812) of cannula (800). It should be understood that piercing tip (222) may be resiliently biased such that if piercing tip (222) is deformed while being driven through cannula (800), piercing tip (222) would return to its initial form once driven through opening (808). Substantial alignment of the top edge and the bottom edge of piercing tip (222) with exterior surface (812) of cannula (800) creates a more streamlined profile which may reduce the force required to insert cannula (800) and obturator (92) into a patient's breast. Such an alignment may also reduce the force required to rotate cannula (800) and obturator (92) in a patient's breast.

It should be understood that, although pair of longitudinal openings (814) of the present example do not extend the length of hollow shaft (806), pair of longitudinal openings (814) may extend the length of hollow shaft (806) in some versions. In at least some such versions, there would be no need for piercing tip (222) to be resiliently biased because the top edge and/or the bottom edge of piercing tip (222) would pass through pair of longitudinal openings (814) as piercing tip (222) is driven through hollow shaft (806) in such versions.

F. Sixth Exemplary Alternative Obturator and Cannula Tip

Figure 24:
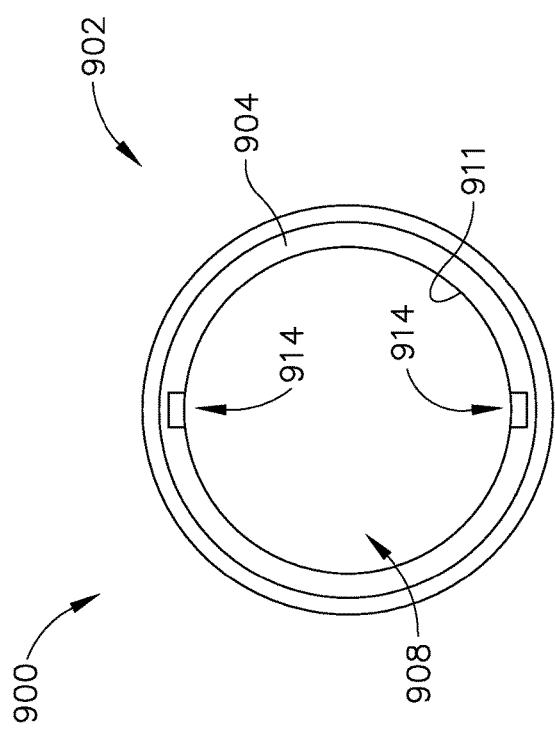
FIG. 24 depicts a front elevational view of the cannula of FIG. 23.

FIGS. 23-26 show yet another merely exemplary variation of a cannula (900). Cannula (900) is configured to function substantially similar to cannula (94) described above. For instance, cannula (900) is configured to receive obturator (92) and the combination is configured to be guided through a guide cube to a biopsy site within a patient's breast. Cannula (900) includes a hollow shaft (906) that is proximally attached to a cylindrical hub (not shown) and has a lateral aperture (910) proximal to an opening (908) defined within a distal end (902) of cannula (900). Opening (908) defines an edge (904). As best seen in FIG. 24, distal end (902) presents a pair of longitudinal channels (914) defined in a top and bottom of an interior surface (911) of cannula (900) and extending to edge (904). Longitudinal channels (914), however, do not extend fully to an exterior surface (912) of cannula (900). Shaft (214) of obturator (92) is longitudinally sized such that piercing tip (222) extends out of opening (908) of cannula (900).

Figure 25:
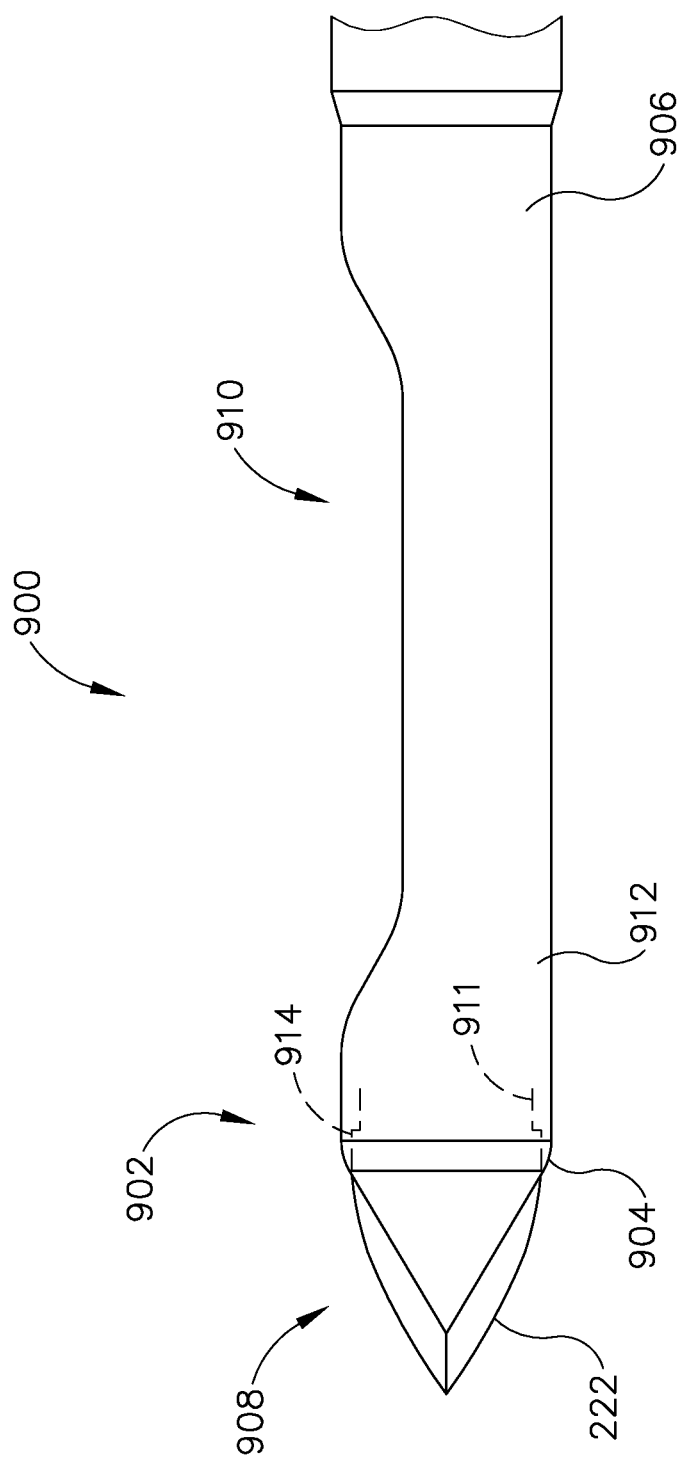
FIG. 25 depicts a partial side elevational view of the cannula of FIG. 23 with an obturator inserted therein.
Figure 26:
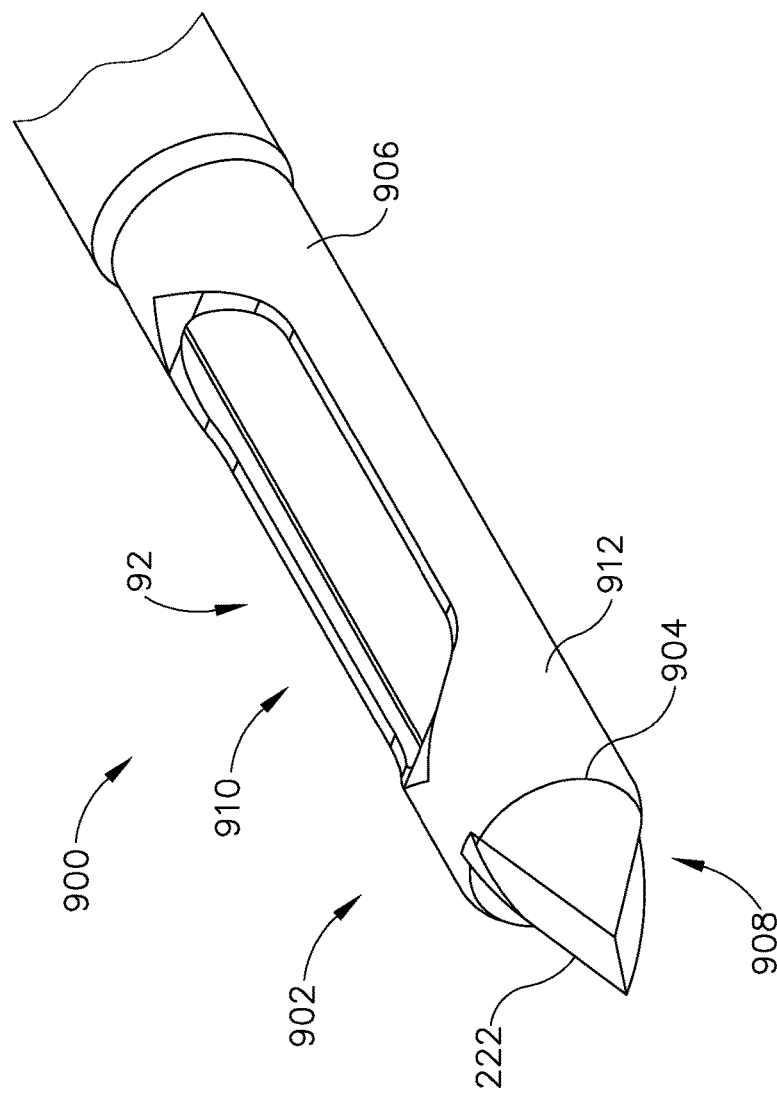
FIG. 26 depicts a partial perspective view of the cannula and obturator of FIG. 25.
Figure 27:
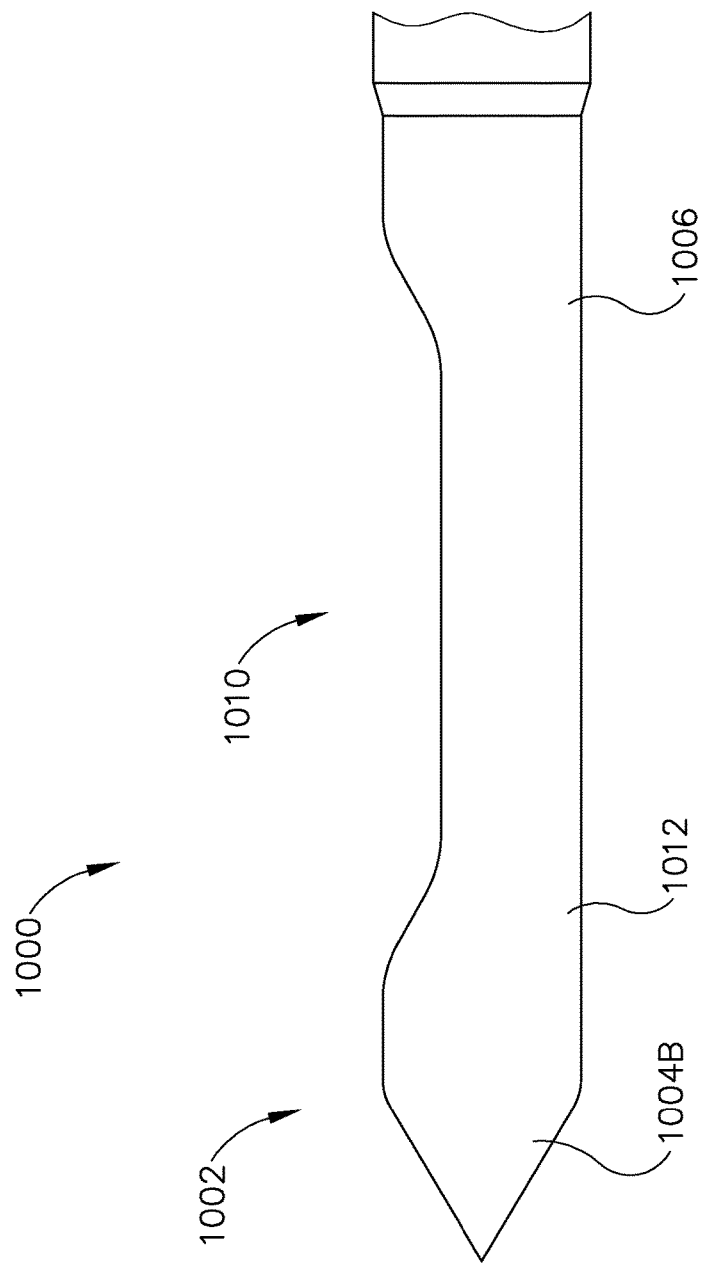
FIG. 27 depicts a partial side elevational view of yet another exemplary alternative cannula that may be used with the biopsy system of FIG. 1.

As shown in FIGS. 25-26, each channel of pair of longitudinal channels (914) is configured to receive a top edge and a bottom edge of piercing tip (222) such that the top edge and the bottom edge of piercing tip (222) are positioned substantially proximal to an exterior surface (912) of cannula (900). Edge (904) may be beveled or chamfered to provide a smoother transition between an exterior surface of shaft (214) and exterior surface (912) of cannula (900) and/or to position the top edge and the bottom edge of piercing tip (222) more proximally to exterior surface (912) of cannula (900). It should be understood that piercing tip (222) may be resiliently biased such that if piercing tip (222) is deformed while being driven through cannula (900), piercing tip (222) would return to its initial form once driven through opening (908). Substantial proximity of the top edge and the bottom edge of piercing tip (222) with exterior surface (912) of cannula (900) creates a more streamlined profile which may reduce the force required to insert cannula (900) and obturator (92) into a patient's breast. Such an alignment may also reduce the force required to rotate cannula (900) and obturator (92) in a patient's breast.

It should be understood that, although pair of longitudinal channels (914) of the present example do not extend the length of hollow shaft (906), pair of longitudinal channels (914) may extend the length of hollow shaft (906) in some versions. In at least some such versions, there would be no need for piercing tip (222) to be resiliently biased because the top edge and/or the bottom edge of piercing tip (222) would pass through pair of longitudinal channels (914) as piercing tip (222) is driven through hollow shaft (906) in such versions.

G. Seventh Exemplary Alternative Obturator and Cannula Tip

Figure 28:
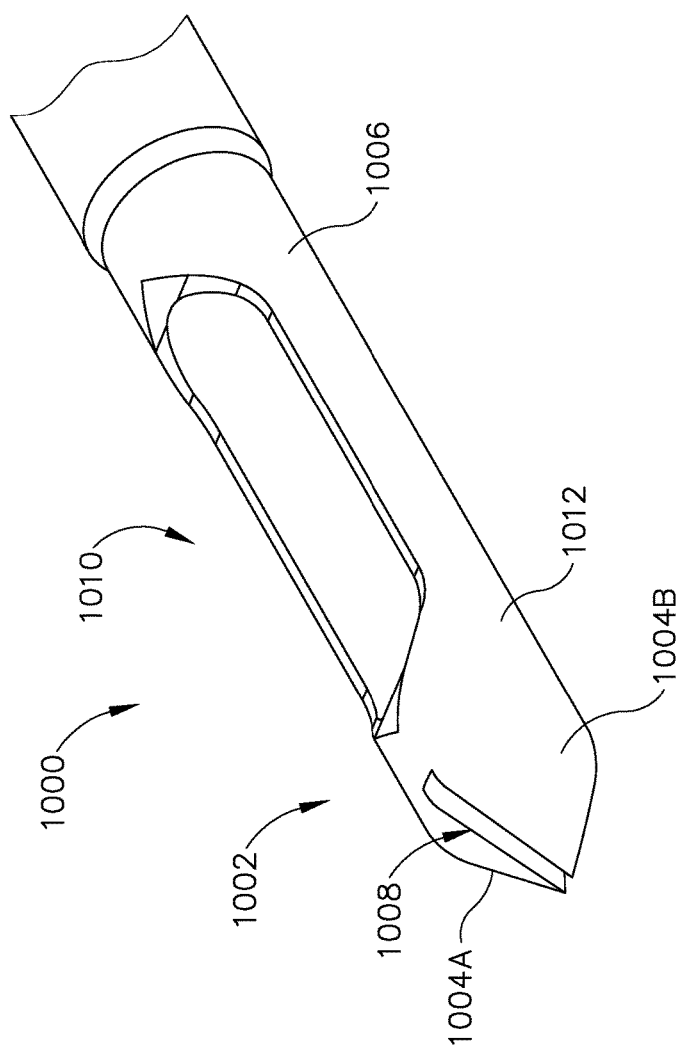
FIG. 28 depicts a partial perspective view of the cannula of FIG. 27.

FIGS. 27-30 show yet another merely exemplary variation of a cannula (1000). Cannula (1000) is configured to function substantially similar to cannula (94) described above. For instance, cannula (1000) is configured to receive obturator (92) and the combination is configured to be guided through a guide cube to a biopsy site within a patient's breast. Cannula (1000) includes a hollow shaft (1006) that is proximally attached to a cylindrical hub (not shown) and has a lateral aperture (1010) proximal to a vertical slot (1008) defined within a distal conical end (1002) of cannula (1000). As best seen in FIG. 28, vertical slot (1008) is bounded by a first conical portion (1004A) and a second conical portion (1004B).

Figure 29:
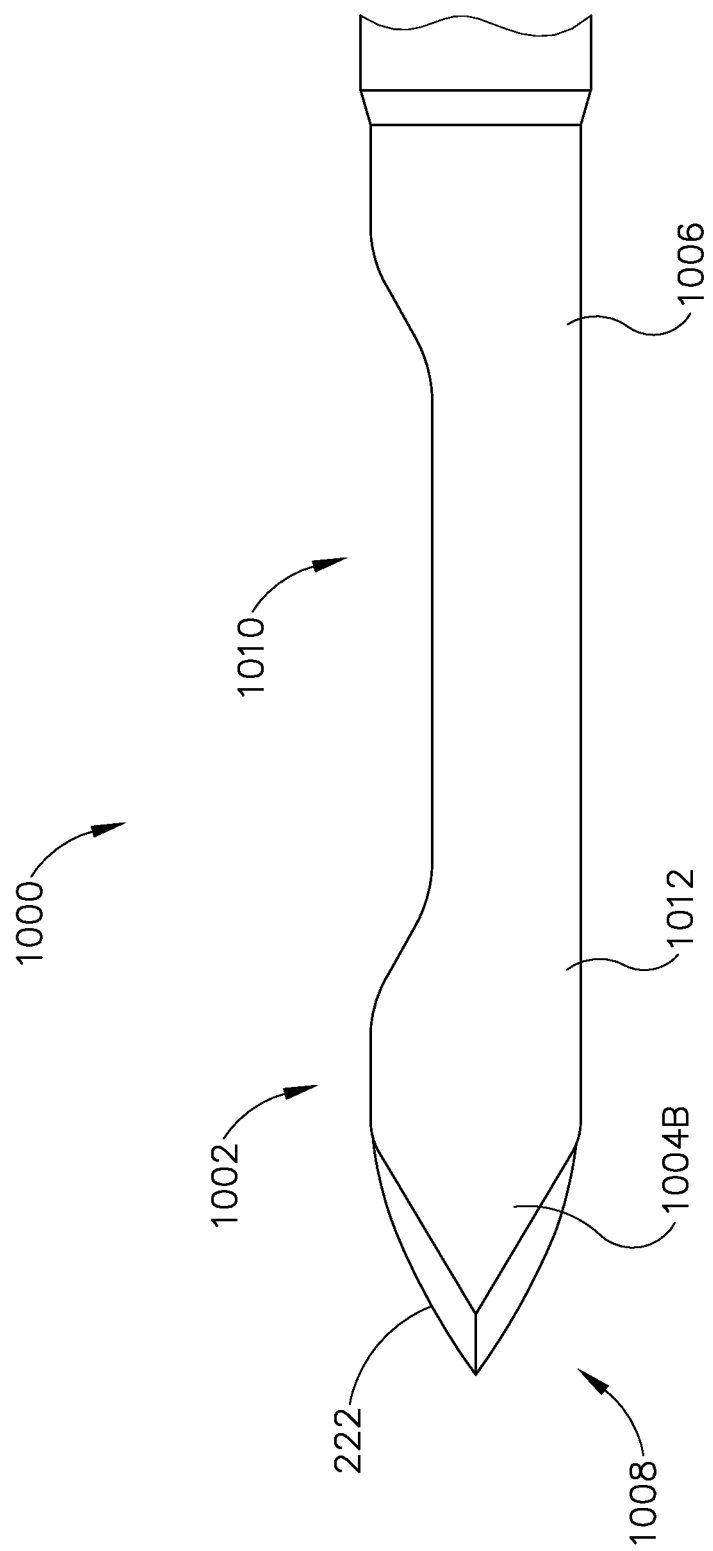
FIG. 29 depicts a partial side elevational view of the cannula of FIG. 27 with an obturator inserted therein.

As shown in FIGS. 29-30, shaft (214) of obturator (92) is longitudinally sized such that piercing tip (222) extends out of vertical slot (1008) of cannula (1000). As best seen in FIG. 30, interior surfaces of first conical portion (1004A) and second conical portion (1004B) are positioned substantially proximal to an exterior surface of piercing tip (222) as piercing tip (222) is extended out of vertical slot (1008). In some versions of cannula (1000), conical portions (1004A, 1004B) may be resiliently-inwardly biased such that interior surfaces of first conical portion (1004A) and second conical portion (1004B) are configured to contact the exterior surface of piercing tip (222) as piercing tip (222) is extended out of vertical slot (1008). First conical portion (1004A) and second conical portion (1004B) are configured to house piercing tip (222) and to provide an angular transition from piercing tip (222) and vertical slot (1008) to exterior surface (1012). Such an angular transition creates a more streamlined profile which may reduce the force required to insert cannula (1000) and obturator (92) into a patient's breast. Such an angular transition may also reduce the force required to rotate cannula (1000) and obturator (92) in a patient's breast.

H. Eighth Exemplary Alternative Obturator and Cannula Tip

Figure 31A:
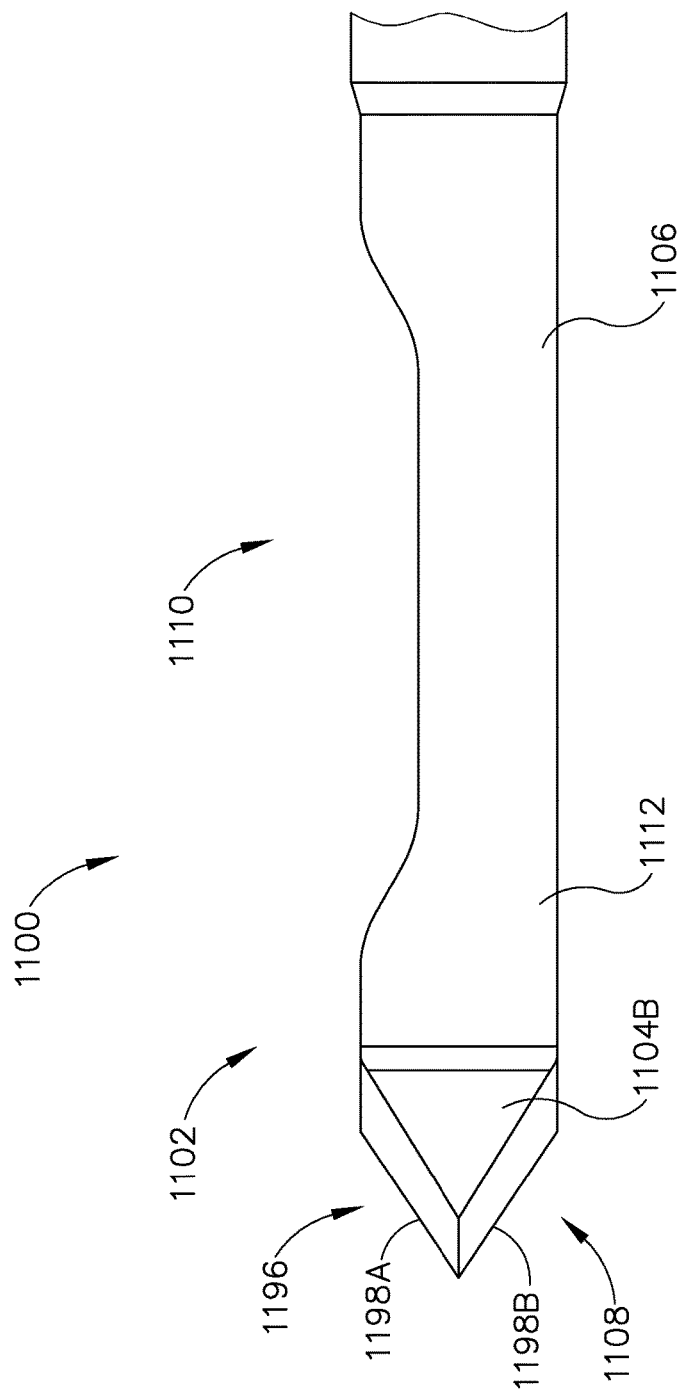
FIG. 31A depicts a partial side elevational view of yet another exemplary alternative cannula with an exemplary alternative obturator having a pair of adjustable blades in an extended position.
Figure 31B:
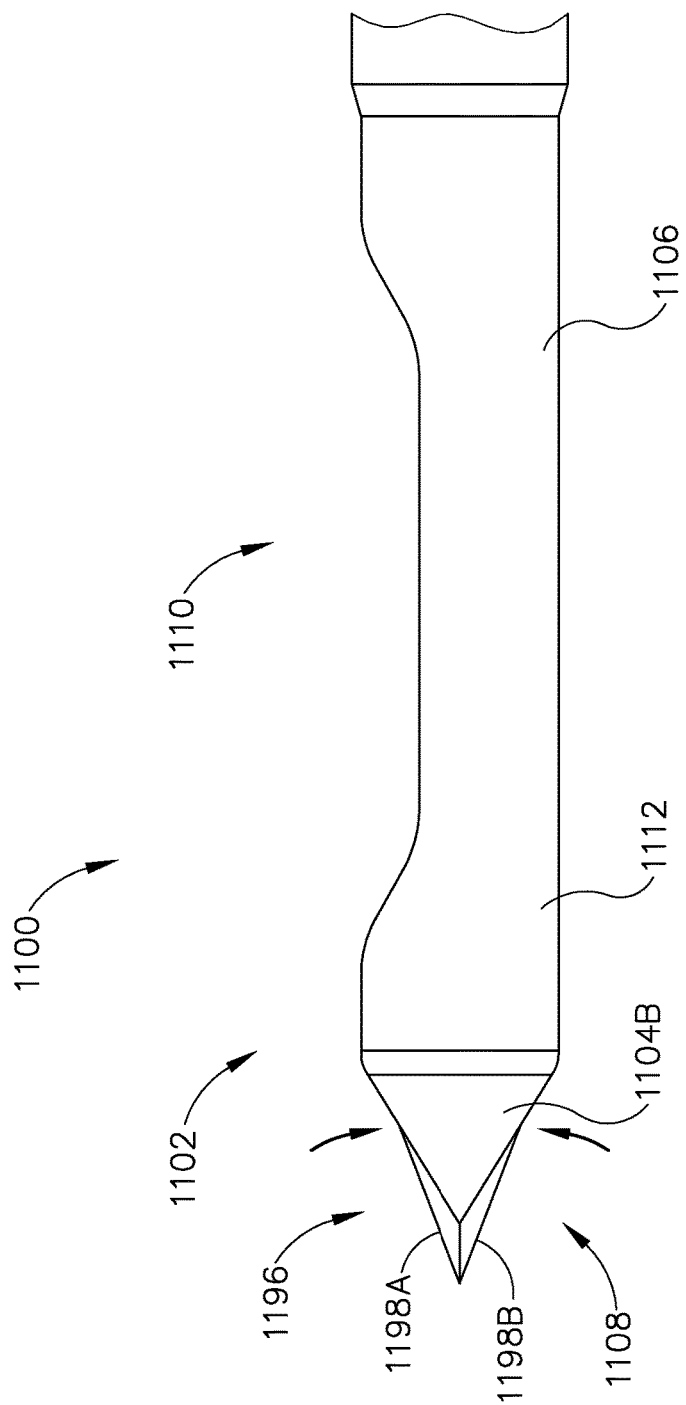
FIG. 31B depicts a partial side elevational view of the cannula and obturator of FIG. 31A with the pair of adjustable blades in a retracted position.
Figure 32A:
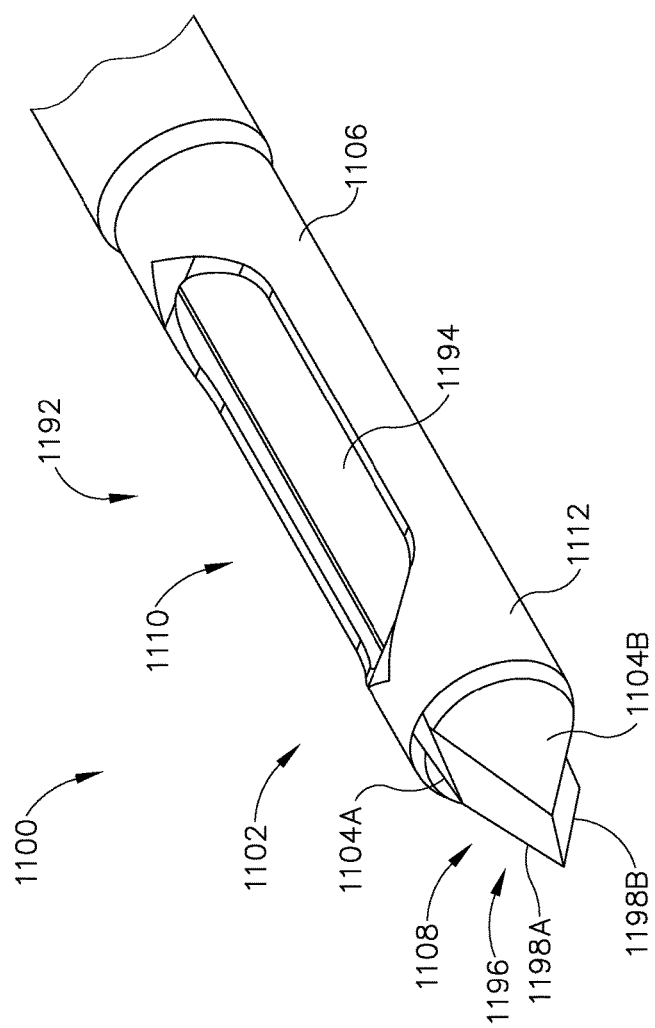
FIG. 32A depicts a partial perspective view of the cannula and obturator of FIG. 31A with the pair of adjustable blades in the extended position.
Figure 32B:
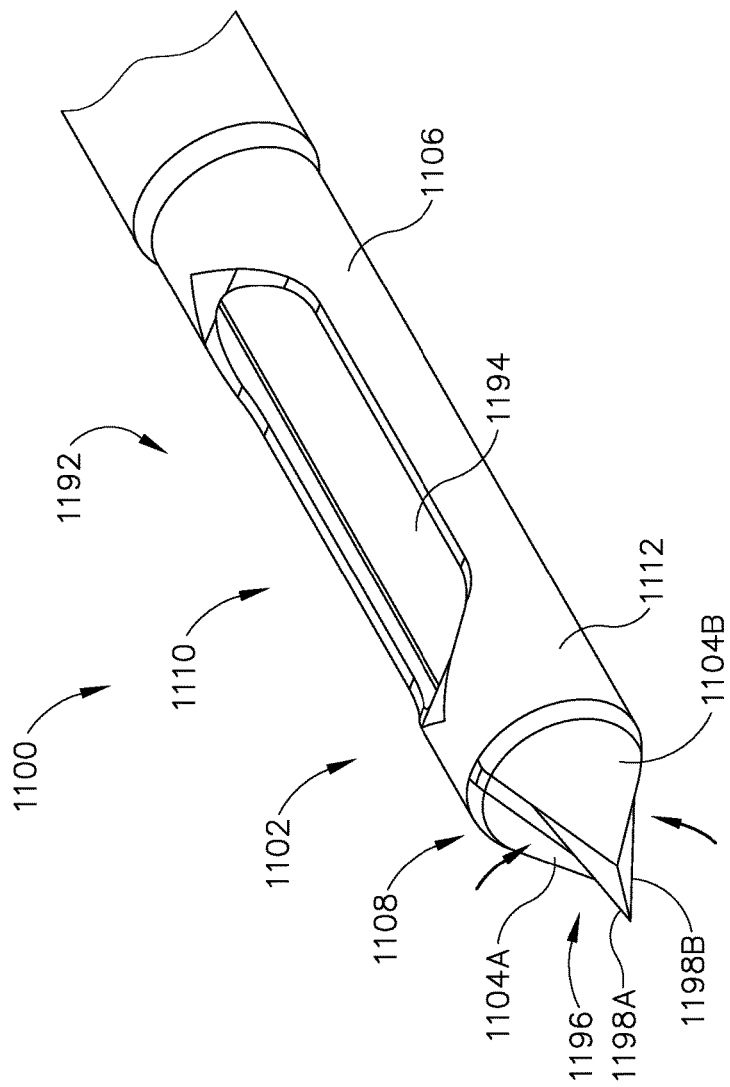
FIG. 32B depicts a partial perspective view of the cannula and obturator of FIG. 31A with the pair of adjustable blades in the retracted position.

FIGS. 31A-32B show yet another merely exemplary variation of a cannula (1100). Cannula (1100) is configured to function substantially similar to cannula (94) described above. For instance, cannula (1100) is configured to receive an obturator (1192) and the combination is configured to be guided through a guide cube to a biopsy site within a patient's breast. Cannula (1100) includes a hollow shaft (1106) that is proximally attached to a cylindrical hub (not shown) and has a lateral aperture (1110) proximal to a vertical slot (1108) defined within a distal conical end (1102) of cannula (1100). As best seen in FIGS. 32A-32B, vertical slot (1108) is bounded by a first conical portion (1104A) and a second conical portion (1104B).

As shown in FIGS. 32A-32B, a shaft (1194) of obturator (1192) is longitudinally sized such that a piercing tip (1196) extends out of vertical slot (1008) of cannula (1100). Interior surfaces of first conical portion (1104A) and second conical portion (1104B) are configured to be positioned substantially proximal to an exterior surface of piercing tip (1196) as piercing tip (1196) is extended out of vertical slot (1108). In some versions of cannula (1100), conical portions (1104A, 1104B) may be resiliently-inwardly biased such that interior surfaces of first conical portion (1104A) and second conical portion (1104B) are configured to contact the exterior surface of piercing tip (1196) as piercing tip (1196) is extended out of vertical slot (1108). First conical portion (1104A) and second conical portion (1104B) are configured to house piercing tip (1196) and to provide an angular transition from piercing tip (1196) and vertical slot (1108) to exterior surface (1112).

Also as shown in FIGS. 31A-32B, piercing tip (1196) comprises a pair of adjustable blades (1198A, 1198B). Pair of blades (1198A, 1198B) may be moved radially inwardly and outwardly to extend and retract relative to a longitudinal axis defined by obturator (1192). Pair of blades (1198A, 1198B) is movable between an extended position as shown in FIGS. 31A and 32A and a retracted position as shown in FIGS. 31B and 32B. Such radial motion allows a user to manipulate the profile of piercing tip (1196). Radial movement of pair of blades (1198A, 1198B) may be actuated by a mandrel, pivot links, a pinion and arcuate racks, and/or any other suitable features as will be apparent to those of ordinary skill in the art in view of the teachings herein.

Manipulation of the profile of piercing tip (1196) may reduce the force required to insert cannula (1100) and obturator (1192) into a patient's breast. Manipulation of piercing tip (1196) may also reduce the force required to rotate cannula (1100) and obturator (1192) in a patient's breast. For instance, during insertion, a user may find it advantageous to leave piercing tip (1196) in the extended position such that breast tissue may be better transitioned along pair of blades (1198A, 1198B) to exterior surface (1112) of cannula (1100). On the other hand, during rotation, a user may find it advantageous to pivot transition piercing tip (1196) to the retracted position such that there is less surface area of pair of blades (1198A, 1198B) to prevent rotation.

I. Exemplary Cannula with Integral Blade

Figure 33:
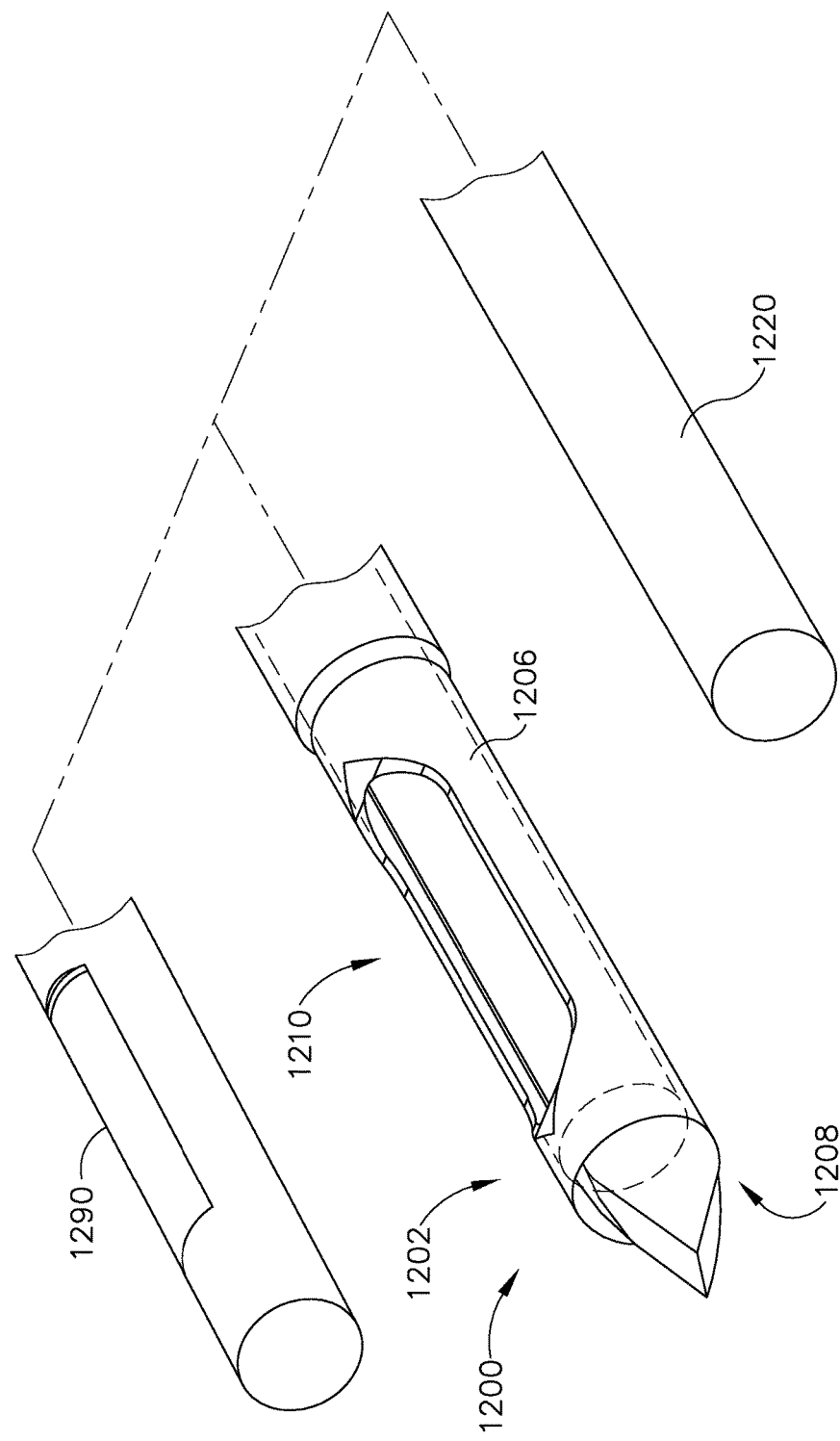
FIG. 33 depicts a partial exploded perspective view of yet another exemplary alternative cannula with an integral tissue piercing tip that may be used with the biopsy system of FIG. 1.
Figure 34:
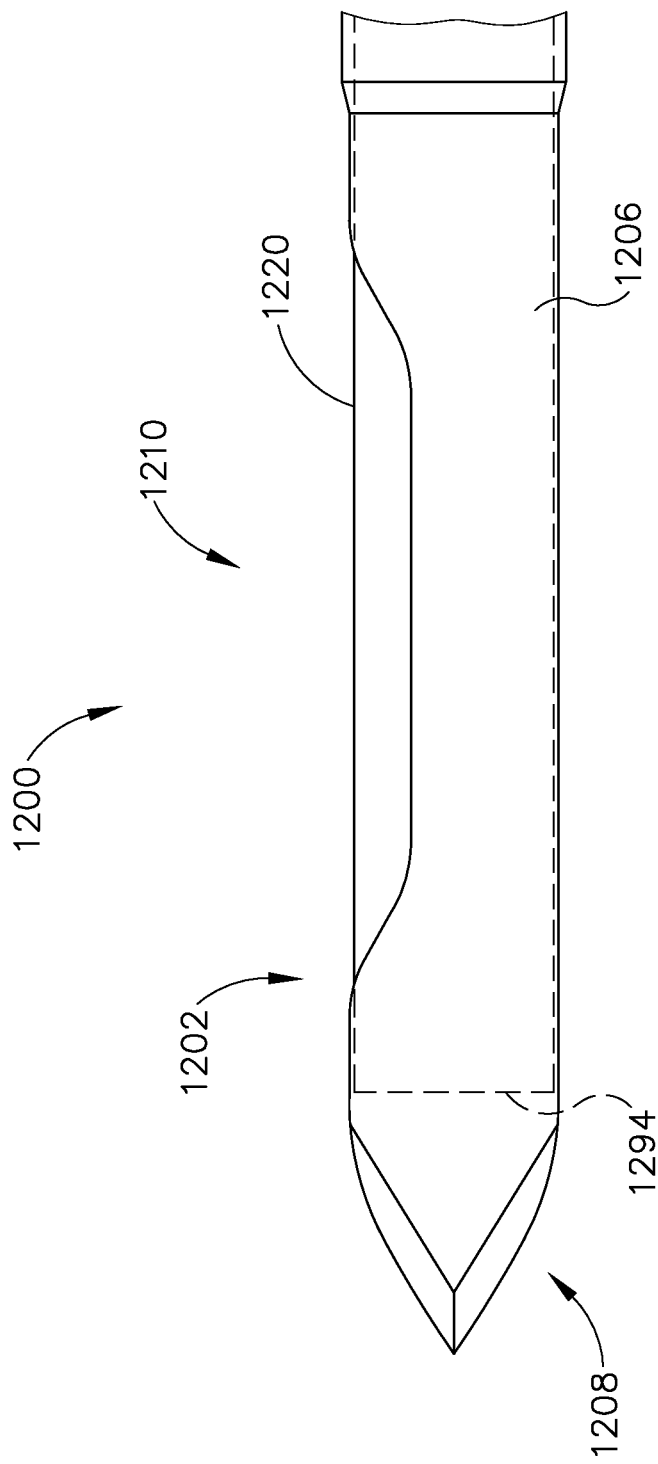
FIG. 34 depicts a partial side elevational view of the cannula of FIG. 33 with an obturator inserted therein.

FIGS. 33-34 show yet another merely exemplary variation of a cannula (1200). Cannula (1200) includes a hollow shaft (1206) that is proximally attached to a cylindrical hub (not shown) and has a lateral aperture (1210) proximal to a piercing tip (1208) located at a distal end (1202) of cannula (1200). Piercing tip (1208) is configured to operate substantially similar to piercing tip (222) of obturator (92) discussed above. Cannula (1200) is configured to slidably receive a blunt tipped obturator (1220) or a blunt tipped needle (1290) of a biopsy probe. Blunt-tipped obturator (1220) is configured to operate substantially similar to obturator (92) discussed above. For instance, and as shown in FIG. 34, blunt tipped obturator (1220) is inserted into cannula (1220) during insertion and targeting of cannula (1220) within a patient's breast. Blunt-tipped obturator (1220) is then removed and replaced with needle (1290) of probe (91) to obtain tissue samples.

VI. Exemplary Depth Stop Member With Alternative Cannula

Figure 35:
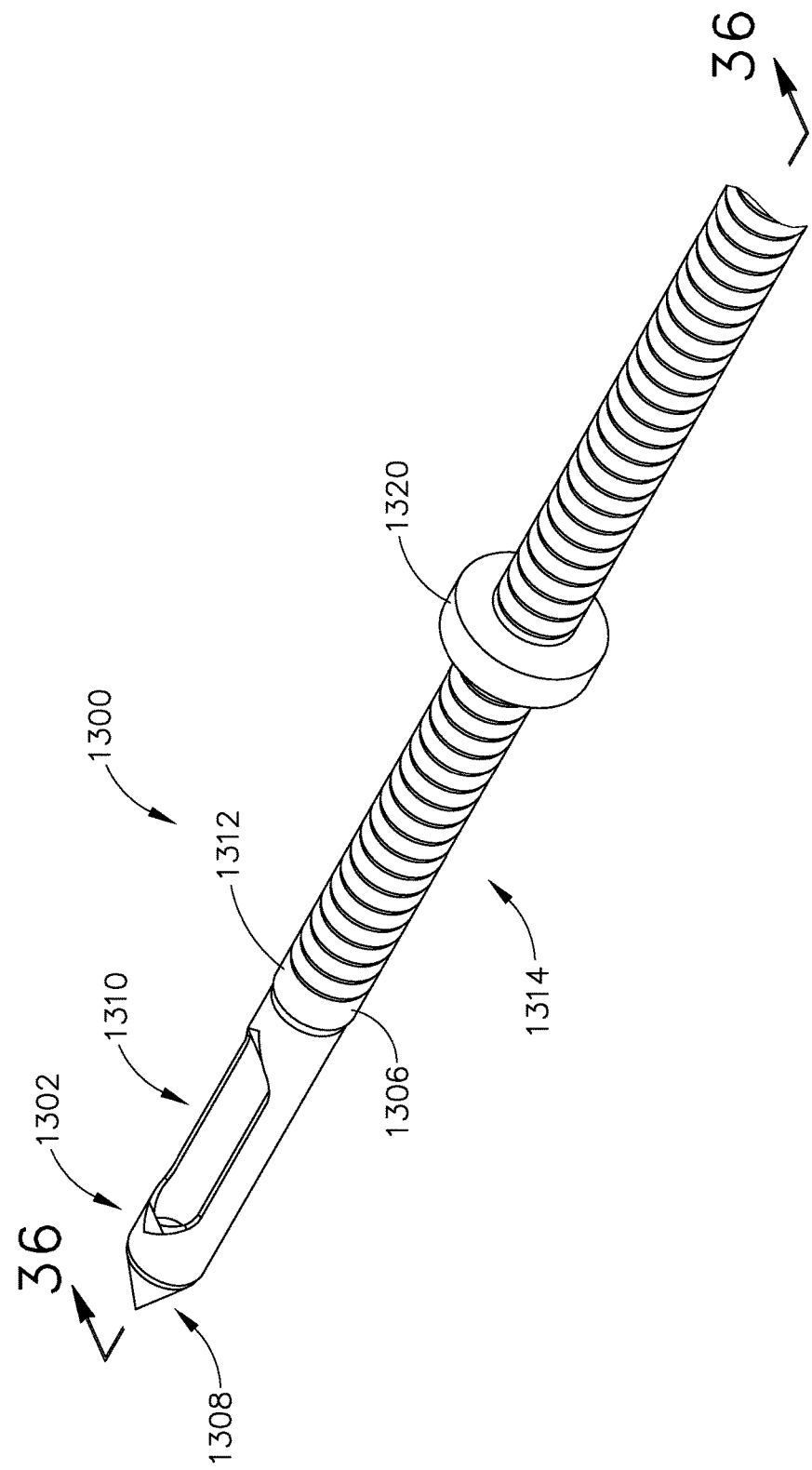
FIG. 35 depicts a perspective view of another exemplary alternative cannula with an integral tissue piercing tip that may be used with the biopsy system of FIG. 1.
Figure 36:
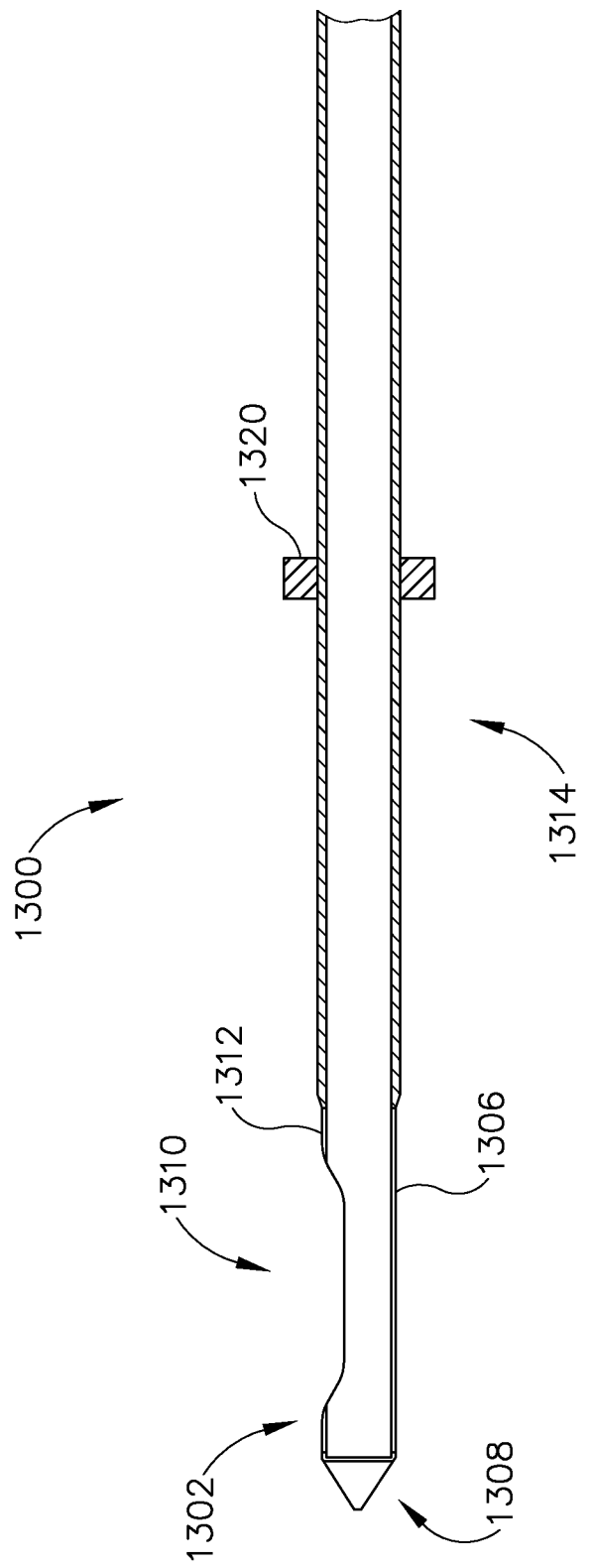
FIG. 36 depicts a cross-sectional view of the cannula of FIG. 35 taken along line 36-36 of FIG. 35.

As noted above, a depth stop device (95) may be coupled with a cannula (94) to controllably restrict the depth of insertion of cannula (94) into a patient's breast. By way of example only, depth stop device (95) may be configured in accordance with at least some of the teachings of U.S. Pat. No. 7,507,210, the disclosure of which is incorporated by reference herein. As described in greater detail below, FIGS. 35-36 show an exemplary alternative form that depth stop device (95) may take. As also described in greater detail below with reference to FIGS. 39-40, this exemplary alternative form of depth stop device (95) may also be used to selectively prevent proximal retraction of a cannula relative to a patient's breast; in addition to restricting the depth of insertion into the patient's breast.

FIGS. 35-36 show one merely exemplary variation of a cannula (1300). Cannula (1300) is configured to function substantially similar to cannula (94) described above. For instance, cannula (1300) is configured to receive obturator (92) and the combination is configured to be guided through a guide cube to a biopsy site within a patient's breast. Cannula (1300) includes a hollow shaft (1306) that is proximally attached to a cylindrical hub (not shown) and has a lateral aperture (1310) proximal to an opening (1308) defined within a distal end (1302) of cannula (1300). An exterior surface (1312) of cannula (1300) presents an exterior threaded region (1314) located proximally of lateral aperture (1310). A lock nut (1320) presents an interior threaded region and is configured to be matingly threaded onto exterior threaded region (1314). Lock nut (1320) is configured to translate longitudinally relative to cannula (1300) as lock nut (1320) is rotated. Lock nut (1320) is further configured such that lock nut (1320) cannot pass through guide holes of the guide cube, thereby preventing cannula (1300) from moving further into a patient's breast. Lock nut (1320) thus serves as a variation of depth stop device (95). Prior to guiding cannula (1300) into the guide cube, a user may rotate lock nut (1320) until lock nut (1320) is translated into a desired longitudinal position along cannula (1300). With lock nut (1320) in this desired position, cannula (1300) will be prevented from moving beyond this position and further into a patient's breast.

It should be understood that although cannula (1300) of the present example utilizes a single lock nut (1320), other versions of cannula (1300) may utilize multiple lock nuts (1320) in order to prevent any incidental rotation of lock nut (1320). It should also be understood that lock nut (1320) may comprise any appropriate thickness or shape. Finally, it should be understood that any of the cannulas referred to herein may include threaded region (1314) and thus be configured to receive lock nut (1320).

VII. Exemplary Alternative Guide Cubes

As a variation of guide cube (104) discussed above, guide cube (104) may be arranged to prevent backing-out of guide cube (104) relative to grid plate (96) and/or to prevent backing-out of cannula (1300) relative to guide cube (104). Various examples of how guide cube (104) may be reconfigured to prevent backing-out of guide cube (104) and/or cannula (1300) will be described in greater detail below; while other examples will be apparent to those of ordinary skill in the art according to the teachings herein. It should be understood that the guide cube examples described below may function substantially similar to guide cube (104) described above. In particular, the guide cube examples described below may be inserted into grid plate (96) and used to guide a cannula and obturator into a patient's breast. It should be understood that the guide cube examples discussed below may be used with any of the biopsy devices discussed above or disclosed herein.

Figure 37:
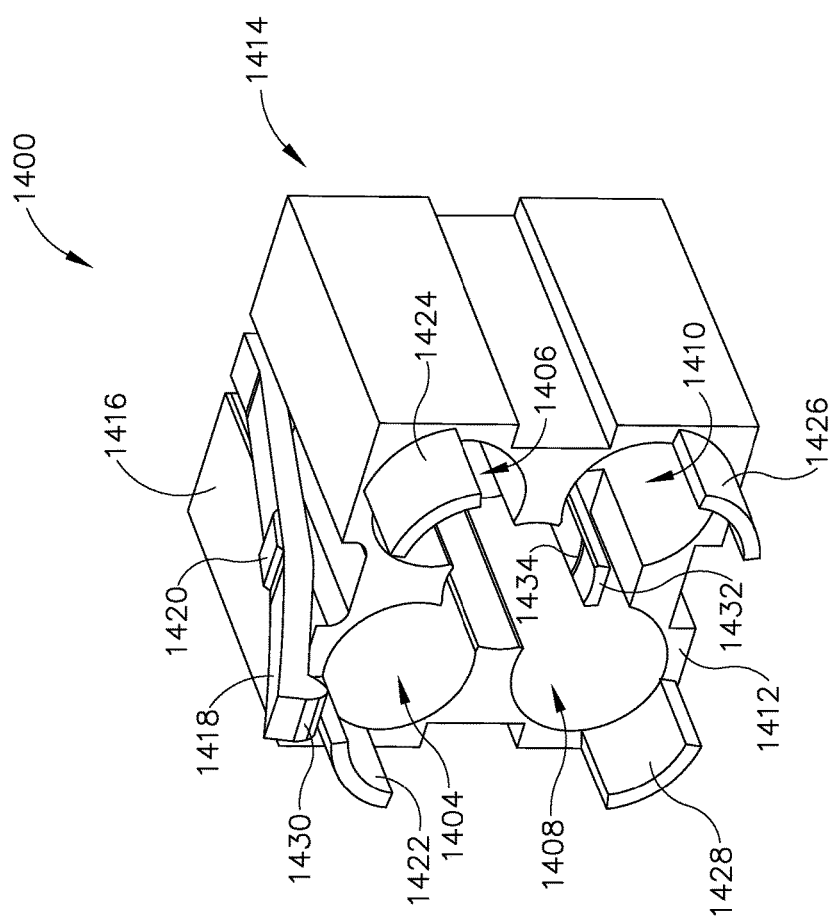
FIG. 37 depicts a perspective view of an exemplary alternative guide cube suitable for use with the biopsy system of FIG. 1.
Figure 38:
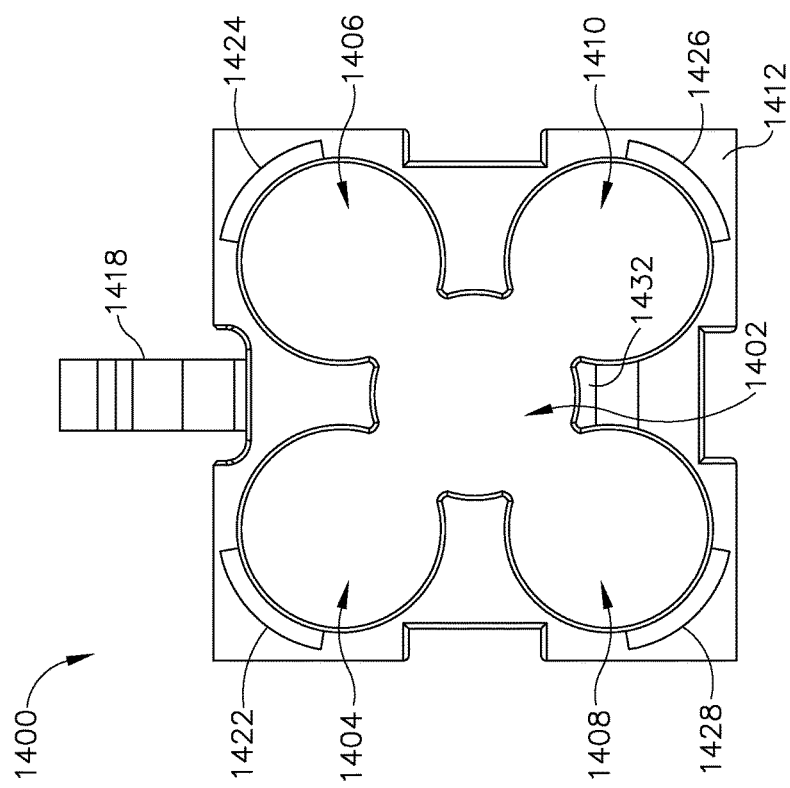
FIG. 38 depicts a front elevational view of the guide cube of FIG. 37.
Figure 39:
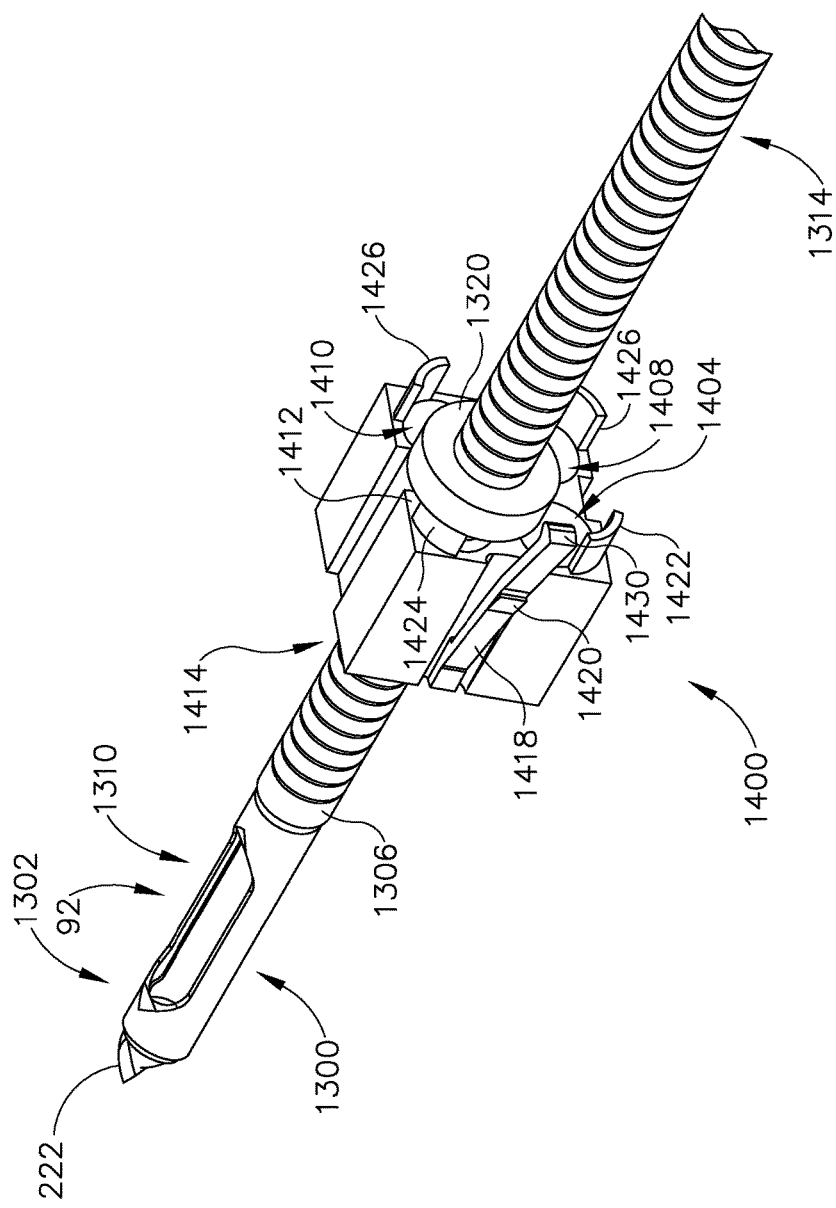
FIG. 39 depicts a perspective view of the cannula of FIG. 35 inserted through a guide hole of the guide cube of FIG. 37.

FIGS. 37-38 show one merely exemplary variation of a guide cube (1400). Guide cube (1400) comprises a central guide hole (1402) and four corner guide holes (1404, 1406, 1408, 1410) that pass through guide cube (1400) from a first surface (1412) to a second surface (1414). Guide holes (1402, 1404, 1406, 1408, 1410) are configured to receive cannula (1300). As best seen in FIG. 37, guide cube (1400) further comprises a plurality of arcuate projections (1422, 1424, 1426, 1428) extending from first surface (1412) and adjacent to guide holes (1404, 1406, 1408, 1410). Projections (1422, 1424, 1426, 1428) are configured to engage lock nut (1320) of cannula (1300) such that cannula (1300) cannot be inserted beyond a position where projections (1422, 1424, 1426, 1428) engage lock nut (1320). As shown in FIG. 39, and as discussed above, lock nut (1320) prevents cannula (1300) from moving further into a patient's breast by resting against an outer surface of projections (1422, 1424, 1426, 1428) guide cube (1400).

Guide cube (1400) is sized for insertion from a proximal side into one of a plurality of square recesses (130) in grid plate (96). Guide cube (1400) is prevented from passing through grid plate (96) by backing substrate (136) attached to a front face of grid plate (96). Backing substrate (136) includes respective square opening (138) centered within each square recess (130), forming lip (140) sufficient to capture second surface (1414) of guide cube (1400) but not so large as to obstruct guide holes (1402, 1404, 1406, 1408, 1410). The depth of square recesses (130) is less than guide cube (1400), thereby exposing a proximal portion of guide cube (1400) for seizing and extraction from grid plate (96).

Figure 40:
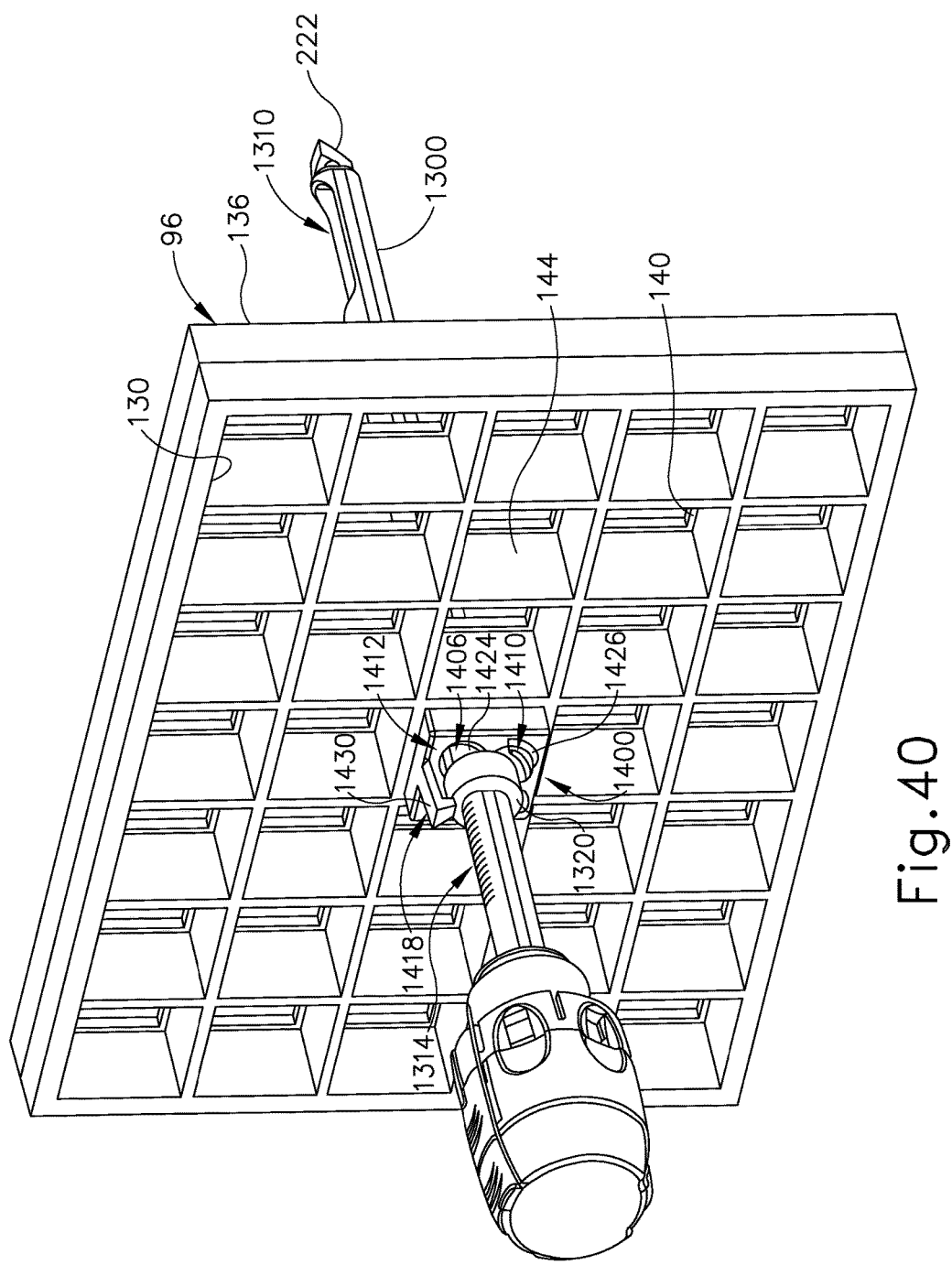
FIG. 40 depicts a perspective view of the cannula of FIG. 35 inserted through the guide cube of FIG. 37, with the guide cube disposed in the grid plate of FIG. 6.

A third surface (1416) of guide cube (1400) comprises a resilient arm (1418). As shown in FIG. 40, arm (1418) is outwardly biased such that when guide cube (1400) is inserted into a particular square recess of the plurality of square recesses (130), arm (1418) is forced inwardly such that arm (1418) bears against and exerts pressure upon an interior surface (144) of the particular square recess. This pressure exerted upon interior surface (144) may create friction that substantially prevents guide cube (1400) from backing-out of the particular square recess. This pressure may also enable guide cube (1400) to fit securely in grid plates with various aperture sizes. Arm (1418) comprises a bearing surface (1420) configured to bear against interior surface (144) of the particular square recess to thereby further prevent backing-out of the particular square recess. Bearing surface (1420) may comprise any suitable material. For instance, bearing surface (1420) may comprise an elastomeric material such as rubber or any other material having a high coefficient of friction.

Arm (1418) further comprises a tab (1430) extending inwardly from an interior surface of arm (1418). As shown in FIG. 40, as arm (1418) is forced inwardly, tab (1430) is forced inwardly as well into a closed position. In this closed position, tab (1430) extends over lock nut (1320) such that neither lock nut (1320) nor cannula (1300) can back-out of guide cube (1400). In some versions, guide cube (1400) may comprise further arms to prevent backing-out of cannula (1300) from guide cube (1400) additionally or in lieu of arm (1418). For instance, as best seen in FIG. 37, central guide hole (1402) comprises a central resilient arm (1432) having a projection (1434). Projection (1434) is configured to engage threaded region (1314) of cannula (1300) to prevent backing-out of cannula (1300) from central guide hole (1402) of guide cube (1400).

Guide cube (1400) may be inserted into grid plate (96), driving arm (1418) (including tab (1430)) into an inward position. As cannula (1300) is then inserted into guide cube (1400), lock nut (1320) engages tab (1430) and drives the exposed portion of arm (1418) outwardly until lock nut (1320) is positioned between tab (1430) and a particular projection of projections (1422, 1424, 1426, 1428). Once lock nut (1320) clears tab (1430), arm (1418) snaps back inwardly, such that lock nut (1320) is captured between tab (1430) and a particular projection of projections (1422, 1424, 1426, 1428). Tab (1422) may include a chamfer, curved surface, or other camming feature configured to facilitate clearance of tab (1430) by lock nut (1320) during insertion of cannula (1300) into guide cube (1400). To withdraw cannula (1300), an operator may push outwardly on arm (1418) to provide clearance between tab (1430) and lock nut (1320).

It should be understood that, although the present example of guide cube (1400) comprises only a single arm (1418) on a single surface of guide cube (1400), guide cube (1400) may comprise any number of arms (1418) located on any number of surfaces of guide cube (1400). For instance, guide cube (1400) may comprise two arms (1418) on opposite surfaces or adjacent surfaces of guide cube (1400). Guide cube (1400) may alternatively comprise three arms (1418) or four arms (1418) located on opposite surfaces, adjacent surfaces, or each surface of guide cube (1400).

FIGS. 41-45 show another merely exemplary variation of a guide cube (1500). Guide cube (1500) comprises a central guide hole (1520) that passes through guide cube (1500)

from a first side surface (1502) to a second side surface (1504). Guide cube (1500) further comprises a pair of offset guide holes (1540, 1560) that passes through guide cube (1500) from a third side surface (1506) to a fourth side surface (1508). Guide holes (1520, 1540, 1560) are configured to receive any of the cannulas described herein. Referring to cannula (1300) as just one merely illustrative example, upon insertion of cannula (1300) into guide holes (1520, 1540, 1560), side surfaces (1502, 1504, 1506, 1508) engage lock nut (1320) of cannula (1300) such that cannula (1300) cannot be inserted beyond a position where side surfaces (1502, 1504, 1506, 1508) engage lock nut (1320). As discussed above, lock nut (1320) prevents cannula (1300) from moving further into a patient's breast by resting against side surfaces (1502, 1504, 1506, 1508) of guide cube (1500).

Figure 41:
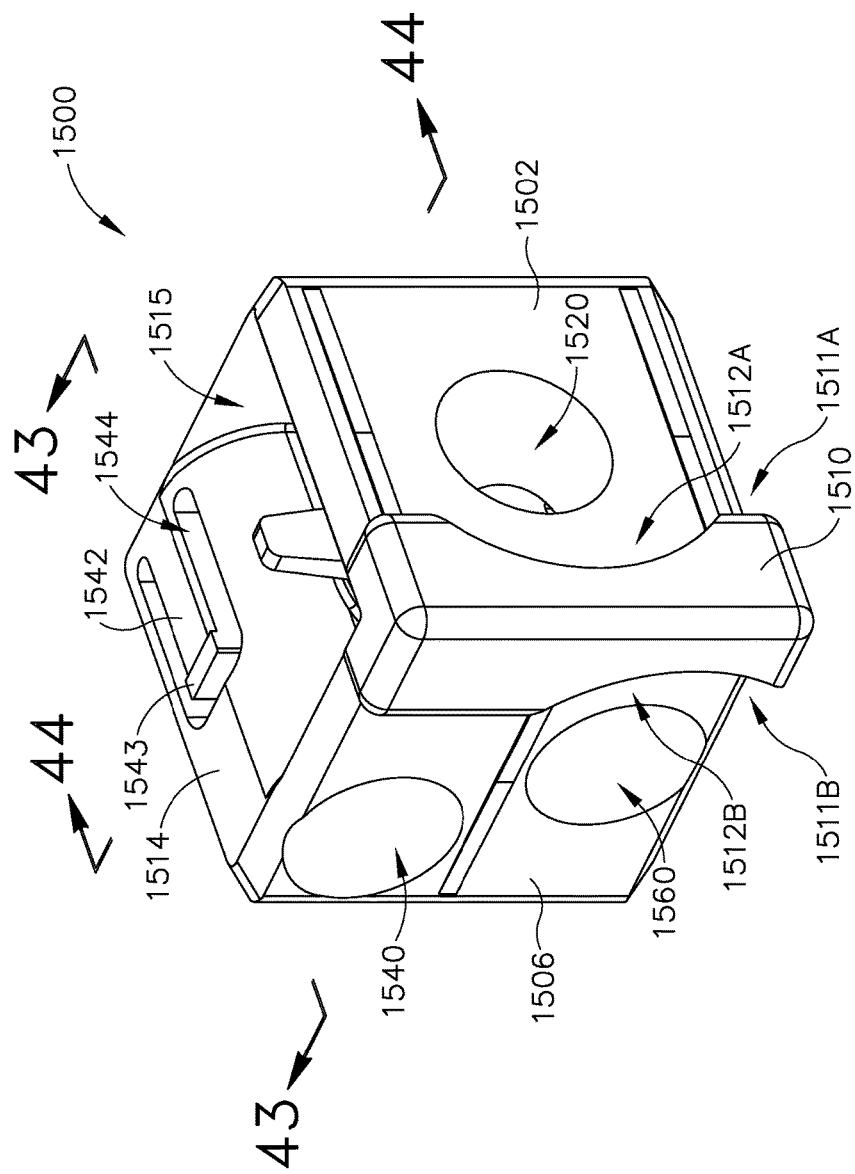
FIG. 41 depicts a perspective view of another exemplary alternative guide cube suitable for use with the biopsy system of FIG. 1.

Guide cube (1500) is sized for insertion from a proximal side into a selected square recess (130) in grid plate (96). As best seen in FIG. 41, guide cube (1500) comprises a projection (1510) extending from a corner of guide cube (1500) adjacent to first side surface (1502) and third side surface (1506). Projection (1510) defines a first face (1511A) extending perpendicularly from first side surface (1502) and a second face (1511B) extending perpendicularly from third side surface (1506). With guide cube (1500) oriented such that third side surface (1506) and fourth side surface (1508) are parallel with a front surface of grid plate (96), first face (1511A) is configured to contact the front surface of grid plate (96) upon being inserted into a square recess (130) to thereby prevent guide cube (1500) from passing into square recess (130) beyond first face (1511A). With guide cube (1500) oriented such that first side surface (1502) and second side surface (1504) are parallel with the front surface of grid plate (96), second face (1511B) is configured to contact the front surface of grid plate (96) upon being inserted into square recess (130) to thereby prevent guide cube (1500) from passing into square recess (130) beyond second face (1511B).

Guide cube (1500) may be further prevented from passing through grid plate (96) by backing substrate (136) attached to the front face of grid plate (96). Backing substrate (136) includes respective square opening (138) centered within each square recess (130), forming lip (140) sufficient to capture second side surface (1504) or fourth side surface (1508) of guide cube (1500) but not so large as to obstruct guide holes (1520, 1540, 1560). The depth of square recesses (130) is less than guide cube (1500), thereby exposing a proximal portion of guide cube (1500) for seizing and extraction from grid plate (96).

As shown in FIG. 41, first face (1511A) and second face (1511B) respectively define a first annular recess (1512A) and a second annular recess (1512B). Annular recesses (1512A, 1512B) are configured to accommodate lock nut (1320) as lock nut (1320) engages side surfaces (1502, 1504, 1506, 1508).

Figure 43:
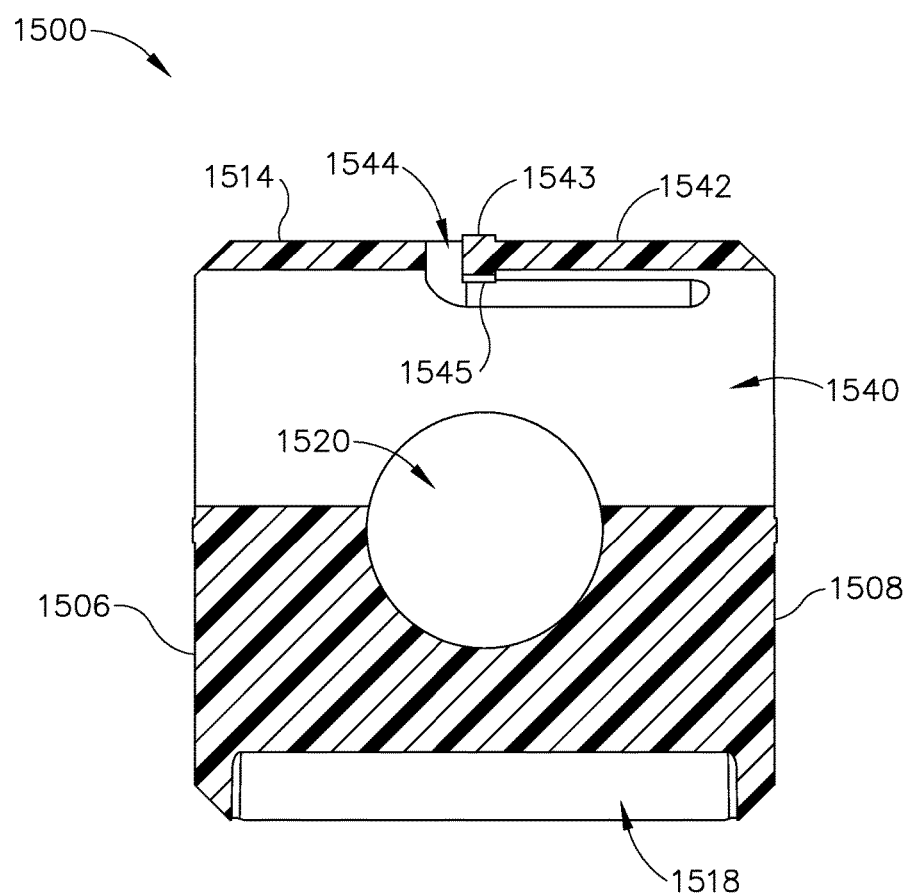
FIG. 43 depicts a cross-sectional view of the guide cube of FIG. 41 taken along line 43-43 of FIG. 41.

Also as shown in FIG. 41, a recess (1515) is formed in a top surface (1514) of guide cube (1500). A portion of recess (1515) is defined by an exterior surface of a portion of guide cube (1500) that defines guide hole (1540). As shown in FIGS. 41 and 43, an opening (1544) is formed in top surface (1514) and the exterior surface of guide hole (1540) and extends into guide hole (1540). A resilient arm (1542) extends longitudinally within opening (1544) relative to guide hole (1540). A free end of resilient arm (1542) comprises a first tab (1543) extending outwardly such that first tab (1543) extends beyond top surface (1514). The free end of resilient arm (1542) further comprises a second tab (1545) extending inwardly such that second tab (1545) extends into guide hole (1540).

As guide cube (1500) is inserted into a particular square recess (130) of the plurality of square recesses (130), first tab (1543) of resilient arm (1542) engages an interior surface (144) of the particular square recess (130) such that resilient arm (1542) is forced inwardly and further such that first tab (1543) of resilient arm (1542) bears against and exerts pressure upon interior surface (144) of the particular square recess (130). Furthermore, as cannula (1300) is inserted into guide hole (1540), an exterior surface of cannula (1300) engages second tab (1545) of resilient arm (1542) and forces resilient arm (1542) outwardly such that first tab (1543) of resilient arm (1542) further bears against and exerts further pressure upon interior surface (144) of the particular square recess (130) of grid plate (96). This pressure exerted upon interior surface (144) may create friction that substantially prevents guide cube (1500) from backing-out of the particular square recess (130). This pressure may also enable guide cube (1500) to fit securely in grid plates with various aperture sizes. First tab (1543) may comprise any suitable material. For instance, first tab (1543) may comprise an elastomeric material such as rubber or any other material having a high coefficient of friction.

It should be understood that, as first tab (1543) exerts pressure upon interior surface (144), second tab (1545) will exert pressure upon the exterior surface of cannula (1300) to substantially resist backing-out of cannula (1300) from guide cube (1500). Second tab (1545) may comprise any suitable material. For instance, second tab (1545) may comprise an elastomeric material such as rubber or any other material having a high coefficient of friction. In some versions of guide cube (1500), second tab (1545) may be configured to engage threaded region (1314) of cannula (1300) to further prevent cannula (1300) from backing-out of guide cube (1500).

Figure 42:
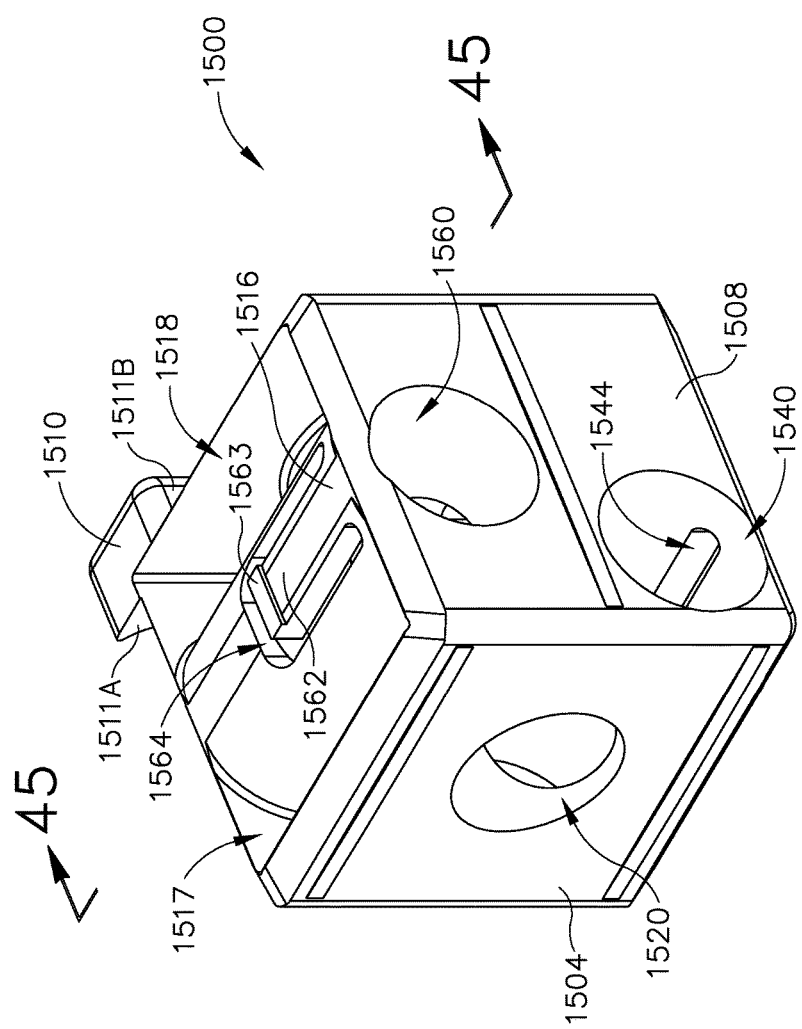
FIG. 42 depicts another perspective view of the guide cube of FIG. 41.
Figure 45:
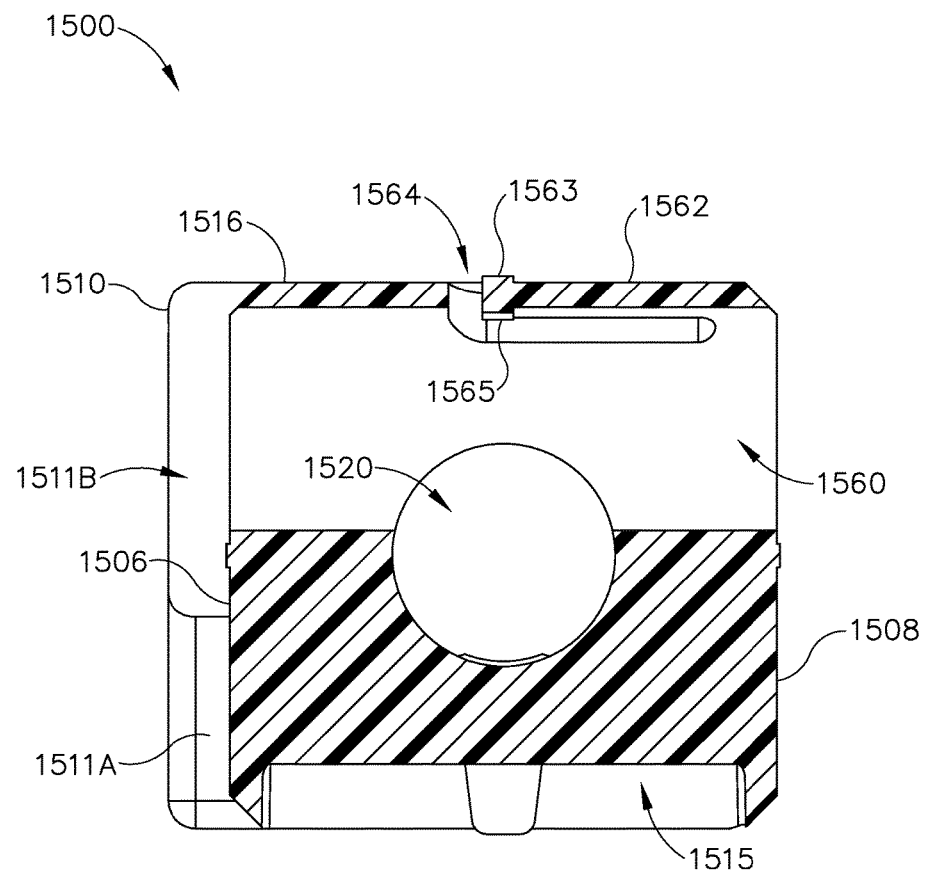
FIG. 45 depicts a cross-sectional view of the guide cube of FIG. 41 taken along line 45-45 of FIG. 42.
Figure 46:
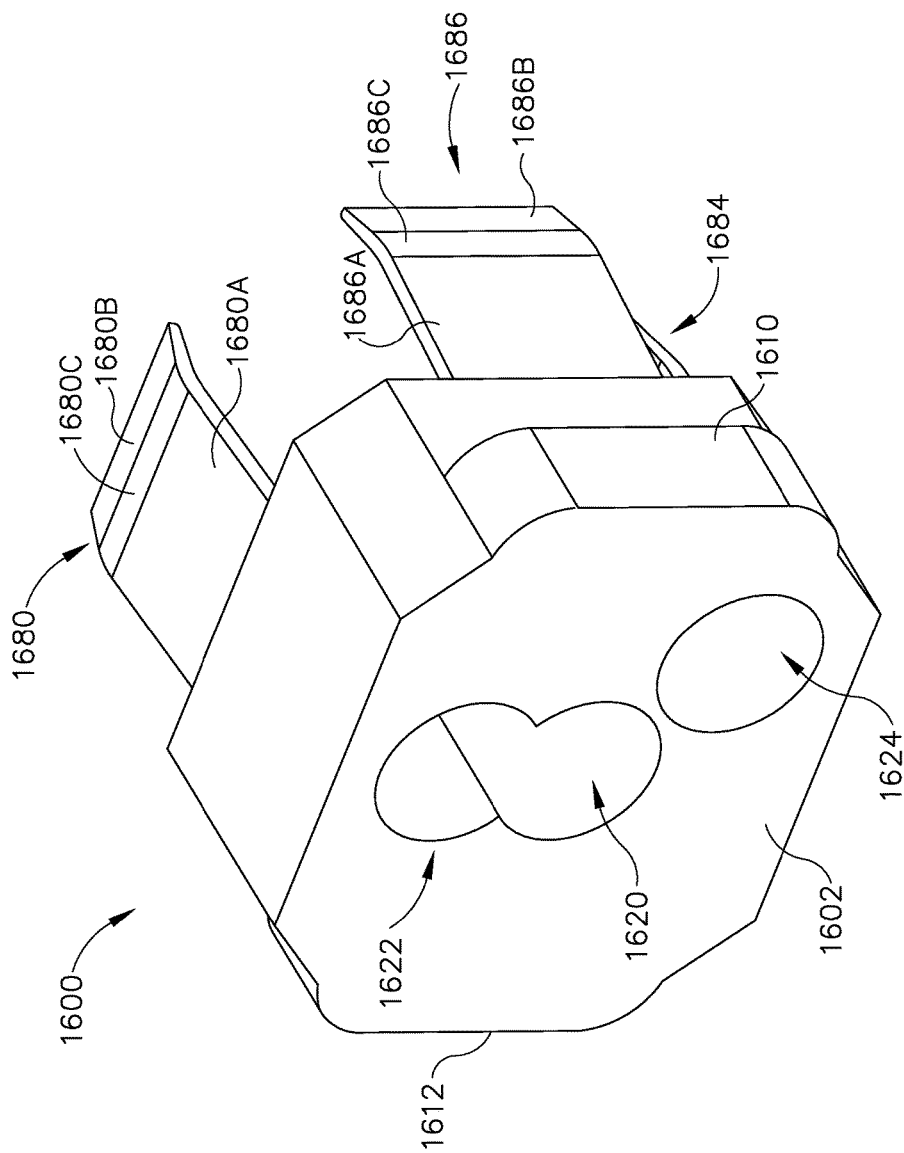
FIG. 46 depicts a perspective view of yet another exemplary alternative guide cube suitable for use with the biopsy system of FIG. 1.
Figure 47:
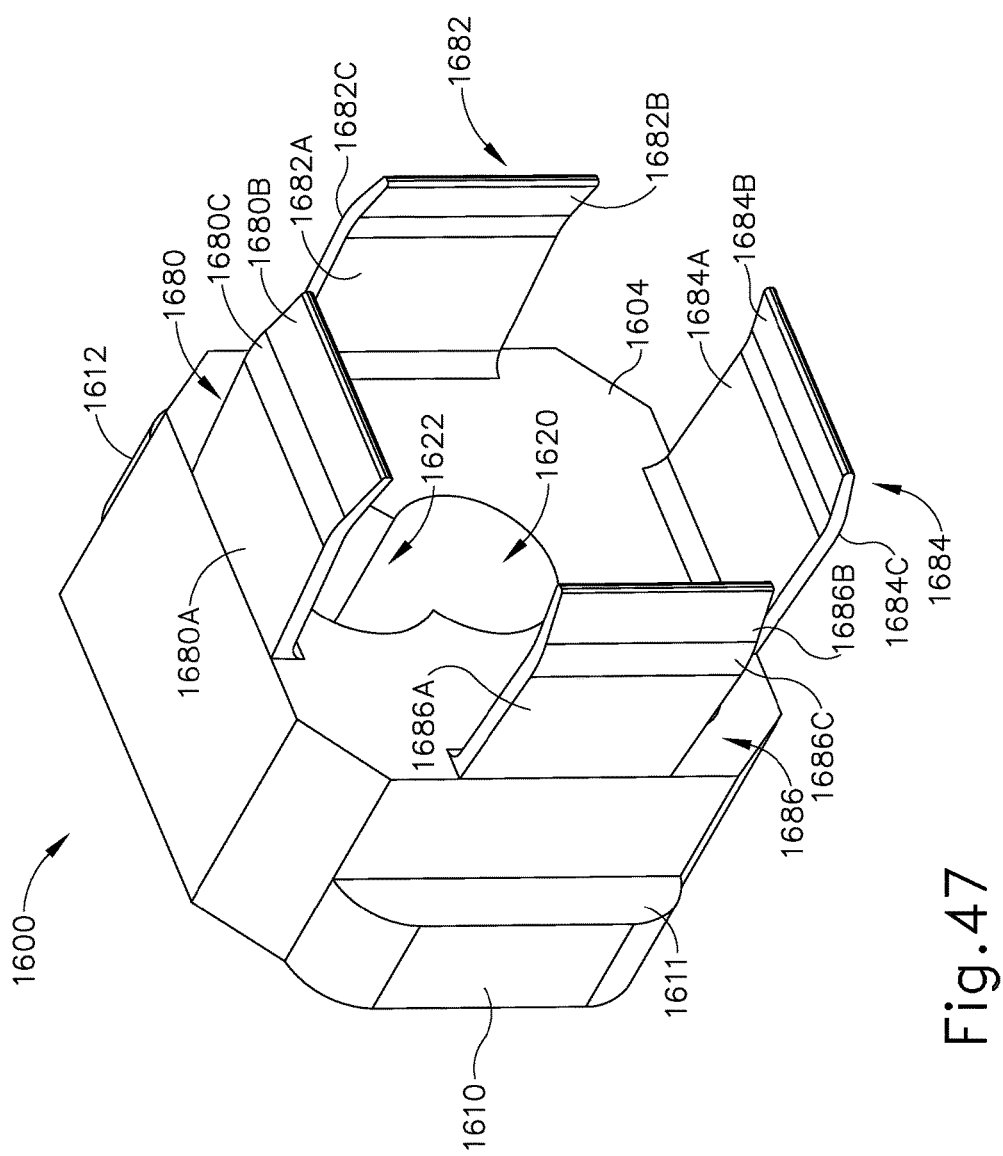
FIG. 47 depicts another perspective view of the guide cube of FIG. 46.
Figure 48:
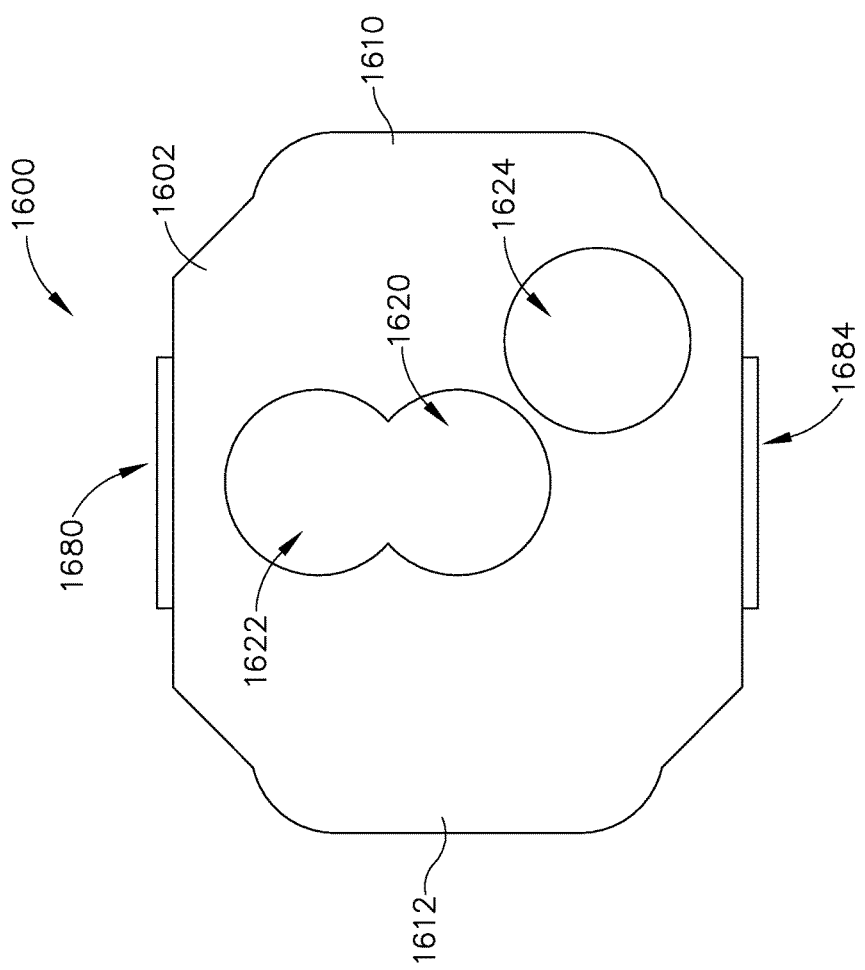
FIG. 48 depicts a front elevational view of the guide cube of FIG. 46.

As shown in FIG. 42, a pair of recesses (1517, 1518) are formed in a bottom surface (1516) of guide cube (1500). A portion of recess (1517) and portion of recess (1518) are defined by an exterior surface of a portion of guide cube (1500) that defines guide hole (1560). As shown in FIGS. 42 and 45, an opening (1564) is formed in bottom surface (1516) and the exterior surface of guide hole (1560) and extends into guide hole (1560). A resilient arm (1562) extends longitudinally within opening (1564) relative to guide hole (1560). A free end of resilient arm (1562) comprises a first tab (1563) extending outwardly such that first tab (1563) extends beyond bottom surface (1516). The free end of resilient arm (1562) further comprises a second tab (1565) extending inwardly such that second tab (1565) extends into guide hole (1560).

As guide cube (1500) is inserted into a particular square recess (130) of the plurality of square recesses (130), first tab (1563) of resilient arm (1562) engages an interior surface of (144) the particular square recess (130) such that resilient arm (1562) is forced inwardly and further such that first tab (1563) of resilient arm (1562) bears against and exerts pressure upon interior surface (144) of the particular square recess (130). Furthermore, as cannula (1300) is inserted into guide hole (1560), an exterior surface of cannula (1300) engages second tab (1565) of resilient arm (1562) and forces resilient arm (1562) outwardly such that first tab (1563) of resilient arm (1562) further bears against and exerts further pressure upon interior surface (144) of the particular square recess (130) of grid plate (96). This pressure exerted upon interior surface (144) may create friction that substantially prevents guide cube (1500) from backing-out of the particular square recess (130). This pressure may also enable guide cube (1500) to fit securely in grid plates with various aperture sizes. First tab (1563) may comprise any suitable material. For instance, first tab (1563) may comprise an elastomeric material such as rubber or any other material having a high coefficient of friction.

It should be understood that, as first tab (1563) exerts pressure upon interior surface (144), second tab (1565) will exert pressure upon the exterior surface of cannula (1300) to substantially resist backing-out of cannula (1300) from guide cube (1500). Second tab (1565) may comprise any suitable material. For instance, second tab (1565) may comprise an elastomeric material such as rubber or any other material having a high coefficient of friction. In some versions of guide cube (1500), second tab (1565) may be configured to engage threaded region (1314) of cannula (1300) to further prevent cannula (1300) from backing-out of guide cube (1500).

Figure 44:
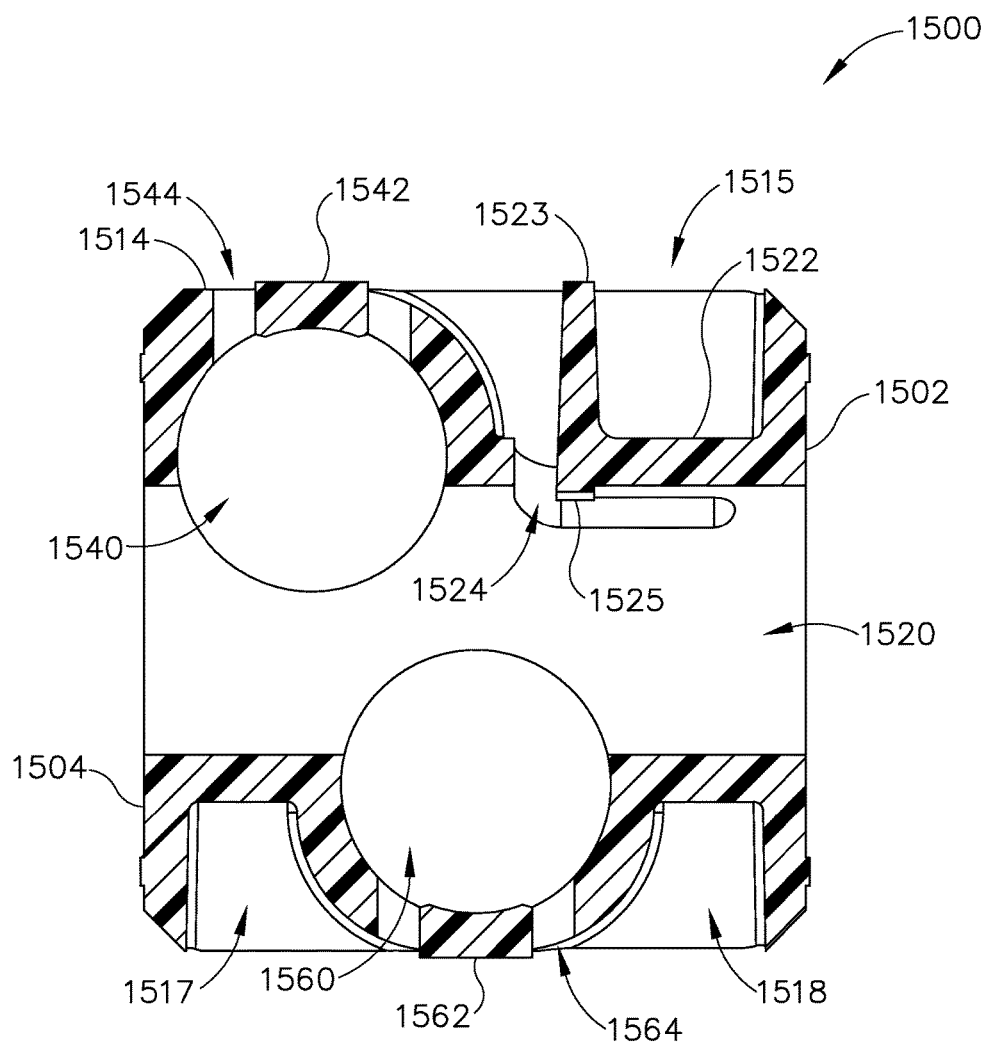
FIG. 44 depicts a cross-sectional view of the guide cube of FIG. 41 taken along line 44-44 of FIG. 41.

As shown in FIG. 44, an opening (1524) is formed in an exterior surface of guide hole (1520) and extends into guide hole (1520). A resilient arm (1522) extends longitudinally within opening (1524) relative to guide hole (1520). A free end of resilient arm (1522) comprises a first tab (1523) extending outwardly through recess (1515) such that first tab (1523) extends beyond top surface (1514). The free end of resilient arm (1522) further comprises a second tab (1525) extending inwardly such that second tab (1525) extends into guide hole (1520).

As guide cube (1500) is inserted into a particular square recess (130) of the plurality of square recesses (130), first tab (1523) of resilient arm (1522) engages an interior surface of the particular square recess (130) such that resilient arm (1522) is forced inwardly and further such that first tab (1523) of resilient arm (1522) bears against and exerts pressure upon interior surface (144) of the particular square recess (130). Furthermore, as cannula (1300) is inserted into guide hole (1520), an exterior surface of cannula (1300) engages second tab (1525) of resilient arm (1522) and forces resilient arm (1522) outwardly such that first tab (1523) of resilient arm (1522) further bears against and exerts further pressure upon interior surface (144) of the particular square recess (130) of grid plate (96). This pressure exerted upon interior surface (144) may create friction that substantially prevents guide cube (1500) from backing-out of the particular square recess (130). This pressure may also enable guide cube (1500) to fit securely in grid plates with various aperture sizes. First tab (1523) may comprise any suitable material. For instance, first tab (1523) may comprise an elastomeric material such as rubber or any other material having a high coefficient of friction.

As first tab (1523) exerts pressure upon interior surface (144), second tab (1525) will exert pressure upon the exterior surface of cannula (1300) to substantially resist backing-out of cannula (1300) from guide cube (1500). Second tab (1525) may comprise any suitable material. For instance, second tab (1525) may comprise an elastomeric material such as rubber or any other material having a high coefficient of friction. In some versions of guide cube (1500), second tab (1525) may be configured to engage threaded region (1314) of cannula (1300) to further prevent cannula (1300) from backing-out of guide cube (1500).

It should be understood that, as guide cube (1500) is inserted into a particular square recess (130) of the plurality of square recesses (130), first tab (1523) of resilient arm (1522), first tab (1543) of resilient arm (1542), and first tab (1563) of resilient arm (1562) will concurrently engage and exert pressure upon respective interior surfaces (144) of the particular square recess (130) regardless of the orientation of guide cube (1500) and/or the guide hole (1520, 1540, 1560) into which cannula (1300) is inserted.

FIGS. 46-51 show another merely exemplary variation of a guide cube (1600). Guide cube (1600) comprises a central guide hole (1620) that passes through guide cube (1600) from a first surface (1602) to a second surface (1604). Guide cube (1600) further comprises a pair of offset guide holes (1622, 1624) that also pass through guide cube (1600) from first surface (1602) to second surface (1604). In the present example guide hole (1620) and guide hole (1622) overlap one another in a manner such that guide holes (1620, 1622) are arranged vertically relative to one another. Guide holes (1620, 1622, 1624) are configured to receive any of the cannulas described herein and provide structural support to the inserted cannula. Referring to cannula (1300) as just one merely illustrative example, upon insertion of cannula (1300) into guide holes (1620, 1622, 1624), first side surface (1602) engages lock nut (1320) of cannula (1300) such that cannula (1300) cannot be inserted beyond a position where first side surface (1602) engages lock nut (1320). As discussed above, lock nut (1320) prevents cannula (1300) from moving further into a patient's breast by abutting first side surface (1602) of guide cube (1600).

Figure 49:
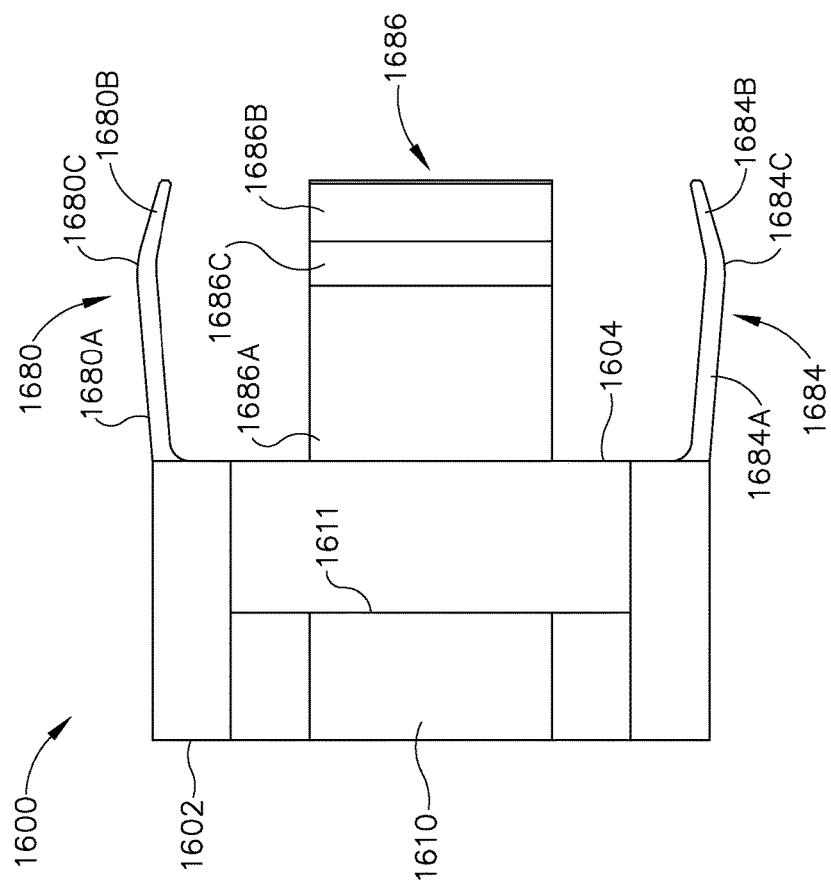
FIG. 49 depicts a side elevational view of the guide cube of FIG. 46.

Guide cube (1600) is sized for insertion from a proximal side into a selected square recess (130) in grid plate (96). Guide cube (1600) comprises a plurality of resilient members (1680, 1682, 1684, 1686) extending distally from second side surface (1604). As best seen in FIG. 49, resilient members (1680, 1682, 1684, 1686) each comprise a first portion (1680A, 1682A, 1684A, 1686A) extending distally and outwardly from second side surface (1604), at an oblique angle away from a center of guide cube (1600). Resilient members (1680, 1682, 1684, 1686) each further comprise a second portion (1680B, 1682B, 1684B, 1686B) extending distally and inwardly from first portions (1680A, 1682A, 1684A, 1686A) respectively, at an oblique angle toward the center of guide cube (1600). An apex (1680C, 1682C, 1684C, 1686C) is formed between respective first portions (1680A, 1682A, 1684A, 1686A) and second portions (1680B, 1682B, 1684B, 1686B) of each resilient member (1680, 1682, 1684, 1686). As will be discussed in more detail below, resilient members (1680, 1682, 1684, 1686) are flexible to provide for insertion of guide cube (1600) into square recesses of varying sizes. Resilient members (1680, 1682, 1684, 1686) are biased toward an initial position as shown in FIG. 49. As guide cube (1600) is inserted into a selected square recess (130) in grid plate (96), resilient members (1680, 1682, 1684, 1686) are driven inwardly toward the center of guide cube (1600) via contact between interior surfaces of a selected square recess (130) and apexes (1680C, 1682C, 1684C, 1686C) of resilient members (1680, 1682, 1684, 1686). As such, it should be understood that the bias of resilient members (1680, 1682, 1684, 1686) toward the initial position of FIG. 49, will exert pressure upon respective interior surfaces (144) of a selected recess (130) to thereby provide for retention of guide cube (1600) within a selected square recess (130) of grid plate (96). It should also be understood that resilient members (1680, 1682, 1684, 1686) will exert pressure upon the respective interior surfaces (144) of selected square recess (130) of grid plate (96) regardless of the orientation of guide cube (1600) and/or the guide hole (1620, 1622, 1624) into which cannula (1300) is inserted.

Figure 50:
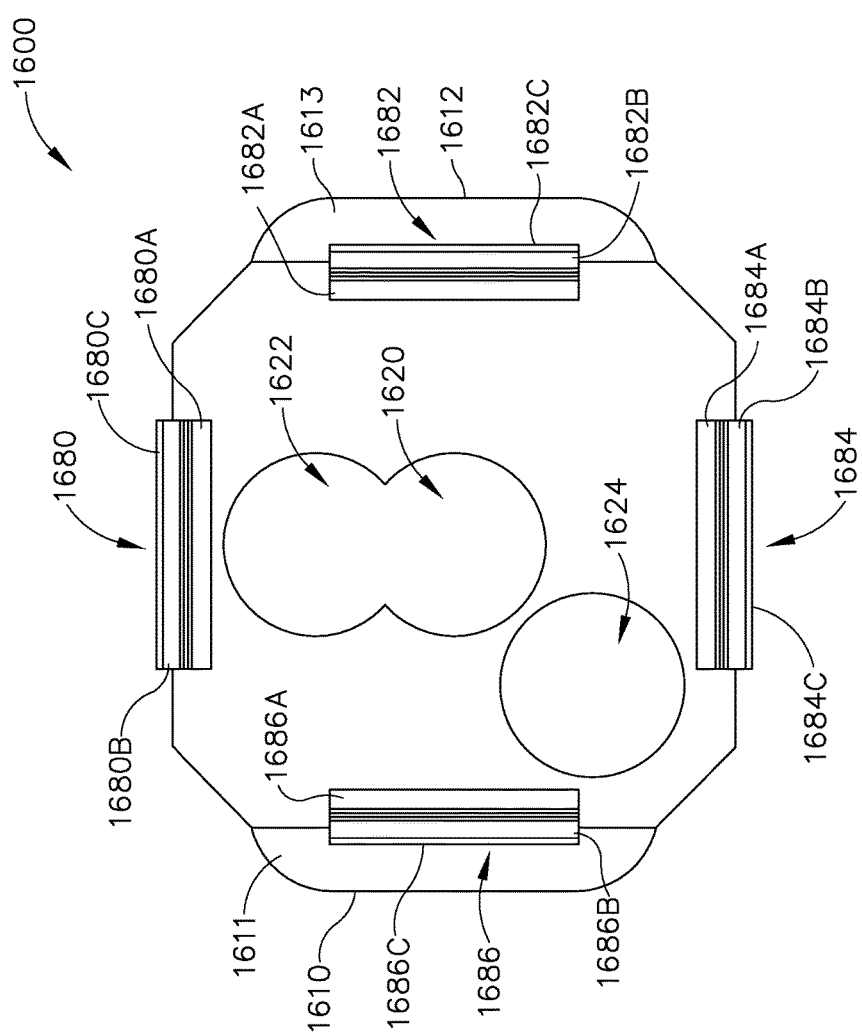
FIG. 50 depicts a back elevational view of the guide cube of FIG. 46.
Figure 51:
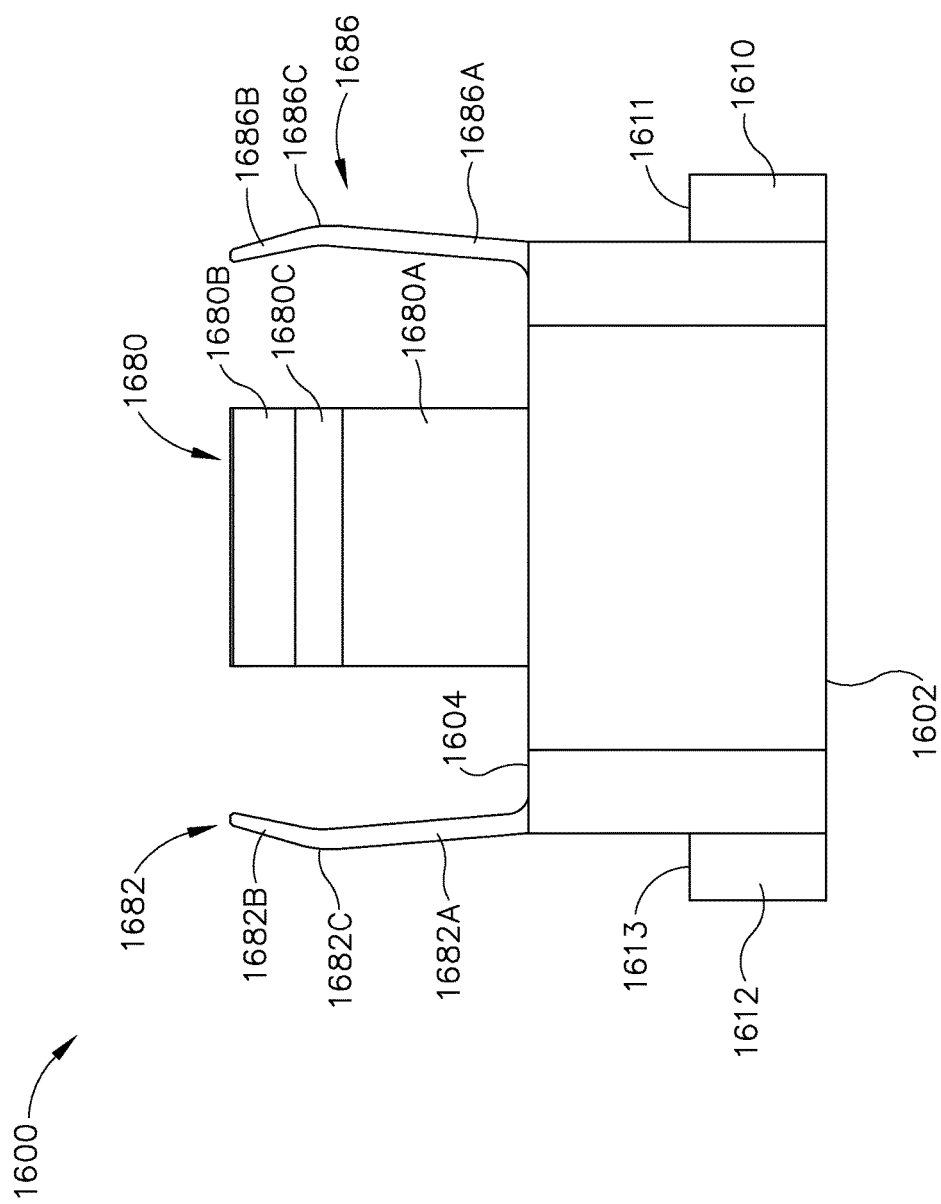
FIG. 51 depicts a top view of the guide cube of FIG. 46.

As discussed above, guide cube (1600) is sized for insertion from a proximal side into a selected square recess (130) in grid plate (96). Guide cube (1600) comprises a pair of projections (1610, 1612) extending from opposite sides of guide cube (1600) adjacent to first side surface (1602). Projections (1610, 1612) are configured to prevent the insertion of guide cube (1600) too deeply within the selected recess (130) of grid plate (96). As best seen in FIG. 50, projections (1610, 1612) each define a distal surface (1611, 1613). With guide cube (1600) oriented such that distal surfaces (1611, 1613) are parallel with the front surface of grid plate (96), distal surfaces (1611, 1613) are configured to contact the front surface of grid plate (96) upon guide cube (1600) being inserted into a square recess (130) to thereby prevent guide cube (1600) from passing into square recess (130) beyond distal surfaces (1611, 1613).

Guide cube (1600) may be further prevented from passing through grid plate (96) by backing substrate (136) attached to the front face of grid plate (96). Backing substrate (136) includes respective square opening (138) centered within each square recess (130), forming lip (140) sufficient to contact a distal tip of each resilient member (1680, 1682, 1684, 1686) so as to prevent guide cube (1600) from passing further into grid plate (96) but not so large as to obstruct guide holes (1620, 1622, 1624). The depth of square recesses (130) is less than guide cube (1600), thereby exposing a proximal portion of guide cube (1600) for seizing and extraction from grid plate (96).

Figure 52:
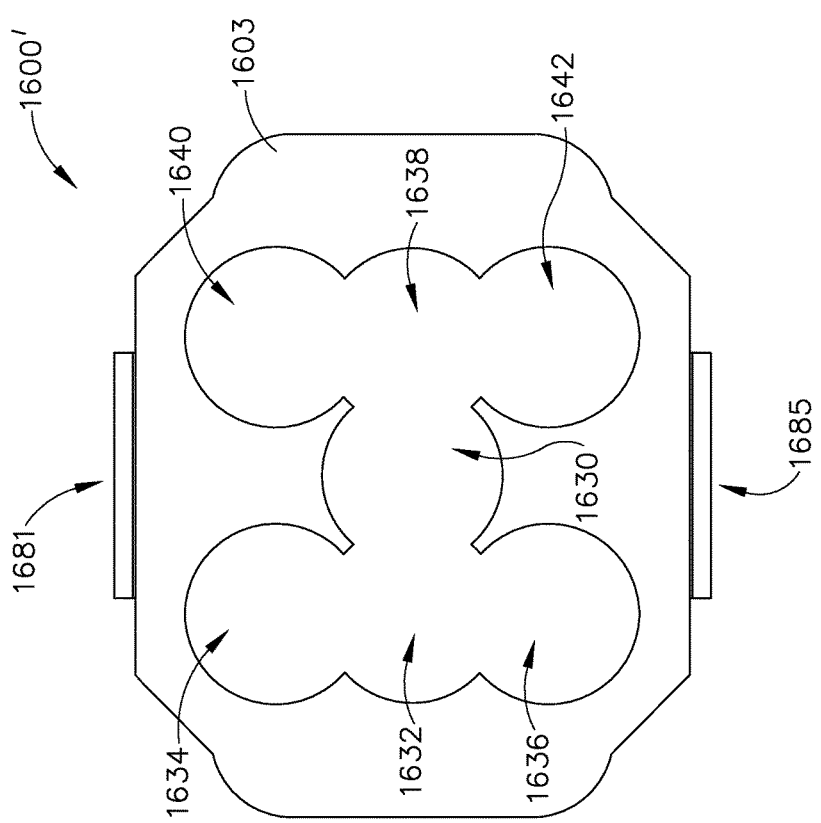
FIG. 52 depicts a front view of yet another exemplary alternative guide cube suitable for use with the biopsy system of FIG. 1.

FIG. 52 shows an exemplary variation of guide cube (1600), guide cube (1600'), having a merely exemplary variation of the orientation of the guide holes of guide cube (1600). Unless otherwise noted below, all features of guide cube (1600') are substantially similar to guide cube (1600). For instance, guide cube (1600') is shown as having resilient members (1681, 1685) which are substantially similar to resilient members (1680, 1684). Additionally, other features of guide cube (1600), although not shown in FIG. 52, may be incorporated into guide cube (1600') and may be substantially similar to those corresponding features in guide cube (1600).

Guide cube (1600') of the present example comprises a central guide hole (1630) that passes through guide cube (1600') from first surface (1603) to second surface (1605). Like with second surface (1604) of guide cube (1600), second surface (1605) of guide cube (1600') is on the opposite side of first surface (1603). Guide cube (1600') further comprises a plurality of offset guide holes (1632, 1634, 1636, 1638, 1640, 1642) that also pass through guide cube (1600') from first surface (1603) to second surface (1605). Guide holes (1630, 1632, 1634, 1636, 1638, 1640, 1642) are arranged in an H-shape as shown in FIG. 52. In the present example, guide hole (1630) and guide hole (1632) overlap one another on a first side of guide hole (1630), while guide hole (1630) and guide hole (1638) overlap one another on a second side of guide hole (1630) in a manner such that guide holes (1630, 1632, 1638) are arranged horizontally relative to one another. Guide hole (1632) and guide hole (1634) overlap one another on a first side of guide hole (1632), while guide hole (1632) and guide hole (1636) overlap one another on a second side of guide hole (1632) in a manner such that guide holes (1632, 1634, 1636) are arranged vertically relative to one another. Guide hole (1638) and guide hole (1640) overlap one another on a first side of guide hole (1638), while guide hole (1638) and guide hole (1642) overlap one another on a second side of guide hole (1638) such that guide holes (1638, 1640, 1642) are arranged vertically relative to one another. Guide holes (1632, 1634, 1636, 1638, 1640, 1642) are configured to receive any of the cannulas described herein and provide structural support to the inserted cannula. Referring to cannula (1300) as just one merely illustrative example, upon insertion of cannula (1300) into guide holes (1632, 1634, 1636, 1638, 1640, 1642), first side surface (1603) engages lock nut (1320) of cannula (1300) such that cannula (1300) cannot be inserted beyond a position where first side surface (1603) engage lock nut (1320). As discussed above, lock nut (1320) prevents cannula (1300) from moving further into a patient's breast by abutting first side surface (1603) of guide cube (1600').

Figure 53:
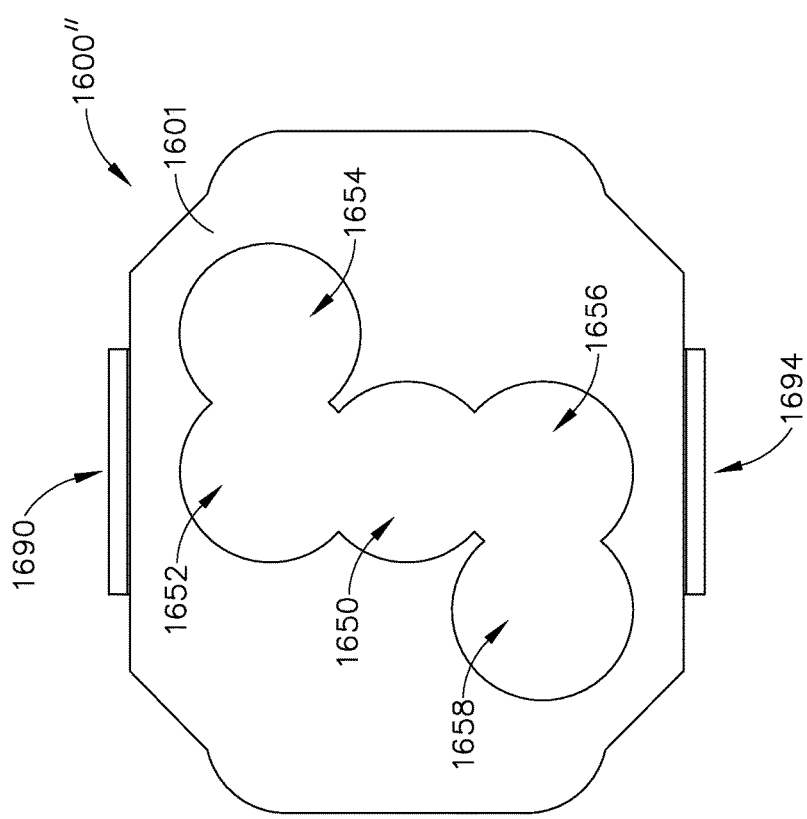
FIG. 53 depicts a front view of yet another exemplary alternative guide cube suitable for use with the biopsy system of FIG. 1.
Figure 54:
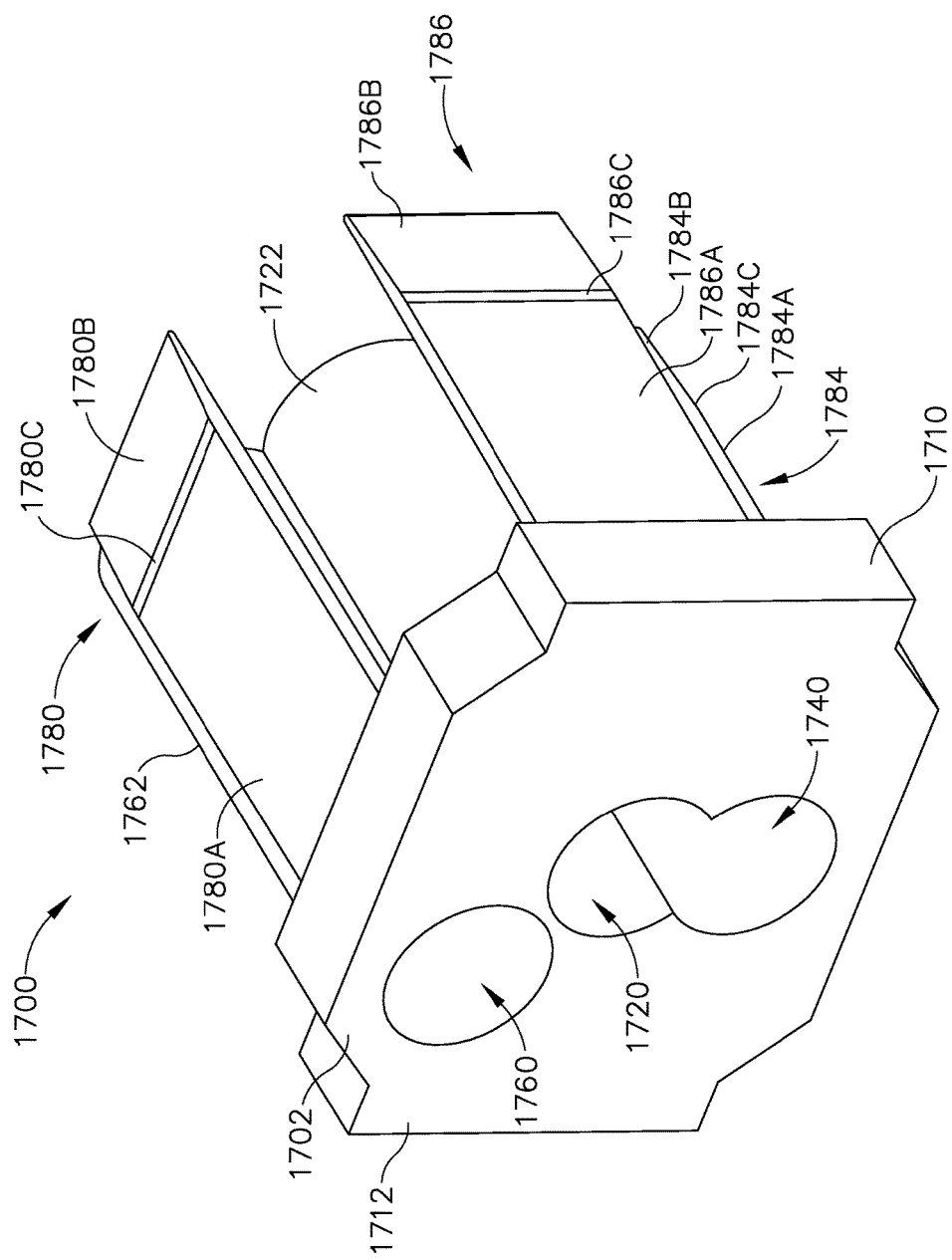
FIG. 54 depicts a perspective view of yet another exemplary alternative guide cube suitable for use with the biopsy system of FIG. 1.

FIG. 53 shows another exemplary variation of guide cube (1600), guide cube (1600") having another merely exemplary variation of the orientation of the guide holes of guide cube (1600). Unless otherwise noted below, all features of guide cube (1600") are substantially similar to guide cube (1600). For instance, guide cube (1600") is shown as having resilient member (1690, 1694) which are substantially similar to resilient members (1680, 1684). Additionally, other features of guide cube (1600), although not shown in FIG. 53, may be incorporated into guide cube (1600") and may be substantially similar to those corresponding features in guide cube (1600).

Guide cube (1600") of the present example comprises a central guide hole (1650) that passes through guide cube (1600") from first surface (1601) to second surface (1607). Like with second surface (1604) of guide cube (1600), second surface (1607) of guide cube (1600") is on the opposite side of first surface (1601). Guide cube (1600") further comprises a plurality of offset guide holes (1652, 1654, 1656, 1658) that also pass through guide cube (1600") from first surface (1601) to second surface (1607). Guide holes (1650, 1652, 1654, 1656, 1658) are arranged in an S-like-shape as shown in FIG. 53. In the present example, guide hole (1650) and guide hole (1652) overlap one another on a first side of guide hole (1650), while guide hole (1650) and guide hole (1656) overlap one another on a second side of guide hole (1650) in a manner such that guide holes (1650, 1652, 1656) are arranged vertically relative to one another. Guide hole (1652) and guide hole (1654) overlap one another in a manner such that guide holes (1652, 1654) are arranged horizontally relative to one another. Guide hole (1656) and guide hole (1658) overlap one another in a manner such that guide holes (1656, 1658) are arranged horizontally relative to one another. Guide holes (1650, 1652, 1654, 1656, 1658) are configured to receive any of the cannulas described herein and provide structural support to the inserted cannula. Referring to cannula (1300) as just one merely illustrative example, upon insertion of cannula (1300) into guide holes (1650, 1652, 1654, 1656, 1658), first side surface (1601) engages lock nut (1320) of cannula (1300) such that cannula (1300) cannot be inserted beyond a position where first side surface (1602) engages lock nut (1320). As discussed above, lock nut (1320) prevents cannula (1300) from moving further into a patient's breast by abutting first side surface (1601) of guide cube (1600").

Figure 55:
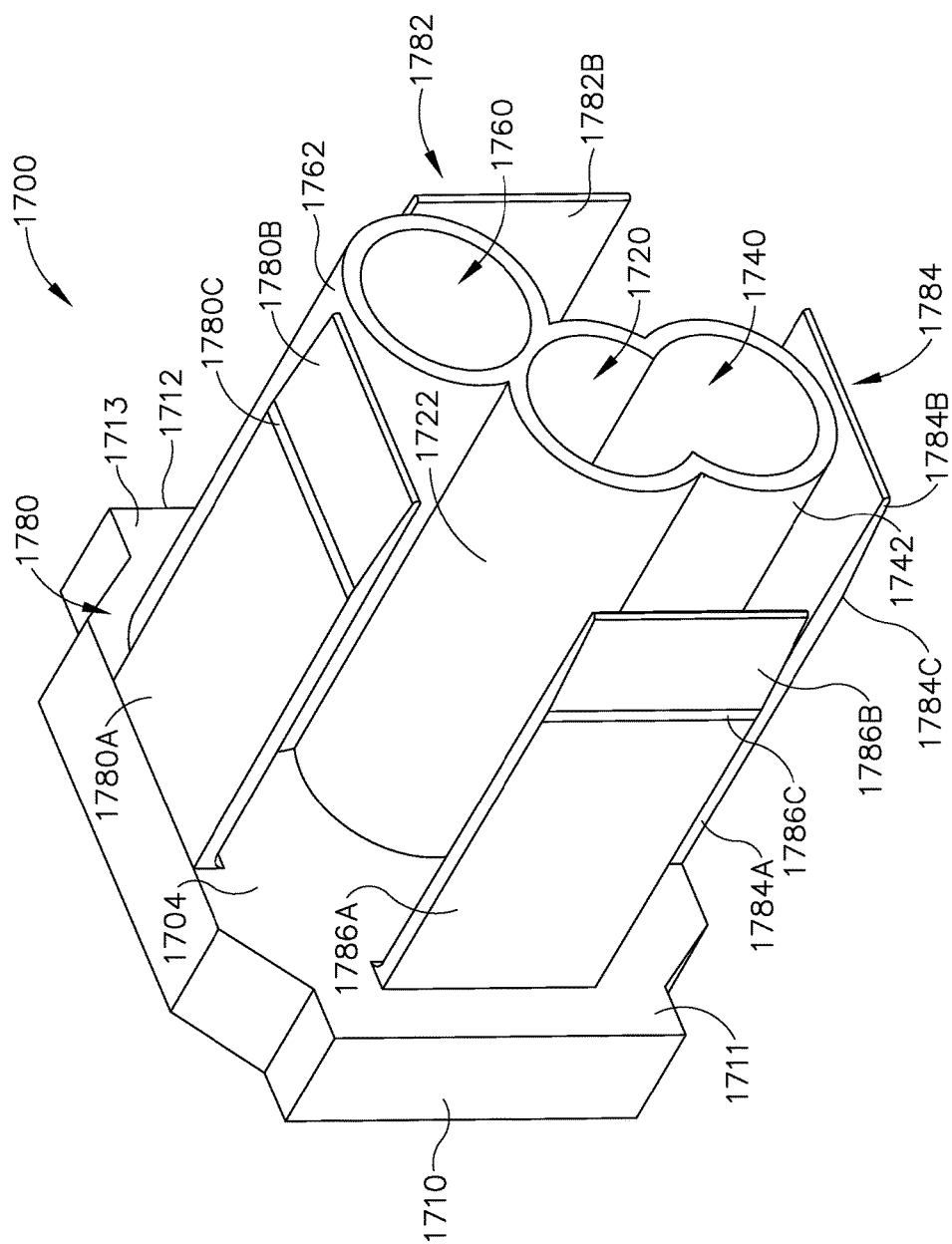
FIG. 55 depicts another perspective view of the guide cube of FIG. 54.
Figure 56:
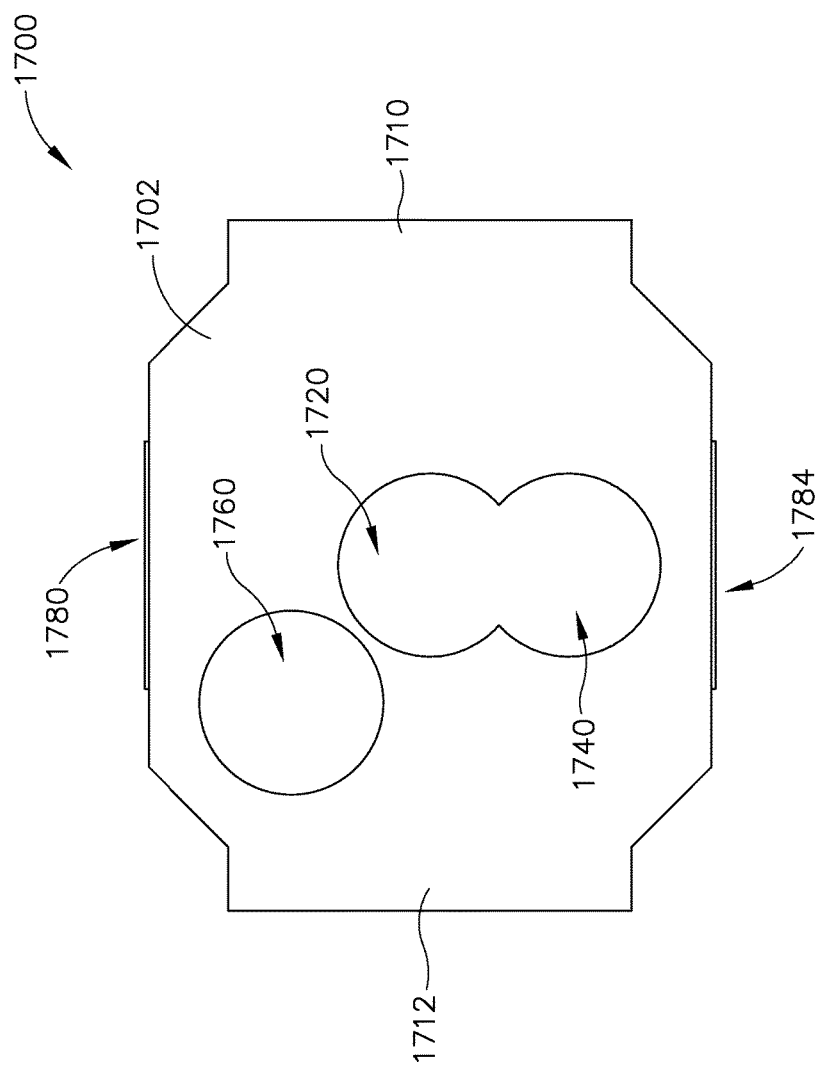
FIG. 56 depicts a front elevational view of the guide cube of FIG. 54.

FIGS. 54-59 show another merely exemplary variation of a guide cube (1700). Guide cube (1700) comprises a central guide hole (1720) that passes through guide cube (1700) from a first surface (1702) to a second surface (1704). Guide cube (1700) further comprises a pair of offset guide holes (1740, 1760) that also pass through guide cube (1700) from first surface (1702) to second surface (1704). As best seen in FIG. 55, guide cube (1700) comprises a plurality of tubular projections (1722, 1742, 1762) extending distally from second surface (1704). Tubular projections (1722, 1742, 1762) are circular or semi-circular in profile, and define a circular or semi-circular hollow interior corresponding to a respective guide hole (1720, 1740, 1760) such that guide holes (1720, 1740, 1760) extend through tubular projections (1722, 1742, 1762). In the present example guide hole (1720) and guide hole (1740) overlap one another in a manner such that guide holes (1720, 1740) are arranged vertically relative to one another. Guide holes (1720, 1740, 1760) are configured to receive any of the cannulas described herein and provide structural support to the inserted cannula. Referring to cannula (1300) as just one merely illustrative example, upon insertion of cannula (1300) into guide holes (1720, 1740, 1760), first side surface (1702) engages lock nut (1320) of cannula (1300) such that cannula (1300) cannot be inserted beyond a position where first side surface (1702) engages lock nut (1320). As discussed above, lock nut (1320) prevents cannula (1300) from moving further into a patient's breast by abutting first side surface (1702) of guide cube (1700).

Figure 57:
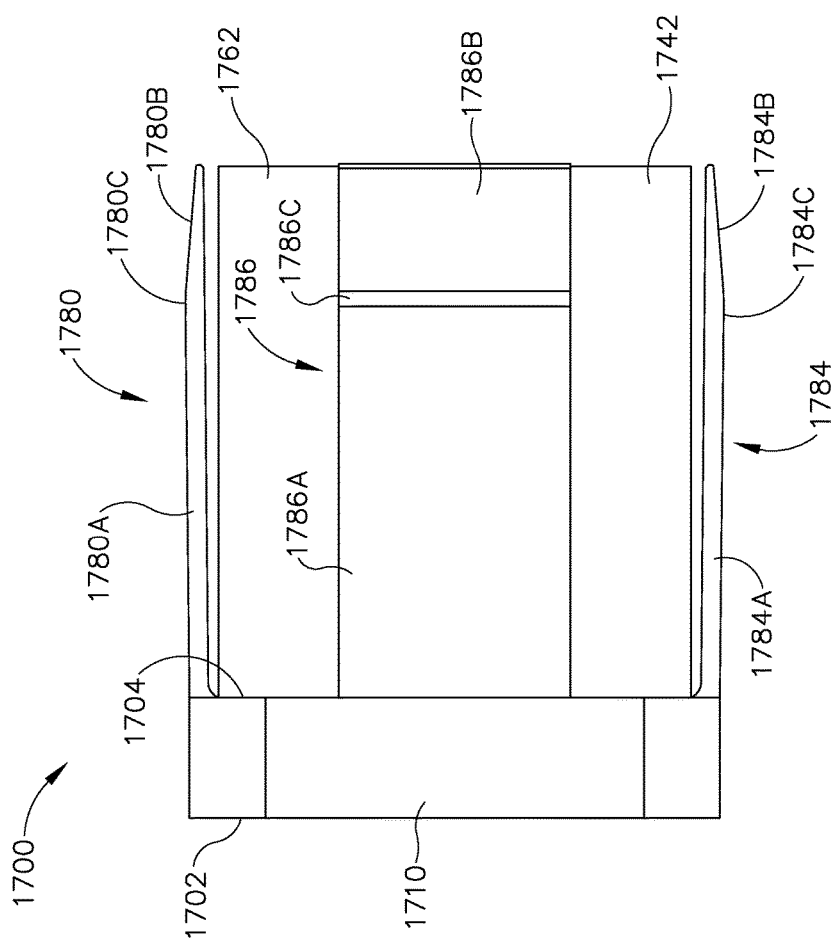
FIG. 57 depicts a side elevational view of the guide cube of FIG. 54.
Figure 58:
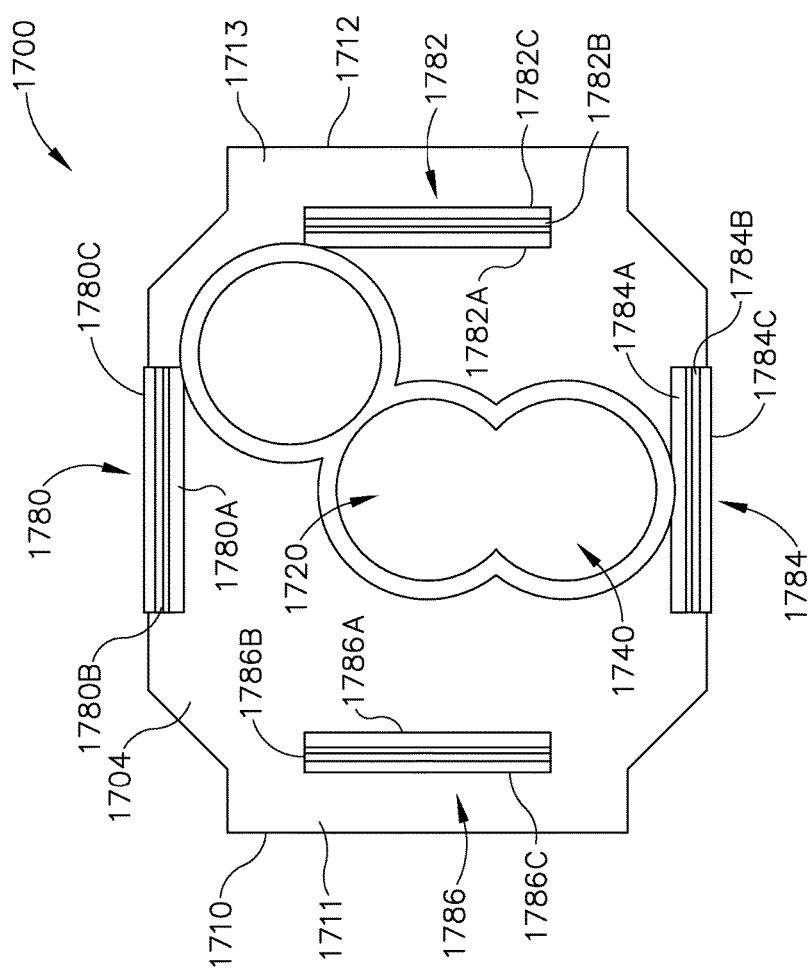
FIG. 58 depicts a back elevational view of the guide cube of FIG. 54.
Figure 59:
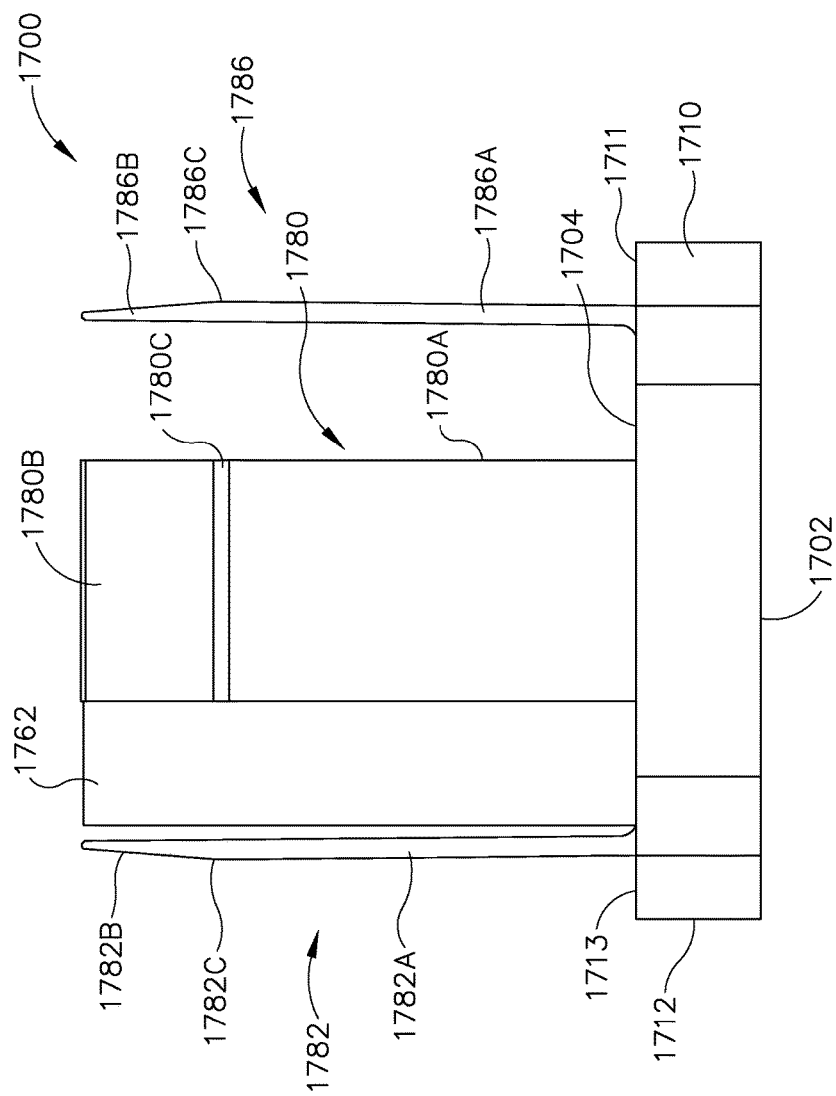
FIG. 59 depicts a top view of the guide cube of FIG. 54.

Guide cube (1700) is sized for insertion from a proximal side into a selected square recess (130) in grid plate (96). Guide cube (1700) comprises a plurality of resilient members (1780, 1782, 1784, 1786) extending distally from second side surface (1704). As best seen in FIG. 57, resilient members (1780, 1782, 1784, 1786) each comprise a first portion (1780A, 1782A, 1784A, 1786A) extending distally and outwardly from second side surface (1704), and at an oblique angle away from a center of guide cube (1700). Resilient members (1780, 1782, 1784, 1786) each further comprise a second portion (1780B, 1782B, 1784B, 1786B) that is tapered and extending distally and inwardly from first portions (1780A, 1782A, 1784A, 1786A) respectively, at an oblique angle toward the center of guide cube (1700). An apex (1780C, 1782C, 1784C, 1786C) is formed between respective first portions (1780A, 1782A, 1784A, 1786A) and second portions (1780B, 1782B, 1784B, 1786B) of each resilient member (1780, 1782, 1784, 1786). As will be discussed in more detail below, resilient members (1780, 1782, 1784, 1786) are flexible to provide for insertion of guide cube (1700) into square recesses of varying sizes. Resilient members (1780, 1782, 1784, 1786) are biased toward an initial position as shown in FIG. 57. As guide cube (1700) is inserted into a selected square recess (130) in grid plate (96), resilient members (1780, 1782, 1784, 1786) are driven inwardly toward the center of guide cube (1700) via contact between interior surfaces of a selected square recess (130) and apexes (1780C, 1782C, 1784C, 1786C) of resilient members (1780, 1782, 1784, 1786). As such, it should be understood that the bias of resilient members (1780, 1782, 1784, 1786) toward the initial position of FIG. 57, will exert pressure upon respective interior surfaces of a selected recess (130) to thereby provide for retention of guide cube (1700) within a selected square recess (130) of grid plate (96). It should also be understood that resilient members (1780, 1782, 1784, 1786) will exert pressure upon the respective interior surfaces (144) of selected square recess (130) of grid plate (96) regardless of the orientation of guide cube (1700) and/or the guide hole (1720, 1740, 1760) into which cannula (1300) is inserted.

As discussed above, guide cube (1700) is sized for insertion from a proximal side into a selected square recess (130) in grid plate (96). Guide cube (1700) comprises a pair of projections (1710, 1712) extending from opposite sides of guide cube (1700) adjacent to first side surface (1702). Projections (1710, 1712) are configured to prevent the insertion of guide cube (1700) too deeply within a selected recess (130) of grid plate (96). As best seen in FIG. 55, projections (1710, 1712) each define a distal surface (1711, 1713). With guide cube (1700) oriented such that distal surfaces (1711, 1713) are parallel with the front surface of grid plate (96), distal surfaces (1711, 1713) are configured to contact the front surface of grid plate (96) upon guide cube (1700) being inserted into a square recess (130) to thereby prevent guide cube (1700) from passing into square recess (130) beyond distal surfaces (1711, 1713).

Guide cube (1700) may be further prevented from passing through grid plate (96) by backing substrate (136) attached to the front face of grid plate (96). Backing substrate (136) includes respective square opening (138) centered within each square recess (130), forming lip (140) sufficient to contact a distal tip of each resilient member (1780, 1782, 1784, 1786) so as to prevent guide cube (1700) from passing further into grid plate (96) but not so large as to obstruct guide holes (1720, 1740, 1760). The depth of square recesses (130) is less than guide cube (1700), thereby exposing a proximal portion of guide cube (1700) for seizing and extraction from grid plate (96).

Figure 60:
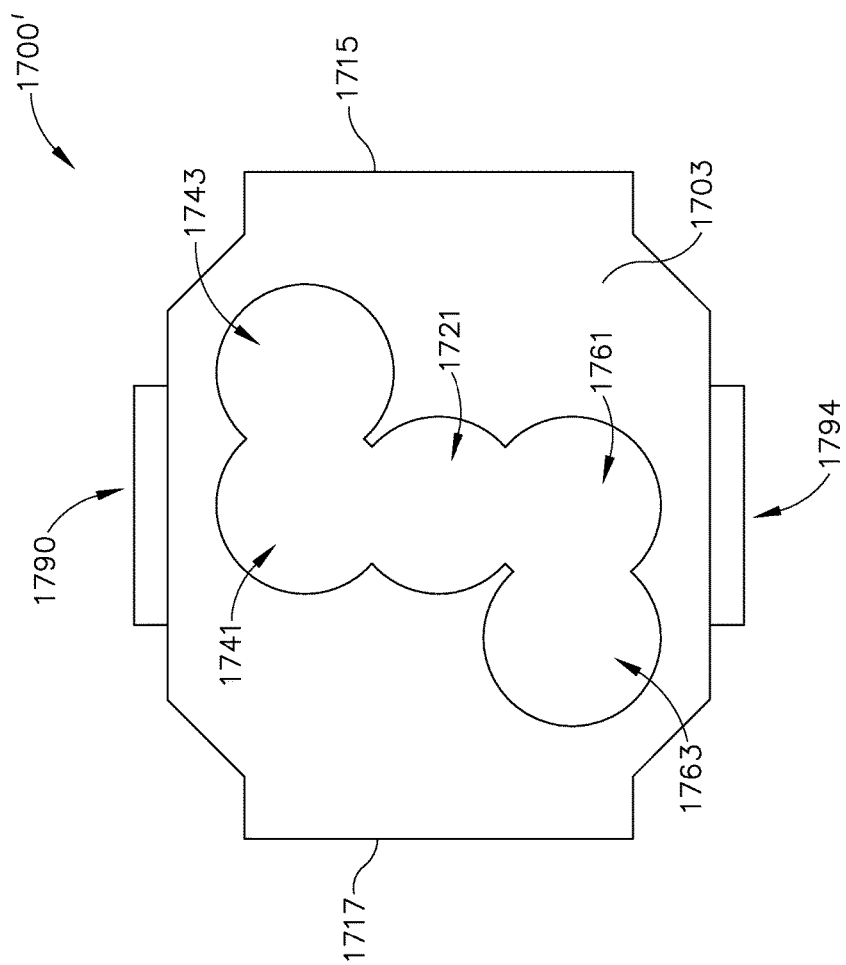
FIG. 60 depicts a front view of yet another exemplary alternative guide cube suitable for use with the biopsy system of FIG. 1.
Figure 61:
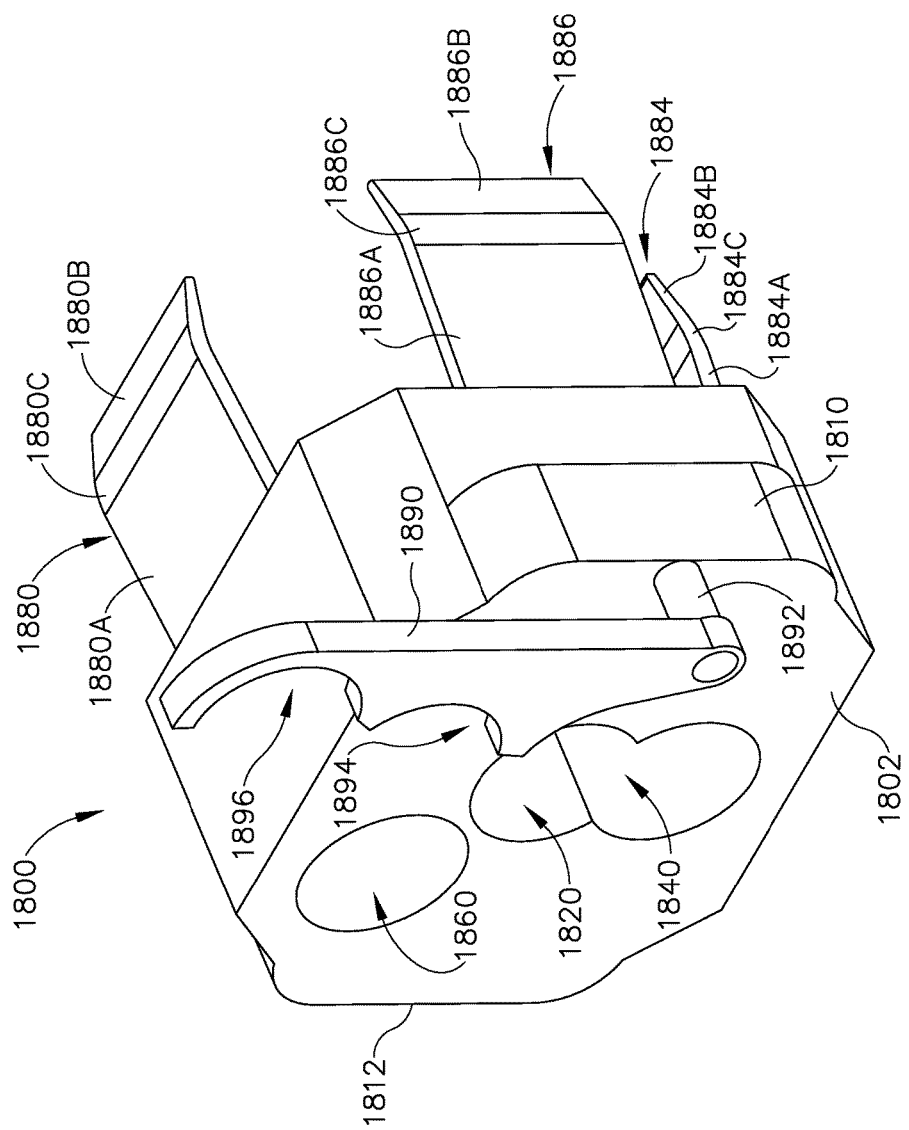
FIG. 61 depicts a perspective view of yet another exemplary alternative guide cube suitable for use with the biopsy system of FIG. 1.

FIG. 60 shows an exemplary variation of guide cube (1700), guide cube (1700'), having a merely exemplary variation of the orientation of the guide holes of guide cube (1700). Unless otherwise noted below, all features of guide cube (1700') are substantially similar to guide cube (1700). For instance, guide cube (1700') is shown as having resilient members (1790, 1794) which are substantially similar to resilient members (1780, 1784). Similarly, guide cube (1700') is shown as having projections (1715, 1717) which are substantially similar to projections (1710, 1712) of guide cube (1700). Additionally, other features of guide cube (1600), although not shown in FIG. 53, may be incorporated into guide cube (1600") and may be substantially similar to those corresponding features in guide cube (1600).

Guide cube (1700') of the present example comprises a central guide hole (1721) that passes through guide cube (1700') from first surface (1703) to second surface (not shown). Guide cube (1700') further comprises a plurality of offset guide holes (1741, 1743, 1761, 1763) that also pass through guide cube (1700') from first surface (1703) to second surface (not shown). Guide holes (1721, 1741, 1743, 1761, 1763) are arranged in an S-like shape as shown in FIG. 60. In the present example, guide hole (1721) and guide hole (1741) overlap one another on a first side of guide hole (1721), while guide hole (1721) and guide hole (1761) overlap one another on a second side of guide hole (1721) in a manner such that guide holes (1721, 1743, 1761) are arranged vertically relative to one another. Guide hole (1741) and guide hole (1743) overlap one another in a manner such that guide holes (1741, 1743) are arranged horizontally relative to one another. Guide hole (1761) and guide hole (1763) overlap one another in a manner such that guide holes (1761, 1763) are arranged horizontally relative to one another. Guide holes (1721, 1741, 1743, 1761, 1763) are configured to receive any of the cannulas described herein and provide structural support to the inserted cannula. Referring to cannula (1300) as just one merely illustrative example, upon insertion of cannula (1300) into guide holes (1721, 1741, 1743, 1761, 1763), first side surface (1703) engages lock nut (1320) of cannula (1300) such that cannula (1300) cannot be inserted beyond a position where first side surface (1703) engages lock nut (1320). As discussed above, lock nut (1320) prevents cannula (1300) from moving further into a patient's breast by abutting first side surface (1703) of guide cube (1700').

FIGS. 61-68 show yet another merely exemplary variation of a guide cube (1800). Guide cube (1800) comprises a central guide hole (1820) that passes through guide cube (1800) from a first surface (1802) to a second surface (1804). Guide cube (1800) further comprises a pair of offset guide holes (1840, 1860) that also pass through guide cube (1800) from first surface (1802) to second surface (1804). In the present example guide hole (1820) and guide hole (1840) overlap one another in a manner such that guide holes (1820, 1840) are arranged vertically relative to one another. Guide holes (1820, 1840, 1860) are configured to receive any of the cannulas described herein and provide structural support to the inserted cannula. Referring to cannula (1300) as just one merely illustrative example, and as shown in FIGS. 67A-67C, upon insertion of cannula (1300) into guide holes (1820, 1840, 1860), first side surface (1802) engages lock nut (1320) of cannula (1300) such that cannula (1300) cannot be inserted beyond a position where first side surface (1802) engages lock nut (1320). As discussed above, lock nut (1320) prevents cannula (1300) from moving further into a patient's breast by abutting first side surface (1802) of guide cube (1800).

Guide cube (1800) is sized for insertion from a proximal side into a selected square recess (130) in grid plate (96). Guide cube (1800) comprises a plurality of resilient members (1880, 1882, 1884, 1886) extending distally from second side surface (1804). As best seen in FIG. 49, resilient members (1880, 1882, 1884, 1886) each comprise a first portion (1880A, 1882A, 1884A, 1886A) extending distally and outwardly from second side surface (1804), at an oblique angle away from a center of guide cube (1800). Resilient members (1880, 1882, 1884, 1886) each further comprise a second portion (1880B, 1882B, 1884B, 1886B) extending distally and inwardly from first portions (1880A, 1882A, 1884A, 1886A) respectively, at an oblique angle toward the center of guide cube (1800). An apex (1880C, 1882C, 1884C, 1886C) is formed between respective first portions (1880A, 1882A, 1884A, 1886A) and second portions (1880B, 1882B, 1884B, 1886B) of each resilient member (1880, 1882, 1884, 1886). As will be discussed in more detail below, resilient members (1880, 1882, 1884, 1886) are flexible to provide for insertion of guide cube (1800) into square recesses of varying sizes. Resilient members (1880, 1882, 1884, 1886) are biased toward an initial position as shown in FIG. 64. As guide cube (1800) is inserted into a selected square recess (130) in grid plate (96), resilient members (1880, 1882, 1884, 1886) are driven inwardly toward the center of guide cube (1800) via contact between interior surfaces of a selected square recess (130) and apexes (1880C, 1882C, 1884C, 1886C) of resilient members (1880, 1882, 1884, 1886). As such, it should be understood that the bias of resilient members (1880, 1882, 1884, 1886) toward the initial position of FIG. 64, will exert pressure upon respective interior surfaces of a selected recess (130) to thereby provide for retention of guide cube (1800) within a selected square recess (130) of grid plate (96). It should also be understood that resilient members (1880, 1882, 1884, 1886) will exert pressure upon the respective interior surfaces of selected square recess (130) of grid plate (96) regardless of the orientation of guide cube (1800) and/or the guide hole (1820, 1840, 1860) into which cannula (1300) is inserted.

Figure 65:
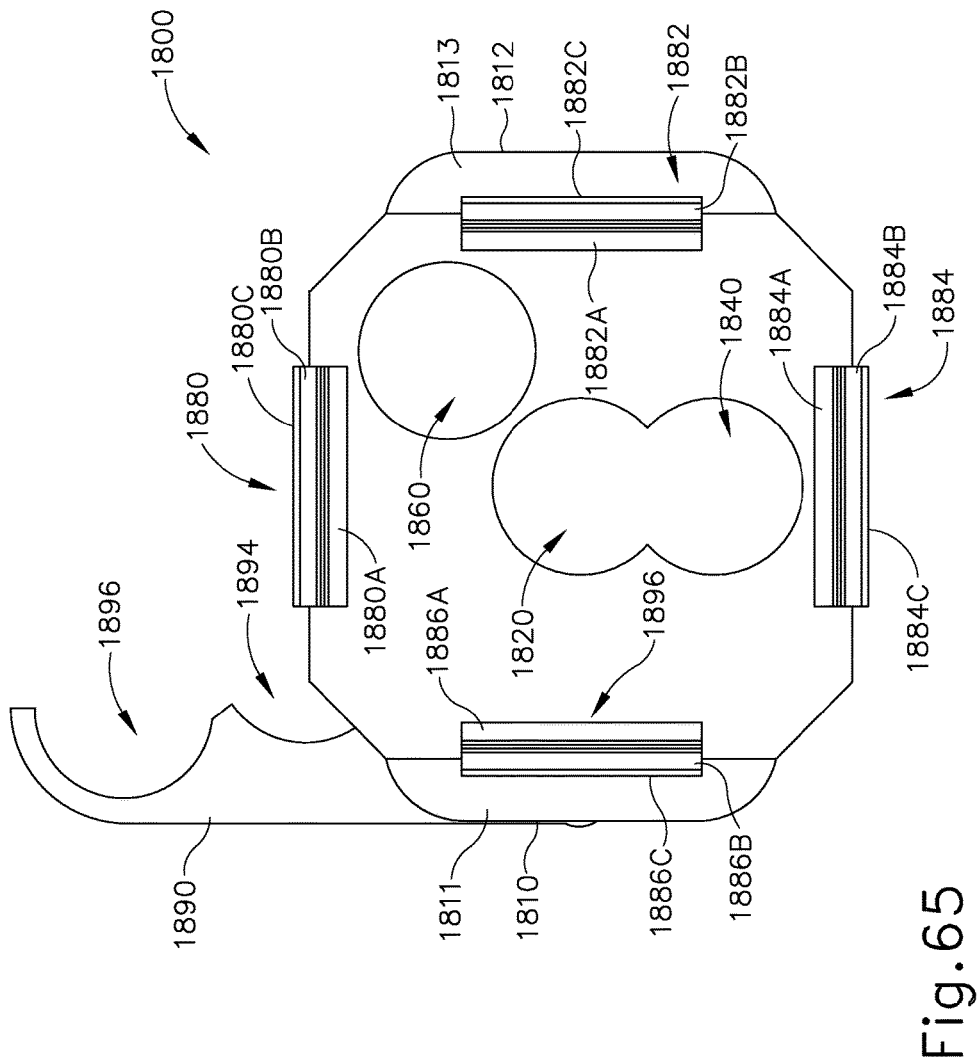
FIG. 65 depicts a back elevational view of the guide cube of FIG. 61.
Figure 66:
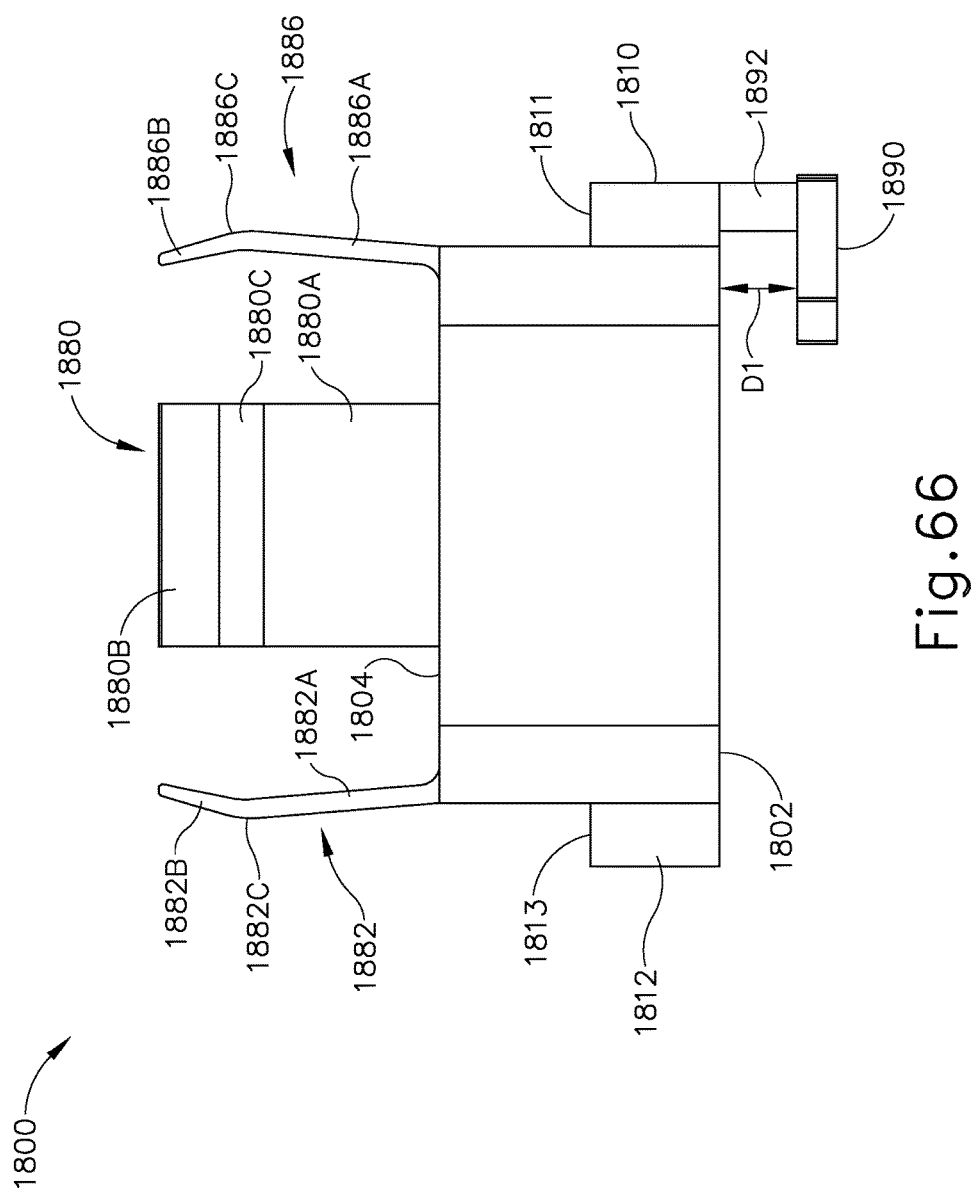
FIG. 66 depicts a top view of the guide cube of FIG. 61.

As discussed above, guide cube (1800) is sized for insertion from a proximal side into a selected square recess (130) in grid plate (96). Guide cube (1800) comprises a pair of projections (1810, 1812) extending from opposite sides of guide cube (1800) adjacent to first side surface (1802). Projections (1810, 1812) are configured to prevent the insertion of guide cube (1800) too deeply within a selected recess (130) of grid plate (96). As best seen in FIG. 65, projections (1810, 1812) each define a distal surface (1811, 1813). With guide cube (1800) oriented such that distal surfaces (1811, 1813) are parallel with the front surface of grid plate (96), distal surfaces (1811, 1813) are configured to contact the front surface of grid plate (96) upon guide cube (1800) being inserted into a square recess (130) to thereby prevent guide cube (1800) from passing into square recess (130) beyond distal surfaces (1811, 1813).

Guide cube (1800) may be further prevented from passing through grid plate (96) by backing substrate (136) attached to the front face of grid plate (96). Backing substrate (136) includes respective square opening (138) centered within each square recess (130), forming lip (140) sufficient to contact a distal tip of each resilient member (1880, 1882, 1884, 1886) so as to prevent guide cube (1800) from passing further into grid plate (96) but not so large as to obstruct guide holes (1820, 1840, 1860). The depth of square recesses (130) is less than guide cube (1800), thereby exposing a proximal portion of guide cube (1800) for seizing and extraction from grid plate (96).

Figure 63A:
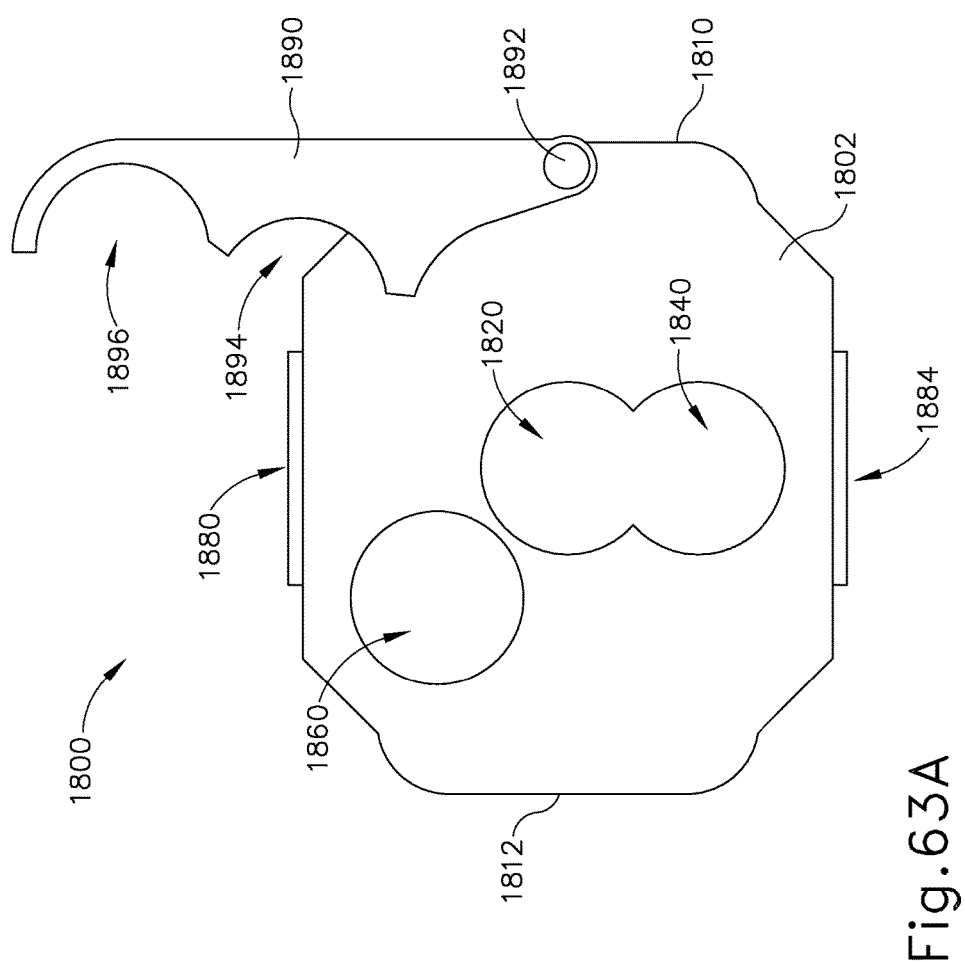
FIG. 63A depicts a front elevational view of the guide cube of FIG. 61 with a locking feature in a first rotational position.
Figure 63B:
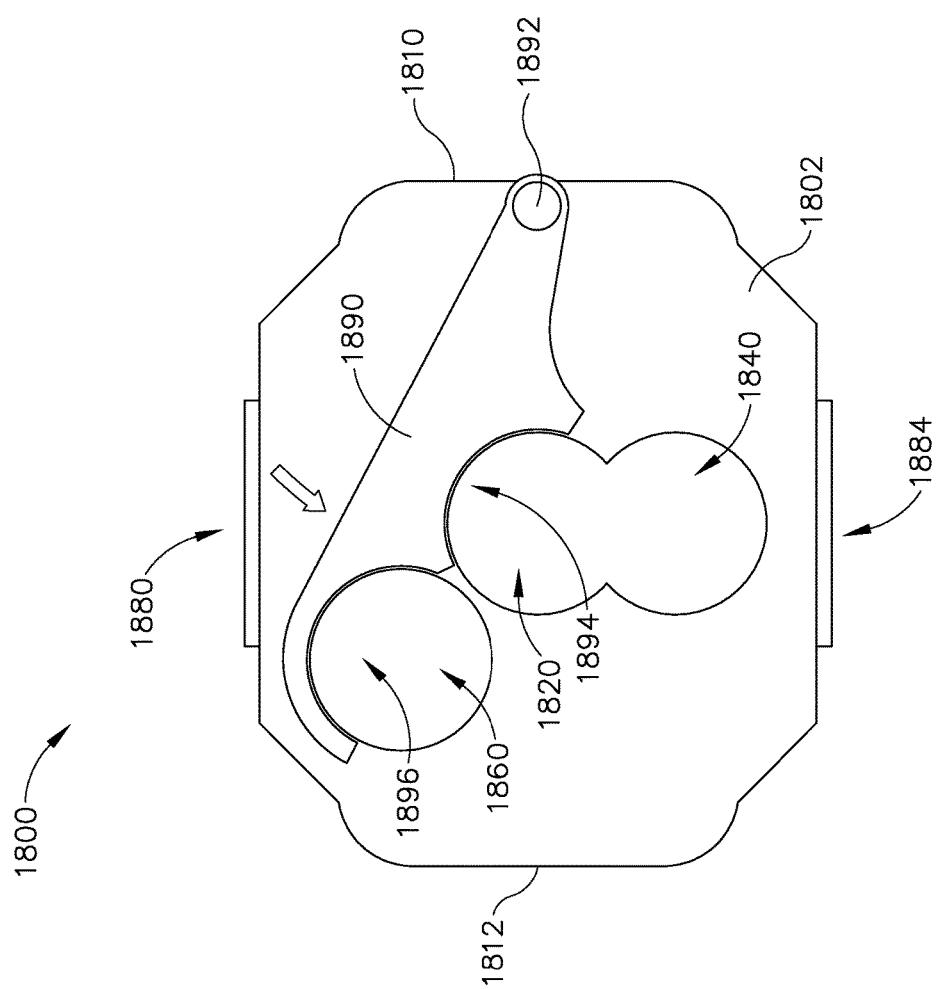
FIG. 63B depicts a front elevational view of the guide cube of FIG. 61 with the locking feature of FIG. 63A moved into a second rotational position.

Guide cube (1800) comprises a locking member (1890) rotatably coupled to guide cube (1800) via a pin (1892) extending from first surface (1802) such that locking member (1890) is operable to rotate about pin (1892) along a plane parallel with first surface (1802). As best seen in FIG. 64, locking member (1890) is secured to pin (1892) at a distance (D1) from first surface (1802) of guide cube (1800) such that distance (D1) exists between first surface (1802) of guide cube (1800) and the plane along which locking member (1890) rotates. As will be discussed in more detail below, distance (D1) is substantially similar to a thickness of lock nut (1320) of cannula (1300). Also as will be discussed in more detail below, and as shown in FIGS. 63A and 63B, locking member (1890) is operable to rotate between an unlocked position (FIG. 63A) and a locked position (FIG. 63B) to thereby selectively lock and/or unlock any of the cannulas described herein within guide cube (1800).

Figure 67B:
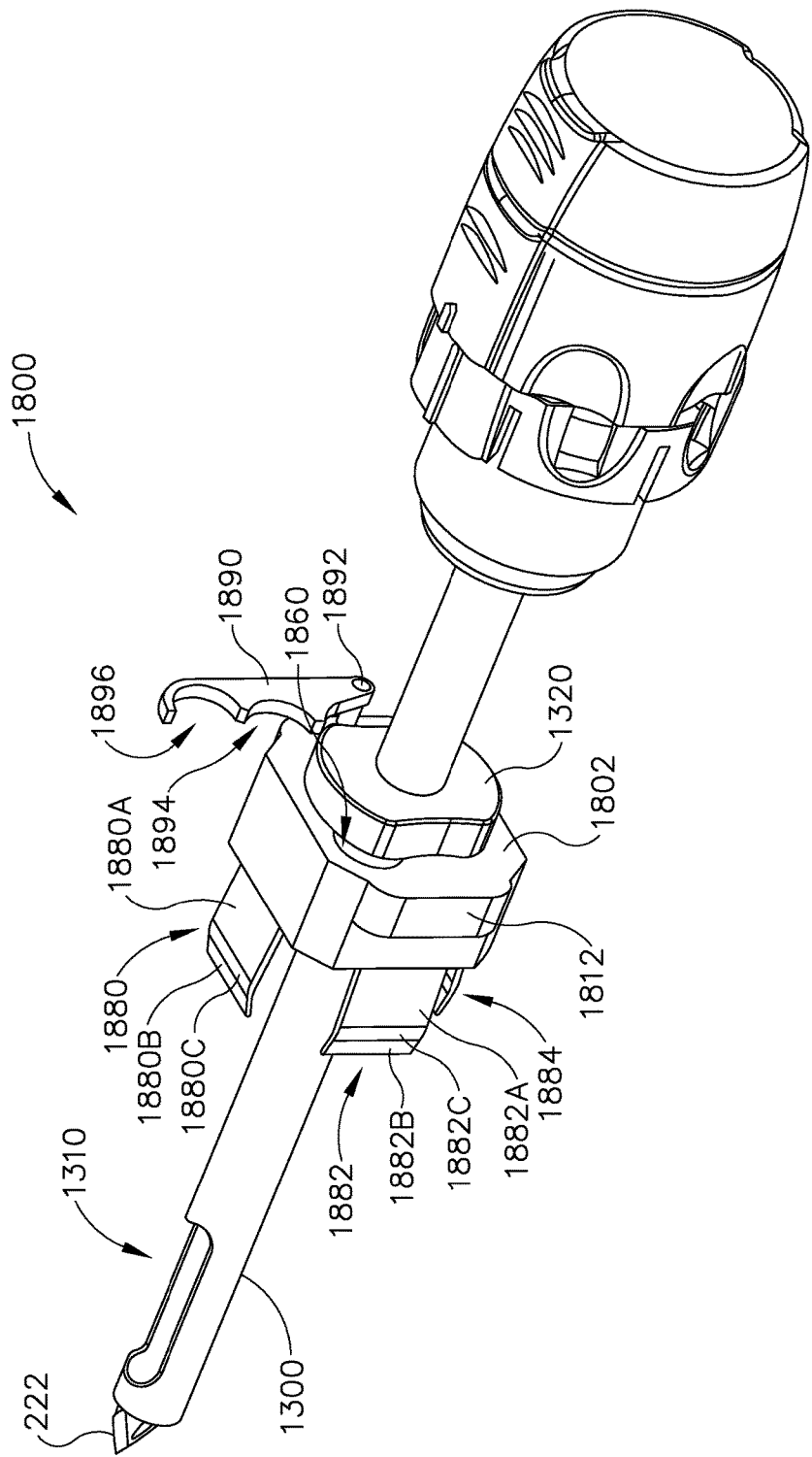
FIG. 67B depicts a perspective view of the guide cube of FIG. 61 with the locking feature of FIG. 63A remaining in the first rotational position of FIG. 63A, and with the cannula of FIG. 67A moved into a second longitudinal position.
Figure 67C:
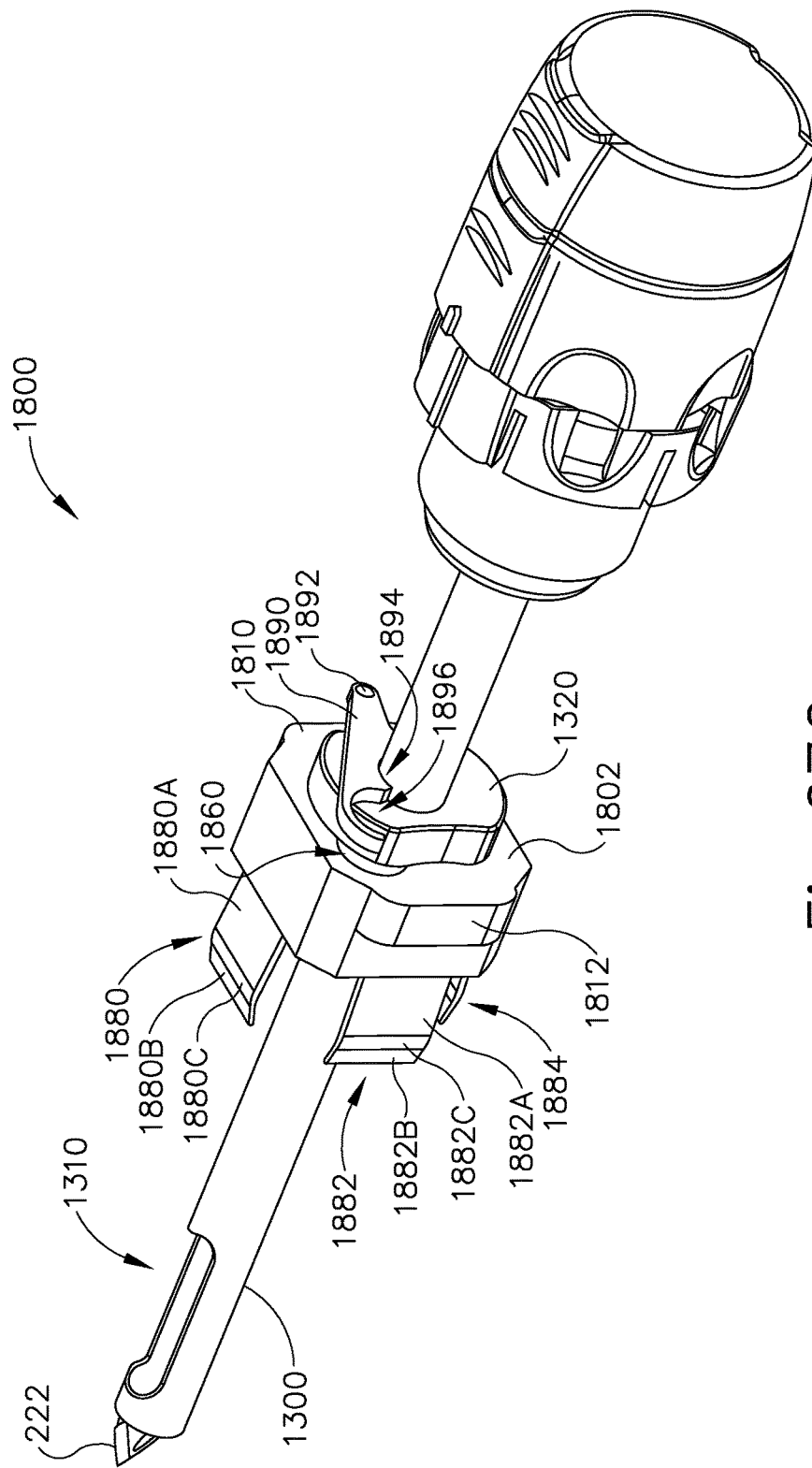
FIG. 67C depicts a perspective view of the guide cube of FIG. 61 with the locking feature of FIG. 63A moved into the second rotational position of FIG. 63B, and with the cannula of FIG. 67A remaining in the second longitudinal position.
Figure 68:
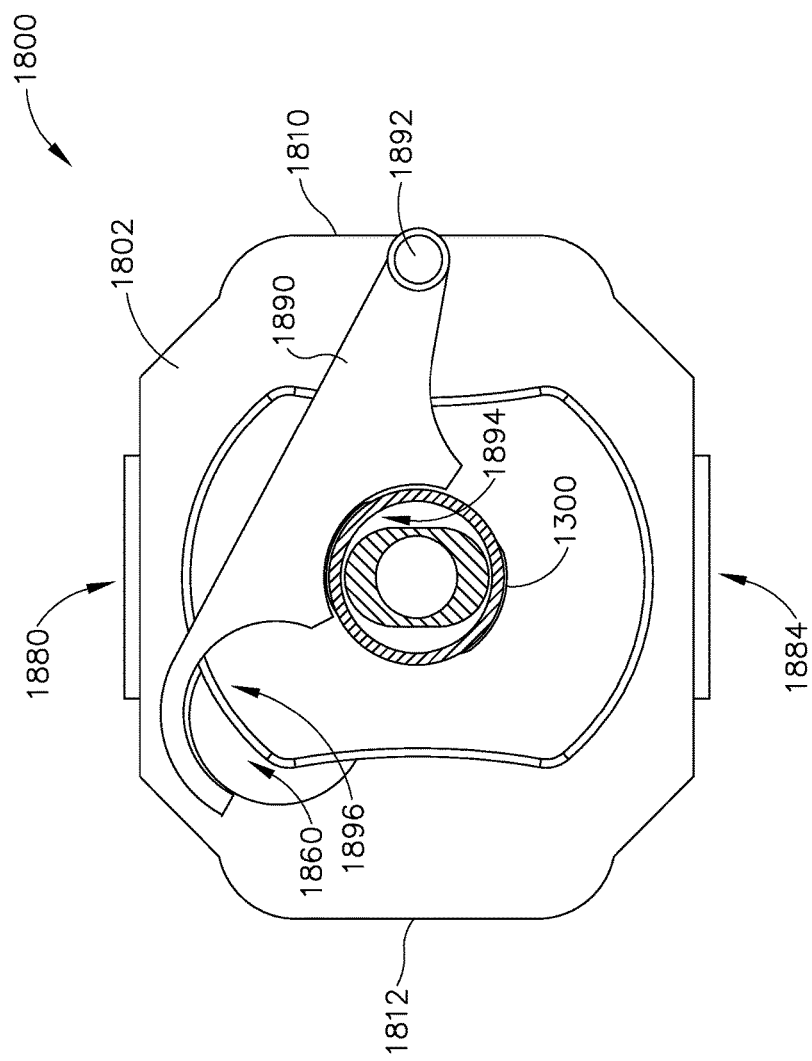
FIG. 68 depicts a cross-sectional view of the cannula of FIG. 67A in the second longitudinal position, and with the locking feature of FIG. 63A in the second rotational position of FIG. 63B.

Locking member (1890) comprises a pair of arcuate recesses (1894, 1896). As shown in FIG. 63B, when in the locked position, arcuate recesses (1894, 1896) are configured to lay adjacent to the circular profile of guide holes (1820, 1840) respectively. FIGS. 67A-68 show the steps of locking cannula (1300) within guide hole (1820) of guide cube (1800). FIG. 67A shows cannula (1300) in a first longitudinal position removed from guide cube (1800). With cannula (1300) in this position, locking member (1890) is in the unlocked position such that cannula (1300) may be received within guide hole (1820) of guide cube (1800). Cannula (1300) is then moved into a second longitudinal position such that cannula (1300) is passed into guide hole (1820) to a point where a distal surface of lock nut (1320) engages first surface (1802) of guide cube (1800) as shown in FIG. 67B. As cannula (1300) is moved into this position, locking member (1890) remains in the unlocked position such that cannula (1300) may be received within guide hole (1820) of guide cube (1800). Once cannula (1300) has been passed within guide hole (1820) to the point where the distal surface of lock nut (1320) engages first surface (1802) of guide cube (1800), locking member (1890) is rotated into the locked position as shown in FIGS. 67C and 68. In the locked position, locking member (1890) engages a proximal surface of lock nut (1320) such that cannula (1300) is locked within guide hole (1820) of guide cube (1800). In other words, guide cube (1800) cooperates with lock nut (1320) to restrict distal movement of cannula (1300) relative to guide cube (1800); while locking member (1890) cooperates with lock nut (1320) to restrict proximal movement of cannula (1300) relative to guide cube (1800).

FIGS. 69-79 show another merely exemplary variation of a guide cube (1900). Guide cube (1900) comprises a central guide hole (1920) that passes through guide cube (1900) from a first side surface (1902) to a second side surface (1904). Guide cube (1900) further comprises a pair of offset guide holes (1940, 1960) that passes through guide cube (1900) from a third side surface (1906) to a fourth side surface (1908). Guide holes (1920, 1940, 1960) are configured to receive any of the cannulas described herein and provide structural support to the inserted cannula. Referring to cannula (1300) as just one merely illustrative example, upon insertion of cannula (1300) into guide holes (1920, 1940, 1960), side surfaces (1902, 1906) engage lock nut (1320) of cannula (1300) such that cannula (1300) cannot be inserted beyond a position where side surfaces (1902, 1906) engage lock nut (1320). As discussed above, lock nut (1320) prevents cannula (1300) from moving further into a patient's breast by abutting side surfaces (1902, 1906) of guide cube (1900).

Figure 69:
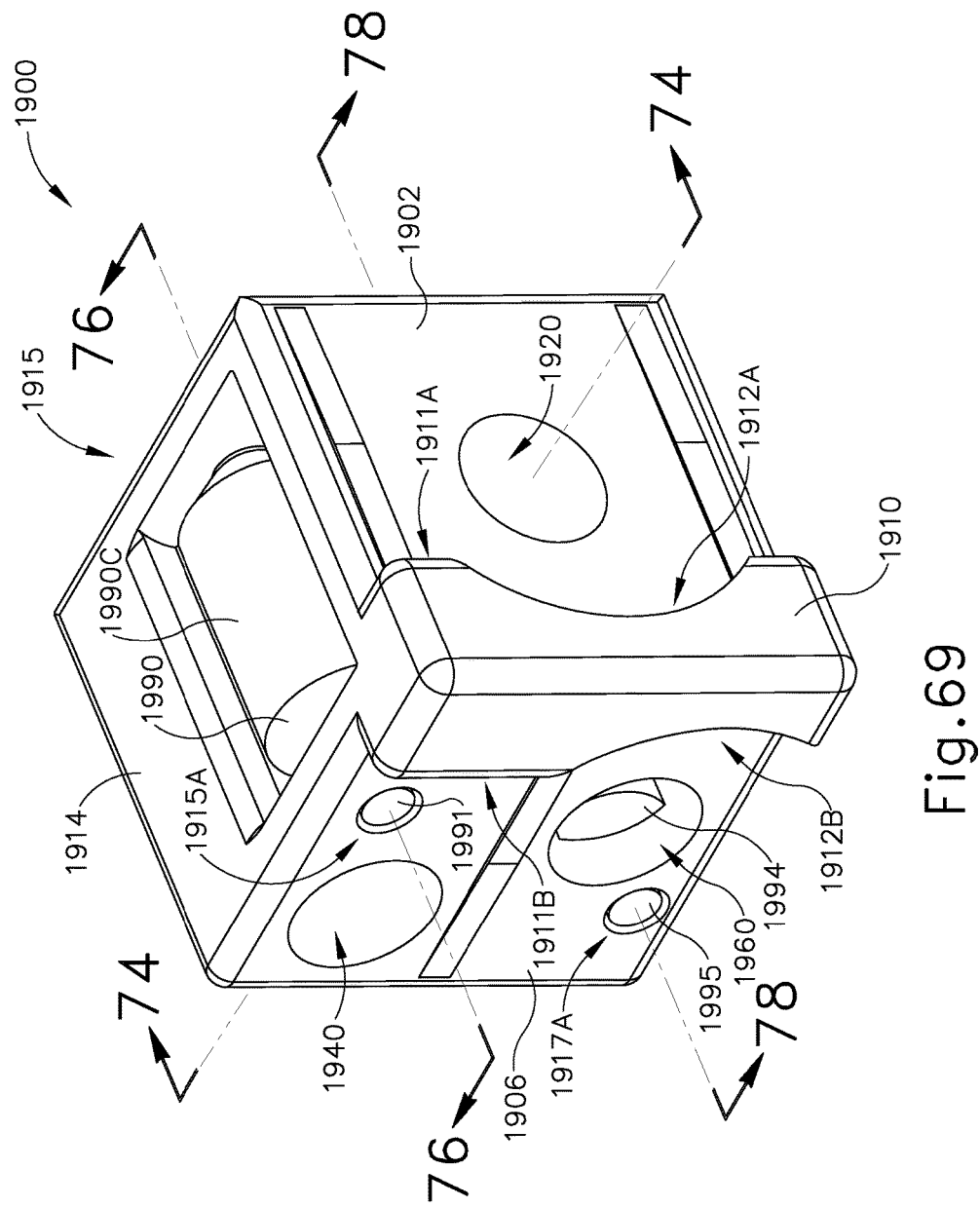
FIG. 69 depicts a perspective view of yet another exemplary alternative guide cube suitable for use with the biopsy system of FIG. 1.

Guide cube (1900) is sized for insertion from a proximal side into a selected square recess (130) in grid plate (96). As best seen in FIG. 69, guide cube (1900) comprises a projection (1910) extending from a corner of guide cube (1900) adjacent to first side surface (1902) and third side surface (1906). Projection (1910) defines a first face (1911A) extending perpendicularly from first side surface (1902) and a second face (1911B) extending perpendicularly from third side surface (1906). With guide cube (1900) oriented such that third side surface (1906) and fourth side surface (1908) are parallel with a front surface of grid plate (96), first face (1911A) is configured to contact the front surface of grid plate (96) upon being inserted into a square recess (130) to thereby prevent guide cube (1900) from passing into square recess (130) beyond first face (1911A). With guide cube (1900) oriented such that first side surface (1902) and second side surface (1904) are parallel with the front surface of grid plate (96), second face (1911B) is configured to contact the front surface of grid plate (96) upon being inserted into square recess (130) to thereby prevent guide cube (1900) from passing into square recess (130) beyond second face (1911B).

Guide cube (1900) may be further prevented from passing through grid plate (96) by backing substrate (136) attached to the front face of grid plate (96). Backing substrate (136) includes respective square opening (138) centered within each square recess (130), forming lip (140) sufficient to capture second side surface (1904) or fourth side surface (1908) of guide cube (1900) but not so large as to obstruct guide holes (1920, 1940, 1960). The depth of square recesses (130) is less than guide cube (1900), thereby exposing a proximal portion of guide cube (1900) for seizing and extraction from grid plate (96).

As shown in FIG. 69, first face (1911A) and second face (1911B) respectively define a first annular recess (1912A) and a second annular recess (1912B). Annular recesses (1912A, 1912B) are configured to accommodate lock nut (1320) as lock nut (1320) engages side surfaces (1902, 1906).

Figure 74:
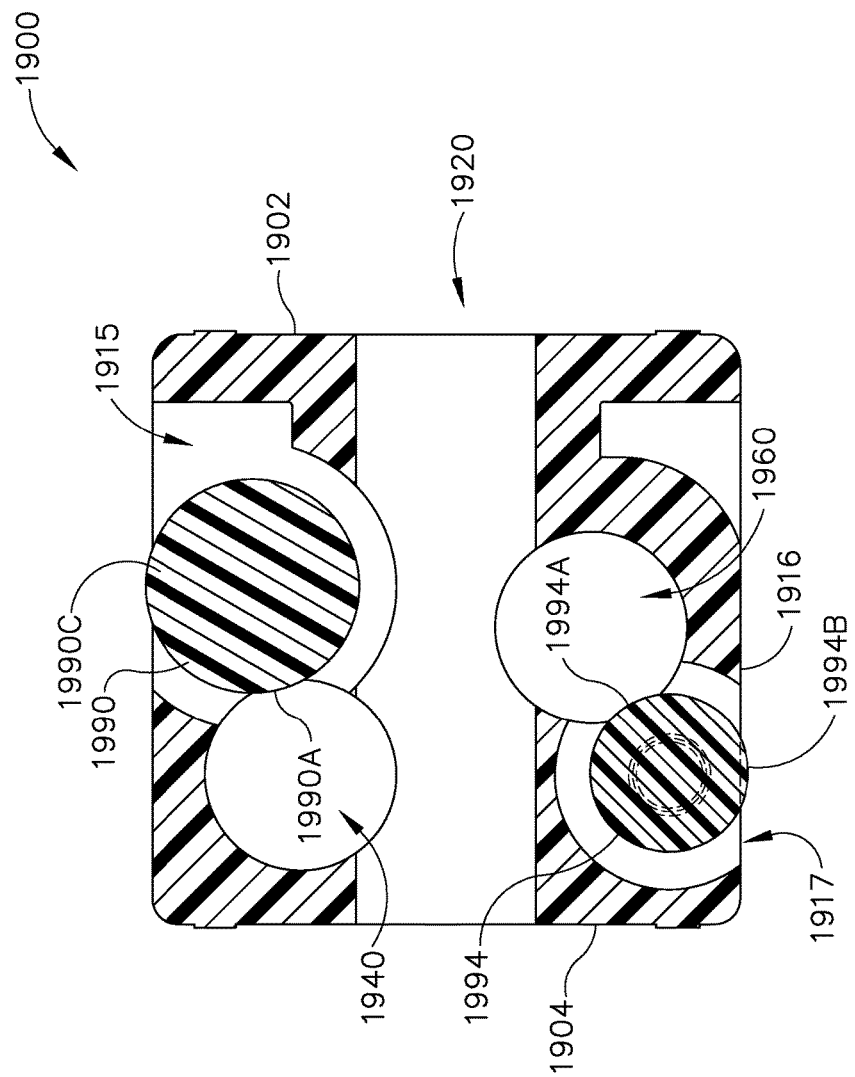
FIG. 74 depicts a cross-sectional view of the guide cube of FIG. 69 taken along line 74-74 of FIG. 69.
Figure 76:
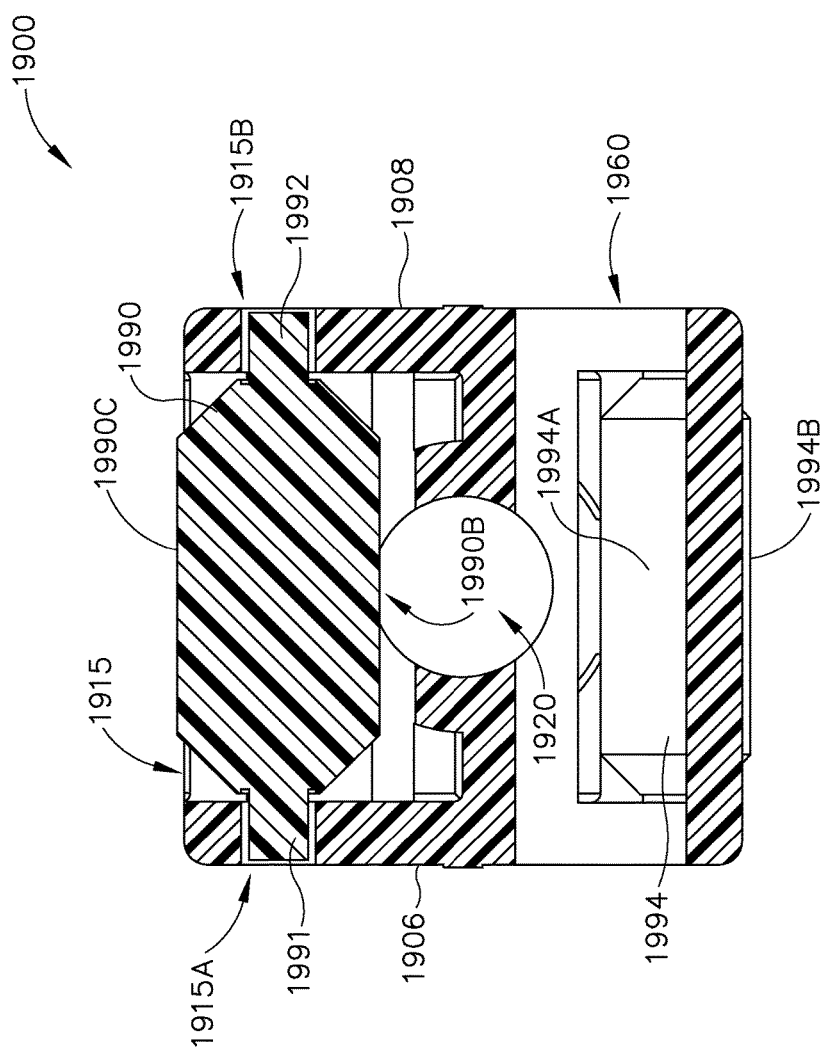
FIG. 76 depicts a cross-sectional view of the guide cube of FIG. 69 taken along line 76-76 of FIG. 69.
Figure 77:
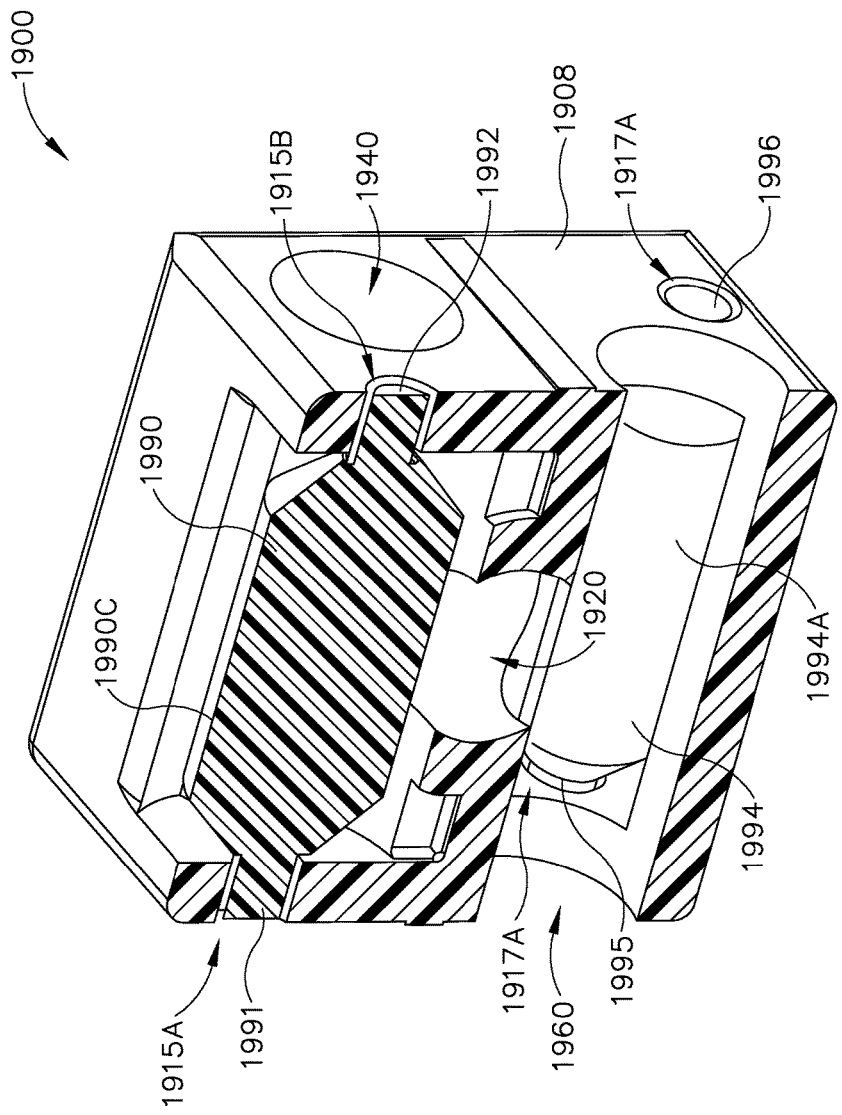
FIG. 77 depicts a cross-sectional perspective view of the guide cube of FIG. 69 taken along line 76-76 of FIG. 69.
Figure 78:
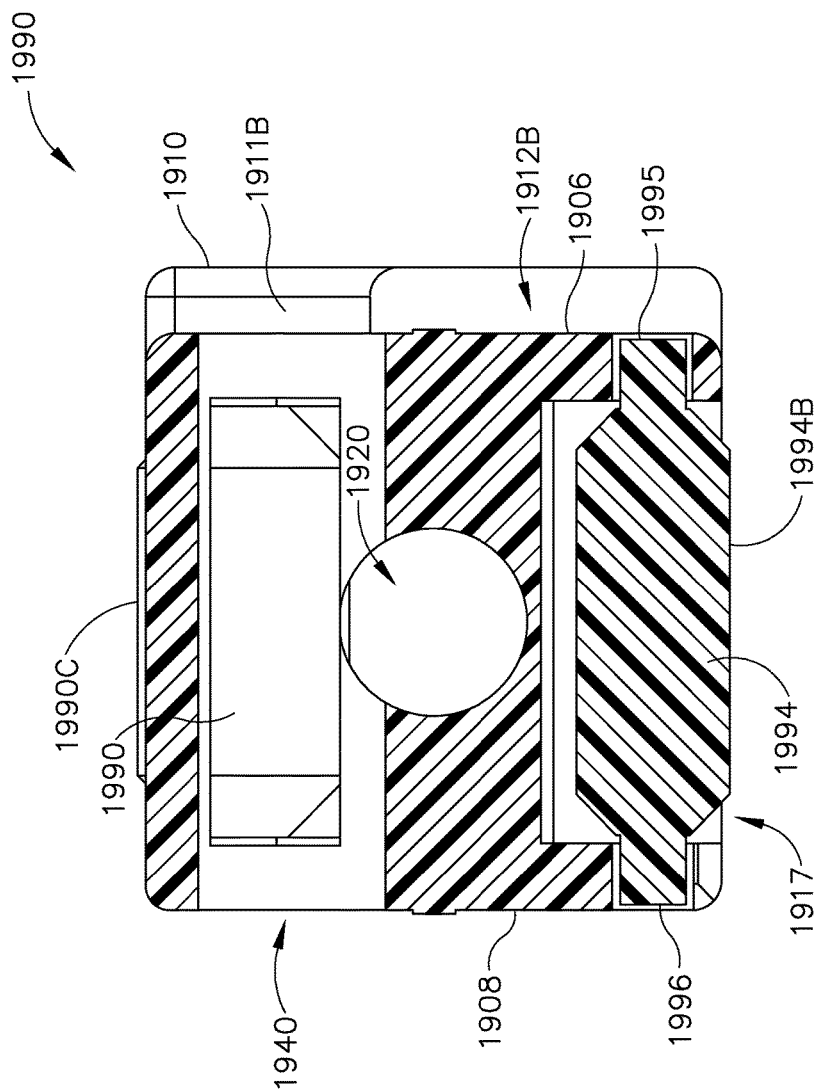
FIG. 78 depicts a cross-sectional view of the guide cube of FIG. 69 taken along line 78-78 of FIG. 69.
Figure 79:
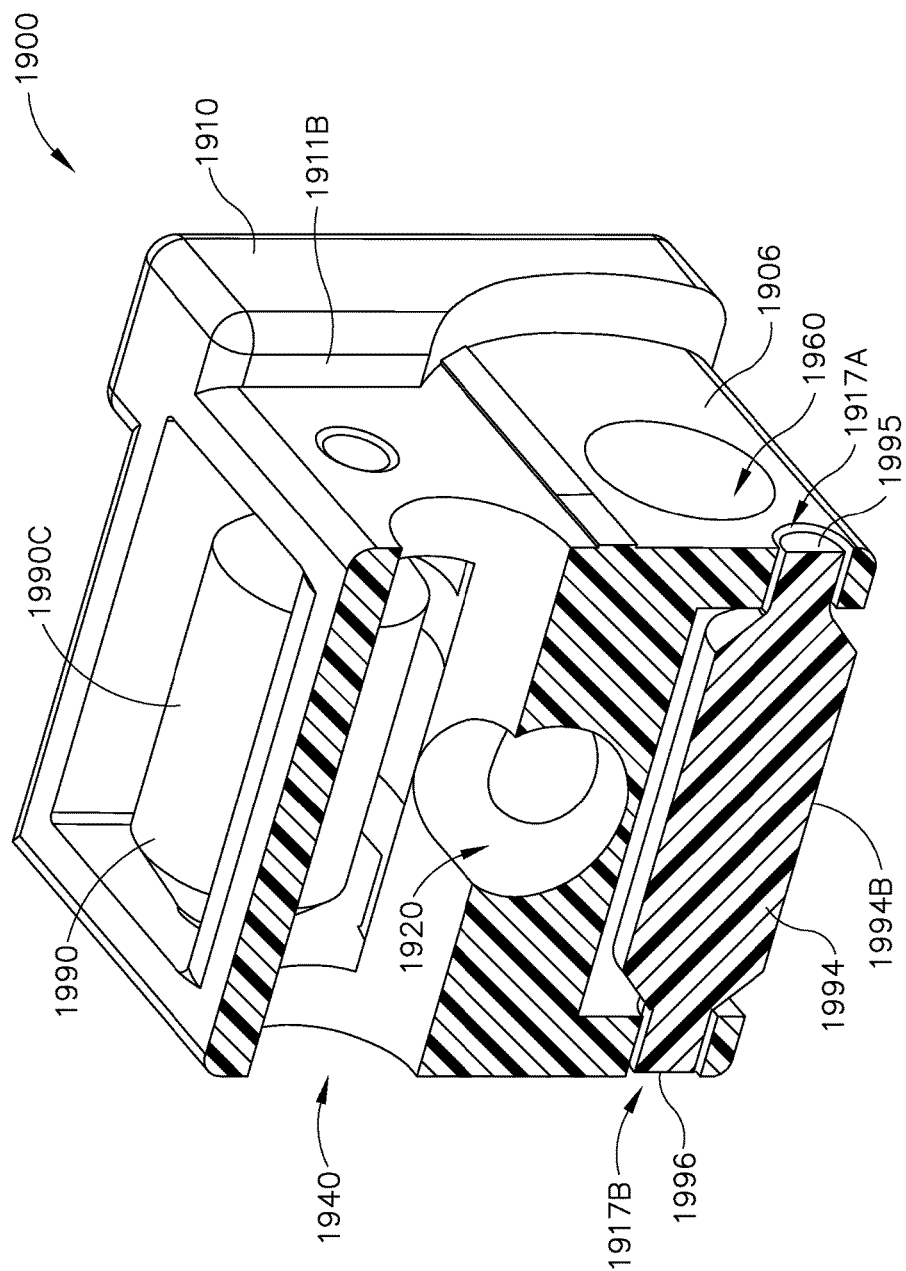
FIG. 79 depicts a cross-sectional perspective view of the guide cube of FIG. 69 taken along line 78-78 of FIG. 69.

Also as shown in FIG. 69, a recess (1915) is formed in a top surface (1914) of guide cube (1900). As best seen in FIG. 74, recess (1915) extends through a sidewall of guide hole (1940) such that recess (1915) is in fluid communication with the interior of guide hole (1940). A first through bore (1915A) passes from third side surface (1906) into recess (1915). A second through bore (1915B) passes from fourth side surface (1908) into recess (1915). As best seen in FIG. 76, a roller (1990) is rotatably disposed within recess (1915) and secured therein by a pair of pegs (1991, 1992) rotatably disposed within through bores (1915A, 1915B). As best seen in FIG. 74, roller (1990) is sized such that a portion (1990A) of roller (1990) extends from recess (1915) and into guide hole (1940) such that portion (1990A) of roller (1990) will engage cannula (1300) when cannula (1300) is disposed within guide hole (1940). It should therefore be understood that roller (1990) may provide frictional retention of cannula (1300) within guide hole (1940). Roller (1990) may comprise an elastomeric or otherwise deformable material.

As best seen in FIG. 76, recess (1915) also extends through a sidewall of guide hole (1920) such that recess (1915) is in fluid communication with the interior of guide hole (1920). Roller (1990) is sized such that a portion (1990B) of roller (1990) also extends from recess (1915) and into guide hole (1920) such that portion (1990B) of roller (1990) will engage cannula (1300) when cannula (1300) is disposed within guide hole (1920). It should therefore be understood that roller (1990) may provide frictional retention of cannula (1300) within guide hole (1920).

Figure 75:
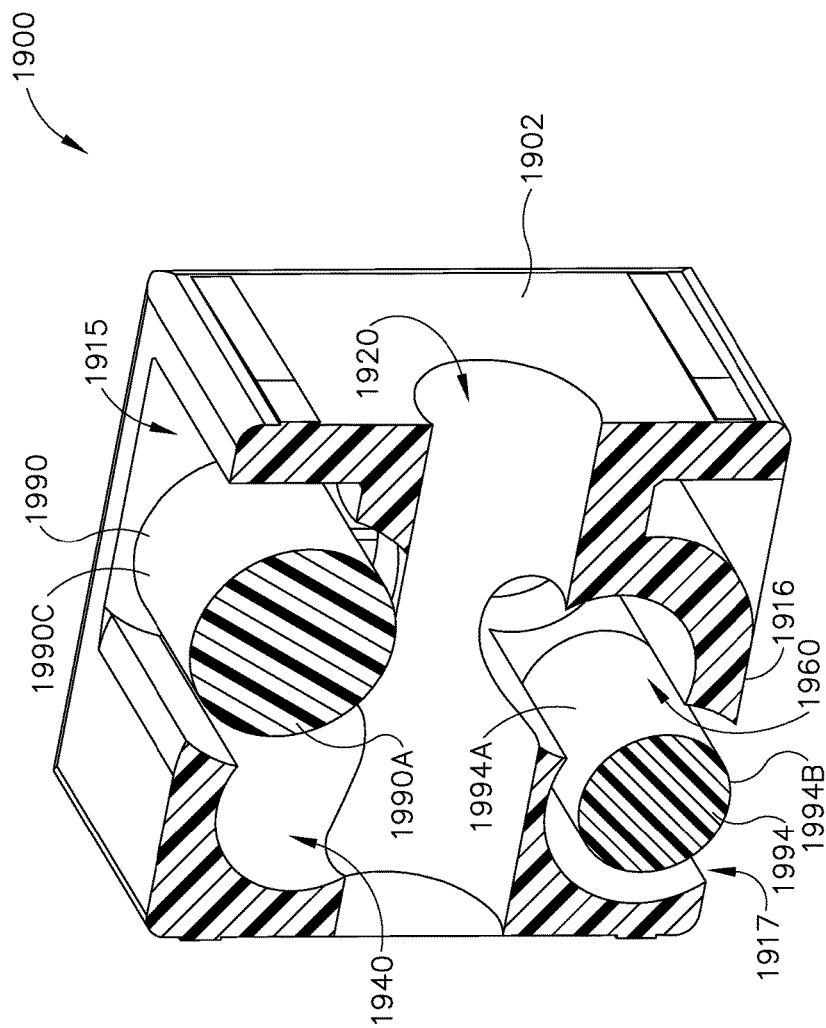
FIG. 75 depicts a cross-sectional perspective view of the guide cube of FIG. 69 taken along line 74-74 of FIG. 69.

As shown in FIGS. 74 and 75, a recess (1917) is formed in a bottom surface (1916) of guide cube (1900). Recess (1917) extends through a sidewall of guide hole (1960) such that recess (1917) is in fluid communication with the interior of guide hole (1960). A first through bore (1917A) passes from third side surface (1906) into recess (1917). A second through bore (1917B) passes from fourth side surface (1908) into recess (1917). As best seen in FIG. 76, a roller (1994) is rotatably disposed within recess (1917) and secured therein by a pair of pegs (1995, 1996) rotatably disposed within through bores (1917A, 1917B). As best seen in FIG. 74, roller (1994) is sized such that a portion (1994A) of roller (1994) extends from recess (1917) and into guide hole (1960) such that portion (1994A) of roller (1994) will engage cannula (1300) when cannula (1300) is disposed within guide hole (1960). It should therefore be understood that roller (1994) may provide frictional retention of cannula (1300) within guide hole (1960).

Figure 70:
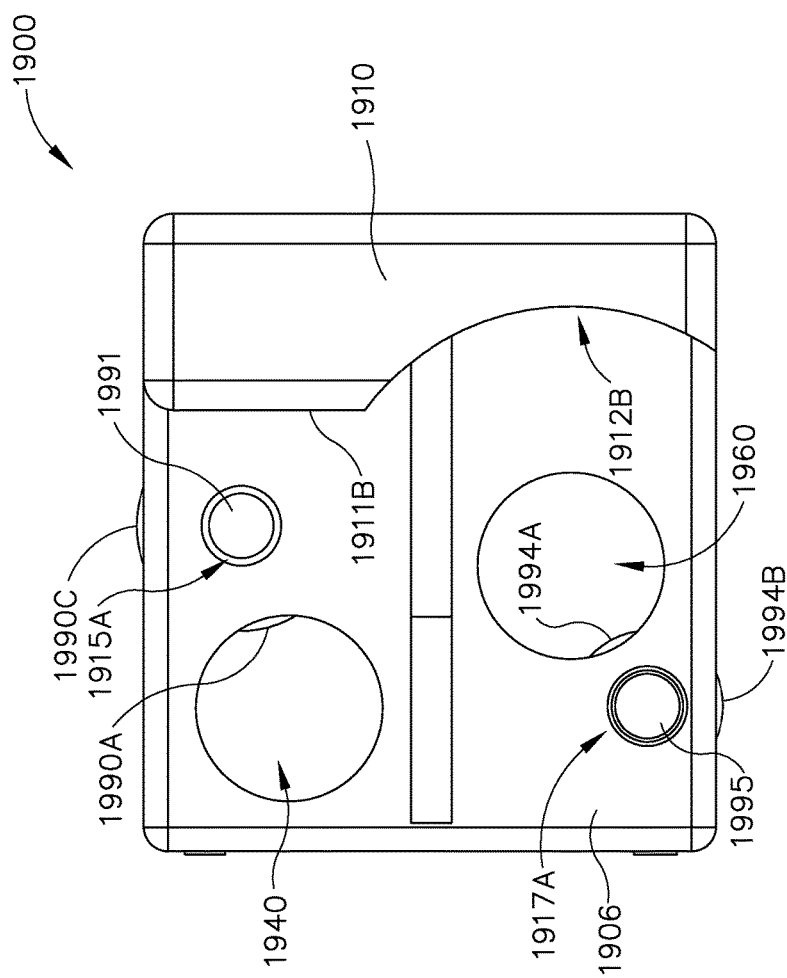
FIG. 70 depicts a front elevational view of the guide cube of FIG. 69.
Figure 71:
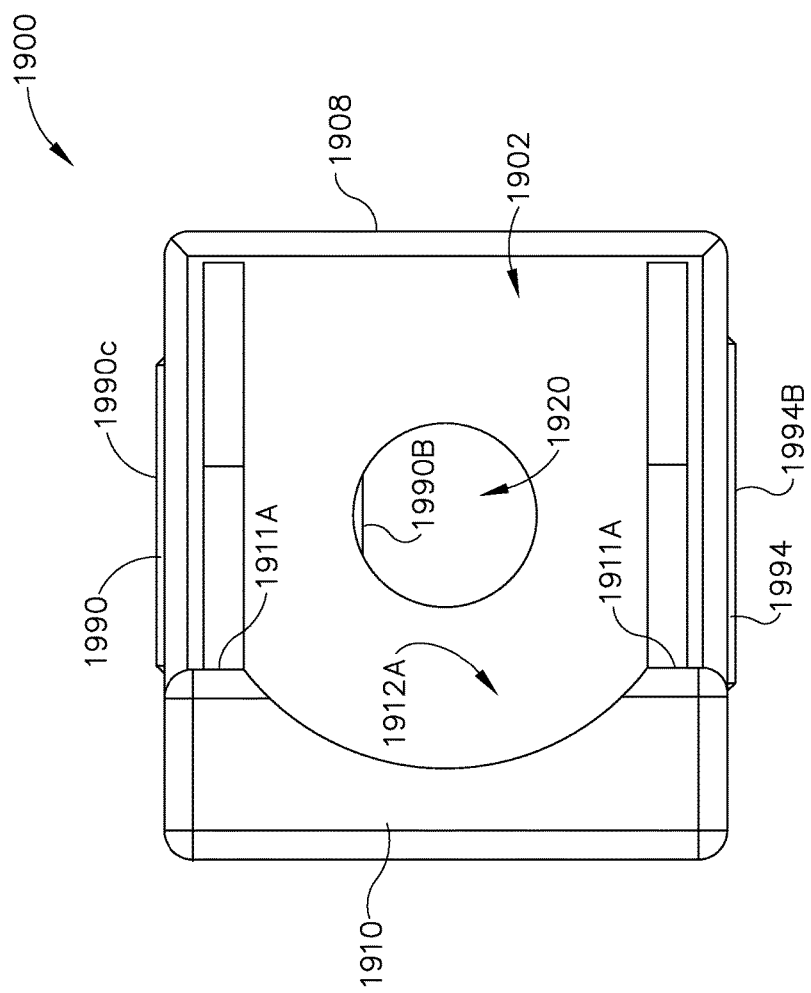
FIG. 71 depicts a side elevational view of the guide cube of FIG. 69.
Figure 72:
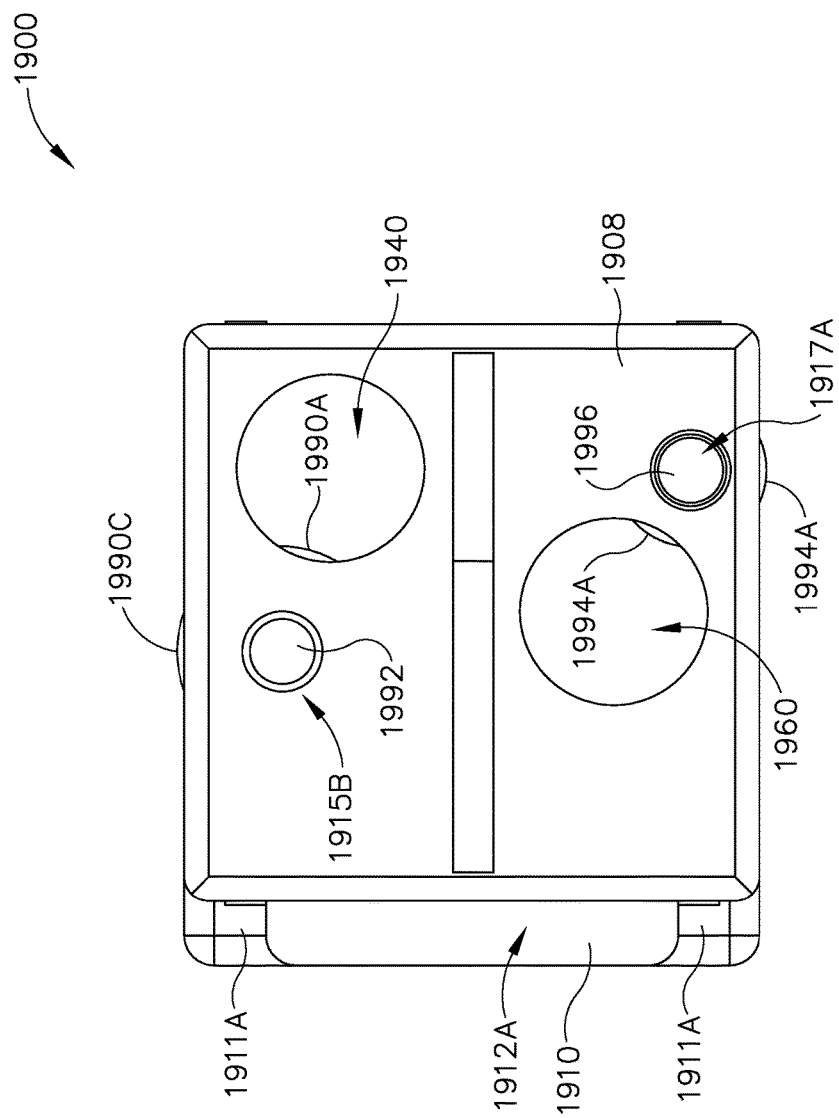
FIG. 72 depicts a back elevational view of the guide cube of FIG. 69.
Figure 73:
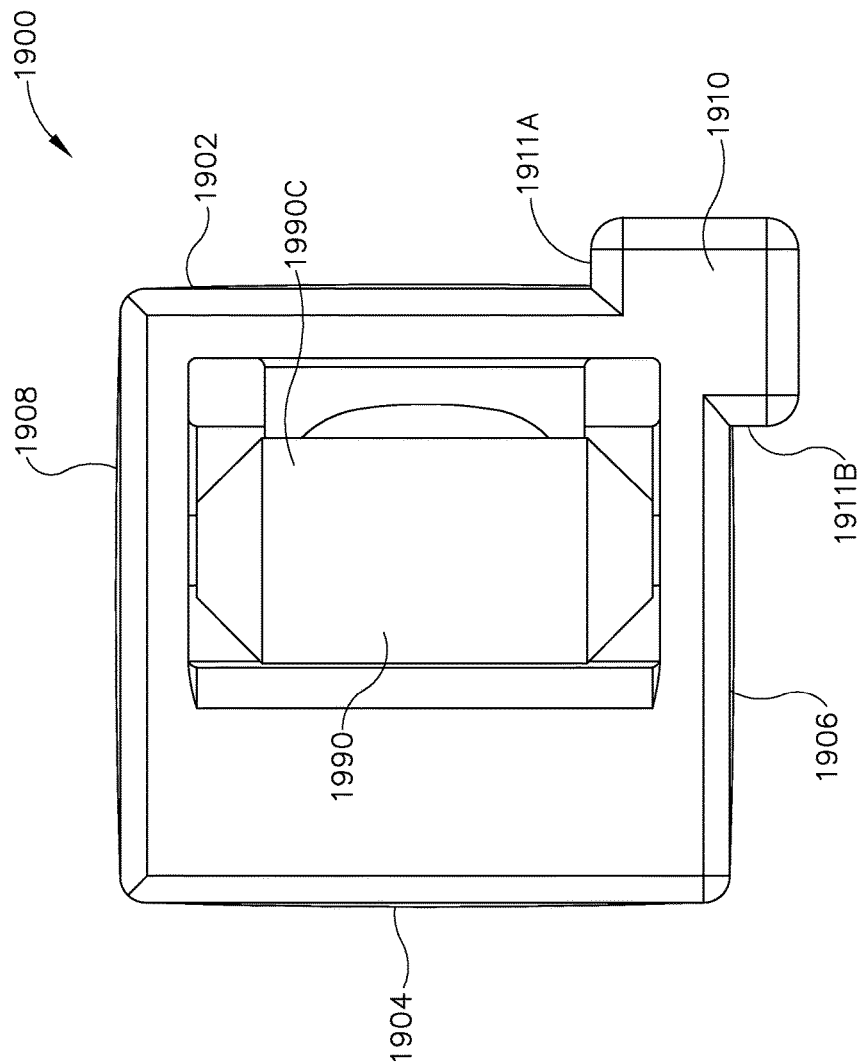
FIG. 73 depicts a top view of the guide cube of FIG. 69.

As best seen in FIG. 70, a portion (1990C) of roller (1990) extends outwardly from top surface (1914) from recess (1915), and a portion (1994B) of roller (1994) extends outwardly from bottom surface (1916) from recess (1917). It should be understood that as guide cube (1900) is inserted into a selected square recess (130) in grid plate (96), portions (1990C, 1994B) of rollers (1990, 1994) will exert pressure upon respective interior surfaces (144) of a selected recess (130) to thereby provide for retention of guide cube (1900) within a selected square recess (130) of grid plate (96). It should also be understood that portions (1990C, 1994B) of rollers (1990, 1994) will exert pressure upon the respective interior surfaces of selected square recess (130) of grid plate (96) regardless of the orientation of guide cube (1900) and/or the guide hole (1920, 1940, 1960) into which cannula (1300) is inserted.

It should be understood that rollers (1990, 1994) may comprise a flexible material, such as rubber, urethane, silicone, or a more rigid material. Other suitable materials and combinations of materials that may be used to form rollers (1990, 1994) will be apparent to those of ordinary skill in the art in view of the teachings herein.

VIII. Exemplary Z-Stop Locking Devices

Figure 80:
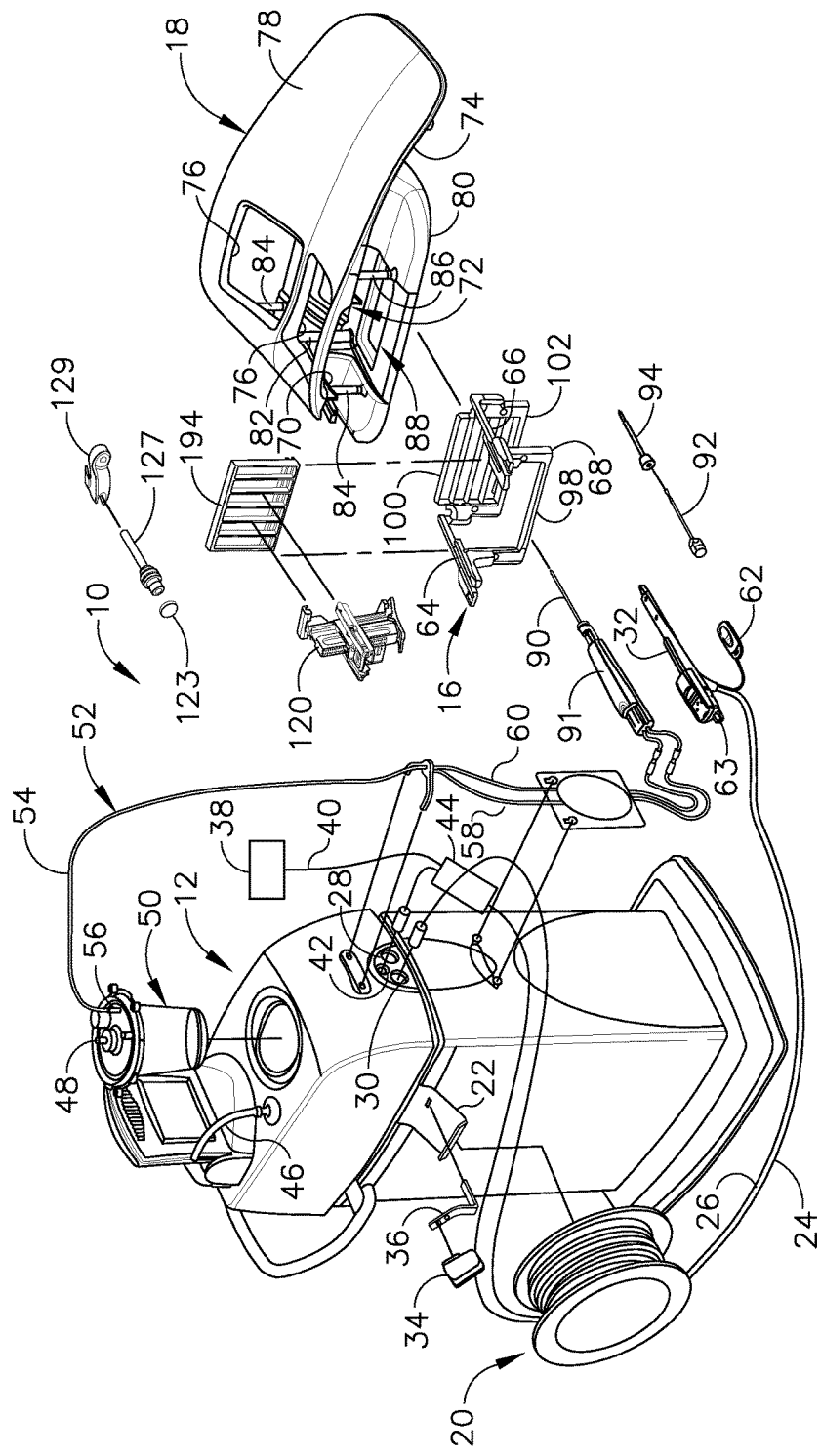
FIG. 80 depicts a perspective view of a biopsy system including a control module remotely coupled to a biopsy device, and including a localization fixture with a lateral fence and pedestal operable to position an obturator or a probe of the biopsy device to a desired insertion depth.

In FIG. 80, grid plate (96) and guide cube (104) of biopsy system (10) of FIG. 1, have been replaced with a lateral fence (194) and a pedestal (120) supported by lateral fence (194). Lateral fence (194) and pedestal (120), best seen in FIG. 81, may be configured and operable in accordance with the teachings of U.S. Pub. No. 2006/0258956, entitled "MRI Biopsy Device," published Nov. 16, 2006, the disclosure of which is incorporated by reference herein. Like grid plate (96) discussed above, lateral fence (194) is downwardly received into three-sided frame (98) of the localization framework (68), defining an X-Y plane. Perpendicular to this X-Y plane extending toward the medial side of the breast is the Z-axis, which typically corresponds to the orientation and depth of insertion of probe (91). An origin of the spatial coordinates may be imaging the dents imparted to the tissue by the lateral fence (194). Alternatively, a disposable fiducial pointer (127) held by a fiducial holder (129) is filled with an MM imageable material (e.g., KY jelly, saline, gadolinium) and sealed with a cap (123).

Figure 81:
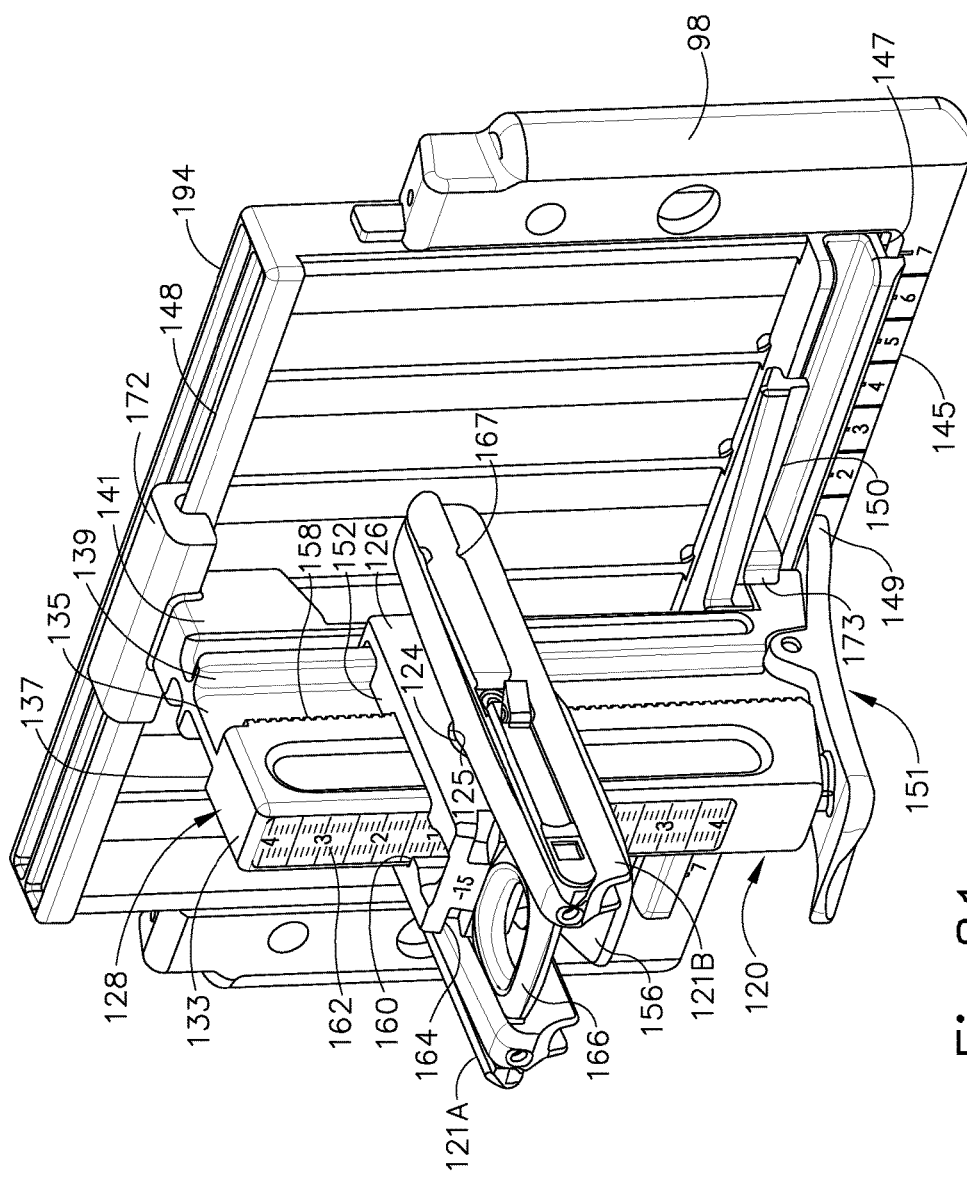
FIG. 81 depicts a perspective view of the lateral fence and pedestal of the localization fixture of the biopsy system of FIG. 80.
Figure 83:
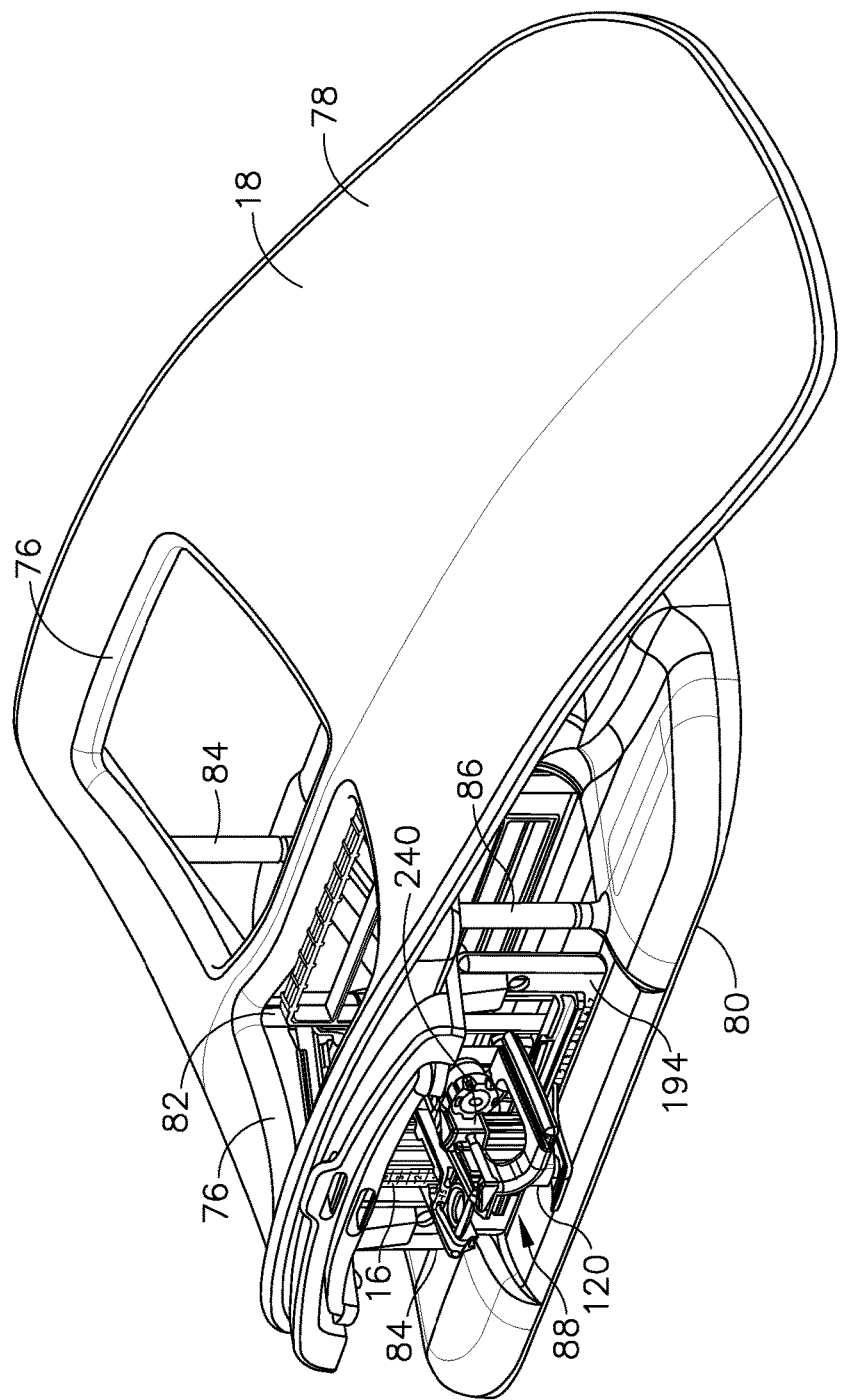
FIG. 83 depicts a perspective view of a breast coil receiving the localization fixture of FIG. 80.
Figure 84:
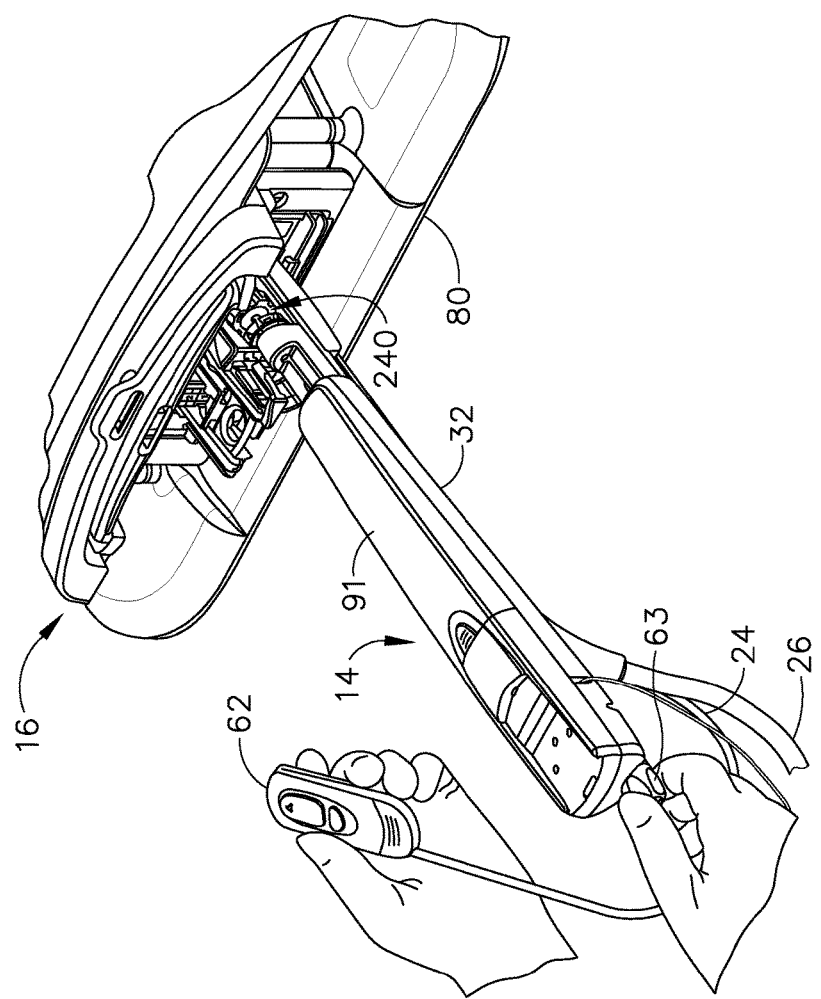
FIG. 84 depicts a perspective view of a biopsy device inserted through a locking device of the localization fixture attached to the breast coil of FIG. 83.
Figure 85:
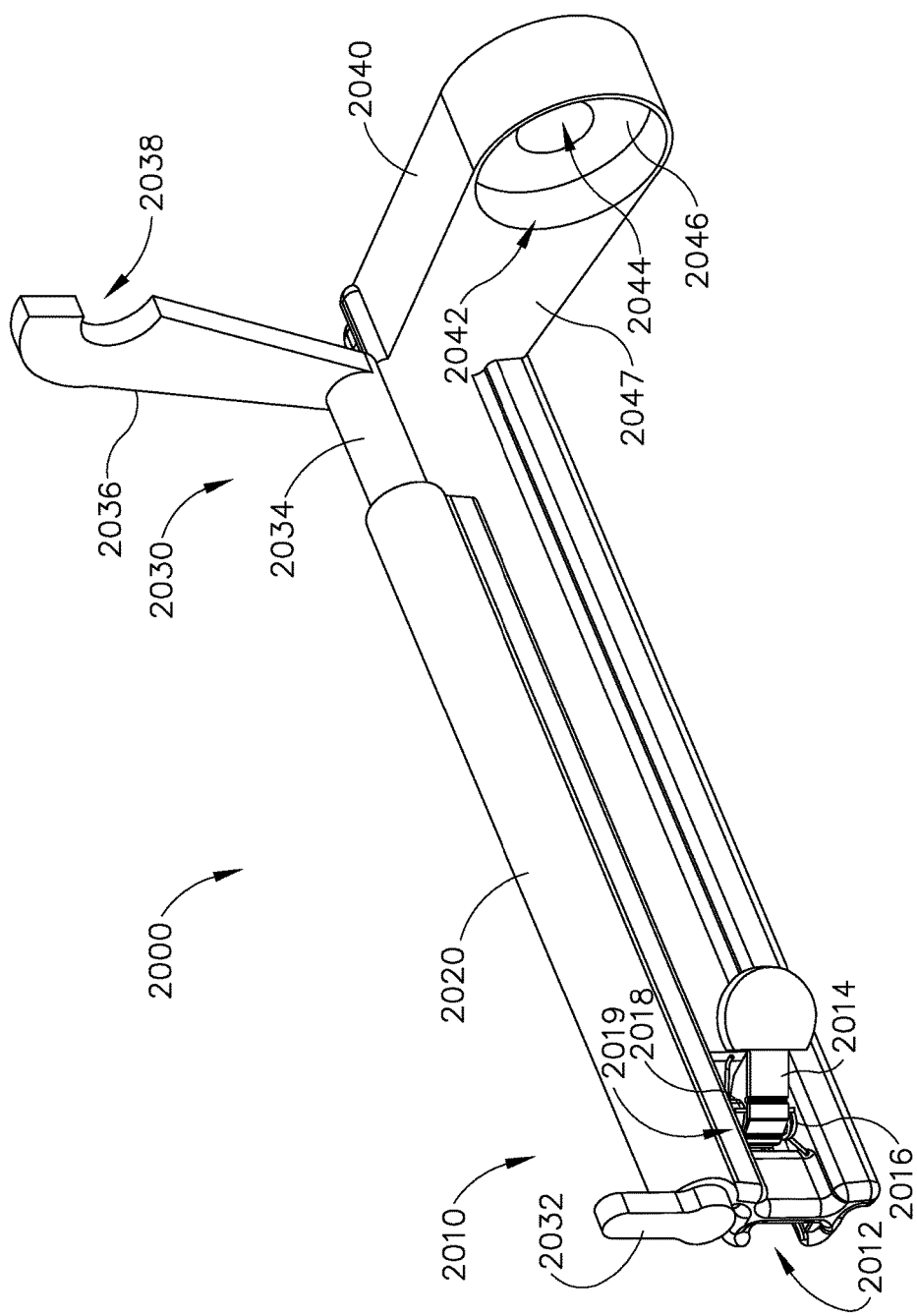
FIG. 85 depicts a perspective view of a locking device suitable for use with the biopsy system of FIG. 80.
Figure 86:
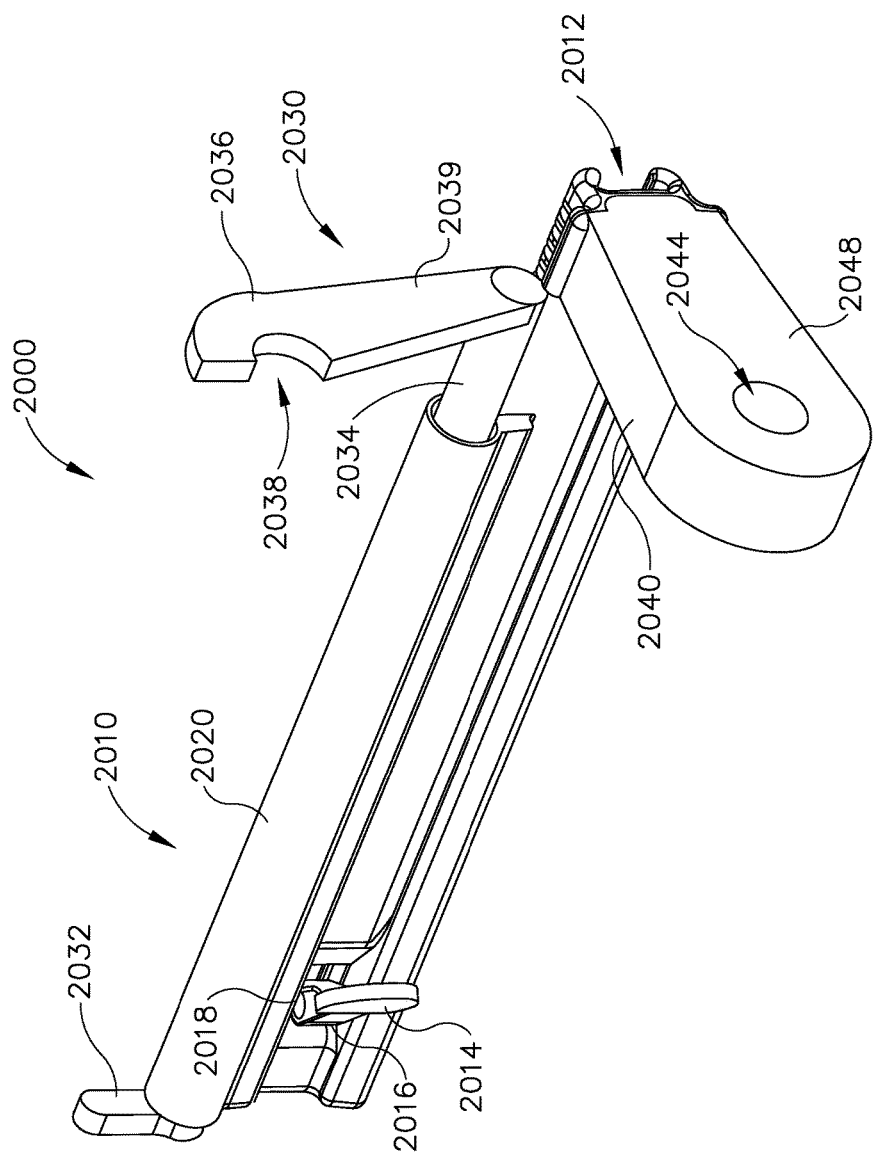
FIG. 86 depicts another perspective view of the locking device of FIG. 85.

As shown in FIGS. 83 and 84, probe (91), cannula (94), and fiducial pointer (127) are guided by localization fixture (16). With particular reference to FIG. 81, pedestal (120) spatially positions left and right primary targeting rails (121A, 121B) that in turn guide fiducial pointer (127), cannula (94), or probe (91) of biopsy device (10). Primary targeting rails (121A, 121B) each include an attachment axle (124) that receives in either a left or right side an axle hub (125) of a (Y-axis) height yoke (126) that is vertically adjustable upon a pedestal main body (128), that in turn is laterally adjustable upon lateral fence (194). Alternatively, a breast coil may enable mounting the pedestal main body on the medial plate (100) for accessing medially. The pedestal main body (128) includes a proximal upright rectangular column (133) with a thinner wall (135) projecting from its distal side that flares laterally outward (defining left and right vertical rectangular slots (137, 139)) as part of a bracket (141) with top and bottom hanger arms (172, 173) that slide laterally respectively on a top track (148) and a proximally open lower track (150) formed in lateral fence (194). A lateral (X-axis) adjustment lever (151) may be raised to lift its distal end (149) out of engagement with a bottom track (147) formed in lateral fence (194) as lateral adjustment lever (151) is repositioned to the left or right to a desired location with reference to a lateral measurement guide (145).

Height yoke (126) is a rectangular cuff interrupted in a mid-portion of a distal side to form locking left and right hands (152) respectively which ride vertically in left and right vertical rectangular slots (137, 139). Locking left and right hands (152) have respective ridged proximal surfaces (not shown) that are selectively drawn proximally into locking engagement by a height locking lever (156) with a ridged surface (158) on a proximal side of each vertical rectangular slot (137, 139). Lifting height locking lever (156) takes height yoke (126) out of locking engagement to pedestal main body (128) as height yoke (126) is vertically repositioned. For height adjustment, the proximal top surface of height yoke (126) serves as a sight (160) to read a height measurement scale (162) presented on a proximal surface of height locking lever (156).

Attachment axle (124) allows rotation so the Z-axis include an upward or downward trajectory. In the illustrative version, proximal corners of height yoke (126) include angle detents (164) (e.g., −15°, 0°, +15°) that are selectable by an angle lock lever (166). The primary targeting rail (121B) includes a distal detent (167) that serves as a home reference for fiducial holder (129).

Figure 82:
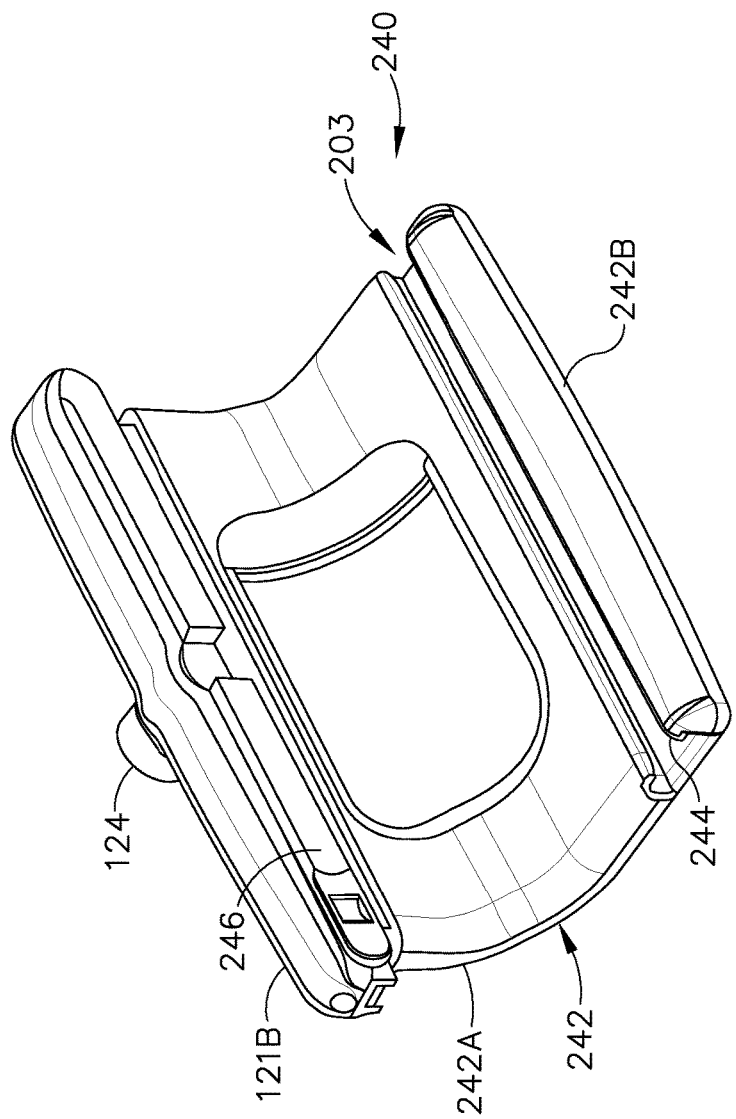
FIG. 82 depicts a perspective view of a guidance member that may be mounted onto the localization fixture of the biopsy system of FIG. 80.

In FIG. 82, a guidance assembly (240), that may be attached to pedestal (120), includes a cradle (242) whose upper lateral side (242A) flares upwardly to engage a bottom channel (243) of primary targeting rail (121B). A lower lateral side (242B) flares horizontally to provide a holster guide track (244) that underlies the Z-axis. Primary targeting rail (121B) includes a longitudinal guide tab (246). Examples of locking devices that may be coupled with pedestal (120) for controlling a depth of penetration of probe (91) will now be discussed.

A. First Exemplary Z-Stop Locking Device

Figure 91A:
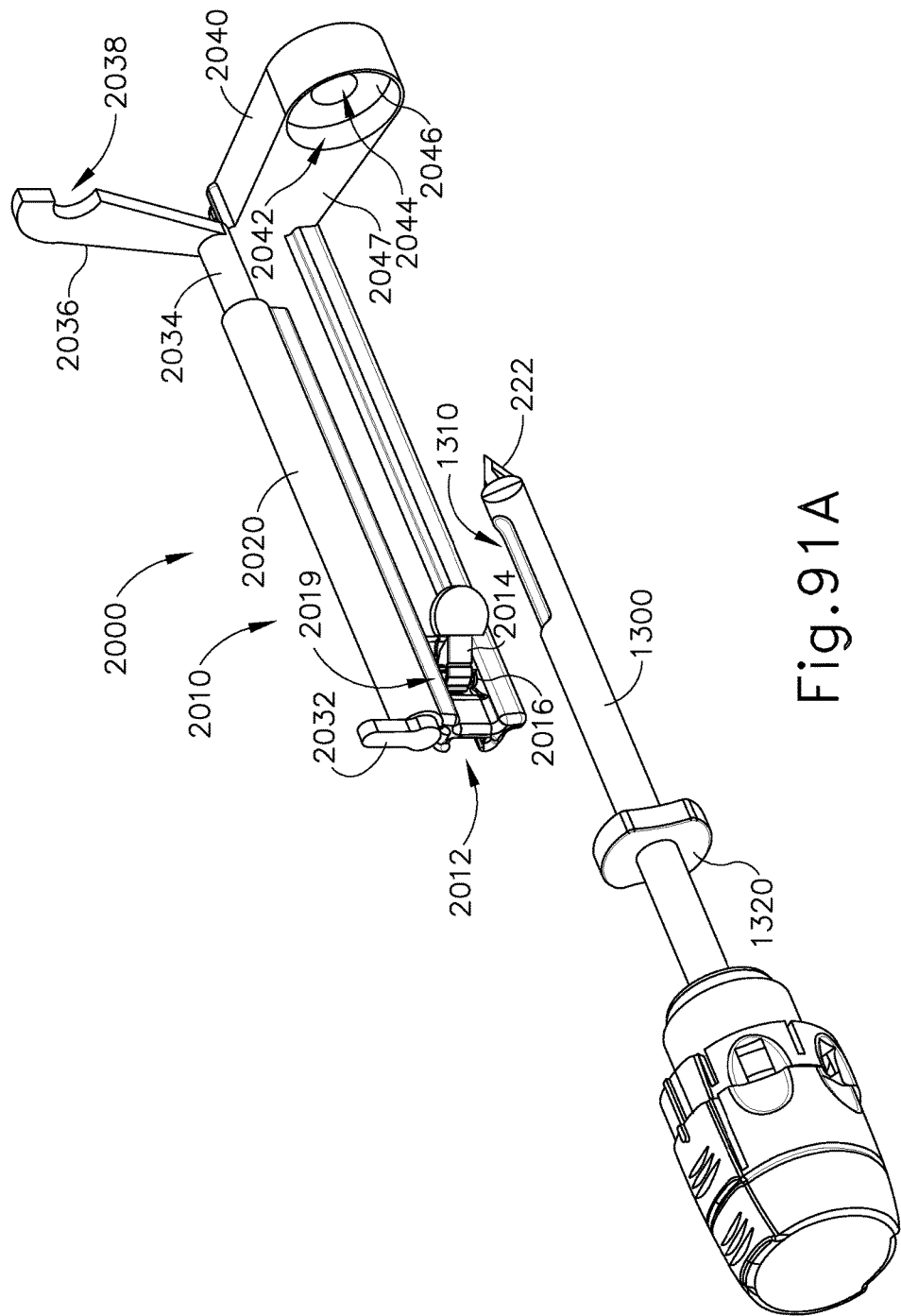
FIG. 91A depicts a perspective view of the locking device of FIG. 85 with the locking feature of FIG. 87A in the first rotational position of FIG. 87A, and with a cannula in a first longitudinal position.
Figure 91B:
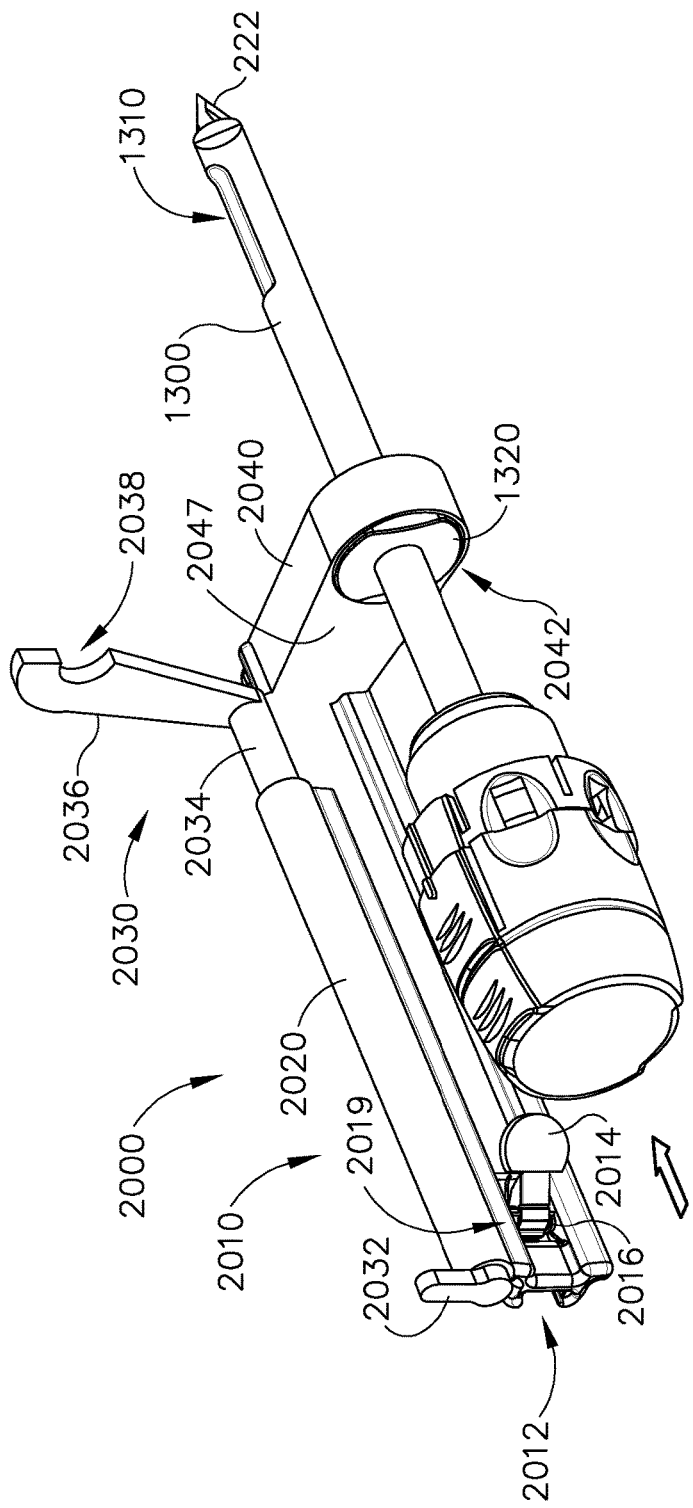
FIG. 91B depicts a perspective view of the locking device of FIG. 85 with the locking feature of FIG. 87A remaining in the first rotational position of FIG. 87A, and with the cannula of FIG. 91A moved into a second longitudinal position.
Figure 91C:
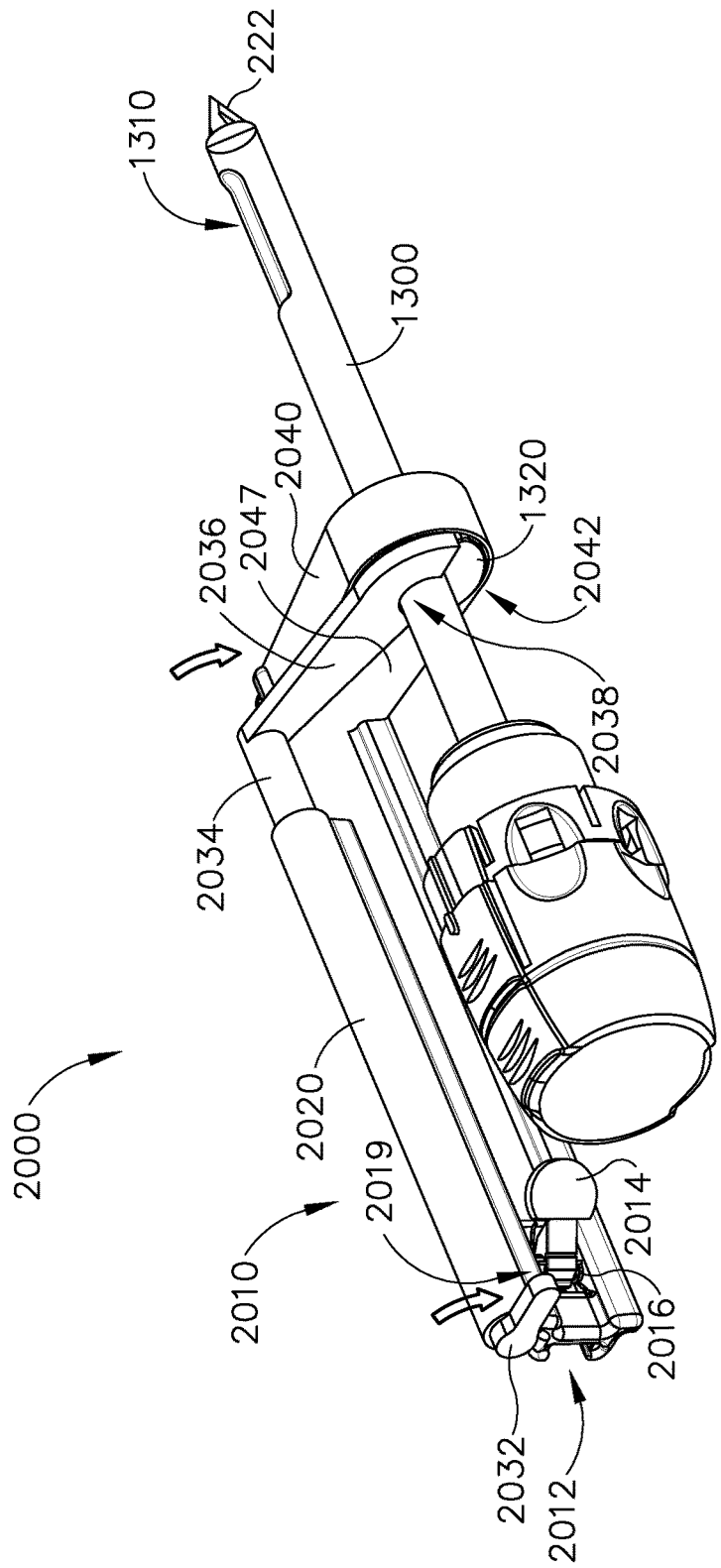
FIG. 91C depicts a perspective view of the locking device of FIG. 85 with the locking feature of FIG. 87A moved into the second rotational position of FIG. 87B, and with the cannula of FIG. 91A remaining in the second longitudinal position.
Figure 92A:
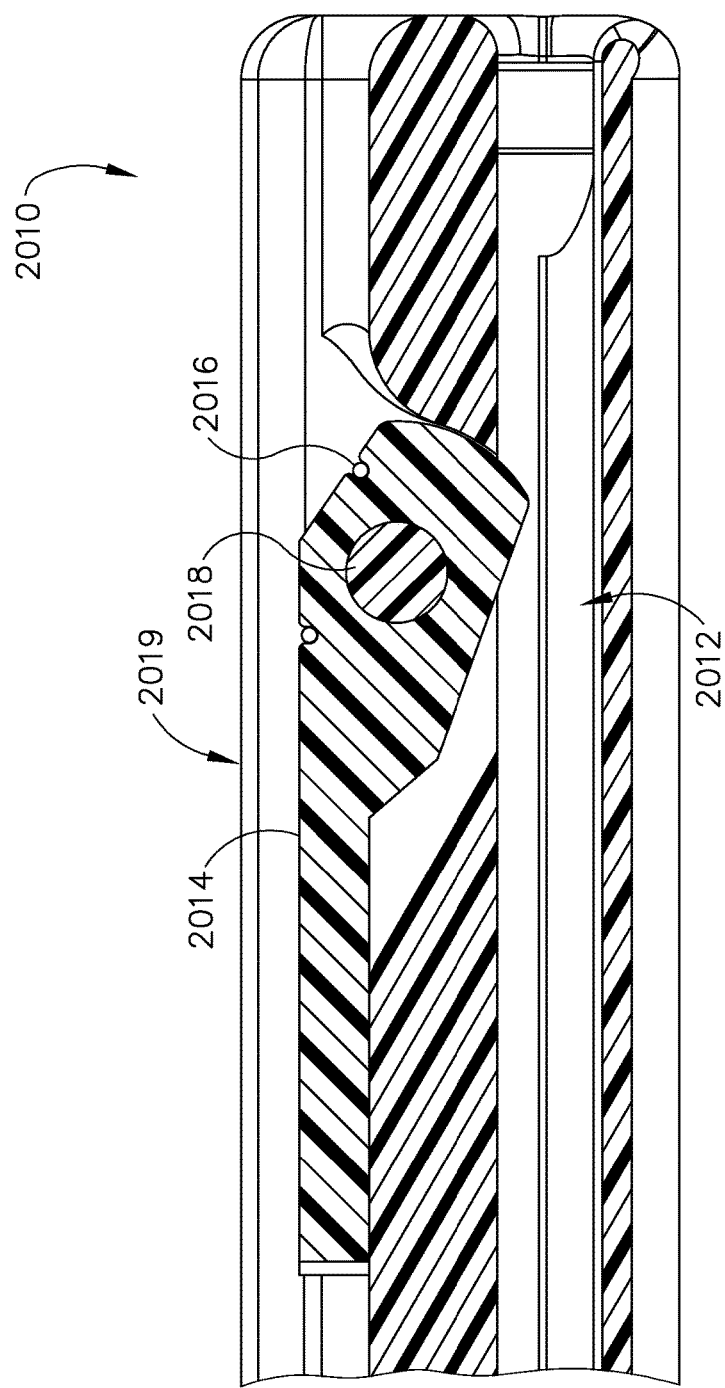
FIG. 92A depicts a cross-sectional view of a tensioning feature of the locking device of FIG. 85 in a first rotational position.
Figure 92B:
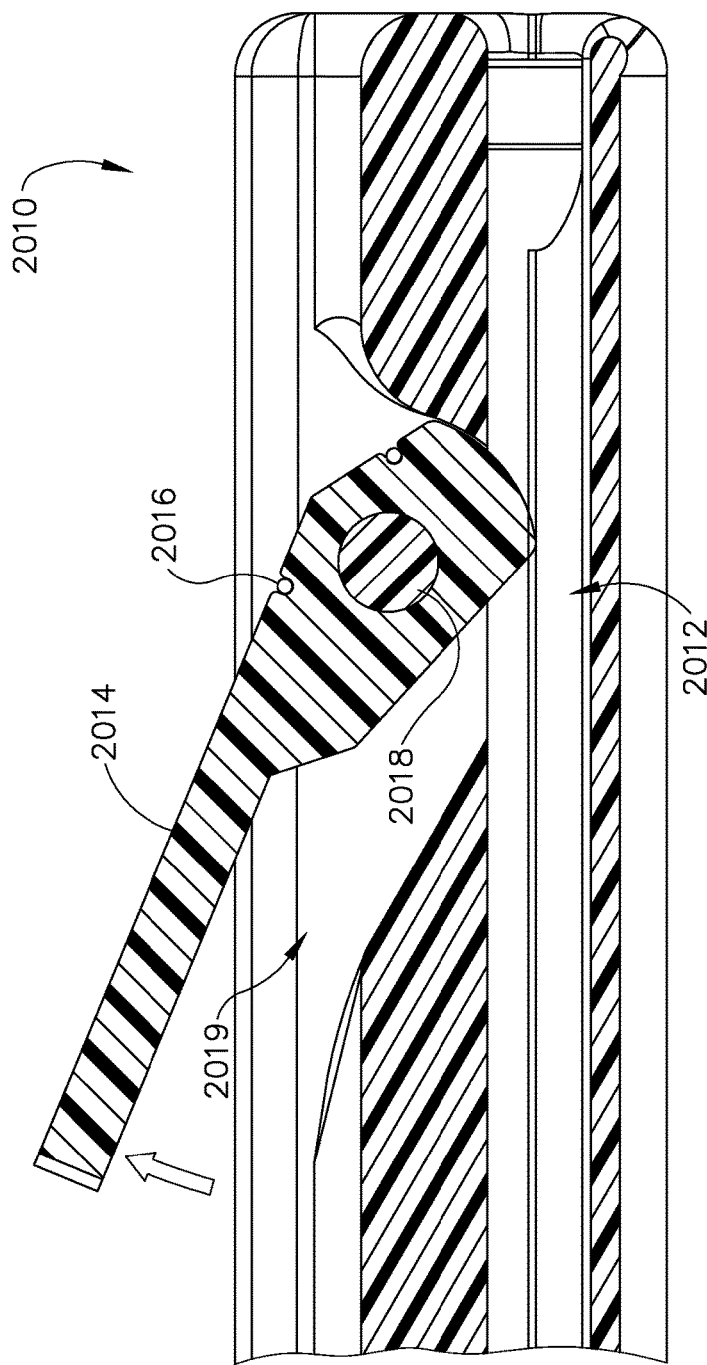
FIG. 92B depicts a cross-sectional view of the tensioning feature of FIG. 92A moved into a second rotational position.

FIGS. 85-92B show an exemplary Z-stop locking device (2000) operable to be used with lateral fence (194) and pedestal (120) to control the depth of penetration of probe (91). To provide additional guidance to the MRI biopsy device (14), locking device (2000) includes a secondary targeting rail (2010) having a lateral channel (2012) that is engageable with and guided along longitudinal guide tab (246) of primary targeting rail (121B) of pedestal (120). When fully engaged thereon, a pawl (2014) pivoting under urging of a pawl spring (2016) about a vertical pawl pin (2018) in a lateral window (2019) engages longitudinal guide tab (246) of primary targeting rail (121B) to thereby retain the position of locking device (2000) relative to longitudinal guide tab (246). In particular, as shown in FIGS. 92A and 92B, pawl (2014) is biased from the position shown in FIG. 92A toward the position shown in FIG. 92B. Such a bias causes pawl (2014) to engage longitudinal guide tab (246) to thereby retain the longitudinal position of locking device (2000) relative to longitudinal guide tab (246). For instance, pawl (2014) may ratchet along a plurality of teeth of guide tab (246); or may frictionally bear against guide tab (246).

Locking device (2000) comprises a stationary member (2040) having a circular recess (2042) formed in a proximal surface (2047) of stationary member (2040). As will be discussed in more detail below, circular recess (2042) is sized to receive lock nut (1320) of cannula (1300). A depth of circular recess (2042) is substantially similar to a thickness of lock nut (1320) of cannula (1300). A guide hole (2044) is defined within a bottom surface (2046) of circular recess (2042). Guide hole (2044) passes through stationary member (2040) from bottom surface (2046) to a distal surface (2048) of stationary member (2040). Guide hole (2044) is configured to receive any of the cannulas described herein. Referring to cannula (1300) as just one merely illustrative example, upon insertion of cannula (1300) into guide hole (2044), bottom surface (2046) engages lock nut (1320) of cannula (1300) such that cannula (1300) cannot be inserted beyond a position where bottom surface (2046) engages lock nut (1320). As discussed above, lock nut (1320) prevents cannula (1300) from moving further into a patient's breast by abutting bottom surface (2046) of stationary member (2040).

Figure 87A:
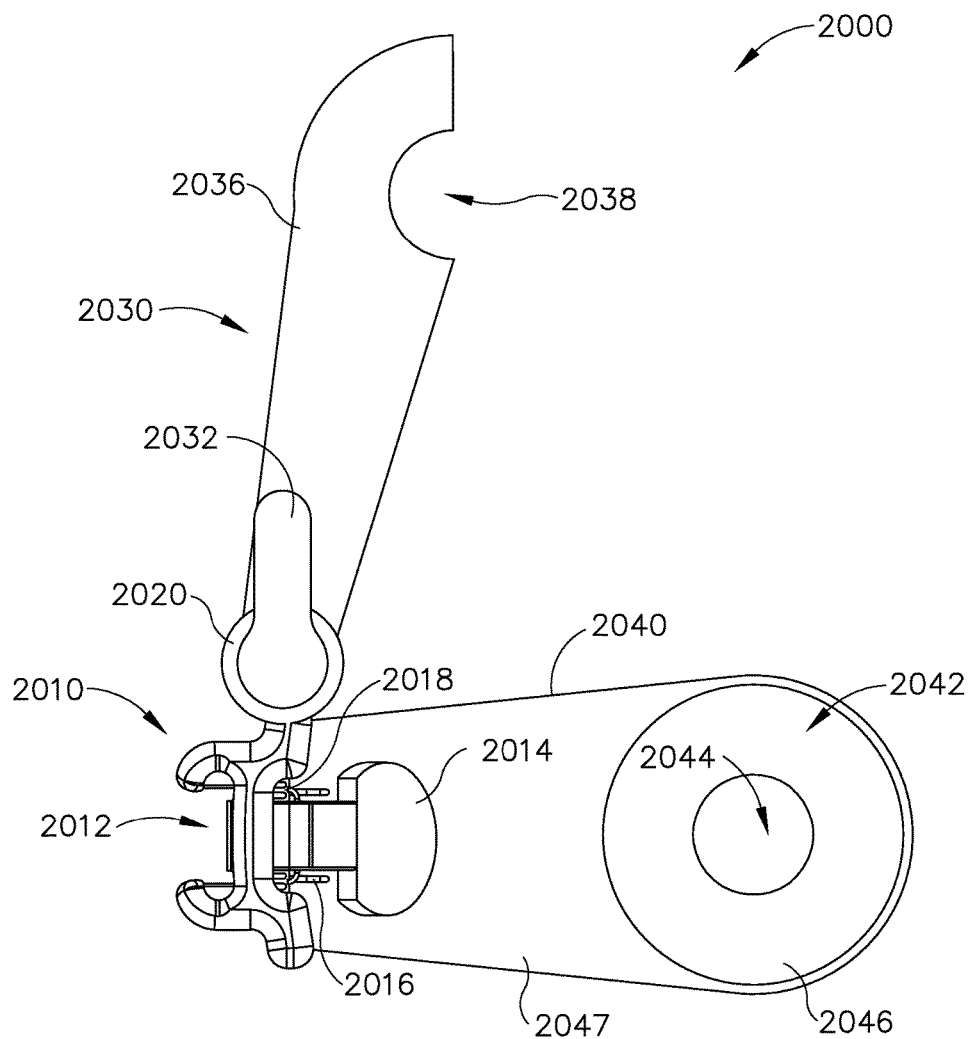
FIG. 87A depicts a front elevational view of the locking device of FIG. 85 with a locking feature in a first rotational position.
Figure 87B:
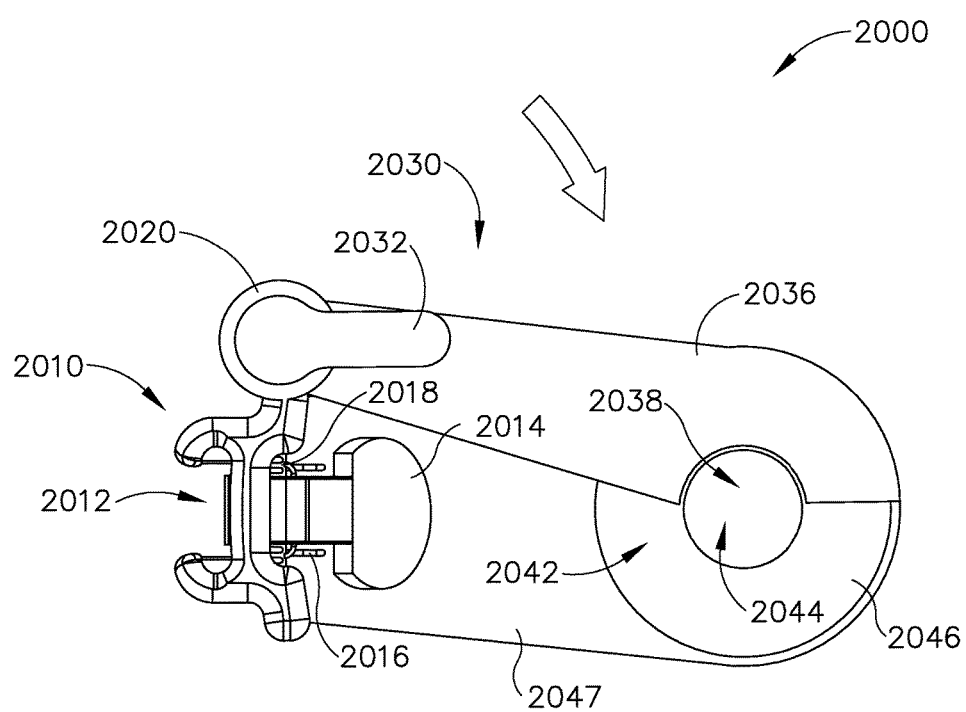
FIG. 87B depicts a front elevational view of the locking device of FIG. 85 with the locking feature of FIG. 87A moved into a second rotational position.
Figure 88:
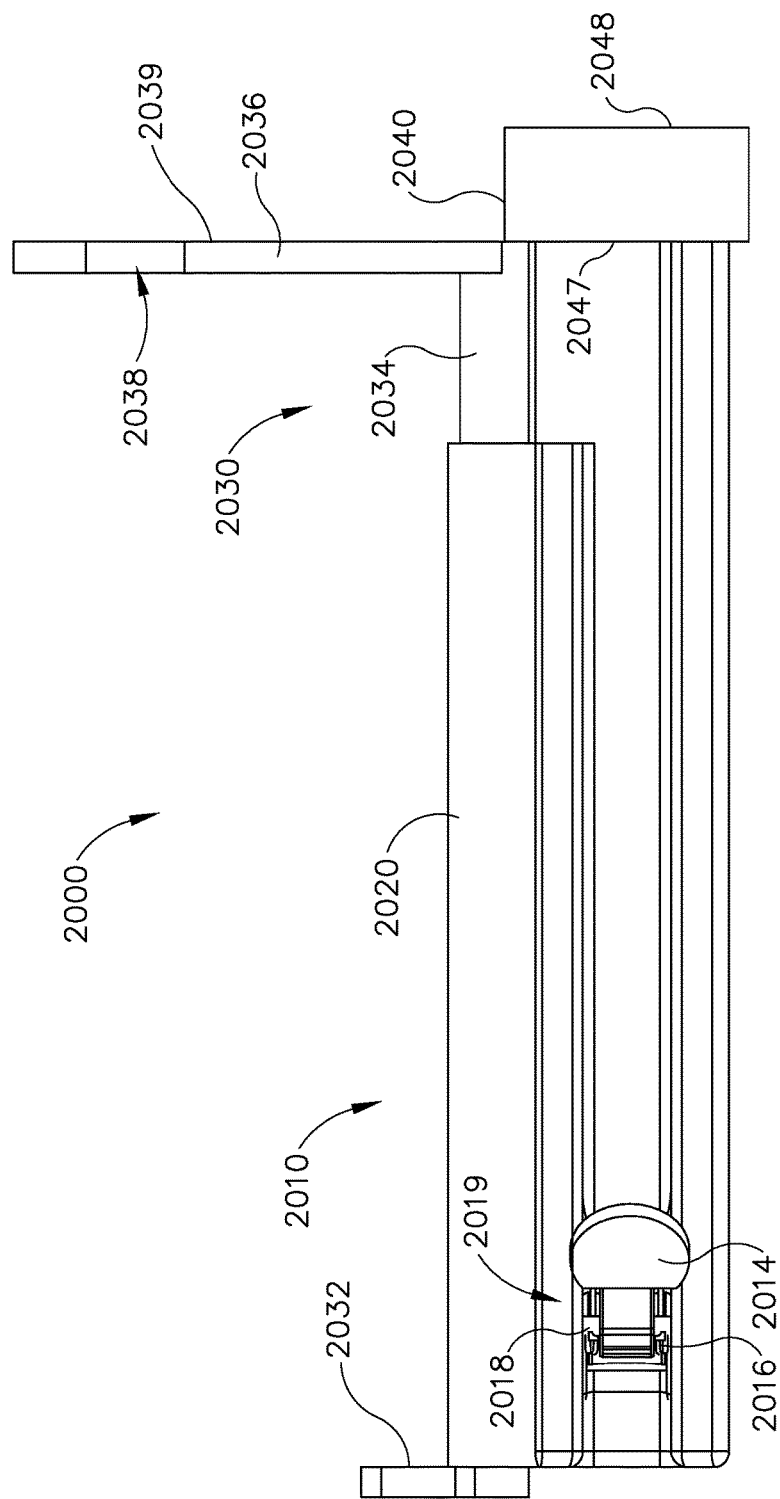
FIG. 88 depicts a side elevational view of the locking device of FIG. 85.
Figure 89:
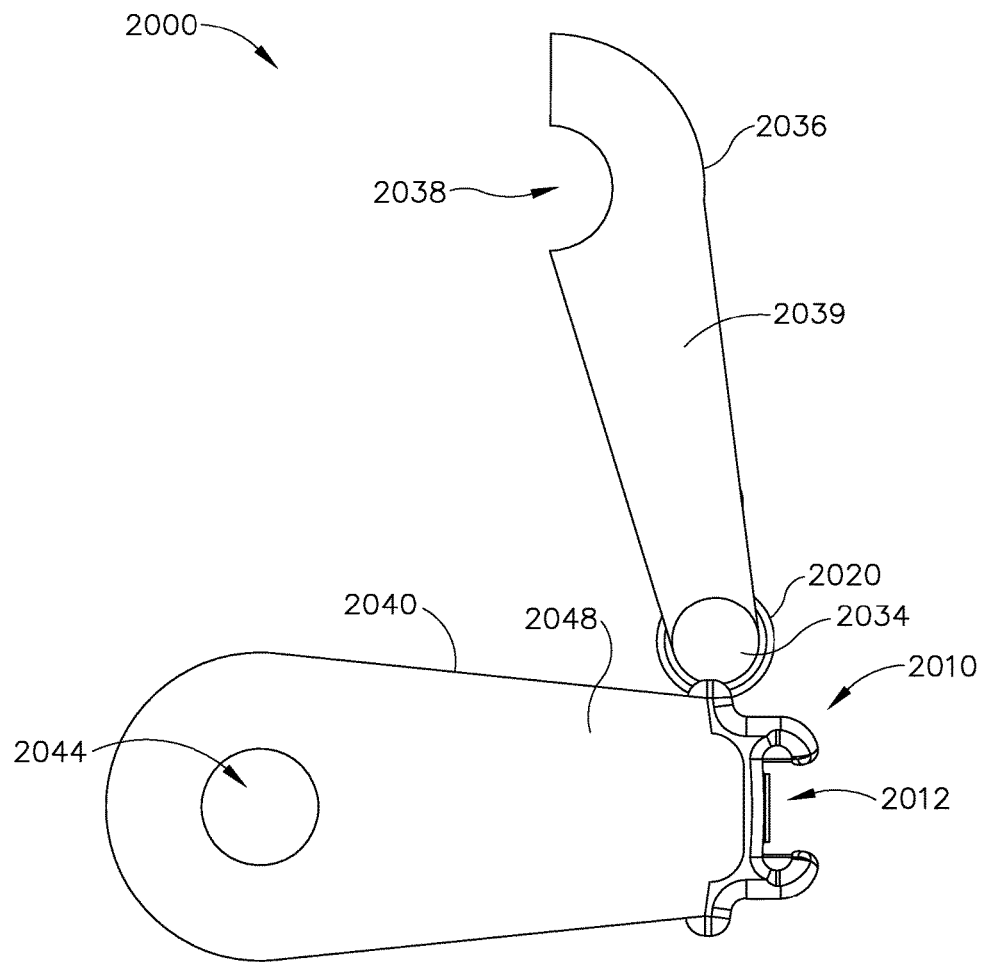
FIG. 89 depicts a back elevational view of the locking device of FIG. 85.
Figure 90:
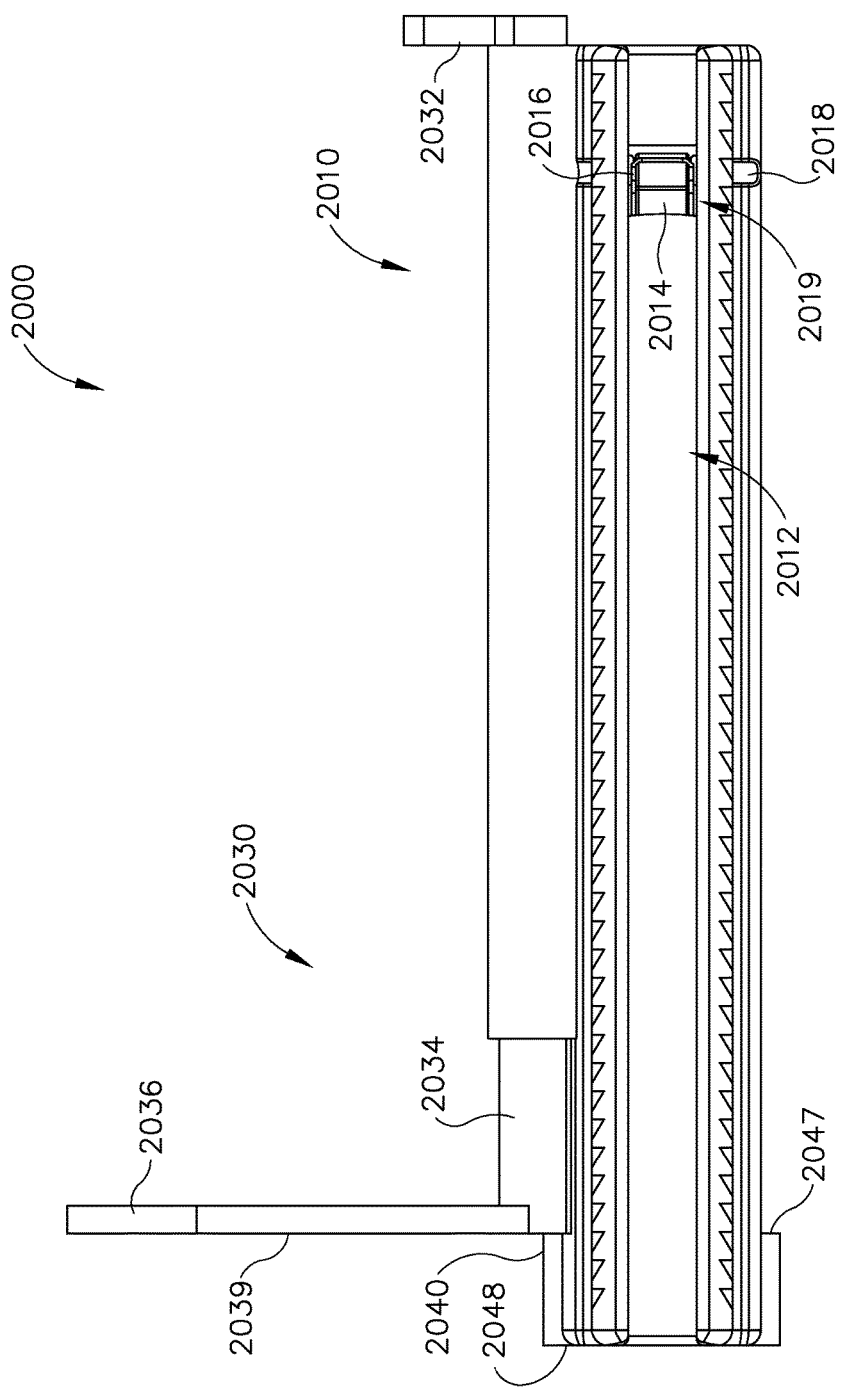
FIG. 90 depicts another side elevational view of the locking device of FIG. 85.

Secondary targeting rail (2010) includes an integral cylindrical tube (2020). A locking member (2030) is rotatably disposed within cylindrical tube (2020) of secondary targeting rail (2010). Locking member (2030) comprises a trigger (2032), a rod (2034), and a locking arm (2036). Rod (2034) is rotatably disposed within cylindrical tube (2020) such that locking member (2030) is operable to rotate between an unlocked position, shown in FIG. 87A, and a locked position, shown in FIG. 87B. Trigger (2032) extends perpendicularly from a first end of rod (2034) while locking arm (2036) extends perpendicularly from a second end of rod (2034). Thus, it should be understood that a user may rotate trigger (2032) to cause concurrent rotation of locking arm (2036). Locking arm (2036) comprises an arcuate recess (2038). As shown in FIG. 87B, when in the locked position, arcuate recess (2038) is configured to lay adjacent to the circular profile of guide hole (2044). As shown in FIG. 88, a distal surface (2039) of locking arm (2036) is substantially proximal to proximal surface (2047) of stationary member (2040) such that in the locked position, distal surface (2039) of locking arm (2036) is adjacent to an opening of circular recess (2042).

FIGS. 91A-91C show the steps of locking cannula (1300) within guide hole (2044) of locking device (2000). FIG. 91A shows cannula (1300) in a first longitudinal position removed from locking device (2000). With cannula (1300) in this position, locking arm (2036) is in the unlocked position such that cannula (1300) may be received within circular recess (2042) and guide hole (2044) of stationary member (2040). Cannula (1300) is then moved into a second longitudinal position such that lock nut (1320) is disposed within circular recess (2042) of stationary member (2040) and such that cannula (1300) is passed into guide hole (2044) to a point where a distal surface of lock nut (1320) engages bottom surface (2046) of circular recess (2042) as shown in FIG. 91B. As cannula (1300) is moved into this position, locking arm (2036) remains in the unlocked position such that lock nut (1320) may be positioned within circular recess (2042) of stationary member (2040) and such that cannula (1300) may be passed into guide hole (2044) of stationary member (2040). Once lock nut (1320) has been positioned within circular recess (2042) and once cannula (1300) has been positioned within guide hole (2044) to the point where the distal surface of lock nut (1320) engages bottom surface (2046) of circular recess (2042), locking arm (2036) is rotated into the locked position by rotation of trigger (2032) of locking member (2030) as shown in FIG. 91C. In the locked position, distal surface (2039) of locking arm (2036) engages a proximal surface of lock nut (1320) such that cannula (1300) is locked within circular recess (2042) and within guide hole (2044) of stationary member (2040) of locking device (2000). In other words, bottom surface (2046) and lock nut (1320) cooperate to restrict distal movement of cannula (1300); while locking arm (2036) and lock nut (1320) cooperate to restrict proximal movement of cannula (1300).

B. Second Exemplary Z-Stop Locking Device

FIGS. 93-103C show an exemplary alternative Z-stop locking device (2100) operable to be used with lateral fence (194) and pedestal (120) to control the depth of penetration of probe (91). To provide additional guidance to the MRI biopsy device (14), locking device (2100) includes a secondary targeting rail (2110) having a lateral channel (2112) that is engageable with and guided along longitudinal guide tab (246) of primary targeting rail (121B) of pedestal (120). When fully engaged thereon, a pawl (2114) pivoting under urging of a pawl spring (2116) about a vertical pawl pin (2118) in a lateral window (2119) engages longitudinal guide tab (246) of primary targeting rail (121B) to thereby retain the position of locking device (2000) relative to longitudinal guide tab (246). In particular, as discussed above with reference to locking device (2000), and as shown in FIGS. 92A and 92B, pawl (2114) of the present example is biased from the position shown in FIG. 92A toward the position shown in FIG. 92B. Such a bias causes pawl (2114) to engage longitudinal guide tab (246) to thereby retain the longitudinal position of locking device (2100) relative to longitudinal guide tab (246). For instance, pawl (2114) may ratchet along a plurality of teeth of guide tab (246); or may frictionally bear against guide tab (246).

Locking device (2100) comprises a stationary member (2140) having a circular recess (2142) formed in a proximal surface (2147) of stationary member (2140). As will be discussed in more detail below, circular recess (2142) is sized to receive lock nut (1320) of cannula (1300). A depth of circular recess (2142) is substantially similar to a thickness of lock nut (1320) of cannula (1300). A guide hole (2144) is defined within a bottom surface (2146) of circular recess (2142). Guide hole (2144) passes through stationary member (2140) from bottom surface (2146) to a distal surface (2148) of stationary member (2140). Guide hole (2144) is configured to receive any of the cannulas described herein and provide structural support to the inserted cannula. Referring to cannula (1300) as just one merely illustrative example, upon insertion of cannula (1300) into guide hole (2144), bottom surface (2146) engages lock nut (1320) of cannula (1300) such that cannula (1300) cannot be inserted beyond a position where bottom surface (2146) engages lock nut (1320). As discussed above, lock nut (1320) prevents cannula (1300) from moving further into a patient's breast by abutting bottom surface (2146) of stationary member (2140).

Figure 97A:
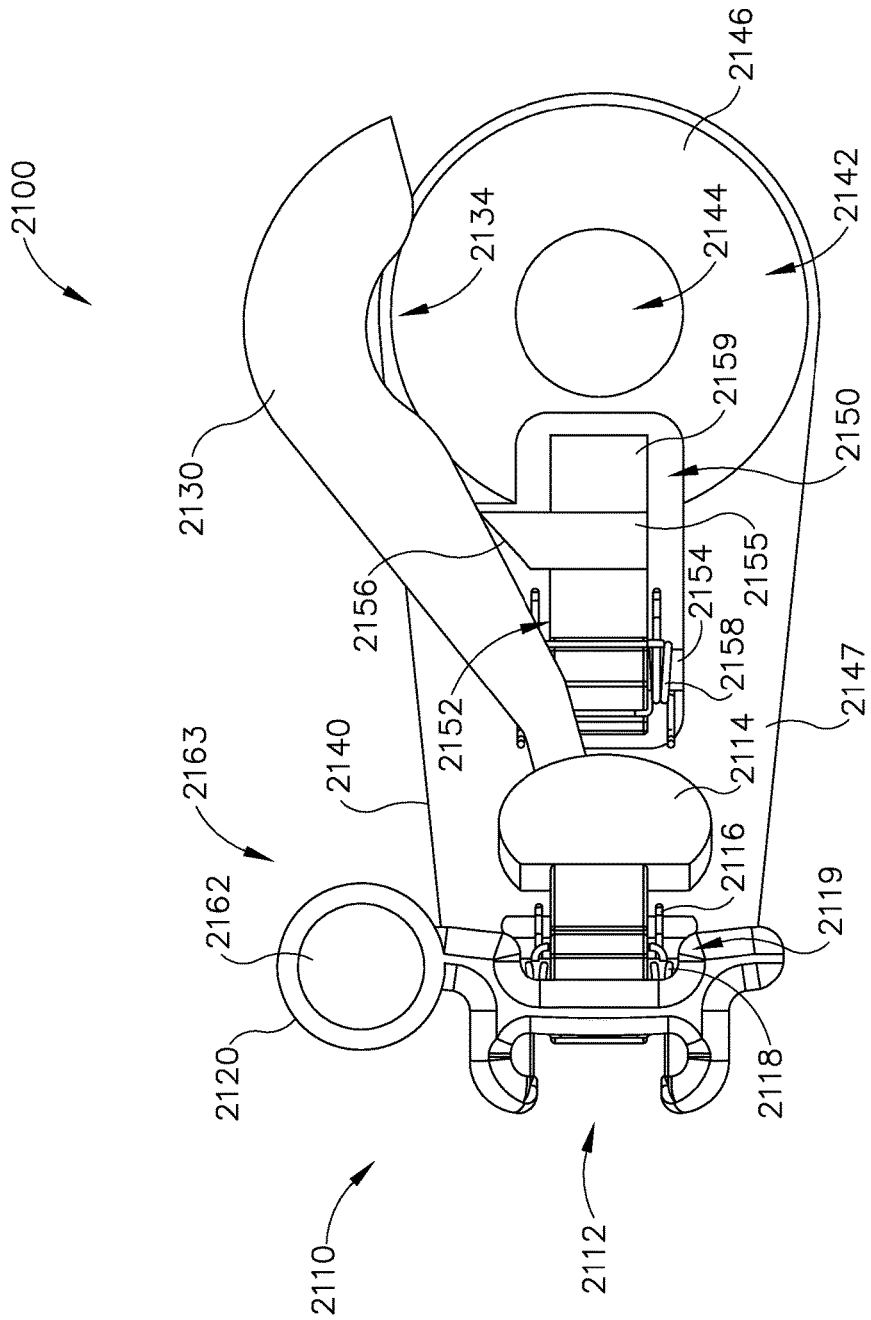
FIG. 97A depicts a front elevational view of the locking device of FIG. 93 with the stabilizing member of FIG. 95 in a first rotational position, and with the locking feature of FIG. 95 also in a first rotational position.
Figure 97B:
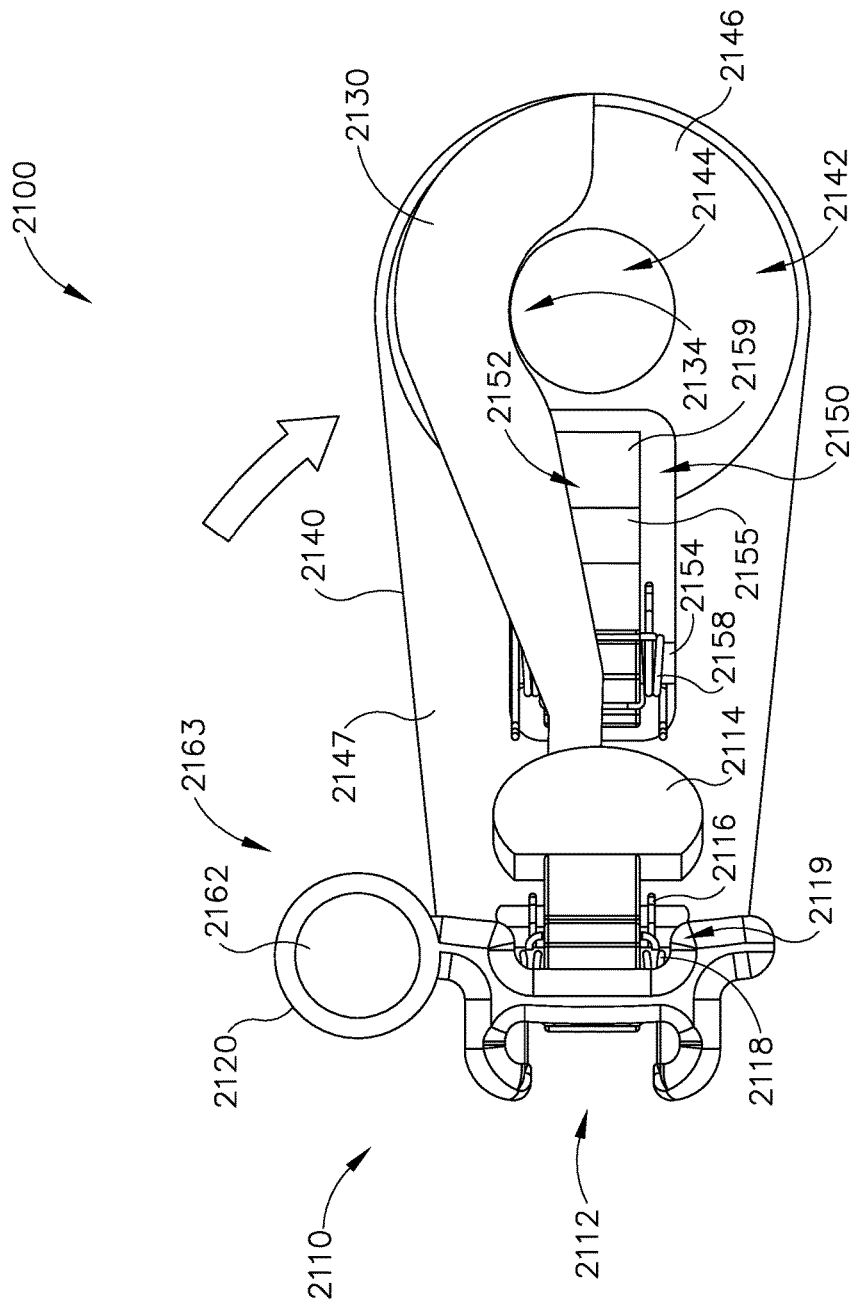
FIG. 97B depicts a front elevational view of the locking device of FIG. 93 with the stabilizing member of FIG. 95 moved into a second rotational position, and with the locking feature of FIG. 95 also moved into a second rotational position.
Figure 98:
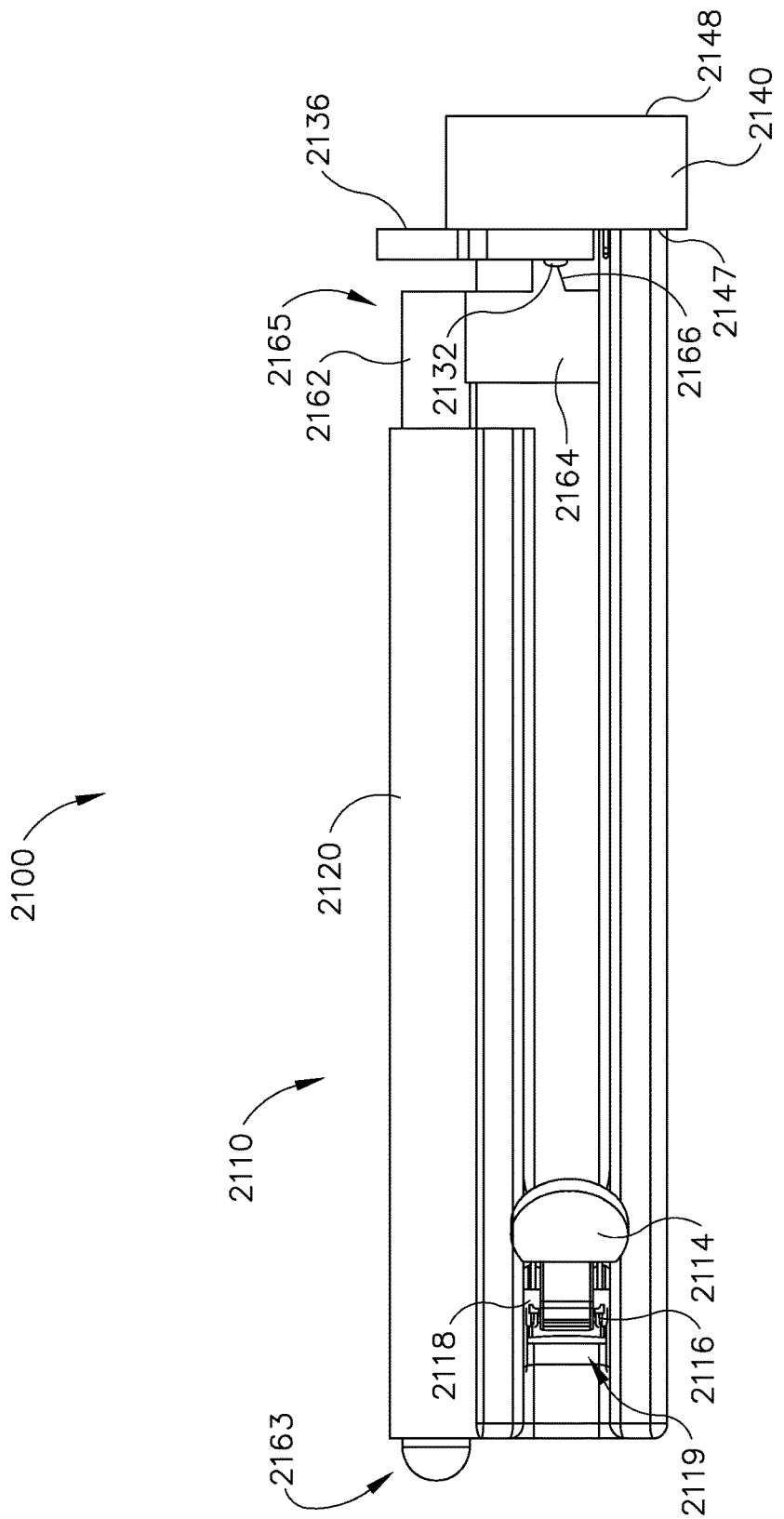
FIG. 98 depicts a side elevational view of the locking device of FIG. 93.
Figure 99:
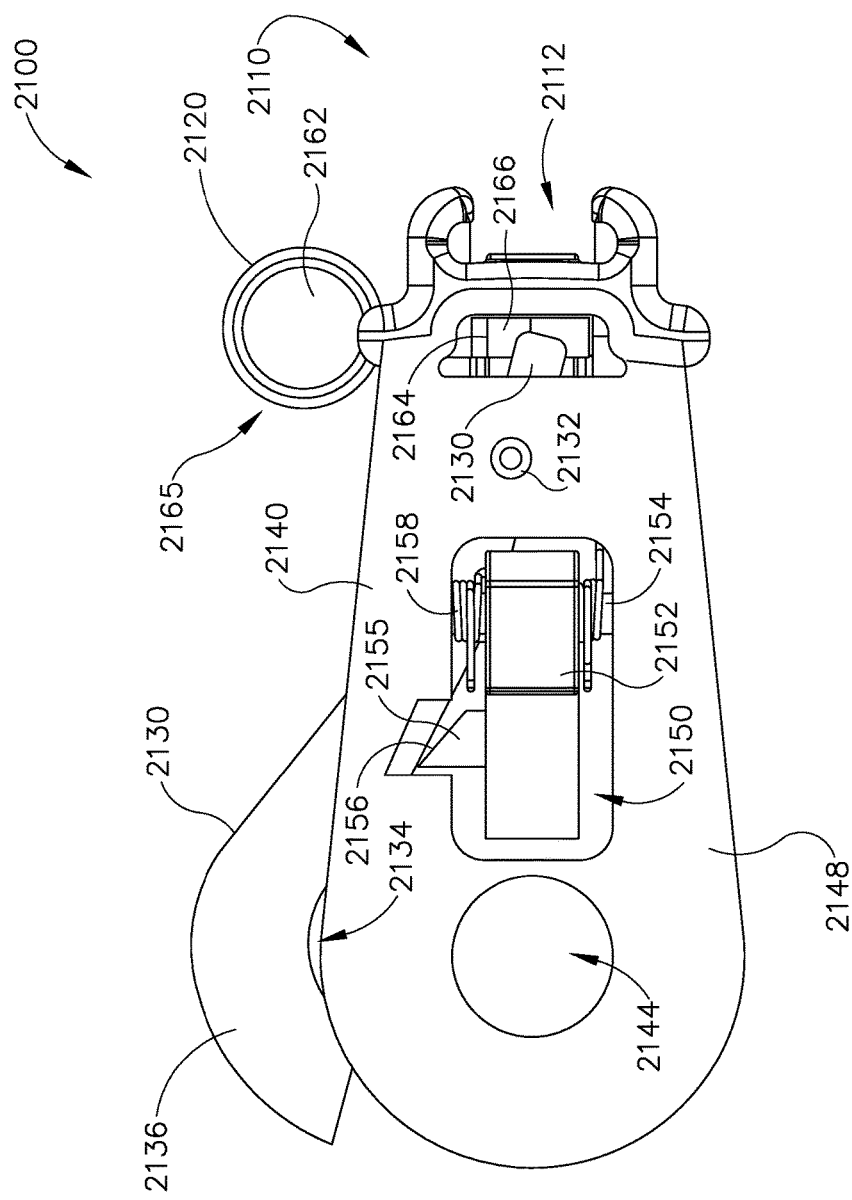
FIG. 99 depicts a back elevational view of the locking device of FIG. 93.
Figure 100:
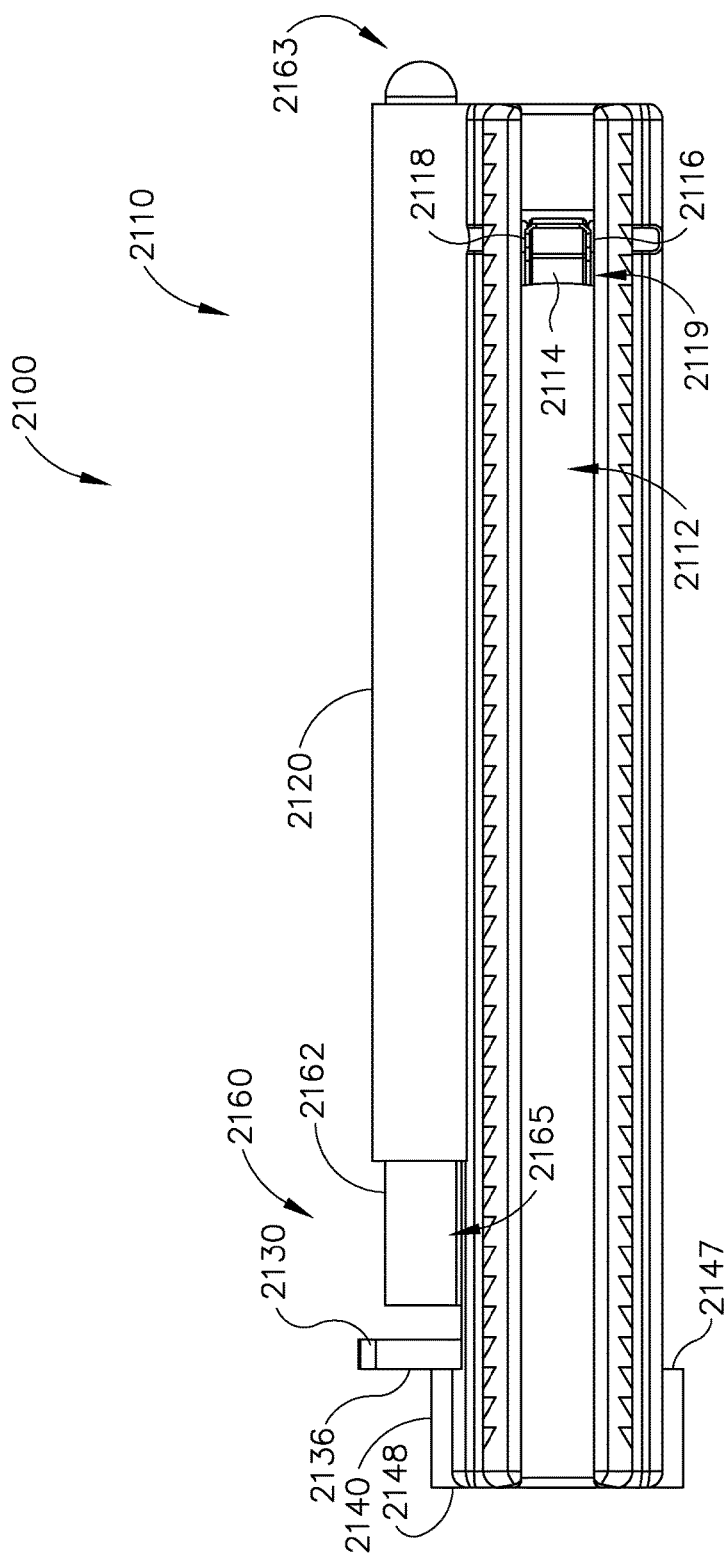
FIG. 100 depicts another side elevational view of the locking device of FIG. 93.

Locking device (2100) further comprises a locking arm (2130) rotatably secured to stationary member (2140) via a pin (2132) such that locking arm (2130) is rotatable about pin (2132) relative to circular recess (2142). As will be discussed in more detail below, locking arm (2130) is operable to be rotated between an unlocked position, shown in FIG. 97A, and a locked position, shown in FIG. 97B. Locking arm (2130) is biased toward the locked position via a spring (not shown). Locking arm (2130) comprises an arcuate recess (2134). As shown in FIG. 97B, when in the locked position, arcuate recess (2134) is configured to lay adjacent to the circular profile of guide hole (2144). As shown in FIG. 98, a distal surface (2136) of locking arm (2130) is substantially proximal to proximal surface (2147) of stationary member (2140) such that in the locked position, distal surface (2136) of locking arm (2130) is adjacent to an opening of circular recess (2142).

Figure 93:
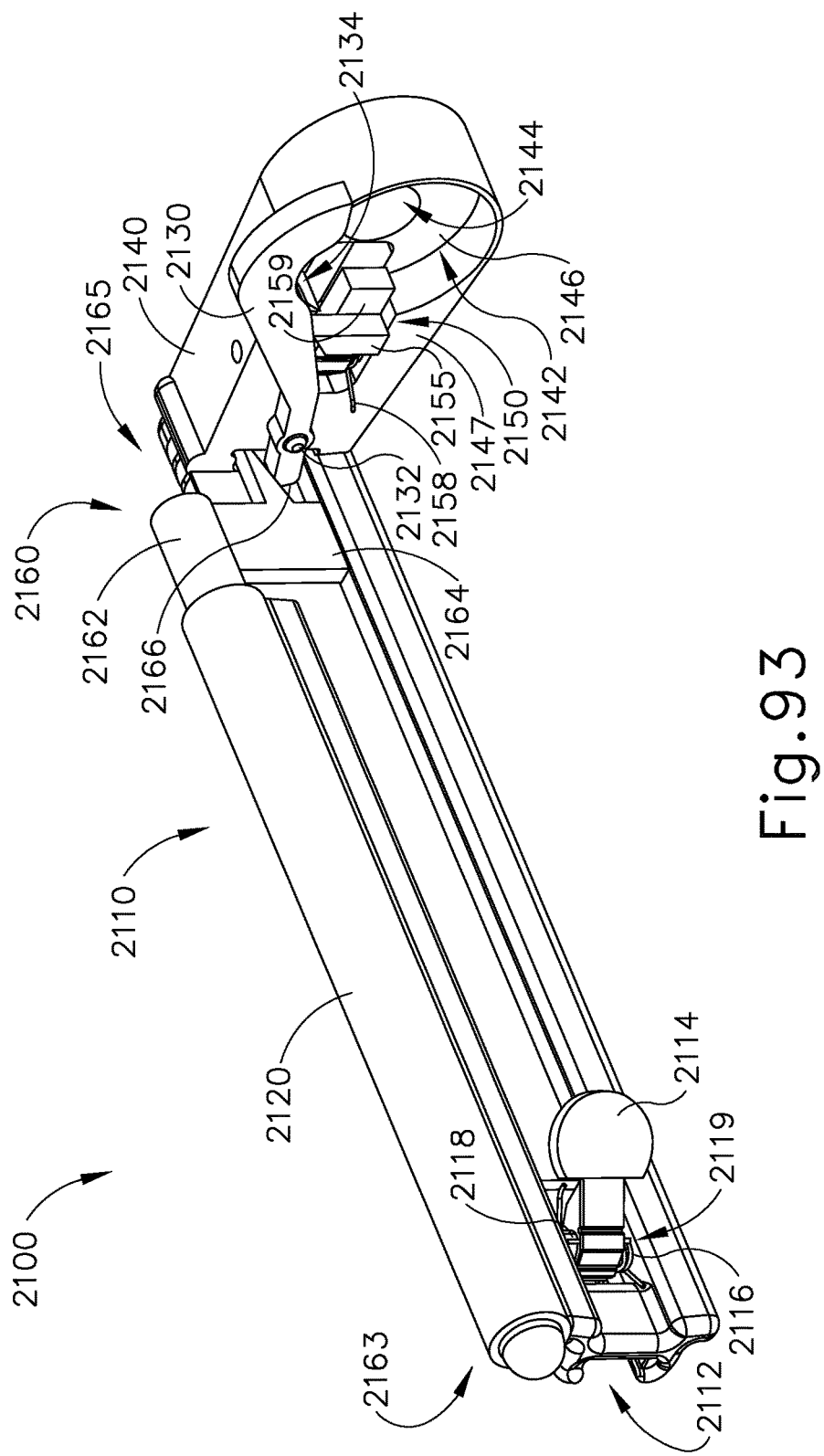
FIG. 93 depicts a perspective view of another locking device suitable for use with the biopsy system of FIG. 80.
Figure 94:
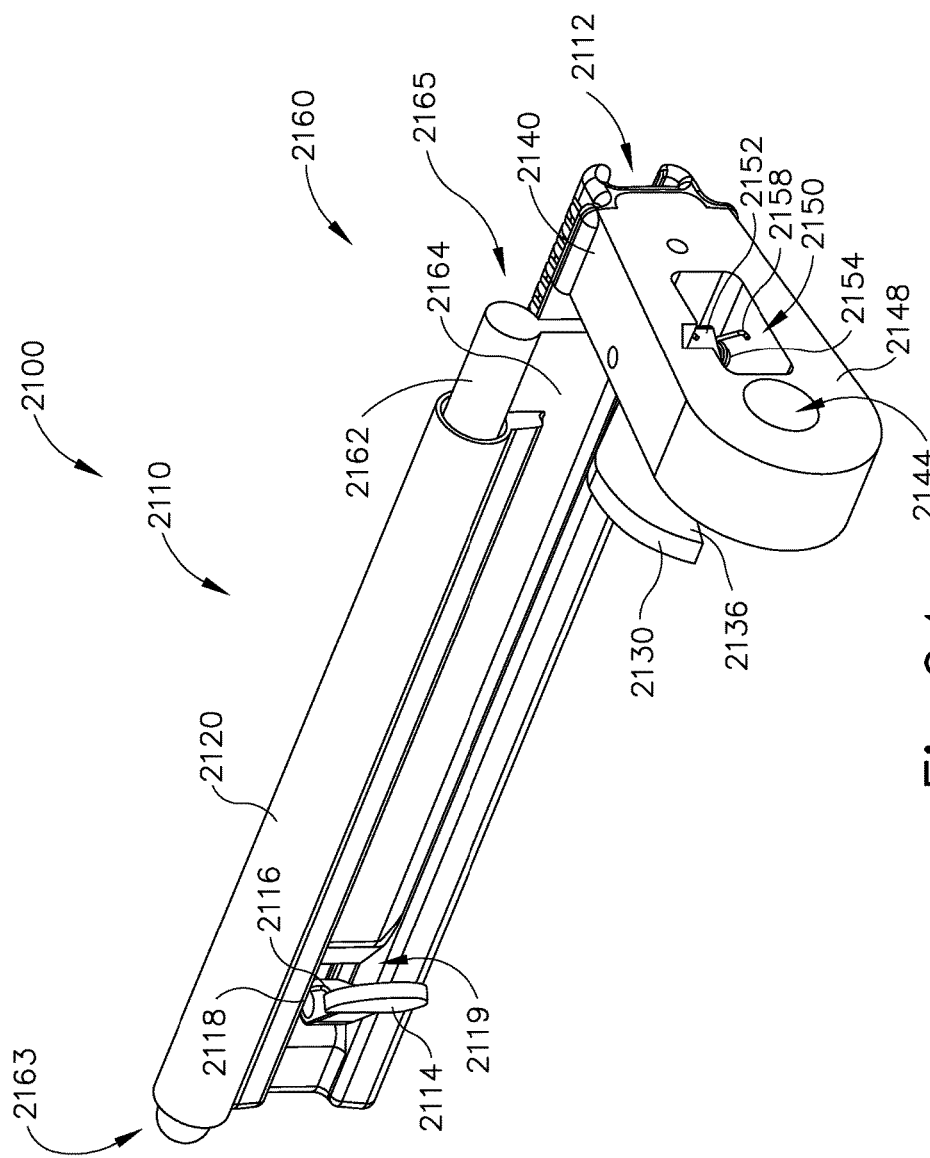
FIG. 94 depicts another perspective view of the locking device of FIG. 93.
Figure 96:
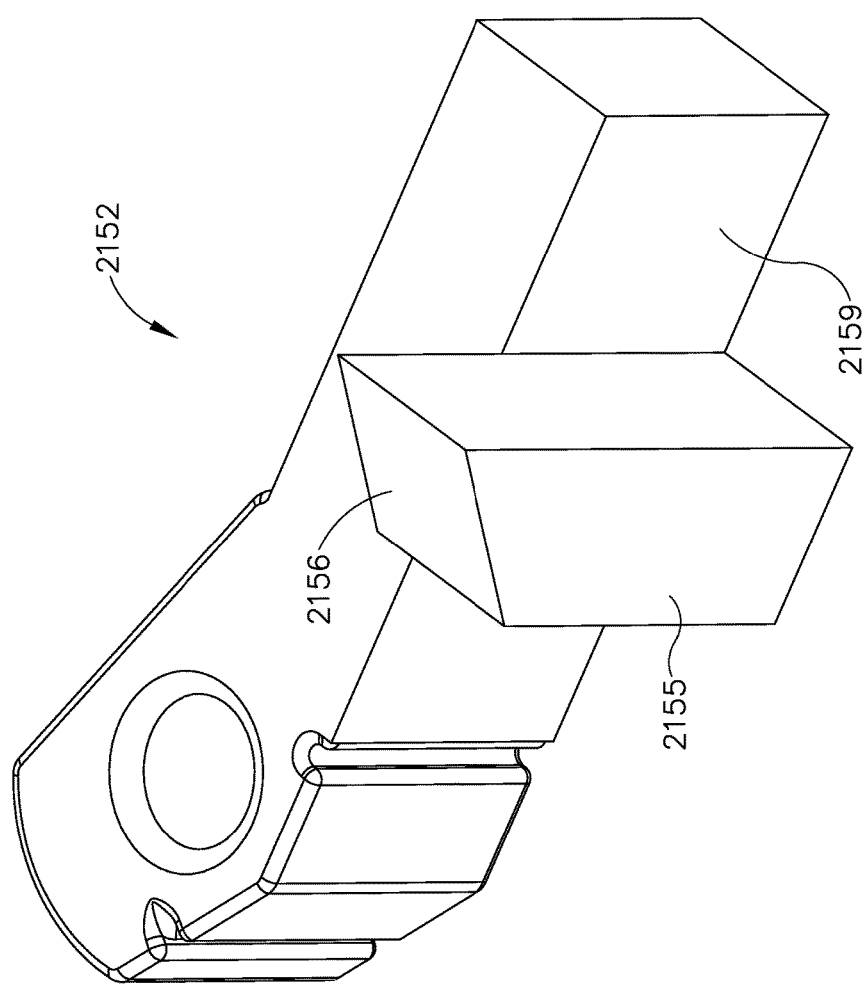
FIG. 96 depicts a perspective view of the stabilizing member of FIG. 95.

Stationary member (2140) further comprises a rounded rectangular through bore (2150). A stabilizing member (2152) is rotatably secured within rounded rectangular through bore (2150) via a pin (2154) such that stabilizing member (2152) is rotatable about pin (2154) relative to stationary member (2140). As best seen in FIG. 96, stabilizing member (2152) comprises a bearing column (2155) having an angled top surface (2156). Stabilizing member (2152) is operable to rotate between a first position, shown in FIG. 97A, where locking arm (2130) bears against top surface (2156) of bearing column (2155) of stabilizing member (2152) such that locking arm (2130) is retained in the unlocked position as shown in FIG. 97A; and a second position, shown in FIG. 97B, where locking arm (2130) no longer bears against top surface (2156) of bearing column (2155) of stabilizing member (2152) such that locking arm (2130) is able to move into the locked position as shown in FIG. 97B. Stabilizing member (2152) is resiliently biased toward the first position, shown in FIG. 97A, via a spring (2158) (i.e. biased to maintain locking arm (2130) in the unlocked position). Stabilizing member (2152) further comprises a bearing surface (2159). As shown in FIG. 93, bearing surface (2159) extends into circular recess (2142). As will be discussed in more detail below, as cannula (1300) is positioned within circular recess (2142) of stabilizing member (2140), a distal surface of lock nut (1320) of cannula (1300) is configured to engage bearing surface (2159) of stabilizing member (2152) to thereby drive stabilizing member (2152) into the second position such that locking arm (2130) is able to move into the locked position as shown in FIG. 97B.

Figure 95:
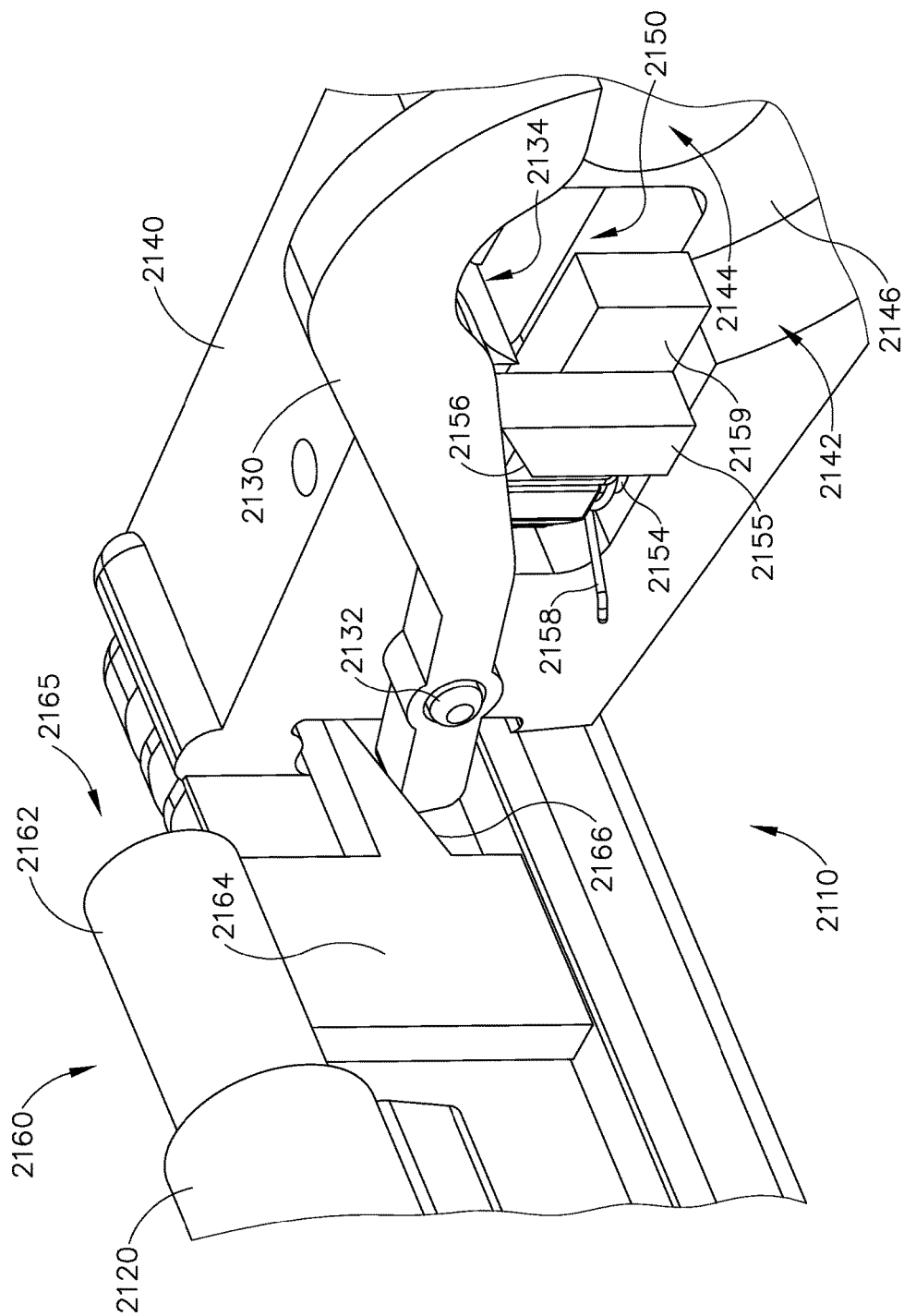
FIG. 95 depicts a detailed perspective view of a translatable member, a stabilizing member, and a locking feature of the locking device of FIG. 93.

Secondary targeting rail (2110) includes an integral cylindrical tube (2120). A translatable member (2160) is slidably disposed within cylindrical tube (2120) of secondary targeting rail (2110). Translatable member (2160) comprises a rod (2162) and a cam member (2164). Rod (2162) is slidably disposed within cylindrical tube (2120) such that translatable member (2160) is operable to translate between a first longitudinal position and a second longitudinal position. A first end (2163) of rod (2162) extends from a first end of cylindrical tube (2120). As best seen in FIG. 95, a second end (2165) of rod (2162) extends from a second end of cylindrical tube (2120) and a cam member (2164) extends perpendicularly from second end (2165) of rod (2162). Cam member (2164) comprises an angled cam surface (2166). Locking arm (2130) is configured to engage angled cam surface (2166) as translatable member (2160) translates between the first longitudinal position and the second longitudinal position and as locking arm (2130) moves between the unlocked position and the locked position. In particular, and as will be discussed in more detail below, movement of arm (2130) from the unlocked position to the locked position is configured to drive locking translatable member (2160) from the first longitudinal position to the second longitudinal position; while movement of translatable member (2160) from the second longitudinal position to the first longitudinal position is configured to drive locking arm (2130) from the locked position to the unlocked position.

Figure 101A:
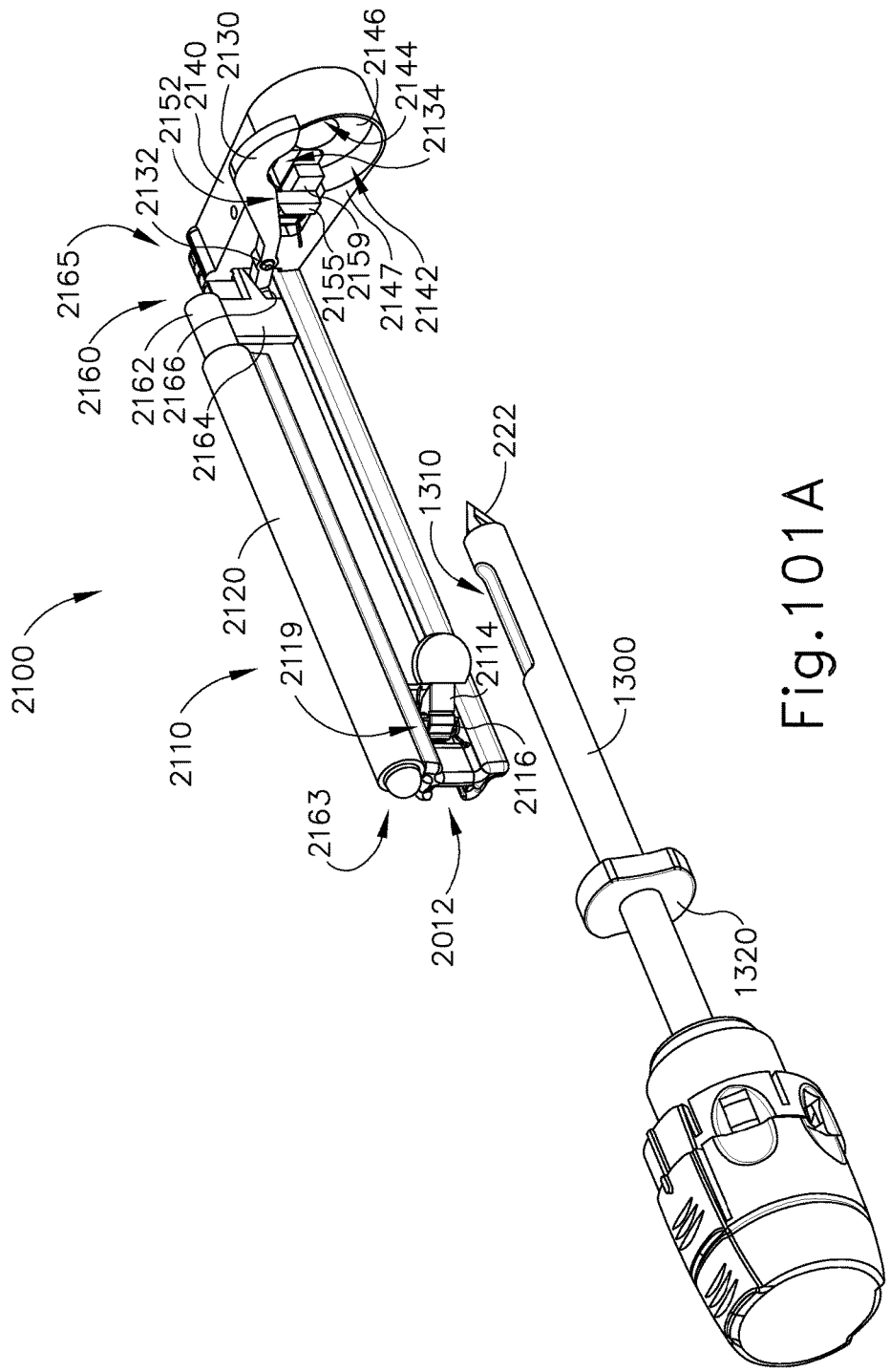
FIG. 101A depicts a perspective view of the locking device of FIG. 93 with the stabilizing member of FIG. 95 in the first rotational position of FIG. 97A, with the locking feature of FIG. 95 in the first rotational position of FIG. 97A, with the translatable member of FIG. 95 in a first longitudinal position, and with a cannula in a first longitudinal position.
Figure 101B:
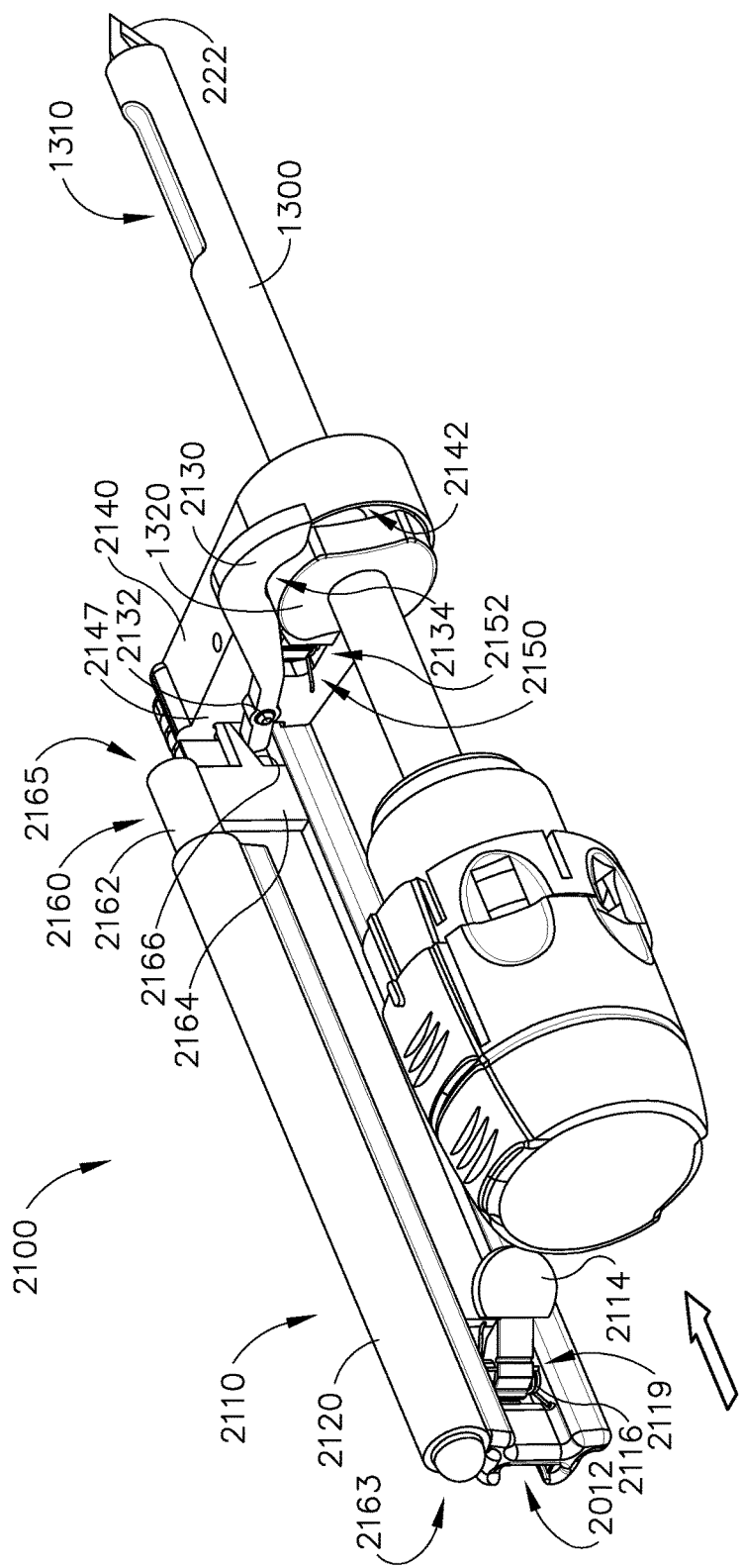
FIG. 101B depicts a perspective view of the locking device of FIG. 93 with the stabilizing member of FIG. 95 remaining in the first rotational position of FIG. 97A, with the locking feature of FIG. 95 remaining in the first rotational position of FIG. 97A, with the translatable member of FIG. 95 remaining in the first longitudinal position of FIG. 101A, and with the cannula of FIG. 101A moved into a second longitudinal position.
Figure 101C:
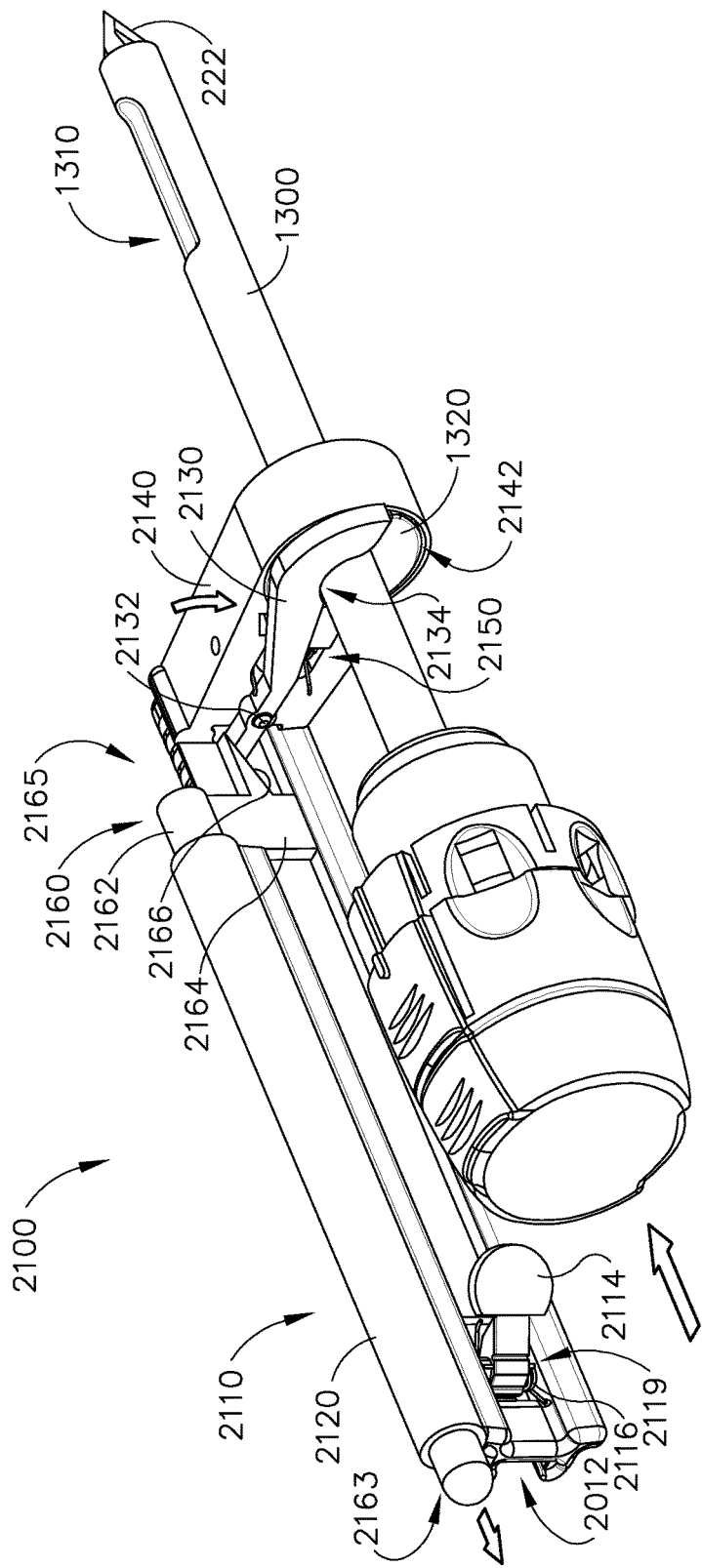
FIG. 101C depicts a perspective view of the locking device of FIG. 93 with the stabilizing member of FIG. 95 moved into the second rotational position of FIG. 97B, with the locking feature of FIG. 95 moved into the second rotational position of FIG. 97B, and with the translatable member of FIG. 95 moved into a second longitudinal position, all by movement of the cannula of FIG. 101 into a third longitudinal position.
Figure 102A:
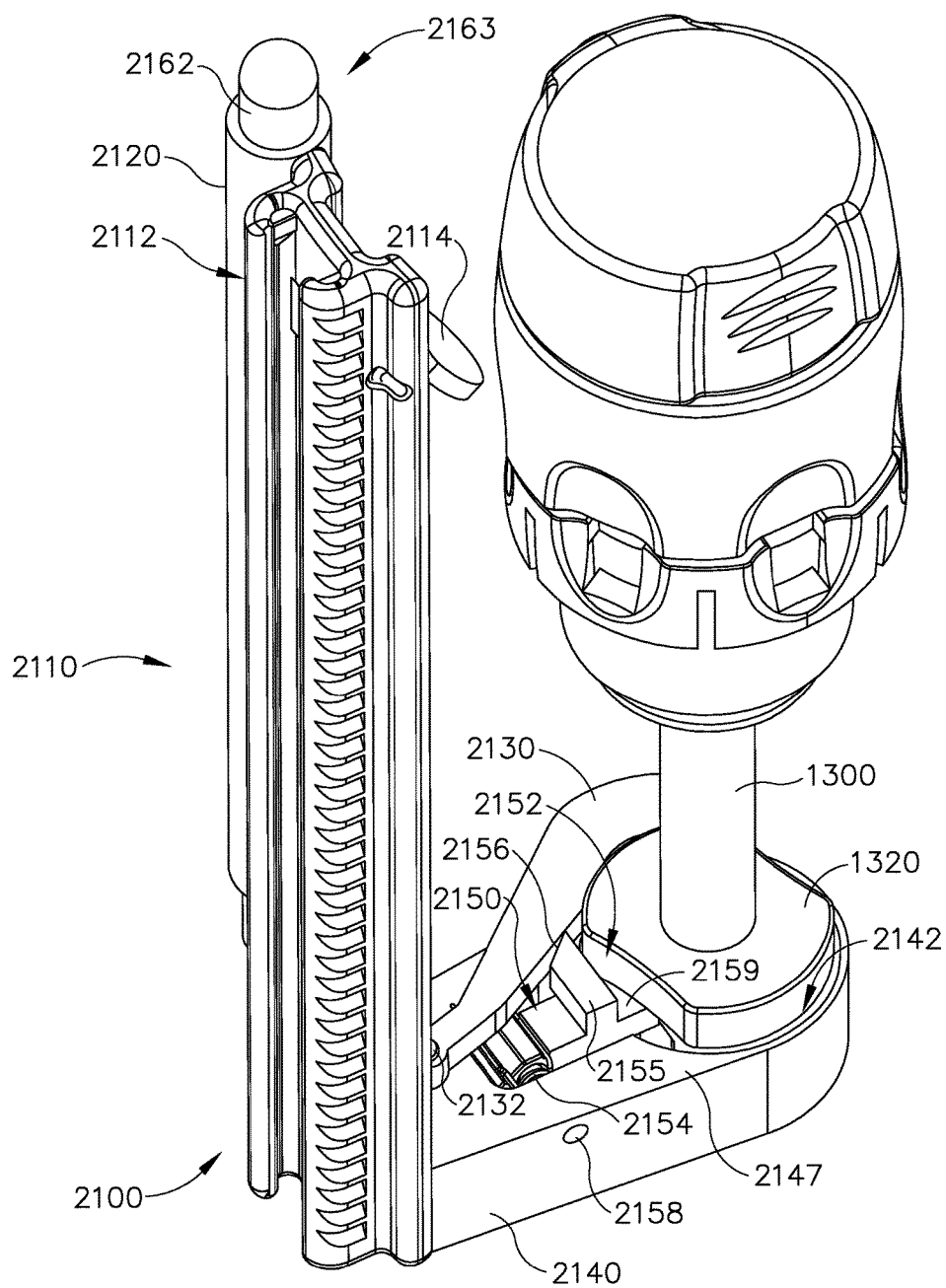
FIG. 102A depicts a detailed perspective view of the locking device of FIG. 93 with the stabilizing member of FIG. 95 in the first rotational position of FIG. 97A, with the locking feature of FIG. 95 in the first rotational position of FIG. 97A, with the translatable member of FIG. 95 in the first longitudinal position of FIG. 101A, and with the cannula of FIG. 101A in the second longitudinal position of FIG. 101B.
Figure 102B:
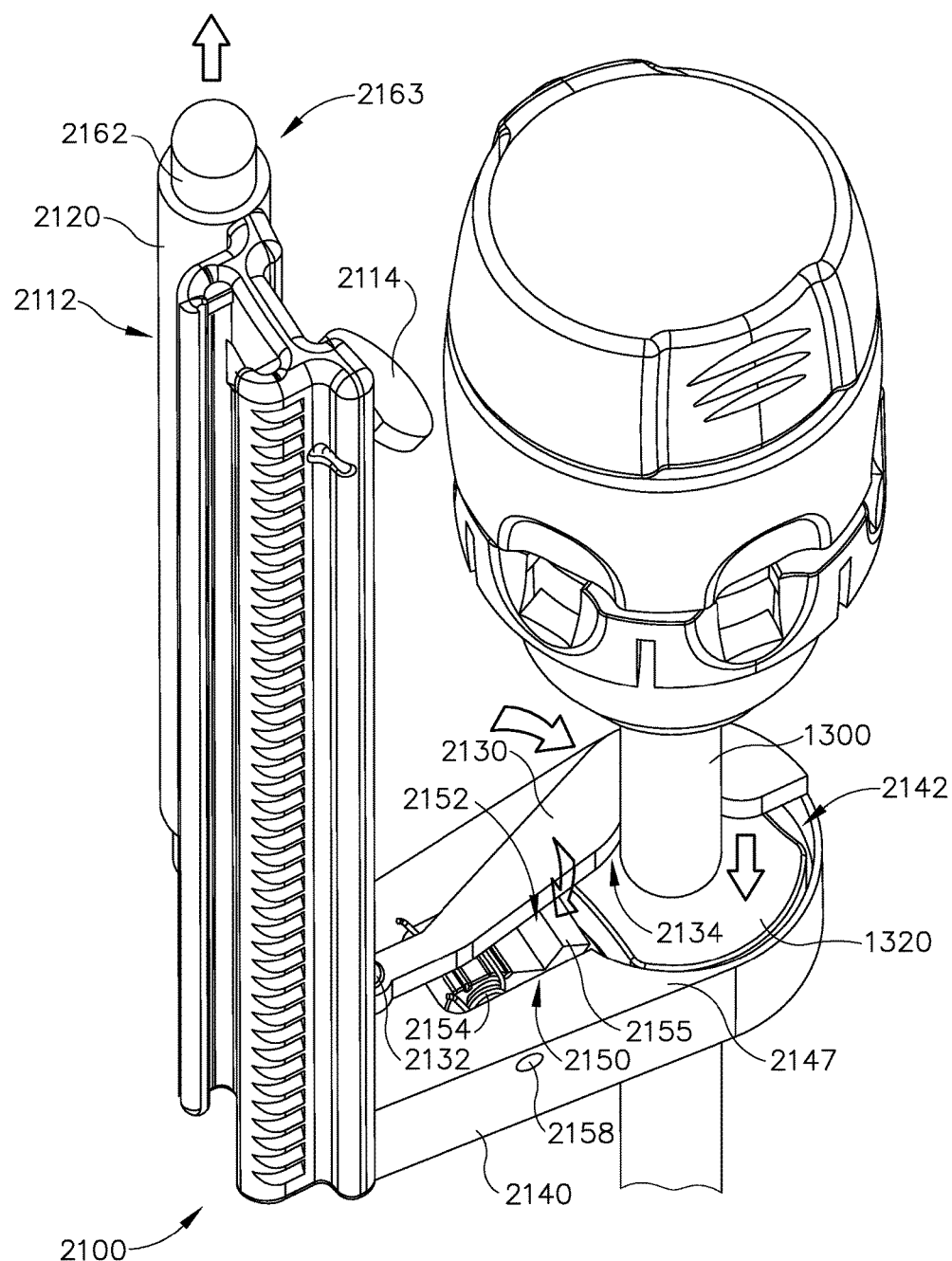
FIG. 102B depicts a detailed perspective view of the locking device of FIG. 93 with the stabilizing member of FIG. 95 moved into the second rotational position of FIG. 97B, with the locking feature of FIG. 95 moved into the second rotational position of FIG. 97B, and with the translatable member of FIG. 95 moved into the second longitudinal position of FIG. 101C, all by movement of the cannula of FIG. 101 into the third longitudinal position of FIG. 101C.

FIGS. 101A-102B show the steps of locking cannula (1300) within guide hole (2144) of locking device (2100). FIG. 101A shows cannula (1300) in a first longitudinal position removed from locking device (2100). With cannula (1300) in this position, locking arm (2130) is retained in the unlocked position by engagement of locking arm (2130) with top surface (2156) of bearing column (2155) of stabilizing member (2152) such that cannula (1300) may be received within circular recess (2142) and guide hole (2144) of stationary member (2140). As discussed above, with locking arm (2130) in the unlocked position, translatable member (2160) is in the first longitudinal position. Cannula (1300) is then moved into a second longitudinal position such that lock nut (1320) is disposed within circular recess (2142) of stationary member (2140) and such that cannula (1300) is passed into guide hole (2144) to a point where a distal surface of lock nut (1320) engages bearing surface (2159) of stabilizing member (2152) as shown in FIG. 101B and in more detail in FIG. 102A. As cannula (1300) is moved into this position, locking arm (2130) remains in the unlocked position such that lock nut (1320) may be positioned within circular recess (2142) of stationary member (2140) and such that cannula (1300) is passed into guide hole (2144) of stationary member (2140). Cannula (1300) is then moved into a third longitudinal position such that lock nut (1320) and cannula (1300) are passed further into circular recess (2142) and guide hole (2144) respectively and such that lock nut (1320) drives stabilizing member (2152) into the second position to thereby enable locking arm (2130) to move into the locked position as shown in FIG. 101C and in more detail in FIG. 102B. A spring (not shown) may drive locking arm (2130) toward the locked position as soon as stabilizing member (2152) pivots toward the second position thereby providing the necessary clearance. As locking arm (2130) moves into the locked position, translatable member (2160) is driven proximally into the second longitudinal position by contact between locking arm (2130) and angled cam surface (2166) of cam member (2164) of translatable member (2160). In the locked position, distal surface (2136) of locking arm (2130) engages a proximal surface of lock nut (1320) such that cannula (1300) is locked within circular recess (2142) and within guide hole (2144) of stationary member (2140) of locking device (2100). In other words, bottom surface (2146) and lock nut (1320) cooperate to restrict distal movement of cannula (1300); while locking arm (2130) and lock nut (1320) cooperate to restrict proximal movement of cannula (1300).

Figure 103A:
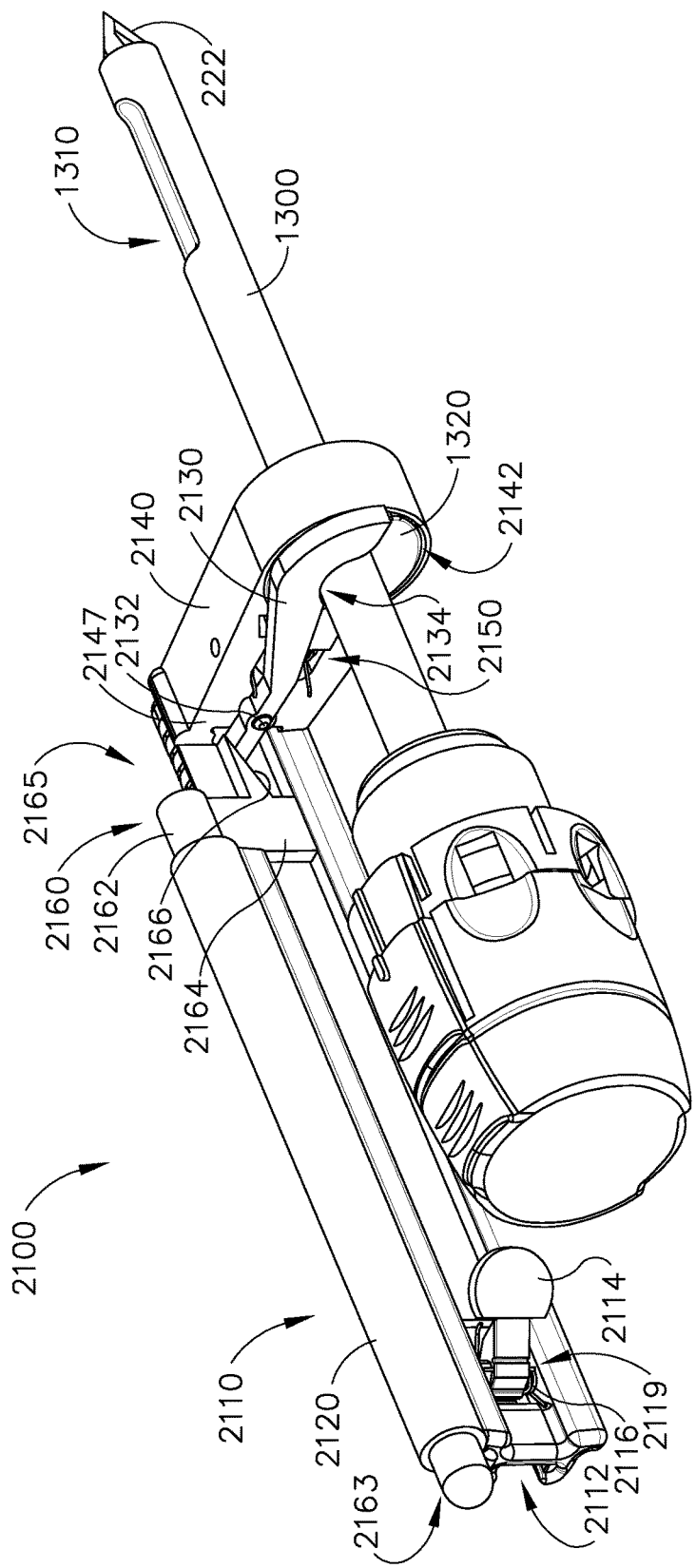
FIG. 103A depicts a perspective view of the locking device of FIG. 93 with the stabilizing member of FIG. 95 in the second rotational position of FIG. 97B, with the locking feature of FIG. 95 in the second rotational position of FIG. 97B, with the translatable member of FIG. 95 moved in the second longitudinal position of FIG. 101C, and with the cannula of FIG. 101 in the third longitudinal position of FIG. 101C.
Figure 103B:
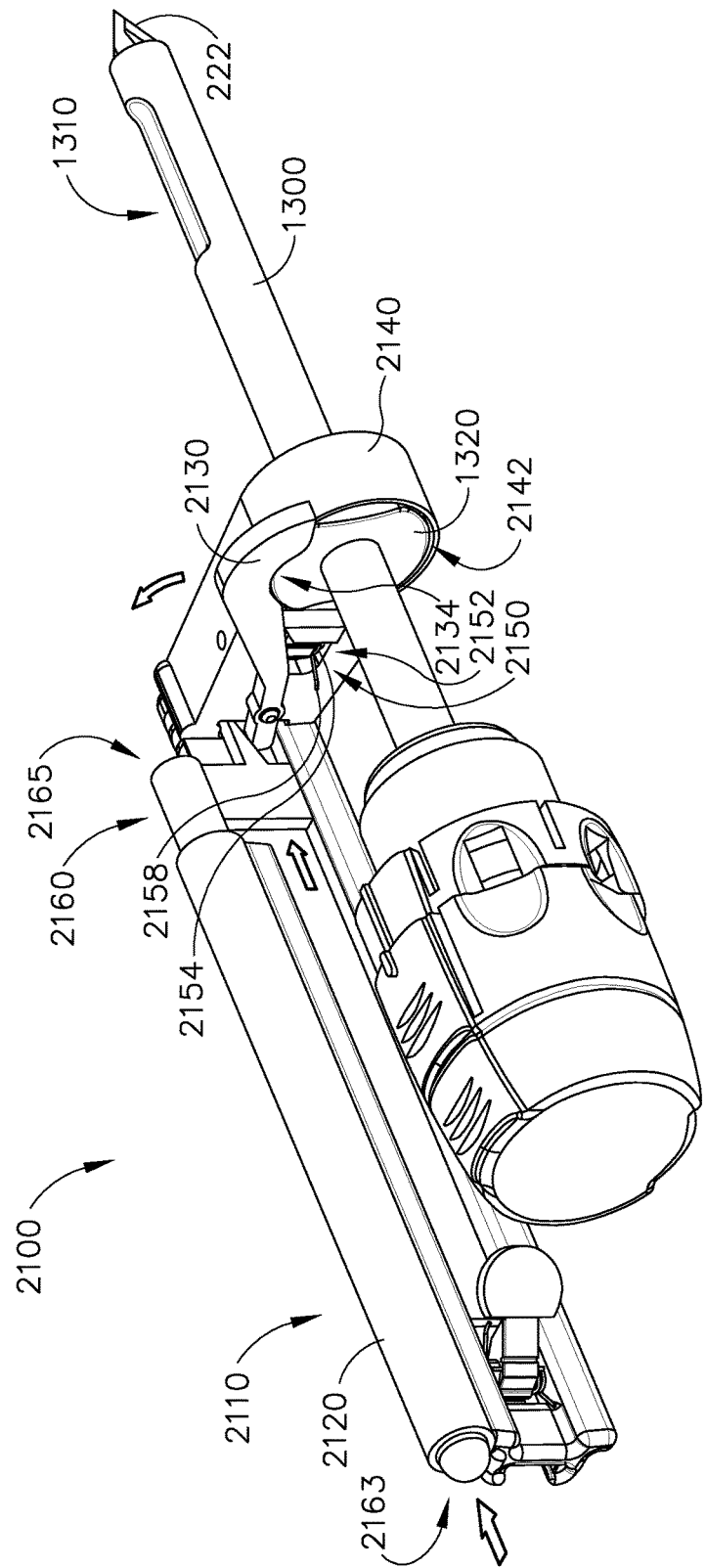
FIG. 103B depicts a perspective view of the locking device of FIG. 93 with the locking feature of FIG. 95 moved back into the first rotational position of FIG. 97A by movement of the translatable member of FIG. 95 back into the first longitudinal position of FIG. 101A, with the stabilizing member of FIG. 95 remaining in the second rotational position of FIG. 97B, and with the cannula of FIG. 101 remaining in the third longitudinal position of FIG. 101C.
Figure 103C:
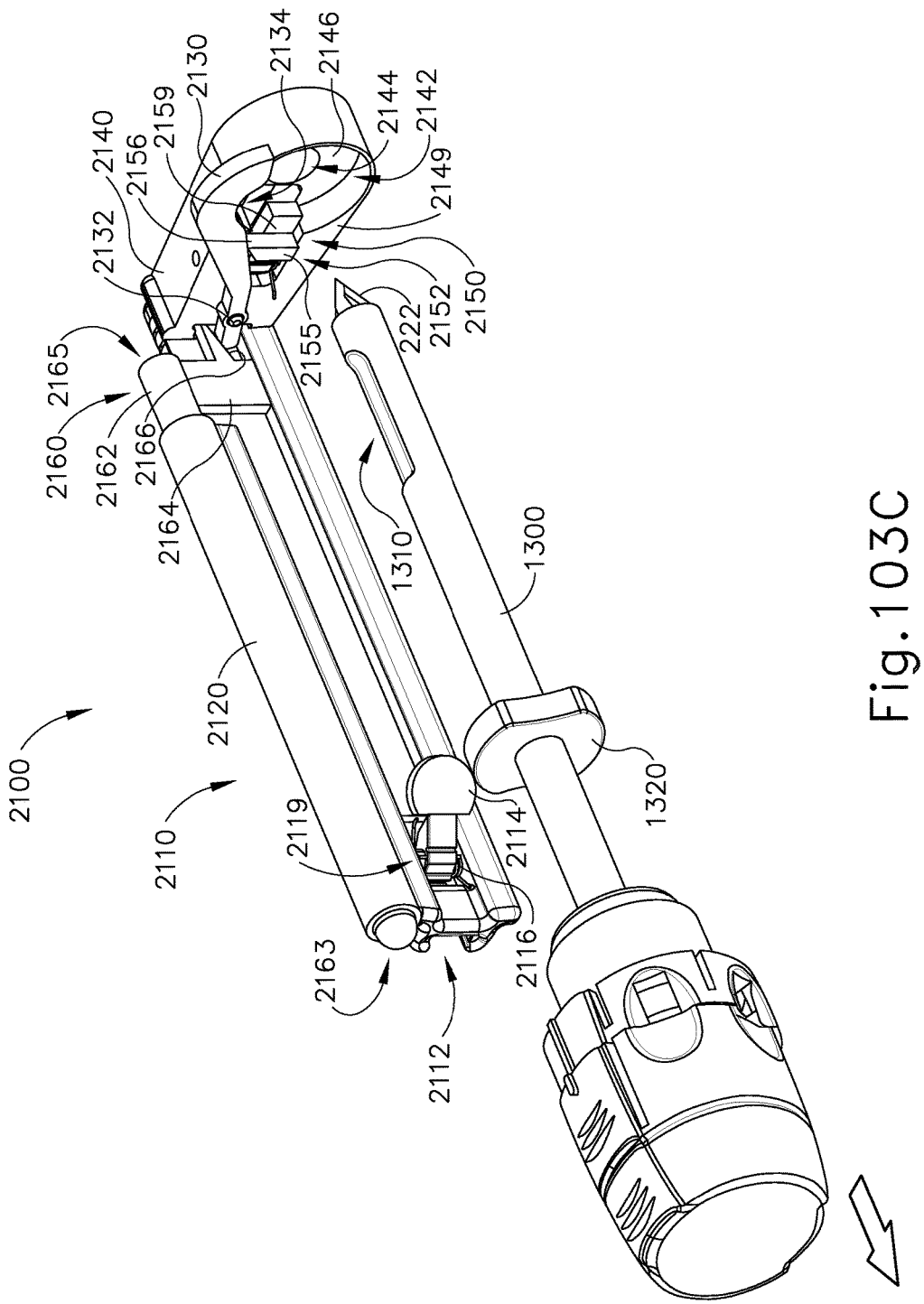
FIG. 103C depicts a perspective view of the locking device of FIG. 93 with the locking feature of FIG. 95 remaining in the first rotational position of FIG. 97A, with the translatable member of FIG. 95 back remaining in the first longitudinal position of FIG. 101A, and with the stabilizing member of FIG. 95 moved back into the first rotational position of FIG. 97A by movement of the cannula of FIG. 101 back into the first longitudinal position of FIG. 101A.

FIGS. 103A-103C show the steps of unlocking cannula (1300) from locking device (2100). FIG. 103A shows translatable member (2160) in the second longitudinal position, locking arm (2130) in the locked position, stabilizing member (2152) in the second position, and cannula (1300) in the third longitudinal position. Translatable member (2160) is driven distally into the first longitudinal position as shown in FIG. 103B. For instance, an operator may simply press distally on exposed first end (2163) of translatable member (2160). As translatable member (2160) is driven into the first longitudinal position, contact between angled cam surface (2166) of cam member (2164) of translatable member (2160) and locking arm (2130) drives locking arm (2130) into the unlocked position. With locking arm (2130) in the unlocked position, stabilizing member (2152) is driven toward the first position via spring (2158) to thereby retain locking arm (2130) in the unlocked position. With locking arm (2130) in the unlocked position, cannula (1300) may be retracted proximally into the first longitudinal position to thereby remove cannula (1300) from locking device (2100).

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for guiding a biopsy instrument into tissue of a patient, the apparatus comprising:
   (a) a cannula, wherein at least a portion of the biopsy instrument is insertable into the cannula;
   (b) a guide device defining a proximal face and a distal face and including at least one guide hole, wherein the at least one guide hole is configured to receive the cannula, wherein the at least one guide hole defines a guide axis;
   (c) a support structure, wherein the support structure is configured to position the guide device relative to a breast of a patient;
   (d) a depth stop device, wherein the depth stop device is configured to selectively lock in position at a plurality of axial positions along the cannula, wherein the depth stop device is configured to engage the guide device to prevent insertion of the cannula beyond a predetermined axial distance; and
   (e) a locking assembly, wherein the locking assembly includes a lock arm defining a proximal face and a distal face, wherein the lock arm is rotatable about an axis parallel with the guide axis such that the lock arm is configured to cooperate with the guide device to capture the depth stop device between the proximal face of the guide device and the distal face of the lock arm to thereby restrict translational movement of the cannula within the guide hole of the guide device.

2. The apparatus of claim 1 further comprising an obturator, wherein the obturator includes a tissue piercing distal tip, wherein the obturator is insertable into the cannula.

3. The apparatus of claim 2, wherein the cannula includes a distal opening, wherein at least a portion of the obturator is configured to extend through the distal opening when the obturator is inserted into the cannula.

4. The apparatus of claim 1, wherein the support structure includes a first plate having a plurality of apertures, wherein the guide device is sized to fit within each aperture of the plurality of apertures.

5. The apparatus of claim 1, wherein the guide device further includes a body and a plurality of resilient members extending distally from the body.

6. The apparatus of claim 5, wherein each resilient member of the plurality of resilient members extends distally and outwardly from the body.

7. The apparatus of claim 5, wherein each resilient member of the plurality of resilient members is configured to engage at least a portion of the support structure to thereby releasably secure the body of the guide device to the support structure.

8. The apparatus of claim 5, wherein each resilient member of the plurality of resilient members includes a first portion and a second portion, wherein the first portion extends outwardly relative to the body, wherein the second portion extends inwardly relative to the body, wherein an apex is defined between the first portion and the second portion.

9. The apparatus of claim 1, wherein the guide device includes a plurality of guide holes, wherein each guide hole of the plurality of guide holes defines a discrete guide axis.

10. The apparatus of claim 9, wherein each guide hole of the plurality of guide holes is positioned such that each discrete guide axis of each guide hole is parallel with all other discrete guide axes.

11. The apparatus of claim 9, wherein at least one guide hole of the plurality of guide holes defines a common open area that is co-defined by another guide hole of the plurality of guide holes.

12. The apparatus of claim 1, wherein the guide device further includes a pair of projections extending on opposite sides of the guide device, wherein each projection of the pair of projections is configured to prevent over insertion of the guide device into the support structure.

13. The apparatus of claim 12, wherein the lock arm of the locking assembly is movably secured to a selected projection of the pair of projections of the guide device such that the lock arm is configured to move relative to the selected projection while remaining secured to the selected projection.

14. The apparatus of claim 1, wherein the lock arm of the locking assembly includes at least one receiving feature, wherein the at least one receiving feature is configured to receive the cannula.

15. The apparatus of claim 14, wherein the at least one receiving feature of the lock arm includes a semi-cylindrical shape.

16. An apparatus for guiding a biopsy instrument into tissue of a patient, the apparatus comprising:

(a) a cannula, wherein at least a portion of the biopsy instrument is insertable into the cannula;
(b) a guide device including at least one guide hole, wherein the at least one guide hole is configured to receive the cannula;
(c) an axial locking feature, wherein the axial locking feature is configured to receive the cannula, wherein the axial locking feature is configured to adjustably engage the cannula to be secured at a predetermined selected axial position along a length of the cannula; and
(d) a locking assembly, wherein the locking assembly includes:
  (i) a pin, and
  (ii) a lock arm,
  wherein the lock arm is configured to pivot relative to the guide device via the pin to a locked position in which a distal face of the lock arm is positioned to engage a proximal face of the axial locking feature to thereby restrict translational movement of the cannula within the guide hole of the guide device, wherein the pin defines a length corresponding to a portion of the axial locking feature such that the lock arm is configured to maintain engagement between the guide device and the axial locking feature.

17. The apparatus of claim 16, wherein the pin of the locking assembly projects proximally from the guide device such that the lock arm is proximally offset from the guide device.

18. The apparatus of claim 16, wherein the lock arm of the locking assembly includes an annular portion.

19. The apparatus of claim 18, wherein the lock arm of the locking assembly is movable between a first positon and a second position, wherein the annular portion of the lock arm is positioned on the lock arm to align with the at least one guide hole when the lock arm is in the second position.

20. An apparatus for guiding a biopsy instrument into tissue of a patient, the apparatus comprising:
(a) a cannula, wherein the cannula is configured to receive at least a portion of the biopsy instrument, wherein the cannula defines a cannula axis;
(b) a guide device including a first pair of opposing faces and a plurality of guide holes extending between the first pair of opposing faces, wherein each guide hole of the plurality of guide holes is configured to receive the cannula such that the cannula is positionable in a plurality of guide positions relative to the guide device;
(c) a depth stop member, wherein the depth stop member is selectively attachable to the cannula along the cannula axis at a plurality of positions along the cannula axis; and
(d) a locking assembly rotatably secured to the guide device, wherein the locking assembly includes a lock arm, wherein the lock arm is configured to rotate about an axis that is parallel with the cannula axis, wherein the lock arm is configured to cooperate with the guide device to capture the depth stop member between the guide device and the lock arm to thereby restrict proximal and distal movement of the cannula within each guide hole of the guide device.

* * * * *